United States Patent
Fan et al.

(10) Patent No.: US 10,968,212 B2
(45) Date of Patent: *Apr. 6, 2021

(54) COMPOUNDS HAVING ESTROGEN RECEPTOR ALPHA DEGRADATION ACTIVITY AND USES THEREOF

(71) Applicant: ACCUTAR BIOTECHNOLOGY INC., Brooklyn, NY (US)

(72) Inventors: Jie Fan, New York, NY (US); Ke Liu, Shanghai (CN)

(73) Assignee: Accutar Biotechnology Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/560,178

(22) Filed: Sep. 4, 2019

(65) Prior Publication Data
US 2020/0024269 A1    Jan. 23, 2020

Related U.S. Application Data

(60) Continuation of application No. 15/883,495, filed on Jan. 30, 2018, now Pat. No. 10,450,307, which is a division of application No. 15/646,793, filed on Jul. 11, 2017, now Pat. No. 9,944,632.

(60) Provisional application No. 62/361,263, filed on Jul. 12, 2016.

(51) Int. Cl.
| C07D 417/12 | (2006.01) |
| A61P 35/00 | (2006.01) |
| A61K 47/55 | (2017.01) |
| C07K 5/062 | (2006.01) |

(52) U.S. Cl.
CPC ............ *C07D 417/12* (2013.01); *A61K 47/55* (2017.08); *A61P 35/00* (2018.01); *C07K 5/06034* (2013.01)

(58) Field of Classification Search
None
See application file for complete search history.

(56) References Cited

U.S. PATENT DOCUMENTS

| 6,207,716 B1 | 3/2001 | Willson |
| 9,944,632 B2 | 4/2018 | Fan |
| 2014/0356322 A1 | 12/2014 | Crews et al. |
| 2016/0136230 A1 | 5/2016 | Campos et al. |

FOREIGN PATENT DOCUMENTS

WO    WO 2014/008159 A1    1/2014

OTHER PUBLICATIONS

Bai, L., et al., "Targeted Degradation of BET Proteins in Triple-Negative Breast Cancers," *Cancer Research* (2017), 77(9):OF1-OF12.
Chi, K.R., "Drug Developers Delve Into the Cell's Trash-Disposal Machinery," *Nature Reviews Drug Discovery* (2016) 15:295-297.
Ciulli, A., et al., "Structural Basis of PROTAC Cooperation Recognition for Selective Protein Degradation," *Nature Chemical Biology* (2017) 13:514-521.
Collins, F. et al. "Expression of oestrogen receptors, ERα, ERβ, and ERβ variants, in endometrial cancers and evidence that prostaglandin F may play a role in regulating expression of ERα." *BMC Cancer,* 2009, 9(330), pp. 1-13.
Collins, I., et al., "Chemical approaches to targeted protein degradation through modulation of the ubiquitin-proteasome pathway," *Biochemical Journal* (2017), 474:1127-1147.
Crews, C.M., et al., "Induced Protein Degradation: An Emerging Drug Discovery Paradigm," *Nature Reviews Drug Discovery* (2017) 16:101-114.
Crews, C.M., et al., "Targeted Protein Degradation by PROTACs," *Pharmacology & Therapeutics* (2017) 174:138-144.
Huang, X., et al., "Drugging the Undruggables: Exploring the Ubiquitin System for Drug Development," *Cell Research* (2016) 26:484-498.
Kawai, H. et al. "Estrogen Receptor α and β are Prognostic Factors in Non-Small Cell Lung Cancer." *Clin. Cancer Res.,* 2005, 11(14), pp. 5084-5089.
Latif, T., et al., "Thalidomide and its analogues in the treatment of Multiple Myeloma," *Experimental Hematology & Oncology* (2012), 1:27.
Lu, J., et al., "Hijacking the E3 Ubiquitin Ligase Cereblon to Efficiently Target BRD4," *Chemistry & Biology* (2015), 22:755-763.
Nozoe, T. et al., "Significance of Immunohistochemical Expression of Estrogen Receptors α and β in Squamous Cell Carcinoma of the Esophagus." *Clin. Cancer Res.,* 2007, 13(14), pp. 4046-4050.
Sudhakar, A., "History of Cancer, Ancient and Modern Treatment Methods." *J. Can. Sci. Ther.,* 2009, 1(2), pp. 1-4.
Van Kruchten, M. et al. "Assessment of Estrogen Receptor Expression in Epithelial Ovarian Cancer Patients Using 16α-[18]Fluoro-17β-Estradiol PET/CT." *J. Nucl. Med.,* 2015, 56(1), pp. 50-55.
Yeh, C-R. et al. "Estrogen receptors in prostate development and cancer." *Am. J. Clin. Exp. Urol.,* 2014, 2(2), pp. 161-168.
PCT Notification of Transmittal of the International Search Report and the Written Opinion of the International Searching Authority issued in International Application No. PCT/US2017/041526, dated Nov. 9, 2017.

*Primary Examiner* — Kamal A Saeed
(74) *Attorney, Agent, or Firm* — Finnegan, Henderson, Farabow, Garrett & Dunner, LLP

(57) ABSTRACT

The present disclosure relates to novel compounds, pharmaceutical compositions containing such compounds, and their use in prevention and treatment of estrogen-related diseases and conditions.

48 Claims, 22 Drawing Sheets

COMPOUNDS HAVING ESTROGEN RECEPTOR ALPHA DEGRADATION ACTIVITY AND USES THEREOF

This application is a continuation of U.S. patent application Ser. No. 15/883,495, filed Jan. 30, 2018, which is a division of U.S. patent application Ser. No. 15/646,793, filed Jul. 11, 2017 (now U.S. Pat. No. 9,944,632, issued Apr. 17, 2018), and claims the benefit of priority to U.S. Provisional Application No. 62/361,263, filed Jul. 12, 2016, all of which are incorporated herein by reference.

The present disclosure relates to novel compounds, pharmaceutical compositions containing such compounds, and their use in prevention and treatment of diseases and conditions.

Estrogen Receptor alpha is a nuclear receptor that is activated by the hormone estrogen. Upon estrogen binding, Estrogen Receptor alpha undergoes a conformational change and dimerizes, which, along with other regulation factors, leads to a proliferation of cancerous cells. Approximately 75% of breast cancers express Estrogen Receptor alpha and exhibit estrogen-dependent proliferation. Morales, A. R., et al. *Am. J. Clin. Path.* 2005; 123: 21-27. Estrogen Receptor alpha is implicated in a variety of cancers, such as, but not limited to, breast cancer, lung cancer, ovarian cancer, endometrial cancer, prostate cancer, and esophageal cancer. Breast cancer is the most common cancer among women, and its incidence rate increases every year.

Selective estrogen receptor modulators (SERMs) are compounds that interact with intracellular Estrogen Receptors and act as agonists or antagonists. SERMs are used for treating various estrogen-related diseases, including breast cancer, infertility, ovulatory dysfunction, postmenopausal osteoporosis, estrogen-related gynecomastia, dyspareunia due to menopause, retroperitoneal fibrosis, and idiopathic sclerosing mesenteritis. It has also been reported that SERMs have beneficial effects on serum lipids in postmenopausal women.

Tamoxifen is the most commonly used SERM and is widely used in treating Estrogen Receptor alpha positive breast cancer. Unfortunately, Tamoxifen activates other genes, which correlates with an increased incidence of other cancers, for example, endometrial cancer. Bernstein, L. et al. *J. Natl Cancer Inst* 1999; 91: 1654-62. Further, many cancer patients who receive Tamoxifen will eventually develop resistance. Ring, A. et al. *Endocr Relat Cancer* 2004; 11: 643-58. Upon failure of Tamoxifen treatment, patients may be prescribed Fulvestrant. Fulvestrant is a selective estrogen receptor degrader via proteasomal degradation.

Tamoxifen competes with estrogen to bind to Estrogen Receptor alpha, whereas Fulvestrant is an antagonist. Fulvestrant's effects are to degrade the Estrogen Receptor alpha protein as opposed to prevent conformational changes and/or dimerization. Although Fulvestrant is an improvement over the deleterious effects of Tamoxifen, Fulvestrant suffers from poor drug-like properties, for example, poor bioavailability and intramuscular administration. Accordingly, there exists a need for an improved method of inhibiting cellular proliferation driven by Estrogen Receptor alpha. Fulvestrant's mechanism of action, where the proteasome is engaged to degrade Estrogen Receptor alpha, provides an alternative mechanism to inhibiting Estrogen Receptor alpha driven cell proliferation. However, general proteasome degradation is not selective, and therefore could lead to deleterious effects. Accordingly, there is a need to discover and develop a drug that could lead to selective Estrogen Receptor alpha degradation, without the side effects caused by Tamoxifen or Fulvestrant.

The present disclosure describes compounds that may be used to bind to both Estrogen Receptor alpha and a ubiquitin ligase. The compounds of the present disclosure possess two binding motifs conjugated via a linker. Without being bound to any theory, it is believed that Estrogen Receptor alpha degradation may occur when both Estrogen Receptor alpha and a ubiquitin ligase are bound and brought into close proximity.

SUMMARY OF THE EMBODIMENTS

In some embodiments, provided herein is a compound of Formula (I), or a pharmaceutically acceptable salt thereof:

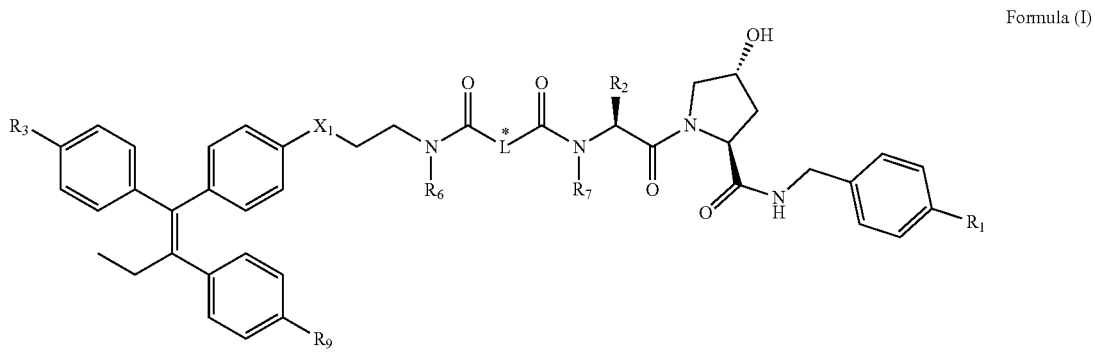

Formula (I)

wherein:

$X^1$ is selected from $CH_2$, $NR^8$, O, and S;

$R^1$ is selected from H, $C_1$-$C_6$ alkyl, halo, heterocycle, and heteroaryl, each of which is substituted with 0, 1, 2, or 3 $R^5$;

$R^2$ is selected from H, $C_1$-$C_6$ alkyl, and $C_3$-$C_6$ cycloalkyl, each of which is substituted with 0, 1, 2, or 3 $R^5$;

$R^3$ is selected from H, $C_1$-$C_6$ alkyl, halo, hydroxy, and sulfhydryl, each of which is substituted with 0, 1, 2, or 3 $R^5$;

$R^4$ is selected from H, $C_1$-$C_6$ alkyl, and acyl, each of which is substituted with 0, 1, 2, or 3 $R^5$;

each $R^5$ is independently selected from $C_1$-$C_6$ alkyl, halo, cyano, and hydroxy;

$R^6$, $R^7$, and $R^8$ are each independently selected from H, $C_1$-$C_6$ alkyl, and acyl, each of which is substituted with 0, 1, 2, or 3 $R^5$;

R⁹ is selected from H, $C_1$-$C_6$ alkyl, halo, hydroxy, and sulfhydryl, each of which is substituted with 0, 1, 2, or 3 R⁵; and L* is a linker of 1 to 16 carbon atoms in length, wherein one or more carbon atoms are optionally replaced by C(O), O, NR⁴, S, $C_2$-alkenyl, $C_2$-alkynyl, cycloalkyl, aryl, heterocycle, or heteroaryl.

In some embodiments, provided herein is a compound of Formula (II), or a pharmaceutically acceptable salt thereof:

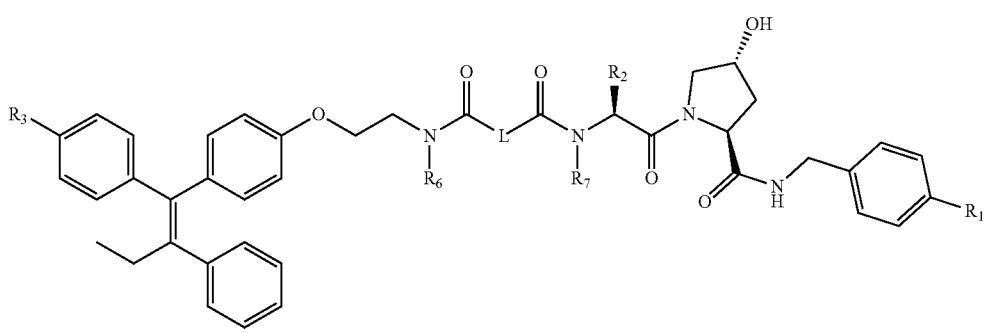

Formula (II)

wherein:
R¹ is selected from H, $C_1$-$C_6$ alkyl, halo, heterocycle, and heteroaryl, each of which is substituted with 0, 1, 2, or 3 R⁵;
R² is selected from H, $C_1$-$C_6$ alkyl, and $C_3$-$C_6$ cycloalkyl, each of which is substituted with 0, 1, 2, or 3 R⁵;
R³ is selected from H, $C_1$-$C_6$ alkyl, halo, and hydroxy, each of which is substituted with 0, 1, 2, or 3 R⁵;
R⁴ is selected from H, $C_1$-$C_6$ alkyl, and acyl, each of which is substituted with 0, 1, 2, or 3 R⁵;
each R⁵ is independently selected from $C_1$-$C_6$ alkyl, halo, cyano, and hydroxy;
R⁶ and R⁷ is each independently selected from H, $C_1$-$C_6$ alkyl, and acyl, each of which is substituted with 0, 1, 2, or 3 R⁵; and
L is a linker of 6 to 16 carbon atoms in length, wherein one or more carbon atoms are optionally replaced by O, NR⁴, S, $C_2$-alkenyl, $C_2$-alkynyl, cycloalkyl, aryl, heterocycle, or heteroaryl.

In some embodiments, provided herein is a compound of Formula (III), or a pharmaceutically acceptable salt thereof:

wherein:
R¹ is selected from H, $C_1$-$C_6$ alkyl, halo, heterocycle, and heteroaryl, each of which is substituted with 0, 1, 2, or 3 R⁵;
R² is selected from H, $C_1$-$C_6$ alkyl, and $C_3$-$C_6$ cycloalkyl, each of which is substituted with 0, 1, 2, or 3 R⁵;
R³ is selected from H, $C_1$-$C_6$ alkyl, halo, and hydroxy, each of which is substituted with 0, 1, 2, or 3 R⁵;
R⁴ is selected from H, $C_1$-$C_6$ alkyl, and acyl, each of which is substituted with 0, 1, 2, or 3 R⁵;
each R⁵ is independently selected from $C_1$-$C_6$ alkyl, halo, cyano, and hydroxy;
R⁶ and R⁷ are each independently selected from H, $C_1$-$C_6$ alkyl, and acyl, each of which is substituted with 0, 1, 2, or 3 R⁵; and
L¹ is a linker of 9 to 10 carbon atoms in length, wherein one or more carbon atoms are optionally replaced by O, NR⁴, S, $C_2$-alkenyl, $C_2$-alkynyl, cycloalkyl, aryl, heterocycle, or heteroaryl.

In some embodiments, L¹ may be

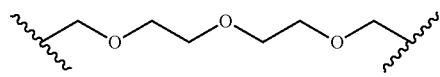

.

In some embodiments, provided herein is a compound of Formula (IV), or a pharmaceutically acceptable salt thereof:

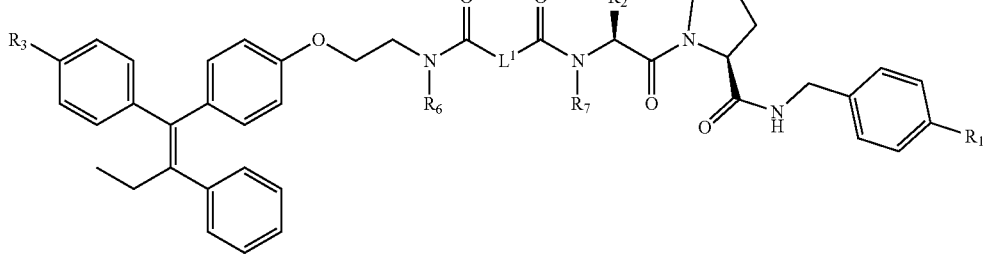

Formula (III)

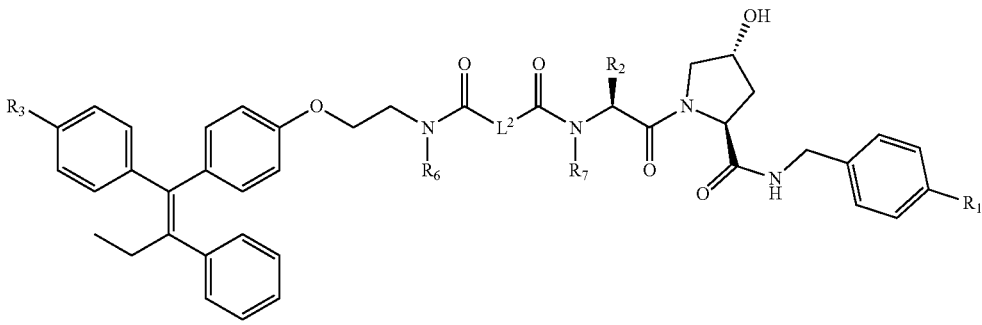

Formual (IV)

wherein:

R[1] is selected from H, $C_1$-$C_6$ alkyl, halo, heterocycle, and heteroaryl, each of which is substituted with 0, 1, 2, or 3 R[5];

R[2] is selected from H, $C_1$-$C_6$ alkyl, and $C_3$-$C_6$ cycloalkyl, each of which is substituted with 0, 1, 2, or 3 R[5];

R[3] is selected from H, $C_1$-$C_6$ alkyl, halo, and hydroxy, each of which is substituted with 0, 1, 2, or 3 R[5];

R[4] is selected from H, $C_1$-$C_6$ alkyl, and acyl, each of which is substituted with 0, 1, 2, or 3 R[5];

each R[5] is independently selected from $C_1$-$C_6$ alkyl, halo, cyano, and hydroxy;

R[6] and R[7] are each independently selected from H, $C_1$-$C_6$ alkyl, and acyl, each of which is substituted with 0, 1, 2, or 3 R[5]; and L[2] is a linker of 6 to 7 carbon atoms in length, wherein one or more carbon atoms are optionally replaced by O, NR[4], S, $C_2$-alkenyl, $C_2$-alkynyl, cycloalkyl, aryl, heterocycle, or heteroaryl.

In some embodiments, L[2] may be

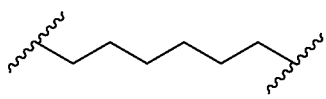

In some embodiments, L may contain at least one O atom. In some embodiments, L may contain at least one aryl. In some embodiments, L may contain at least one $C_2$-alkenyl. In some embodiments, L may contain at least one $C_2$-alkynyl. In some embodiments, L may contain at least one 5-membered heteroaryl. In some embodiments, the at least one 5-membered heteroaryl may be a triazole.

In some embodiments, L[1] may contain at least one O atom. In some embodiments, L[1] may contain at least one aryl. In some embodiments, L[1] may contain at least one $C_2$-alkenyl. In some embodiments, L[1] may contain at least one $C_2$-alkynyl. In some embodiments, L[1] may contain at least one 5-membered heteroaryl. In some embodiments, the at least one 5-membered heteroaryl may be a triazole.

In some embodiments, L[2] may contain at least one O atom. In some embodiments, L[2] may contain at least one aryl. In some embodiments, L[2] may contain at least one $C_2$-alkenyl. In some embodiments, L[2] may contain at least one $C_2$-alkynyl. In some embodiments, L[2] may contain at least one 5-membered heteroaryl. In some embodiments, the at least one 5-membered heteroaryl may be a triazole.

In some embodiments, R[1] may be selected from halo and heteroaryl. In some embodiments, R[1] may be a 5-membered heteroaryl. In some embodiments, R[1] may be methylthiazole. In some embodiments, R[1] may be 4-methylthiazole. In some embodiments, R[1] may be

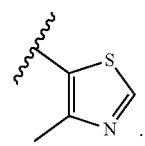 [SMILES: *c1scnc1C]

In some embodiments, R[2] may be $C_1$-$C_6$ alkyl. In some embodiments, R[2] may be tert-butyl. In some embodiments, R[2] may be iso-propyl.

In some embodiments, R[3] may be H. In some embodiments, R[3] may be $C_1$-$C_6$ alkyl. In some embodiments, R[3] may be hydroxy.

In some embodiments, R[4] may be H. In some embodiments, R[4] may be $C_1$-$C_3$ alkyl. In some embodiments, $C_1$-$C_3$ may be methyl. In some embodiments, R[4] may be acyl. In some embodiments, the acyl may be acetyl.

In some embodiments, R[6] may be $C_1$-$C_3$ alkyl. In some embodiments, the $C_1$-$C_3$ alkyl may be methyl. In some embodiments, the R[6] may be H.

In some embodiments, R[7] may be selected from H and $C_1$-$C_3$ alkyl. In some embodiments, R[7] may be H. In some embodiments, R[7] may be $C_1$-$C_3$ alkyl. In some embodiments, the $C_1$-$C_3$ alkyl may be methyl.

In some embodiments, provided herein is the compound:

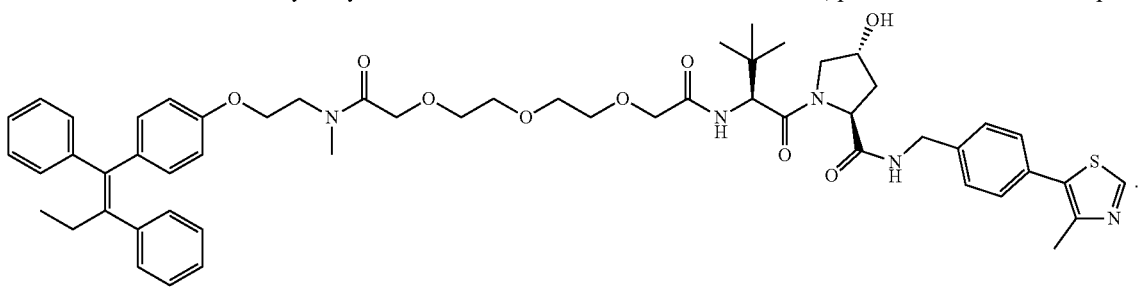

In some embodiments, provided herein is the compound:

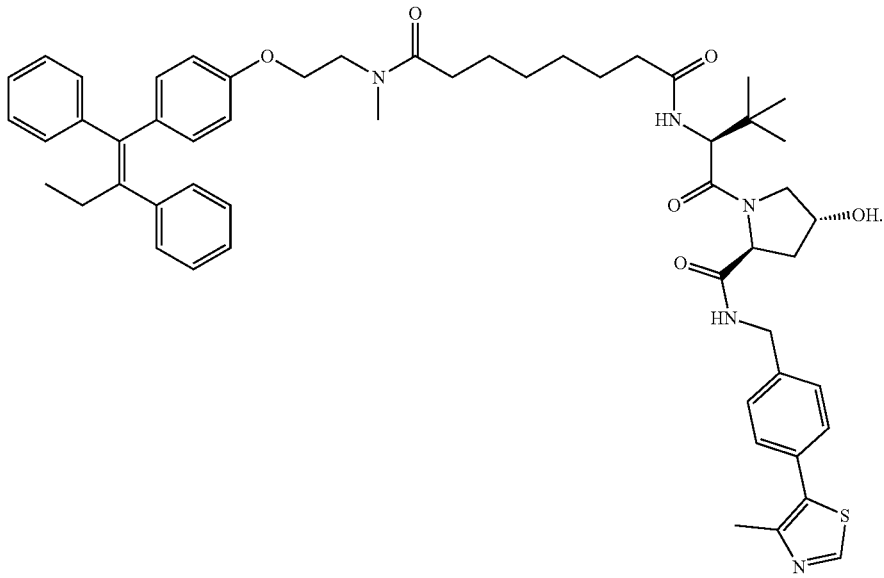 [SMILES: CC/C(=C(\c1ccccc1)c1ccc(OCCN(C)C(=O)CCCCCCC(=O)N[C@H](C(=O)N2C[C@H](O)C[C@H]2C(=O)NCc2ccc(-c3scnc3C)cc2)C(C)(C)C)cc1)c1ccccc1]

In some embodiments, provided herein is a pharmaceutical composition comprising the compound of Formulae (I), (II), (III), or (IV), and at least one additional component selected from pharmaceutically acceptable carriers, pharmaceutically acceptable vehicles, and pharmaceutically acceptable excipients. In some embodiments, provided herein is a pharmaceutical composition wherein the compound may be present in a therapeutically effective amount.

In some embodiments, provided herein is a method of treating cancer in a subject in need thereof, comprising administering to said subject an effective amount of the compound of Formulae (I), (II), (III), or (IV), or of the pharmaceutical composition provided herein, wherein the cancer may be chosen from breast cancer, lung cancer, ovarian cancer, endometrial cancer, prostate cancer, or esophageal cancer. In some embodiments, the cancer may be breast cancer. In some embodiments, the cancer may be positive for Estrogen Receptor alpha. In some embodiments, the subject may have been previously treated with an anti-cancer agent. In some embodiments, the anti-cancer agent may be tamoxifen.

In some embodiments, provided herein is a use of the compound of Formulae (I), (II), (III), or (IV) in a method of therapeutic treatment, wherein said therapeutic treatment may be treatment of breast cancer, lung cancer, ovarian cancer, endometrial cancer, prostate cancer, esophageal cancer, infertility, ovulatory dysfunction, postmenopausal osteoporosis, estrogen-related gynecomastia, dyspareunia due to menopause, retroperitoneal fibrosis, or idiopathic sclerosing mesenteritis. In some embodiments, provided herein is a use of the compound of Formulae (I), (II), (III), or (IV) in the preparation of a medicament.

In some embodiments, provided herein is a method of inhibiting cell growth, comprising contacting a cell with the compound of Formulae (I), (II), or (III), or a pharmaceutical composition provided herein. In some embodiments, the cell may be a cancer cell. In some embodiments, the cell may express Estrogen Receptor alpha.

BRIEF DESCRIPTION OF THE FIGURES

The accompanying drawings, which are incorporated in and constitute a part of this specification, illustrate the disclosed embodiments and, together with the description, serve to explain the principles of the disclosed embodiments. In the drawings.

DETAILED DESCRIPTION

Definitions

Figure 1A:
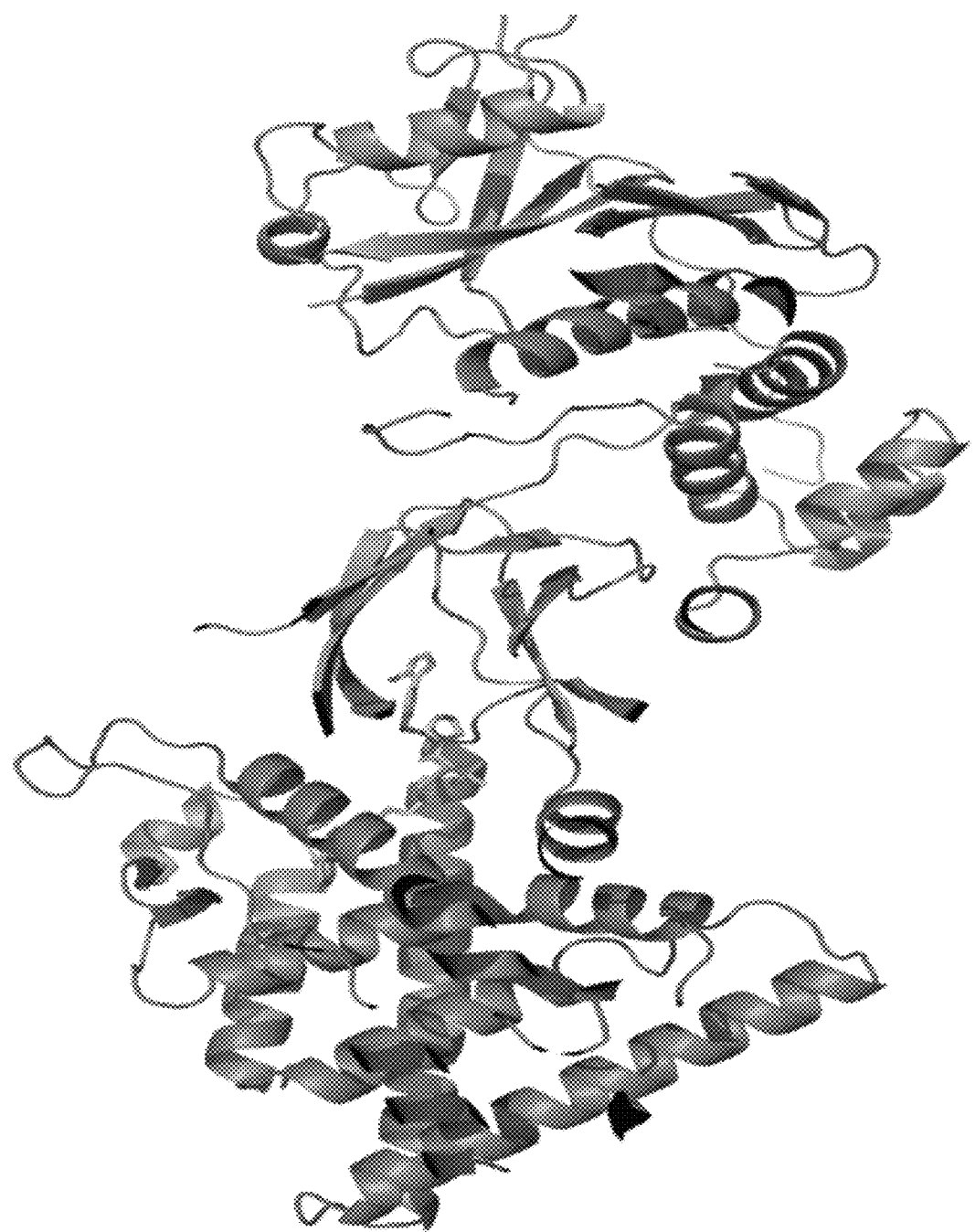
FIG. 1A illustrates Compound 1 bound to Estrogen Receptor alpha and a Von Hippel-Lindau ligase.
Figure 1B:
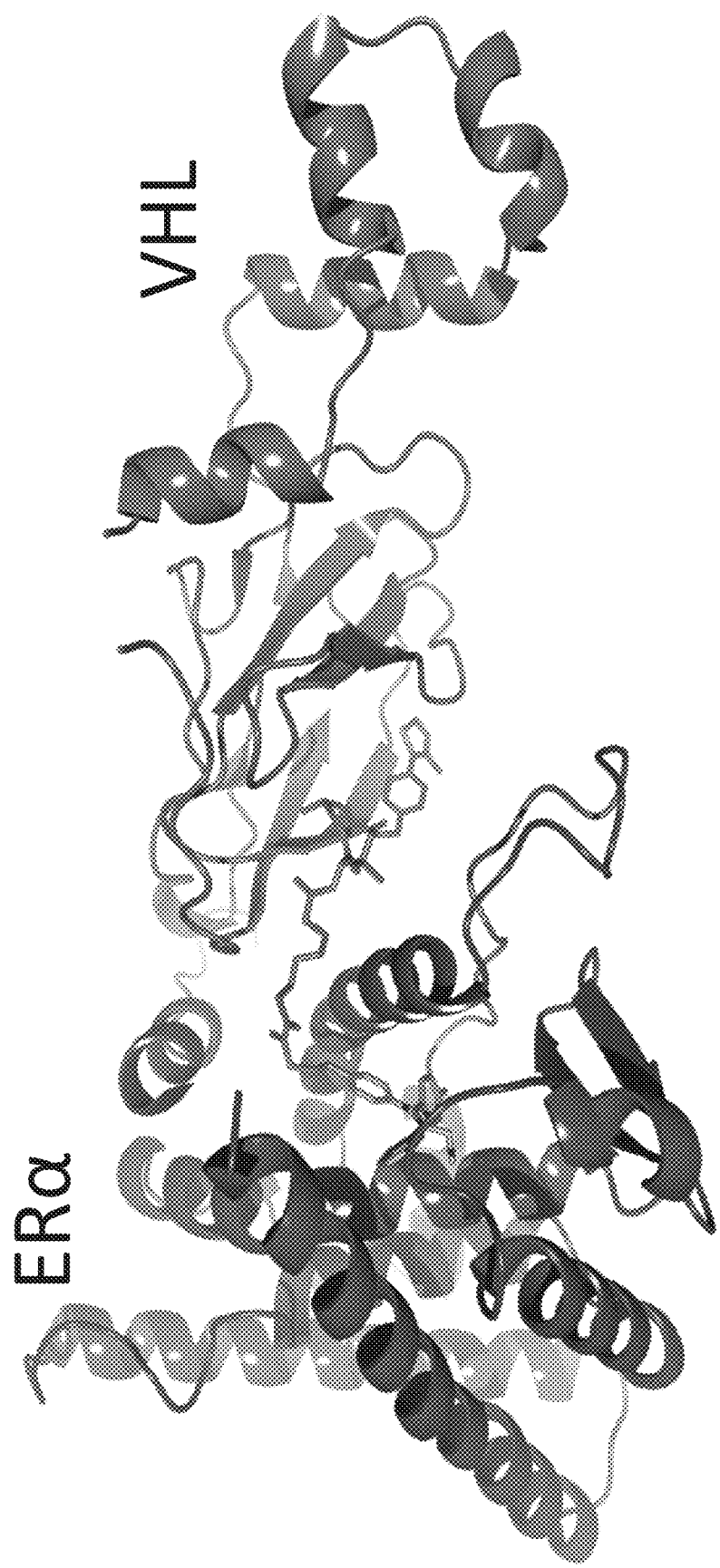
FIG. 1B is an alternative view of the protein-ligand complex illustrated in FIG. 1A.

As used in the present specification, the following words, phrases and symbols are generally intended to have the meanings as set forth below, except to the extent that the context in which they are used indicates otherwise. The following abbreviations and terms have the indicated meanings throughout.

Chemical names were generated using PerkinElmer ChemDraw® Professional, version 15.

As used herein, "cancer" refers to diseases, disorders, and conditions that involve abnormal cell growth with the potential to invade or spread to other parts of the body. Exemplary cancers, include, but are not limited to, breast cancer, lung cancer, ovarian cancer, endometrial cancer, prostate cancer, and esophageal cancer.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CN is attached through the carbon atom.

By "optional" or "optionally" it is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

The term "alkenyl" as used herein refers to an unsaturated straight or branched hydrocarbon having at least one carbon-carbon double bond, such as a straight or branched group of 2-8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkyl" as used herein refers to a saturated straight or branched hydrocarbon, such as a straight or branched group of 1-8 carbon atoms, referred to herein as ($C_1$-$C_8$)alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_8$)alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$C_6$-aryl."

The term "cyano" as used herein refers to —CN.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al, "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

Provided herein are compounds of Formula (I):

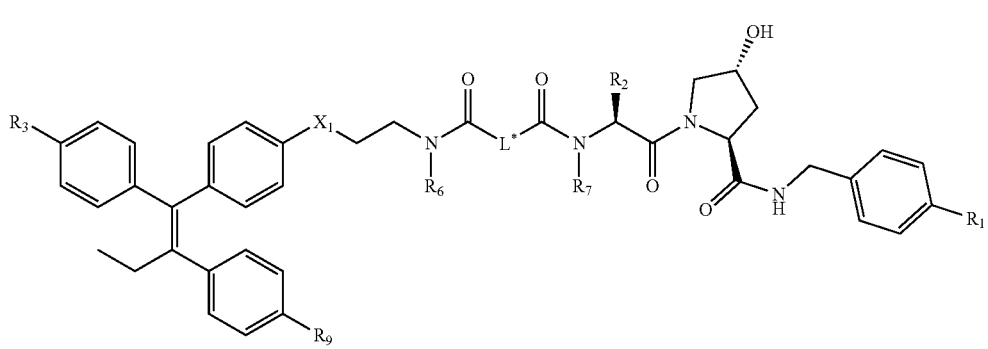

Formula (I)

wherein:

$X^1$ is selected from $CH_2$, $NR^8$, O, and S;

$R^1$ is selected from H, $C_1$-$C_6$ alkyl, halo, heterocycle, and heteroaryl, each of which is substituted with 0, 1, 2, or 3 $R^5$;

$R^2$ is selected from H, $C_1$-$C_6$ alkyl, and $C_3$-$C_6$ cycloalkyl, each of which is substituted with 0, 1, 2, or 3 $R^5$;

$R^3$ is selected from H, $C_1$-$C_6$ alkyl, halo, hydroxy, and sulfhydryl, each of which is substituted with 0, 1, 2, or 3 $R^5$;

$R^4$ is selected from H, $C_1$-$C_6$ alkyl, and acyl, each of which is substituted with 0, 1, 2, or 3 $R^5$;

each $R^5$ is independently selected from $C_1$-$C_6$ alkyl, halo, cyano, and hydroxy;

$R^6$, $R^7$, and $R^8$ are each independently selected from H, $C_1$-$C_6$ alkyl, and acyl, each of which is substituted with 0, 1, 2, or 3 $R^5$;

$R^9$ is selected from H, $C_1$-$C_6$ alkyl, halo, hydroxy, and sulfhydryl, each of which is substituted with 0, 1, 2, or 3 $R^5$; and L* is a linker of 1 to 16 carbon atoms in length, wherein one or more carbon atoms are optionally replaced by C(O), C(NH), C(S), O, $NR^4$, S, $C_2$-alkenyl, $C_2$-alkynyl, cycloalkyl, aryl, heterocycle, or heteroaryl.

Provided herein are compounds of Formula (II):

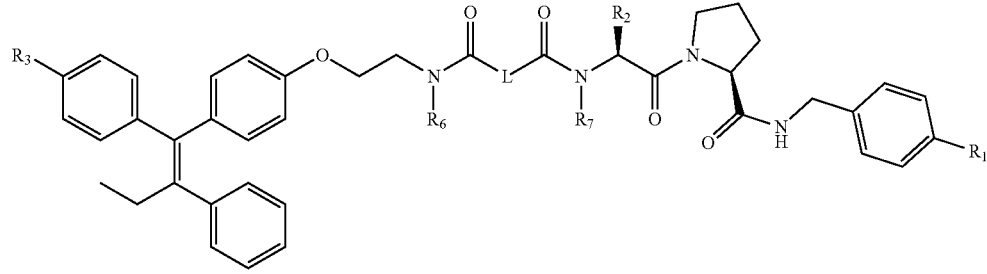

Formula (II)

wherein:

$R^1$ is selected from H, $C_1$-$C_6$ alkyl, halo, heterocycle, and heteroaryl, each of which is substituted with 0, 1, 2, or 3 $R^5$;

$R^2$ is selected from H, $C_1$-$C_6$ alkyl, and $C_3$-$C_6$ cycloalkyl, each of which is substituted with 0, 1, 2, or 3 $R^5$;

$R^3$ is selected from H, $C_1$-$C_6$ alkyl, halo, and hydroxy, each of which is substituted with 0, 1, 2, or 3 $R^5$;

$R^4$ is selected from H, $C_1$-$C_6$ alkyl, and acyl, each of which is substituted with 0, 1, 2, or 3 $R^5$;

each $R^5$ is independently selected from $C_1$-$C_6$ alkyl, halo, cyano, and hydroxy;

$R^6$ and $R^7$ are each independently selected from H, $C_1$-$C_6$ alkyl, and acyl, each of which is substituted with 0, 1, 2, or 3 $R^5$; and L is a linker of 6 to 16 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl.

Provided herein are compounds of Formula (III):

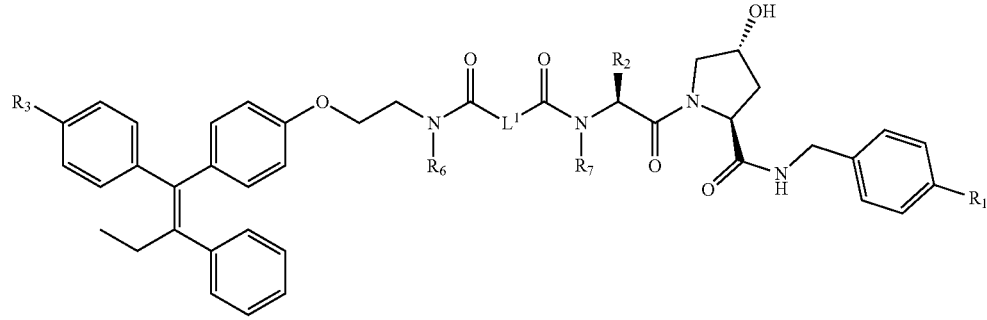

Formula (III)

wherein:

R$^1$ is selected from H, C$_1$-C$_6$ alkyl, halo, heterocycle, and heteroaryl, each of which is substituted with 0, 1, 2, or 3 R$^5$;

R$^2$ is selected from H, C$_1$-C$_6$ alkyl, and C$_3$-C$_6$ cycloalkyl, each of which is substituted with 0, 1, 2, or 3 R$^5$;

R$^3$ is selected from H, C$_1$-C$_6$ alkyl, halo, and hydroxy, each of which is substituted with 0, 1, 2, or 3 R$^5$;

R$^4$ is selected from H, C$_1$-C$_6$ alkyl, and acyl, each of which is substituted with 0, 1, 2, or 3 R$^5$;

each R$^5$ is independently selected from C$_1$-C$_6$ alkyl, halo, cyano, and hydroxy; R$^6$ and R$^7$ are each independently selected from H, C$_1$-C$_6$ alkyl, and acyl, each of which is substituted with 0, 1, 2, or 3 R$^5$; and L$^1$ is a linker of 9 to 10 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl.

Provided herein are compounds of Formula (IV):

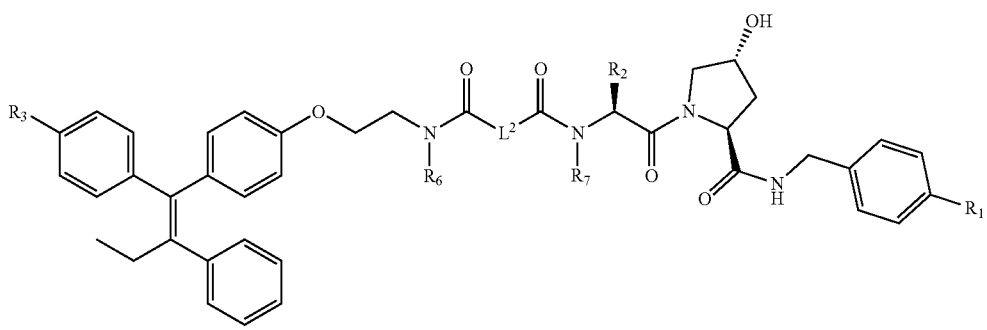

Formual (IV)

wherein:

R$^1$ is selected from H, C$_1$-C$_6$ alkyl, halo, heterocycle, and heteroaryl, each of which is substituted with 0, 1, 2, or 3 R$^5$;

R$^2$ is selected from H, C$_1$-C$_6$ alkyl, and C$_3$-C$_6$ cycloalkyl, each of which is substituted with 0, 1, 2, or 3 R$^5$;

R$^3$ is selected from H, C$_1$-C$_6$ alkyl, halo, and hydroxy, each of which is substituted with 0, 1, 2, or 3 R$^5$;

R$^4$ is selected from H, C$_1$-C$_6$ alkyl, and acyl, each of which is substituted with 0, 1, 2, or 3 R$^5$;

each R$^5$ is independently selected from C$_1$-C$_6$ alkyl, halo, cyano, and hydroxy;

R$^6$ and R$^7$ are each independently selected from H, C$_1$-C$_6$ alkyl, and acyl, each of which is substituted with 0, 1, 2, or 3 R$^5$; and L$^2$ is a linker of 6 to 7 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl.

In some embodiments, L* may range from 1 to 16 carbon atoms in length, wherein one or more carbon atoms are optionally replaced by C(O), C(NH), C(S), O, NR$^4$, S, C$_2$-alkenyl, C$_2$-alkynyl, cycloalkyl, aryl, heterocycle, or heteroaryl. In some embodiments, L* may range from about 6 carbon atoms to about 16 carbon atoms, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may range from about 6 carbon atoms to about 11 carbon atoms, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may range from about 6 carbon atoms to about 9 carbon atoms, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 6 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 7 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 8 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 9 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 10 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 11 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 12 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 13 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 14 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 15 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl. In some embodiments, L* may be 16 carbon atoms in length, wherein one or more carbon atoms are optionally replaced by O, NR$^4$, S, C$_2$-alkenyl, C$_2$-alkynyl, cycloalkyl, aryl, heterocycle, or heteroaryl.

In some embodiments, L* may be 1 carbon atom in length. In some embodiments, L* may be 2 carbon atoms in length. In some embodiments, L* may be 3 carbon atoms in length. In some embodiments, L* may be 4 carbon atoms in length. In some embodiments, L* may be 5 carbon atoms in length. In some embodiments, L* may be 6 carbon atoms in length. In some embodiments, L* may be 7 carbon atoms in length. In some embodiments, L* may be 8 carbon atoms in length. In some embodiments, L* may be 9 carbon atoms in length. In some embodiments, L* may be 10 carbon atoms in length. In some embodiments, L* may be 11 carbon atoms in length. In some embodiments, L* may be 12 carbon atoms in length. In some embodiments, L* may be 13 carbon atoms in length. In some embodiments, L* may be 14 carbon atoms in length. In some embodiments, L* may be 15 carbon atoms in length. In some embodiments, L* may be 16 carbon atoms in length.

In some embodiments, L* may be 6 carbon atoms in length, wherein 2 carbon atoms have been replaced by O. In some embodiments, L* may be 8 carbon atoms in length, wherein 2 carbon atoms have been replaced by O. In some embodiments, L* may be 9 carbon atoms in length, wherein 3 carbon atoms have been replaced by O. In some embodiments, L* may be 11 carbon atoms in length, wherein 3 carbon atoms have been replaced by O. In some embodiments, L* may be 14 carbon atoms in length, wherein 4 carbon atoms have been replaced by O. In some embodiments, L* may be 15 carbon atoms in length, wherein 5 carbon atoms have been replaced by O.

In some embodiments, L* may be 1 carbon atom in length, wherein the one carbon atom is optionally replaced by a cycloalkyl. In some embodiments, L* may be 1 carbon atom in length, wherein the one carbon atom is optionally replaced by a heterocycle. In some embodiments, L* may be 1 carbon atom in length, wherein the one carbon atom is optionally replaced by an aryl. In some embodiments, L* may be 1 carbon atom in length, wherein the one carbon atom is optionally replaced by a heteroaryl. In some embodiments, L* may be 1 carbon atom in length, wherein the one carbon atom is optionally replaced by a $C_2$-alkenyl. In some embodiments, L* may be 1 carbon atom in length, wherein the one carbon atom is optionally replaced by a $C_2$-alkynyl.

In some embodiments, L* may be 2 carbon atoms in length, wherein one carbon atom is optionally replaced by a cycloalkyl. In some embodiments, L* may be 2 carbon atoms in length, wherein one carbon atom is optionally replaced by a heterocycle. In some embodiments, L* may be 2 carbon atoms in length, wherein one carbon atom is optionally replaced by an aryl. In some embodiments, L* may be 2 carbon atoms in length, wherein one carbon atom is optionally replaced by a heteroaryl.

In some embodiments, L* may be 3 carbons in length, wherein one carbon atom is optionally replaced by a $C_2$-alkenyl. In some embodiments, L* may be 4 carbon atoms in length, wherein one carbon atom is optionally replaced by a $C_2$-alkenyl. In some embodiments, L* may be 5 carbon atoms in length, wherein one carbon atom is optionally replaced by a $C_2$-alkenyl. In some embodiments, L* may be 6 carbon atoms in length, wherein one carbon atom is optionally replaced by a $C_2$-alkenyl. In some embodiments, L* may be 3 carbons in length, wherein one carbon atom is optionally replaced by a $C_2$-alkynyl. In some embodiments, L* may be 4 carbon atoms in length, wherein one carbon atom is optionally replaced by a $C_2$-alkynyl. In some embodiments, L* may be 5 carbon atoms in length, wherein one carbon atom is optionally replaced by a $C_2$-alkynyl. In some embodiments, L* may be 6 carbon atoms in length, wherein one carbon atom is optionally replaced by a $C_2$-alkynyl.

In some embodiments, L* may be 4 carbon atoms in length, wherein two carbon atoms are each optionally replaced by a $C_2$-alkenyl. In some embodiments, L* may be 5 carbon atoms in length, wherein two carbon atoms are each optionally replaced by a $C_2$-alkenyl. In some embodiments, L* may be 6 carbon atoms in length, wherein two carbon atoms are each optionally replaced by a $C_2$-alkenyl.

In some embodiments, L* may be 4 carbon atoms in length, wherein two carbon atoms are each optionally replaced by a $C_2$-alkynyl. In some embodiments, L* may be 5 carbon atoms in length, wherein two carbon atoms are each optionally replaced by a $C_2$-alkynyl. In some embodiments, L* may be 6 carbon atoms in length, wherein two carbon atoms are each optionally replaced by a $C_2$-alkynyl.

In some embodiments, L* may be 4 carbon atoms in length, wherein a first carbon atom is optionally replaced by O or $NR^4$ and a second carbon atom is optionally replaced by C(O). In some embodiments, L* may be 5 carbon atoms in length, wherein a first carbon atom is optionally replaced by O or $NR^4$ and a second carbon atom is optionally replaced by C(O). In some embodiments, L* may be 6 carbon atoms in length, wherein a first carbon atom is optionally replaced by O or $NR^4$ and a second carbon atom is optionally replaced by C(O). In some embodiments, L* may be 7 carbon atoms in length, wherein a first carbon atom is optionally replaced by O or $NR^4$ and a second carbon atom is optionally replaced by C(O). In some embodiments, L* may be 8 carbon atoms in length, wherein a first carbon atom is optionally replaced by O or $NR^4$ and a second carbon atom is optionally replaced by C(O). In some embodiments, L* may be 9 carbon atoms in length, wherein a first carbon atom is optionally replaced by O or $NR^4$ and a second carbon atom is optionally replaced by C(O). In some embodiments, L* may be 10 carbon atoms in length, wherein a first carbon atom is optionally replaced by O or $NR^4$ and a second carbon atom is optionally replaced by C(O). In some embodiments, L* may be 11 carbon atoms in length, wherein a first carbon atom is optionally replaced by O or $NR^4$ and a second carbon atom is optionally replaced by C(O). In some embodiments, L* may be 12 carbon atoms in length, wherein a first carbon atom is optionally replaced by O or $NR^4$ and a second carbon atom is optionally replaced by C(O). In some embodiments, L* may be 13 carbon atoms in length, wherein a first carbon atom is optionally replaced by O or $NR^4$ and a second carbon atom is optionally replaced by C(O). In some embodiments, L* may be 14 carbon atoms in length, wherein a first carbon atom is optionally replaced by O or $NR^4$ and a second carbon atom is optionally replaced by C(O). In some embodiments, L* may be 15 carbon atoms in length, wherein a first carbon atom is optionally replaced by O or $NR^4$ and a second carbon atom is optionally replaced by C(O).

In some embodiments, L* may be selected from L, $L^1$, and $L^2$. In some embodiments, L* may be L. In some embodiments, L* may be $L^1$. In some embodiments, L* may be $L^2$.

In some embodiments, L* may be

In some embodiments, L* may be

In some embodiments, L* may be

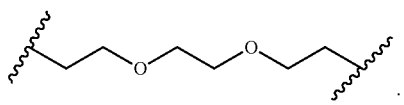 [SMILES: *CCOCCOCC*]

In some embodiments, L* may be

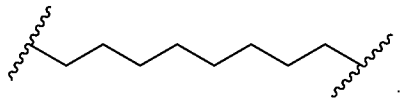 [SMILES: *CCCCCCCC*]

In some embodiments, L* may be

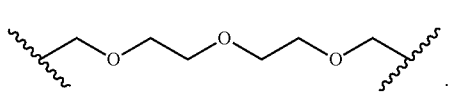 [SMILES: *COCCOCCOC*]

In some embodiments, L* may be

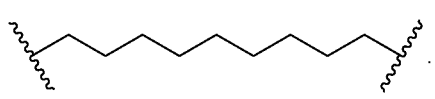 [SMILES: *CCCCCCCCC*]

In some embodiments, L* may be

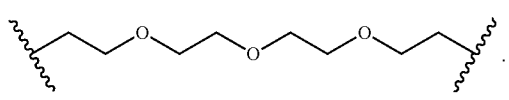 [SMILES: *CCOCCOCCOCC*]

In some embodiments, L* may be

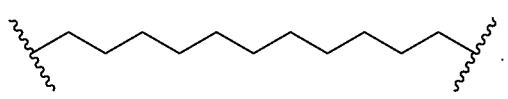 [SMILES: *CCCCCCCCCCC*]

In some embodiments, L* may be

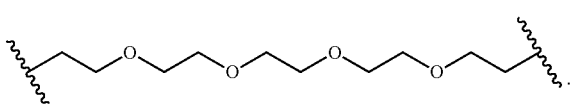 [SMILES: *CCOCCOCCOCCOCC*]

In some embodiments, L* may be

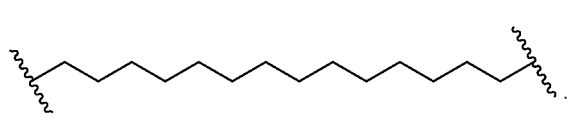 [SMILES: *CCCCCCCCCCCCCC*]

In some embodiments, L* may be

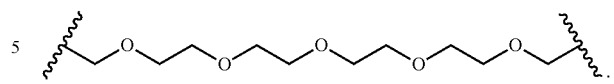

In some embodiments, L* may be

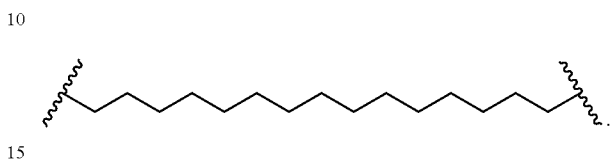

In some embodiments, L* may be

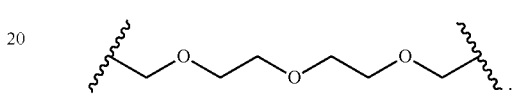

In some embodiments, L* may be

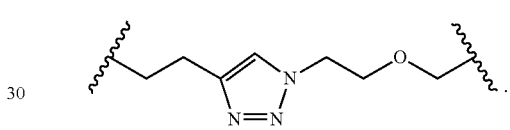

In some embodiments, L* may be

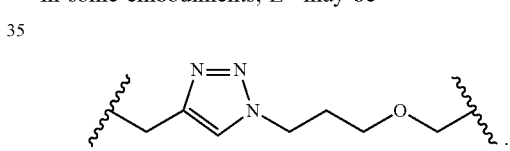

In some embodiments, L* may be

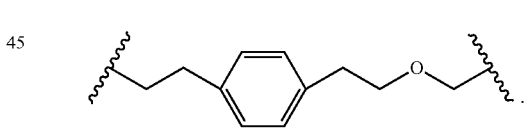

In some embodiments, L* may be

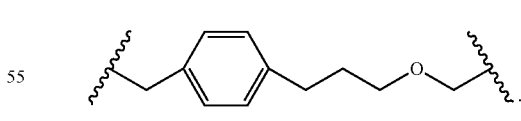

In some embodiments, L* may be

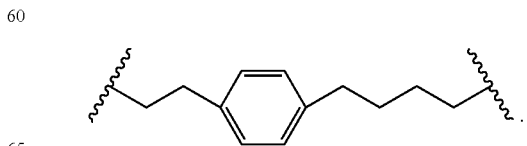

In some embodiments, L* may be

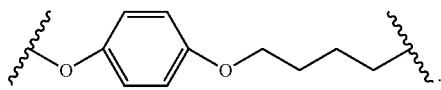

In some embodiments, L* may be

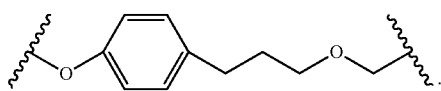 [SMILES: *COCCCc1ccc(O*)cc1]

In some embodiments, L* may be

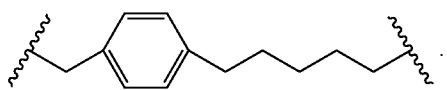 [SMILES: *CCCCCc1ccc(C*)cc1]

In some embodiments, L* may be

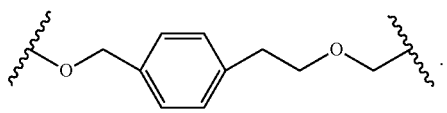 [SMILES: *COCCc1ccc(CO*)cc1]

In some embodiments, L* may be

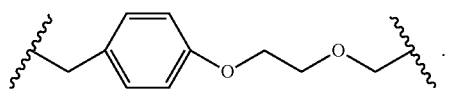

In some embodiments, L* may be

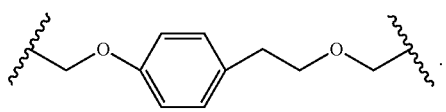 [SMILES: *COCCc1ccc(OC*)cc1]

In some embodiments, L* may be

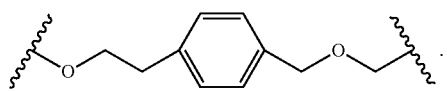

In some embodiments, L* may be

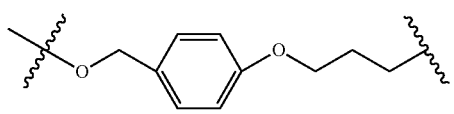

In some embodiments, L* may be

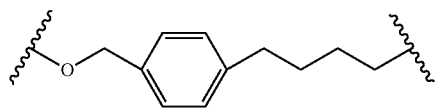

In some embodiments, L* may be

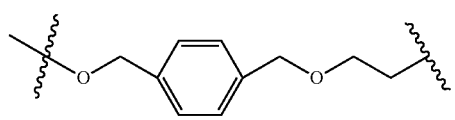

In some embodiments, L* may be

In some embodiments, L* may be

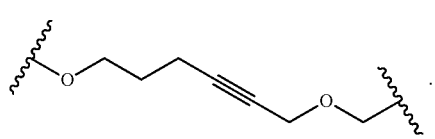 [SMILES: *COCC#CCCCO*]

In some embodiments, L* may be

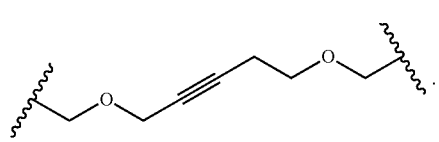 [SMILES: *COCC#CCCOC*]

In some embodiments, L* may be

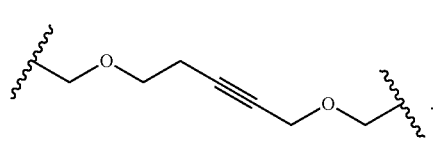 [SMILES: *COCC#CCCOC*]

In some embodiments, L* may be

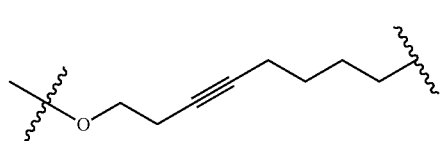

In some embodiments, L* may be

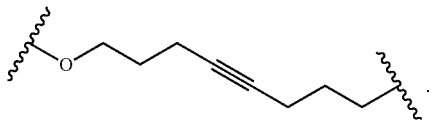 [SMILES: *CCCC#CCCCO*]

In some embodiments, L* may be

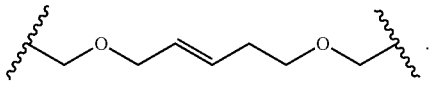 [SMILES: *COC/C=C/CCOC*]

In some embodiments, L* may be

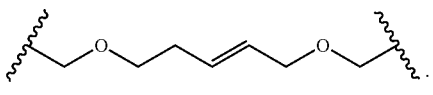 [SMILES: *COC/C=C/CCOC*]

In some embodiments, L* may be

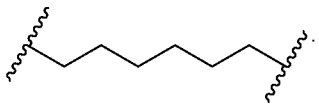 [SMILES: *CCCCCC*]

In some embodiments, L* may be

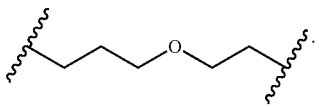 [SMILES: *CCCOCC*]

In some embodiments, L* may be

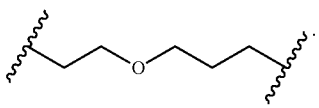 [SMILES: *CCCOCC*]

In some embodiments, L* may be

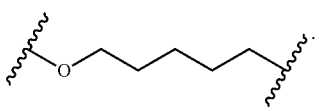 [SMILES: *CCCCCO*]

In some embodiments, L* may be

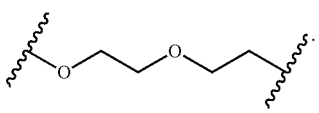 [SMILES: *CCOCCO*]

In some embodiments, L* may be

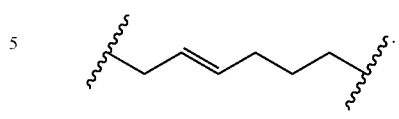

In some embodiments, L* may be

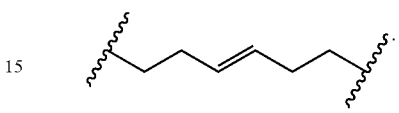

In some embodiments, L* may be

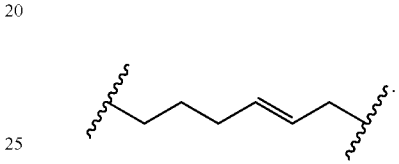

In some embodiments, L* may be

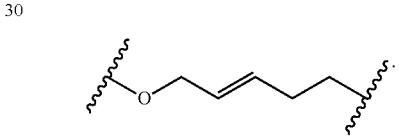

In some embodiments, L* may be

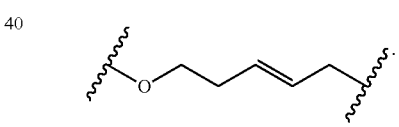

In some embodiments, L* may be

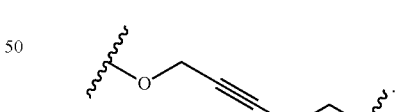

In some embodiments, L* may be

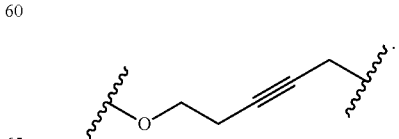

In some embodiments, L* may be
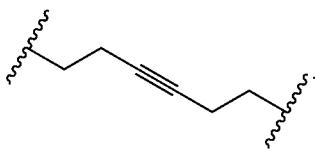 [SMILES: *CCC#CCC*]
In some embodiments, L* may be
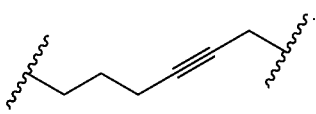 [SMILES: *CC#CCCC*]
In some embodiments, L* may be
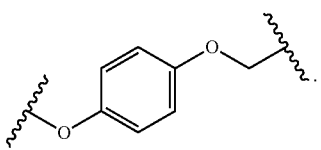 [SMILES: *COc1ccc(O*)cc1]
In some embodiments, L* may be
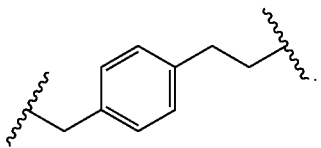 [SMILES: *CCc1ccc(C*)cc1]
In some embodiments, L* may be
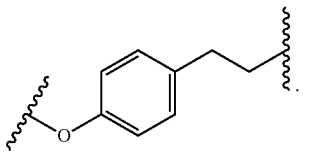 [SMILES: *CCc1ccc(O*)cc1]
In some embodiments, L* may be
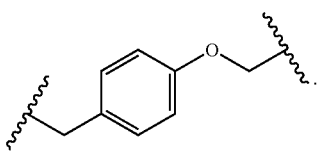 [SMILES: *COc1ccc(C*)cc1]
In some embodiments, L* may be
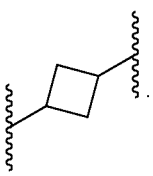 [SMILES: *C1CC(*)C1]
In some embodiments, L* may be
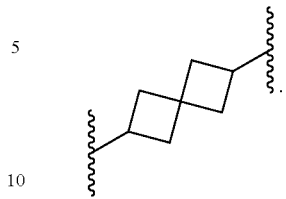
In some embodiments, L* may be
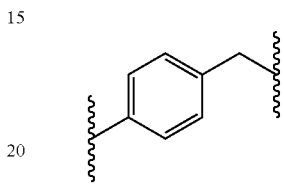
In some embodiments, L* may be
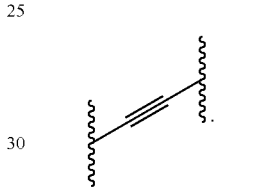
In some embodiments, L* may be
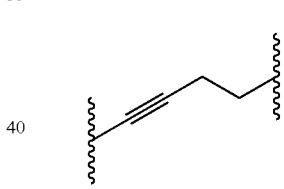
In some embodiments, L* may be
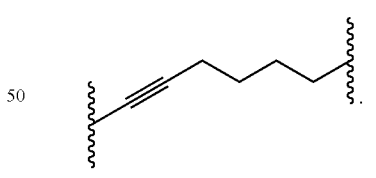
In some embodiments, L* may be
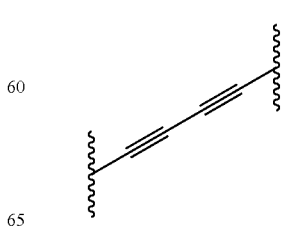

In some embodiments, L* may be

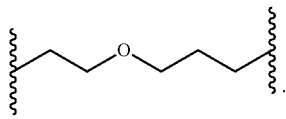 [SMILES: *CCCOCC*]

In some embodiments, L* may be

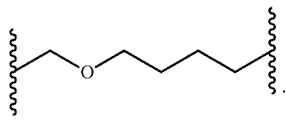 [SMILES: *CCCCOC*]

In some embodiments, L* may be

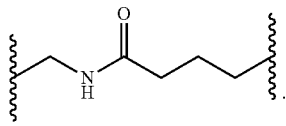 [SMILES: *CCCC(=O)NC*]

In some embodiments, L* may be

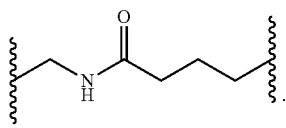 [SMILES: *CCCC(=O)NC*]

In some embodiments, L* may be

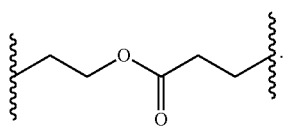 [SMILES: *CCOC(=O)CC*]

In some embodiments, L* may be

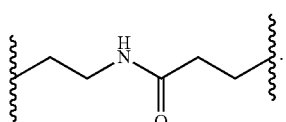

In some embodiments, $X^1$ may be selected from $CH_2$, $NR^8$, O, and S. In some embodiments, $X^1$ may be $CH_2$. In some embodiments, $X^1$ may be $NR^8$. In some embodiments, $X^1$ may be O. In some embodiments, $X^1$ may be S.

In some embodiments, $R^8$ may be selected from H, $C_1$-$C_6$ alkyl, and acyl, each of which may be substituted with 0, 1, 2, or 3 $R^5$. In some embodiments, $R^8$ may be selected from H, $C_1$-$C_6$ alkyl, and acyl. In some embodiments, $R^8$ may be H. In some embodiments, $R^8$ may be $C_1$-$C_6$ alkyl, substituted with 0, 1, 2, or 3 $R^5$. In some embodiments, $R^8$ may be $C_1$-$C_6$ alkyl. In some embodiments, $R^8$ may be $C_1$ alkyl. In some embodiments, $R^8$ may be $C_1$ alkyl, substituted with 0, 1, 2, or 3 $R^5$. In some embodiments, $R^8$ may be acyl. In some embodiments, $R^8$ may be acyl, substituted with 0, 1, 2, or 3 $R^5$.

In some embodiments, $R^9$ may be selected from H, $C_1$-$C_6$ alkyl, halo, hydroxy, and sulfhydryl, each of which is substituted with 0, 1, 2, or 3 $R^5$. In some embodiments, $R^9$ may be H. In some embodiments, $R^9$ may be halo. In some embodiments, $R^9$ may be halo, where the halo is fluoro. In some embodiments, $R^9$ may be halo, where the halo is chloro. In some embodiments, $R^9$ may be hydroxy. In some embodiments, $R^9$ may be sulfhydryl. In some embodiments, $R^9$ may be $C_1$-$C_6$ alkyl. In some embodiments, $R^9$ may be C alkyl. In some embodiments, $R^9$ may be $C_1$ alkyl, substituted with 0, 1, 2, or 3 $R^5$. In some embodiments, $R^9$ may be $C_1$ alkyl.

In some embodiments, L may range from about 6 carbon atoms to about 16 carbon atoms, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may range from about 6 carbon atoms to about 16 carbon atoms, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may range from about 6 carbon atoms to about 11 carbon atoms, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may range from about 6 carbon atoms to about 9 carbon atoms, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 6 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 7 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 8 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 9 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 10 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 11 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 12 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 13 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 14 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 15 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl. In some embodiments, L may be 16 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl.

In some embodiments, L may be 6 carbon atoms in length. In some embodiments, L may be 7 carbon atoms in length. In some embodiments, L may be 8 carbon atoms in length. In some embodiments, L may be 9 carbon atoms in length. In some embodiments, L may be 10 carbon atoms in length. In some embodiments, L may be 11 carbon atoms in length. In some embodiments, L may be 12 carbon atoms in length. In some embodiments, L may be 13 carbon atoms in length. In some embodiments, L may be 14 carbon atoms in length. In some embodiments, L may be 15 carbon atoms in length. In some embodiments, L may be 16 carbon atoms in length.

In some embodiments, L may be 6 carbon atoms in length, wherein 2 carbon atoms have been replaced by O. In some embodiments, L may be 8 carbon atoms in length, wherein 2 carbon atoms have been replaced by O. In some embodiments, L may be 9 carbon atoms in length, wherein 3 carbon atoms have been replaced by O. In some embodiments, L may be 11 carbon atoms in length, wherein 3 carbon atoms have been replaced by O. In some embodiments, L may be 14 carbon atoms in length, wherein 4 carbon atoms have been replaced by O. In some embodiments, L may be 15 carbon atoms in length, wherein 5 carbon atoms have been replaced by O.

In some embodiments, $R^1$ may be $C_1$-$C_6$ alkyl. In some embodiments, $R^1$ may be methyl. In some embodiments, $R^1$ may be ethyl. In some embodiments, $R^1$ may be iso-propyl. In some embodiments, $R^1$ may be tert-butyl.

In some embodiments, $R^1$ may be heterocycle. In some embodiments, $R^1$ may be heteroaryl. In some embodiments, $R^1$ may be a 5-membered heteroaryl. In some embodiments, $R^1$ may be thiazole. In some embodiments, $R^1$ may be oxazole. In some embodiments, $R^1$ may be a 5-membered heteroaryl substituted with 1 $R^5$. In some embodiments, $R^1$ may be a 5-membered heteroaryl substituted with 1 $R^5$, wherein the $R^5$ is methyl. In some embodiments, $R^1$ may be thiazole substituted with 1 $R^5$. In some embodiments, $R^1$ may be thiazole substituted with 1 $R^5$, wherein the $R^5$ is methyl. In some embodiments, $R^1$ may be

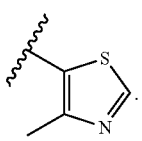

In some embodiments, $R^1$ may be pyrimidine.

In some embodiments, $R^1$ may be halo. In some embodiments, $R^1$ may be fluoro. In some embodiments, $R^1$ may be chloro. In some embodiments, $R^1$ may be bromo. In some embodiments, $R^1$ may be iodo. In some embodiments, $R^1$ may be H.

In some embodiments, $R^2$ may be H. In some embodiments, $R^2$ may be $C_1$-$C_6$ alkyl. In some embodiments, $R^2$ may be $C_1$-$C_3$ alkyl. In some embodiments, $R^2$ may be $C_2$-$C_4$ alkyl. In some embodiments, $R^2$ may be methyl. In some embodiments, $R^2$ may be ethyl. In some embodiments, $R^2$ may be iso-propyl. In some embodiments, $R^2$ may be tert-butyl.

In some embodiments, $R^2$ may be $C_3$-$C_6$ cycloalkyl. In some embodiments, $R^2$ may be cyclopropyl. In some embodiments, $R^2$ may be cyclobutyl. In some embodiments, $R^2$ may be cyclopentyl. In some embodiments, $R^2$ may be cyclohexyl.

In some embodiments, $R^3$ may be H. In some embodiments, $R^3$ may be hydroxy. In some embodiments, $R^3$ may be $C_1$-$C_6$ alkyl. In some embodiments, $R^3$ may be $C_1$-$C_4$ alkyl. In some embodiments, $R^3$ may be methyl. In some embodiments, $R^3$ may be ethyl. In some embodiments, $R^3$ may be iso-propyl. In some embodiments, $R^3$ may be tert-butyl.

In some embodiments, $R^3$ may be halo. In some embodiments, $R^3$ may be fluoro. In some embodiments, $R^3$ may be chloro. In some embodiments, $R^3$ may be chloro. In some embodiments, $R^3$ may be bromo. In some embodiments, $R^3$ may be iodo.

In some embodiments, $R^4$ may be H. In some embodiments, $R^4$ may be $C_1$-$C_6$ alkyl. In some embodiments, $R^4$ may be $C_1$-$C_3$ alkyl. In some embodiments, $R^4$ may be methyl. In some embodiments, $R^4$ may be acyl. In some embodiments, $R^4$ may be acetyl.

In some embodiments, $R^5$ may be $C_1$-$C_6$ alkyl. In some embodiments, $R^5$ may be $C_1$-$C_4$ alkyl. In some embodiments, $R^5$ may be methyl. In some embodiments, $R^5$ may be ethyl. In some embodiments, $R^5$ may be iso-propyl. In some embodiments, $R^5$ may be tert-butyl.

In some embodiments, $R^5$ may be halo. In some embodiments, $R^5$ may be fluoro. In some embodiments, $R^5$ may be chloro. In some embodiments, $R^5$ may be bromo. In some embodiments, $R^5$ may be iodo.

In some embodiments, $R^6$ may be selected from H, $C_1$-$C_6$ alkyl, and acyl, each of which is substituted with 0, 1, 2, or 3 $R^5$. In some embodiments, $R^6$ may be H. In some embodiments, $R^6$ may be $C_1$-$C_6$ alkyl. In some embodiments, $R^6$ may be $C_1$-$C_3$ alkyl. In some embodiments, $R^6$ may be methyl. In some embodiments, $R^6$ may be acyl. In come embodiments, $R^6$ may be $C_1$-$C_3$ acyl. In come embodiments, $R^6$ may be acetyl.

In some embodiments, $R^7$ may be selected from H, $C_1$-$C_6$ alkyl, and acyl, each of which is substituted with 0, 1, 2, or 3 $R^5$. In some embodiments, $R^7$ may be H. In some embodiments, $R^7$ may be $C_1$-$C_6$ alkyl. In some embodiments, $R^7$ may be $C_1$-$C_3$ alkyl. In some embodiments, $R^7$ may be $C_1$-$C_3$ alkyl. In some embodiments, $R^7$ may be methyl. In some embodiments, $R^7$ may be $C_1$-$C_3$ acyl. In some embodiments, $R^7$ may be acetyl.

In some embodiments, L may be

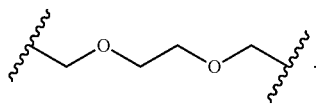 [SMILES: *COCCOC*]

In some embodiments, L may be

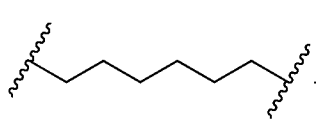

In some embodiments, L may be

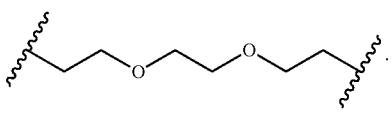 [SMILES: *CCOCCOCC*]

In some embodiments, L may be

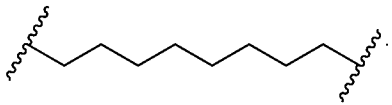 [SMILES: *CCCCCCCC*]

In some embodiments, L may be

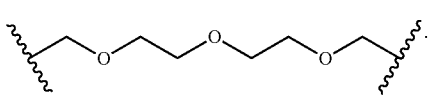 [SMILES: *COCCOCCOC*]

In some embodiments, L may be

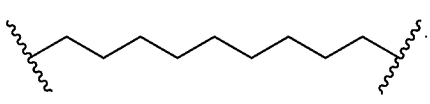 [SMILES: *CCCCCCCCC*]

In some embodiments, L may be

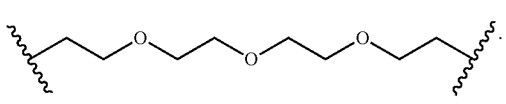 [SMILES: *CCOCCOCCOCC*]

In some embodiments, L may be

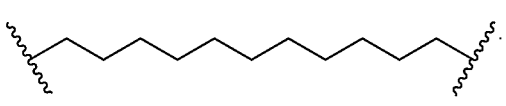 [SMILES: *CCCCCCCCCCC*]

In some embodiments, L may be

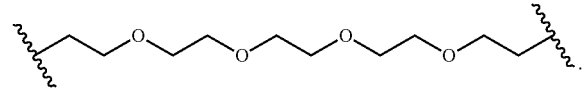 [SMILES: *CCOCCOCCOCCOCC*]

In some embodiments, L may be

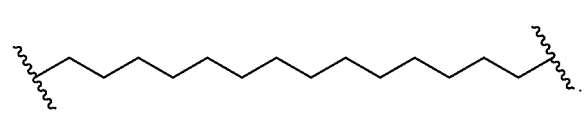 [SMILES: *CCCCCCCCCCCCCC*]

In some embodiments, L may be

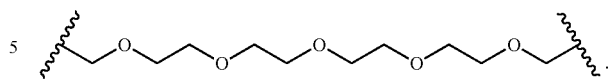

In some embodiments, L may be

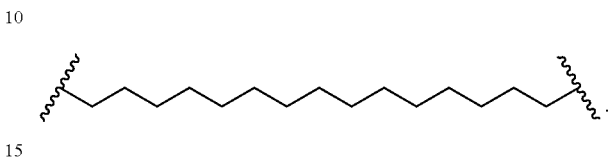

In some embodiments, $L^1$ may be

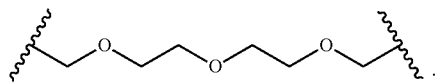 [SMILES: *COCCOCCOC*]

In some embodiments, $L^1$ may be

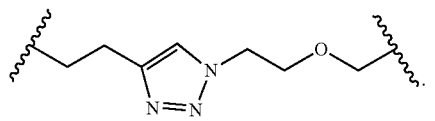 [SMILES: *CCc1cn(CCOC*)nn1]

In some embodiments, $L^1$ may be

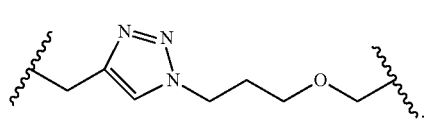 [SMILES: *COCCCn1cc(C*)nn1]

In some embodiments, $L^1$ may be

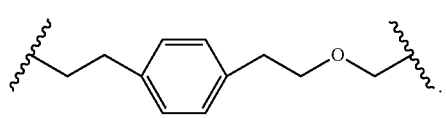

In some embodiments, $L^1$ may be

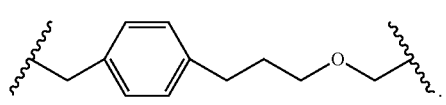 [SMILES: *COCCCc1ccc(C*)cc1]

In some embodiments, $L^1$ may be

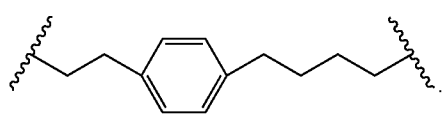 [SMILES: *CCCCc1ccc(CC*)cc1]

In some embodiments, L¹ may be

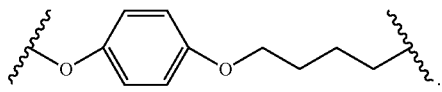 [SMILES: *CCCCOc1ccc(O*)cc1]

In some embodiments, L¹ may be

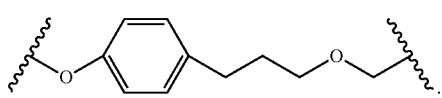

In some embodiments, L¹ may be

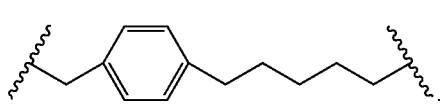 [SMILES: *CCCCCc1ccc(C*)cc1]

In some embodiments, L¹ may be

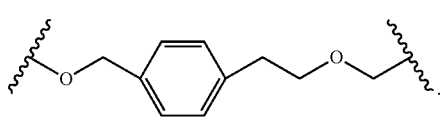

In some embodiments, L¹ may be

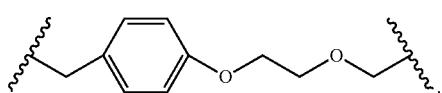

In some embodiments, L¹ may be

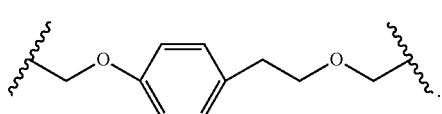

In some embodiments, L¹ may be

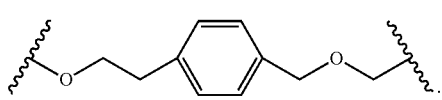 [SMILES: *COCc1ccc(CCO*)cc1]

In some embodiments, L¹ may be

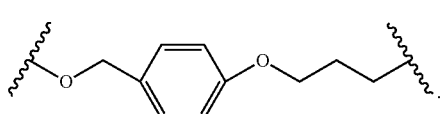

In some embodiments, L¹ may be

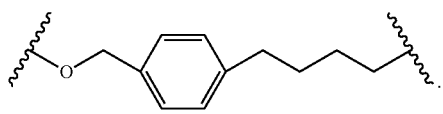 [SMILES: *CCCCc1ccc(CO*)cc1]

In some embodiments, L¹ may be

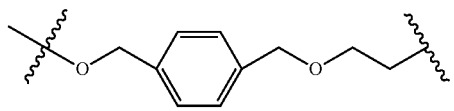

In some embodiments, L¹ may be

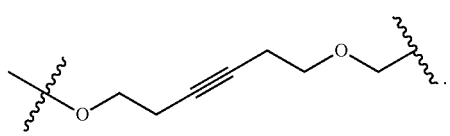 [SMILES: *COCCC#CCCO*]

In some embodiments, L¹ may be

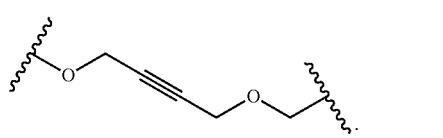 [SMILES: *COCC#CCO*]

In some embodiments, L¹ may be

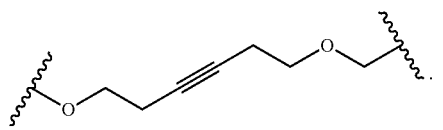 [SMILES: *COCCC#CCCO*]

In some embodiments, L¹ may be

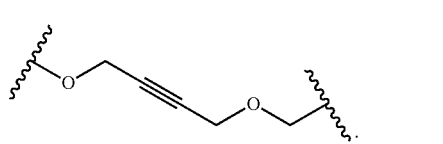 [SMILES: *COCC#CCO*]

In some embodiments, L¹ may be

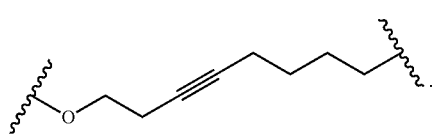 [SMILES: *CCCCC#CCCO*]

In some embodiments, L¹ may be

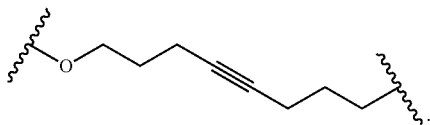 [SMILES: *CCCC#CCCCO*]

In some embodiments, L¹ may be

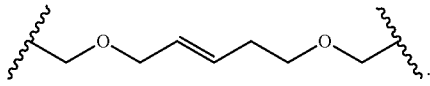 [SMILES: *COC/C=C/CCOC*]

In some embodiments, L¹ may be

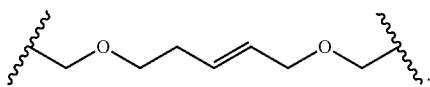 [SMILES: *COC/C=C/CCOC*]

In some embodiments, L² may be

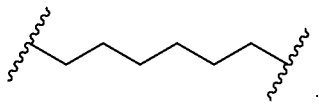 [SMILES: *CCCCCC*]

In some embodiments, L² may be

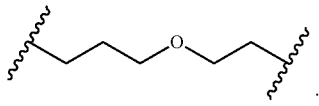 [SMILES: *CCCOCC*]

In some embodiments, L² may be

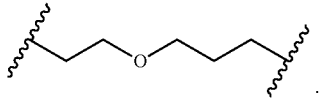 [SMILES: *CCCOCC*]

In some embodiments, L² may be

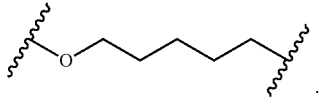 [SMILES: *CCCCCO*]

In some embodiments, L² may be

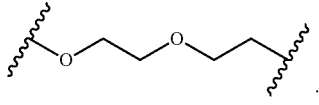 [SMILES: *CCOCCO*]

In some embodiments, L² may be

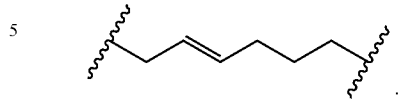

In some embodiments, L² may be

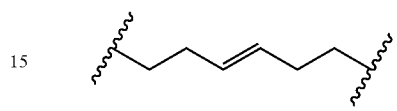

In some embodiments, L² may be

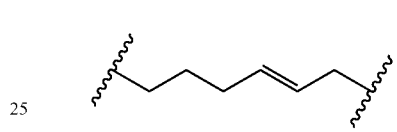

In some embodiments, L² may be

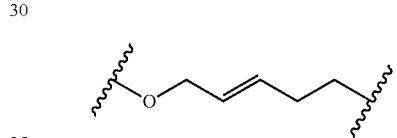

In some embodiments, L² may be

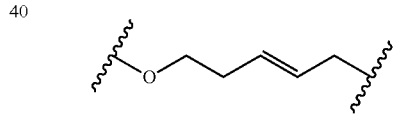

In some embodiments, L² may be

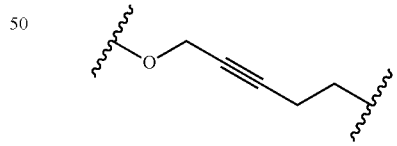

In some embodiments, L² may be

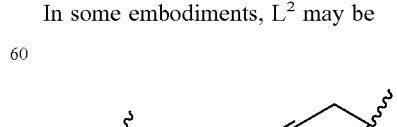

In some embodiments, L² may be

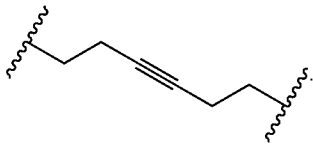 [SMILES: *CCC#CCC*]

In some embodiments, L² may be

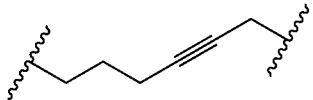

In some embodiments, L² may be

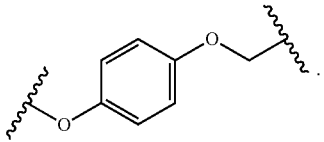 [SMILES: *COc1ccc(O*)cc1]

In some embodiments, L² may be

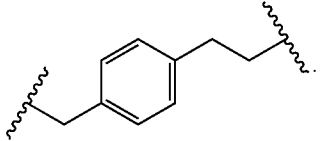 [SMILES: *CCc1ccc(C*)cc1]

In some embodiments, L² may be

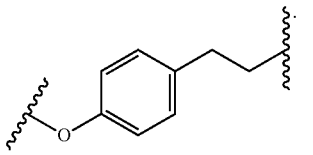 [SMILES: *CCc1ccc(O*)cc1]

In some embodiments, L² may be

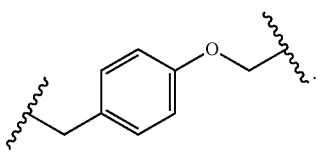

Provided herein is the compound (2S,4R)-1-((S)-2-(tert-butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide. Provided herein is the compound (2S,4R)-1-((S)-2-(2-(4-(3-(2-(4-((Z)-1,2-diphenylbut-1-en-1-yl)phenoxy)ethyl)(methyl)amino)-3-oxopropyl)-1H-1,2,3-triazol-1-yl)ethoxy)acetamido)-3,3-dimethylbutanoyl)-4-hydroxy-N-(4-(4-methylthiazol-5-yl)benzyl)pyrrolidine-2-carboxamide. Provided herein is the compound (2S,4R)-1-((S)-2-(2-(3-(4-(2-((2-(4-((Z)-1,2-diphenylbut-1-en-1-yl)phenoxy)ethyl)(methyl)amino)-2-oxoethyl)-1H-1,2,3-triazol-1-yl)propoxy)acetamido)-3,3-dimethylbutanoyl)-4-hydroxy-N-(4-(4-methylthiazol-5-yl)benzyl)pyrrolidine-2-carboxamide. Provided herein is the compound (2S,4R)-1-((S)-2-(2-(4-(3-((2-(4-((Z)-1,2-diphenylbut-1-en-1-yl)phenoxy)ethyl)(methyl)amino)-3-oxopropyl)phenethoxy)acetamido)-3,3-dimethylbutanoyl)-4-hydroxy-N-(4-(4-methylthiazol-5-yl)benzyl)pyrrolidine-2-carboxamide. Provided herein is the compound (2S,4R)-1-((S)-2-(2-(3-(4-(2-((2-(4-((Z)-1,2-diphenylbut-1-en-1-yl)phenoxy)ethyl)(methyl)amino)-2-oxoethyl)phenyl)propoxy)acetamido)-3,3-dimethylbutanoyl)-4-hydroxy-N-(4-(4-methylthiazol-5-yl)benzyl)pyrrolidine-2-carboxamide. Provided herein is the compound (2S,4R)-1-((S)-2-(5-(4-(3-((2-(4-((Z)-1,2-diphenylbut-1-en-1-yl)phenoxy)ethyl)(methyl)amino)-3-oxopropyl)phenyl)pentanamido)-3,3-dimethylbutanoyl)-4-hydroxy-N-(4-(4-methylthiazol-5-yl)benzyl)pyrrolidine-2-carboxamide. Provided herein is the compound 4-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)oxy)phenyl (2-(4-((Z)-1,2-diphenylbut-1-en-1-yl)phenoxy)ethyl)(methyl)carbamate. Provided herein is the compound 4-(3-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)propyl)phenyl (2-(4-((Z)-1,2-diphenylbut-1-en-1-yl)phenoxy)ethyl)(methyl)carbamate. Provided herein is the compound (2S,4R)-1-((S)-2-(6-(4-(2-((2-(4-((Z)-1,2-diphenylbut-1-en-1-yl)phenoxy)ethyl)(methyl)amino)-2-oxoethyl)phenyl)hexanamido)-3,3-dimethylbutanoyl)-4-hydroxy-N-(4-(4-methylthiazol-5-yl)benzyl)pyrrolidine-2-carboxamide. Provided herein is the compound 4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)benzyl (2-(4-((Z)-1,2-diphenylbut-1-en-1-yl)phenoxy)ethyl)(methyl)carbamate. Provided herein is the compound (2S,4R)-1-((S)-2-(2-(2-(4-(2-((2-(4-((Z)-1,2-diphenylbut-1-en-1-yl)phenoxy)ethyl)(methyl)amino)-2-oxoethyl)phenoxy)ethoxy)acetamido)-3,3-dimethylbutanoyl)-4-hydroxy-N-(4-(4-methylthiazol-5-yl)benzyl)pyrrolidine-2-carboxamide. Provided herein is the compound (2S,4R)-1-((S)-2-(2-(4-(2-((2-(4-((Z)-1,2-diphenylbut-1-en-1-yl)phenoxy)ethyl)(methyl)amino)-2-oxoethoxy)phenethoxy)acetamido)-3,3-dimethylbutanoyl)-4-hydroxy-N-(4-(4-methylthiazol-5-yl)benzyl)pyrrolidine-2-carboxamide. Provided herein is the compound 4-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)methyl)phenethyl (2-(4-((Z)-1,2-diphenylbut-1-en-1-yl)phenoxy)ethyl)(methyl)carbamate. Provided herein is the compound 4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutoxy)benzyl (2-(4-((Z)-1,2-diphenylbut-1-en-1-yl)phenoxy)ethyl)(methyl)carbamate. Provided herein is the compound 4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)benzyl (2-(4-((Z)-1,2-diphenylbut-1-en-1-yl)phenoxy)ethyl)(methyl)carbamate. Provided herein is the compound. Provided herein is the compound 4-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)methyl)benzyl (2-(4-((Z)-1,2-diphenylbut-1-en-1-yl)phenoxy)ethyl)(methyl)carbamate.

Provided herein is the compound 6-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)hex-3-yn-1-yl (2-(4-((Z)-1,2-diphenylbut-1-en-1-yl)phenoxy)ethyl)(methyl)carbamate. Provided herein is the compound 6-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)hex-4-yn-1-yl (2-(4-((Z)-1,2-diphenylbut-1-en-1-yl)phenoxy)ethyl)(methyl)carbamate. Provided herein is the compound (2S,4R)-1-((S)-2-(tert-butyl)-17-(4-((Z)-1,2-diphenylbut-1-en-1-yl)phenoxy)-15-methyl-4,14-dioxo-6,12-dioxa-3,15-diazaheptadec-9-ynoyl)-4-hydroxy-N-(4-(4-methylthiazol-5-yl)benzyl)pyrrolidine-2-carboxamide. Provided herein is the compound (2S,4R)-1-((S)-2-(tert-butyl)-17-(4-((Z)-1,2-diphenylbut-1-en-1-yl)phenoxy)-15-methyl-4,14-dioxo-6,12-dioxa-3,15-diazaheptadec-8-ynoyl)-4-hydroxy-N-(4-(4-methylthiazol-5-yl)benzyl)pyrrolidine-2-carboxamide. Provided herein is the compound 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxonon-3-yn-1-yl (2-(4-((Z)-1,2-diphenylbut-1-en-1-yl)phenoxy)ethyl)(methyl)carbamate. Provided herein is the compound 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxonon-4-yn-1-yl (2-(4-((Z)-1,2-diphenylbut-1-en-1-yl)phenoxy)ethyl)(methyl)carbamate. Provided herein is the compound (2S,4R)-1-((S,E)-2-(tert-butyl)-17-(4-((Z)-1,2-diphenylbut-1-en-1-yl)phenoxy)-15-methyl-4,14-dioxo-6,12-dioxa-3,15-diazaheptadec-9-enoyl)-4-hydroxy-N-(4-(4-methylthiazol-5-yl)benzyl)pyrrolidine-2-carboxamide. Provided herein is the compound (2S,4R)-1-((S,E)-2-(tert-butyl)-17-(4-((Z)-1,2-diphenylbut-1-en-1-yl)phenoxy)-15-methyl-4,14-dioxo-6,12-dioxa-3,15-diazaheptadec-8-enoyl)-4-hydroxy-N-(4-(4-methylthiazol-5-yl)benzyl)pyrrolidine-2-carboxamide.

Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide. Provided herein is the compound (2S,4R)-1-((S)-2-(3-(4-((2-(4-((Z)-1,2-diphenylbut-1-en-1-yl)phenoxy)ethyl)(methyl)amino)-4-oxobutoxy)propanamido)-3,3-dimethylbutanoyl)-4-hydroxy-N-(4-(4-methylthiazol-5-yl)benzyl)pyrrolidine-2-carboxamide. Provided herein is the compound (2S,4R)-1-((S)-2-(4-(3-((2-(4-((Z)-1,2-diphenylbut-1-en-1-yl)phenoxy)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide. Provided herein is the compound 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl (2-(4-((Z)-1,2-diphenylbut-1-en-1-yl)phenoxy)ethyl)(methyl)carbamate. Provided herein is the compound 2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl (2-(4-((Z)-1,2-diphenylbut-1-en-1-yl)phenoxy)ethyl)(methyl)carbamate. Provided herein is the compound (E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-3-enediamide. Provided herein is the compound (E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-4-enediamide. Provided herein is the compound (E)-N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-methyloct-3-enediamide. Provided herein is the compound (E)-6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-2-en-1-yl (2-(4-((Z)-1,2-diphenylbut-1-en-1-yl)phenoxy)ethyl)(methyl)carbamate. Provided herein is the compound (E)-6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-3-en-1-yl (2-(4-((Z)-1,2-diphenylbut-1-en-1-yl)phenoxy)ethyl)(methyl)carbamate. Provided herein is the compound 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-2-yn-1-yl (2-(4-((Z)-1,2-diphenylbut-1-en-1-yl)phenoxy)ethyl)(methyl)carbamate. Provided herein is the compound 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-3-yn-1-yl (2-(4-((Z)-1,2-diphenylbut-1-en-1-yl)phenoxy)ethyl)(methyl)carbamate. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-3-ynediamide. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-4-ynediamide. Provided herein is the compound N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-methyloct-3-ynediamide. Provided herein is the compound 4-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)phenyl (2-(4-((Z)-1,2-diphenylbut-1-en-1-yl)phenoxy)ethyl)(methyl)carbamate. Provided herein is the compound (2S,4R)-1-((S)-2-(3-(4-(2-((2-(4-((Z)-1,2-diphenylbut-1-en-1-yl)phenoxy)ethyl)(methyl)amino)-2-oxoethyl)phenyl)propanamido)-3,3-dimethylbutanoyl)-4-hydroxy-N-(4-(4-methylthiazol-5-yl)benzyl)pyrrolidine-2-carboxamide. Provided herein is the compound 4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)phenyl (2-(4-((Z)-1,2-diphenylbut-1-en-1-yl)phenoxy)ethyl)(methyl)carbamate. Provided herein is the compound (2S,4R)-1-((S)-2-(2-(4-(2-((2-(4-((Z)-1,2-diphenylbut-1-en-1-yl)phenoxy)ethyl)(methyl)amino)-2-oxoethyl)phenoxy)acetamido)-3,3-dimethylbutanoyl)-4-hydroxy-N-(4-(4-methylthiazol-5-yl)benzyl)pyrrolidine-2-carboxamide.

Provided herein is the compound (2S,4R)-1-((1-(4-((Z)-1,2-diphenylbut-1-en-1-yl)phenoxy)-3-methyl-4-oxo-6,9,12-trioxa-3-azatetradecan-14-oyl)-L-valyl)-4-hydroxy-N-(4-(4-methylthiazol-5-yl)benzyl)pyrrolidine-2-carboxamide. Provided herein is the compound (2S,4R)-1-((2-(2-(4-(3-((2-(4-((Z)-1,2-diphenylbut-1-en-1-yl)phenoxy)ethyl)(methyl)amino)-3-oxopropyl)-1H-1,2,3-triazol-1-yl)ethoxy)acetyl)-L-valyl)-4-hydroxy-N-(4-(4-methylthiazol-5-yl)benzyl)pyrrolidine-2-carboxamide. Provided herein is the compound (2S,4R)-1-((2-(3-(4-(2-((2-(4-((Z)-1,2-diphenylbut-1-en-1-yl)phenoxy)ethyl)(methyl)amino)-2-oxoethyl)-1H-1,2,3-triazol-1-yl)propoxy)acetyl)-L-valyl)-4-hydroxy-N-(4-(4-methylthiazol-5-yl)

benzyl)pyrrolidine-2-carboxamide. Provided herein is the compound (2S,4R)-1-((2-(4-(3-((2-(4-((Z)-1,2-diphenylbut-1-en-1-yl)phenoxy)ethyl)(methyl)amino)-3-oxopropyl)phenethoxy)acetyl)-L-valyl)-4-hydroxy-N-(4-(4-methylthiazol-5-yl)benzyl)pyrrolidine-2-carboxamide. Provided herein is the compound (2S,4R)-1-((2-(3-(4-(2-((2-(4-((Z)-1,2-diphenylbut-1-en-1-yl)phenoxy)ethyl)(methyl)amino)-2-oxoethyl)phenyl)propoxy)acetyl)-L-valyl)-4-hydroxy-N-(4-(4-methylthiazol-5-yl)benzyl)pyrrolidine-2-carboxamide. Provided herein is the compound (2S,4R)-1-((5-(4-(3-((2-(4-((Z)-1,2-diphenylbut-1-en-1-yl)phenoxy)ethyl)(methyl)amino)-3-oxopropyl)phenyl)pentanoyl)-L-valyl)-4-hydroxy-N-(4-(4-methylthiazol-5-yl)benzyl)pyrrolidine-2-carboxamide. Provided herein is the compound 4-((5-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-5-oxopentyl)oxy)phenyl (2-(4-((Z)-1,2-diphenylbut-1-en-1-yl)phenoxy)ethyl)(methyl)carbamate. Provided herein is the compound 4-(3-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)propyl)phenyl (2-(4-((Z)-1,2-diphenylbut-1-en-1-yl)phenoxy)ethyl)(methyl)carbamate. Provided herein is the compound (2S,4R)-1-((6-(4-(2-((2-(4-((Z)-1,2-diphenylbut-1-en-1-yl)phenoxy)ethyl)(methyl)amino)-2-oxoethyl)phenyl)hexanoyl)-L-valyl)-4-hydroxy-N-(4-(4-methylthiazol-5-yl)benzyl)pyrrolidine-2-carboxamide. Provided herein is the compound 4-(2-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)ethyl)benzyl (2-(4-((Z)-1,2-diphenylbut-1-en-1-yl)phenoxy)ethyl)(methyl)carbamate. Provided herein is the compound (2S,4R)-1-((2-(2-(4-(2-((2-(4-((Z)-1,2-diphenylbut-1-en-1-yl)phenoxy)ethyl)(methyl)amino)-2-oxoethyl)phenoxy)ethoxy)acetyl)-L-valyl)-4-hydroxy-N-(4-(4-methylthiazol-5-yl)benzyl)pyrrolidine-2-carboxamide. Provided herein is the compound (2S,4R)-1-((2-(4-(2-((2-(4-((Z)-1,2-diphenylbut-1-en-1-yl)phenoxy)ethyl)(methyl)amino)-2-oxoethoxy)phenethoxy)acetyl)-L-valyl)-4-hydroxy-N-(4-(4-methylthiazol-5-yl)benzyl)pyrrolidine-2-carboxamide. Provided herein is the compound 4-((2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)methyl)phenethyl (2-(4-((Z)-1,2-diphenylbut-1-en-1-yl)phenoxy)ethyl)(methyl)carbamate. Provided herein is the compound 4-(4-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-4-oxobutoxy)benzyl (2-(4-((Z)-1,2-diphenylbut-1-en-1-yl)phenoxy)ethyl)(methyl)carbamate. Provided herein is the compound 4-(5-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-5-oxopentyl)benzyl (2-(4-((Z)-1,2-diphenylbut-1-en-1-yl)phenoxy)ethyl)(methyl)carbamate. Provided herein is the compound 4-((3-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-3-oxopropoxy)methyl)benzyl (2-(4-((Z)-1,2-diphenylbut-1-en-1-yl)phenoxy)ethyl)(methyl)carbamate. Provided herein is the compound 6-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)hex-3-yn-1-yl (2-(4-((Z)-1,2-diphenylbut-1-en-1-yl)phenoxy)ethyl)(methyl)carbamate. Provided herein is the compound 6-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)hex-4-yn-1-yl (2-(4-((Z)-1,2-diphenylbut-1-en-1-yl)phenoxy)ethyl)(methyl)carbamate. Provided herein is the compound (2S,4R)-1-((2-((5-(2-((2-(4-((Z)-1,2-diphenylbut-1-en-1-yl)phenoxy)ethyl)(methyl)amino)-2-oxoethoxy)pent-3-yn-1-yl)oxy)acetyl)-L-valyl)-4-hydroxy-N-(4-(4-methylthiazol-5-yl)benzyl)pyrrolidine-2-carboxamide. Provided herein is the compound (2S,4R)-1-((2-((5-(2-((2-(4-((Z)-1,2-diphenylbut-1-en-1-yl)phenoxy)ethyl)(methyl)amino)-2-oxoethoxy)pent-2-yn-1-yl)oxy)acetyl)-L-valyl)-4-hydroxy-N-(4-(4-methylthiazol-5-yl)benzyl)pyrrolidine-2-carboxamide. Provided herein is the compound 9-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-9-oxonon-3-yn-1-yl (2-(4-((Z)-1,2-diphenylbut-1-en-1-yl)phenoxy)ethyl)(methyl)carbamate. Provided herein is the compound 9-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-9-oxonon-4-yn-1-yl (2-(4-((Z)-1,2-diphenylbut-1-en-1-yl)phenoxy)ethyl)(methyl)carbamate. Provided herein is the compound (2S,4R)-1-((2-(((E)-5-(2-((2-(4-((Z)-1,2-diphenylbut-1-en-1-yl)phenoxy)ethyl)(methyl)amino)-2-oxoethoxy)pent-3-en-1-yl)oxy)acetyl)-L-valyl)-4-hydroxy-N-(4-(4-methylthiazol-5-yl)benzyl)pyrrolidine-2-carboxamide. Provided herein is the compound (2S,4R)-1-((2-(((E)-5-(2-((2-(4-((Z)-1,2-diphenylbut-1-en-1-yl)phenoxy)ethyl)(methyl)amino)-2-oxoethoxy)pent-2-en-1-yl)oxy)acetyl)-L-valyl)-4-hydroxy-N-(4-(4-methylthiazol-5-yl)benzyl)pyrrolidine-2-carboxamide. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloctanediamide. Provided herein is the compound (2S,4R)-1-((3-(4-((2-(4-((Z)-1,2-diphenylbut-1-en-1-yl)phenoxy)ethyl)(methyl)amino)-4-oxobutoxy)propanoyl)-L-valyl)-4-hydroxy-N-(4-(4-methylthiazol-5-yl)benzyl)pyrrolidine-2-carboxamide. Provided herein is the compound (2S,4R)-1-((4-(3-((2-(4-((Z)-1,2-diphenylbut-1-en-1-yl)phenoxy)ethyl)(methyl)amino)-3-oxopropoxy)butanoyl)-L-valyl)-4-hydroxy-N-(4-(4-methylthiazol-5-yl)benzyl)pyrrolidine-2-carboxamide. Provided herein is the compound 6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohexyl (2-(4-((Z)-1,2-diphenylbut-1-en-1-yl)phenoxy)ethyl)(methyl)carbamate. Provided herein is the compound 2-(3-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-3-oxopropoxy)ethyl (2-(4-((Z)-1,2-diphenylbut-1-en-1-yl)phenoxy)ethyl)(methyl)carbamate. Provided herein is the compound (E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-3-enediamide. Provided herein is the compound (E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-4-enediamide. Provided herein is the compound (E)-N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N8-methyloct-3-enediamide. Provided herein is the compound (E)-6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-2-en-1-yl (2-(4-((Z)-1,2-diphenylbut-1-en-1-yl)phenoxy)ethyl)(methyl)carbamate. Provided herein is the compound (E)-

6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-3-en-1-yl (2-(4-((Z)-1,2-diphenylbut-1-en-1-yl)phenoxy)ethyl)(methyl)carbamate. Provided herein is the compound 6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-2-yn-1-yl (2-(4-((Z)-1,2-diphenylbut-1-en-1-yl)phenoxy)ethyl)(methyl)carbamate. Provided herein is the compound 6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-3-yn-1-yl (2-(4-((Z)-1,2-diphenylbut-1-en-1-yl)phenoxy)ethyl)(methyl)carbamate. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-3-ynediamide. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-4-ynediamide. Provided herein is the compound N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N8-methyloct-3-ynediamide. Provided herein is the compound 4-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)phenyl (2-(4-((Z)-1,2-diphenylbut-1-en-1-yl)phenoxy)ethyl)(methyl)carbamate. Provided herein is the compound (2S,4R)-1-((3-(4-(2-((2-(4-((Z)-1,2-diphenylbut-1-en-1-yl)phenoxy)ethyl)(methyl)amino)-2-oxoethyl)phenyl)propanoyl)-L-valyl)-4-hydroxy-N-(4-(4-methylthiazol-5-yl)benzyl)pyrrolidine-2-carboxamide. Provided herein is the compound 4-(3-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-3-oxopropyl)phenyl (2-(4-((Z)-1,2-diphenylbut-1-en-1-yl)phenoxy)ethyl)(methyl)carbamate. Provided herein is the compound (2S,4R)-1-((2-(4-(2-((2-(4-((Z)-1,2-diphenylbut-1-en-1-yl)phenoxy)ethyl)(methyl)amino)-2-oxoethyl)phenoxy)acetyl)-L-valyl)-4-hydroxy-N-(4-(4-methylthiazol-5-yl)benzyl)pyrrolidine-2-carboxamide.

Provided herein is the compound (2S,4R)-1-((S)-2-(tert-butyl)-14-(4-((Z)-1,2-diphenylbut-1-en-1-yl)phenoxy)-12-methyl-4,11-dioxo-6,9-dioxa-3,12-diazatetradecanoyl)-4-hydroxy-N-(4-(4-methylthiazol-5-yl)benzyl)pyrrolidine-2-carboxamide. Provided herein is the compound (2S,4R)-1-((2-(2-(2-((2-(4-((Z)-1,2-diphenylbut-1-en-1-yl)phenoxy)ethyl)(methyl)amino)-2-oxoethoxy)ethoxy)acetyl)-L-valyl)-4-hydroxy-N-(4-(4-methylthiazol-5-yl)benzyl)pyrrolidine-2-carboxamide. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloctanediamide. Provided herein is the compound (2S,4R)-1-((S)-2-(tert-butyl)-16-(4-((Z)-1,2-diphenylbut-1-en-1-yl)phenoxy)-14-methyl-4,13-dioxo-7,10-dioxa-3,14-diazahexadecanoyl)-4-hydroxy-N-(4-(4-methylthiazol-5-yl)benzyl)pyrrolidine-2-carboxamide. Provided herein is the compound (2S,4R)-1-((3-(2-(3-((2-(4-((Z)-1,2-diphenylbut-1-en-1-yl)phenoxy)ethyl)(methyl)amino)-3-oxopropoxy)ethoxy)propanoyl)-L-valyl)-4-hydroxy-N-(4-(4-methylthiazol-5-yl)benzyl)pyrrolidine-2-carboxamide. Provided herein is the compound N1-(2-(4-((Z)-1,2-diphenylbut-1-en-1-yl)phenoxy)ethyl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyldecanediamide. Provided herein is the compound N1-(2-(4-((Z)-1,2-diphenylbut-1-en-1-yl)phenoxy)ethyl)-N10-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyldecanediamide. Provided herein is the compound (2S,4R)-1-((S)-2-(tert-butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide. Provided herein is the compound (2S,4R)-1-((1-(4-((Z)-1,2-diphenylbut-1-en-1-yl)phenoxy)-3-methyl-4-oxo-6,9,12-trioxa-3-azatetradecan-14-oyl)-L-valyl)-4-hydroxy-N-(4-(4-methylthiazol-5-yl)benzyl)pyrrolidine-2-carboxamide. Provided herein is the compound N1-(2-(4-((Z)-1,2-diphenylbut-1-en-1-yl)phenoxy)ethyl)-N11-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylundecanediamide. Provided herein is the compound N1-(2-(4-((Z)-1,2-diphenylbut-1-en-1-yl)phenoxy)ethyl)-N11-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methylundecanediamide. Provided herein is the compound (2S,4R)-1-((S)-2-(tert-butyl)-19-(4-((Z)-1,2-diphenylbut-1-en-1-yl)phenoxy)-17-methyl-4,16-dioxo-7,10,13-trioxa-3,17-diazanonadecanoyl)-4-hydroxy-N-(4-(4-methylthiazol-5-yl)benzyl)pyrrolidine-2-carboxamide. Provided herein is the compound (2S,4R)-1-((1-(4-((Z)-1,2-diphenylbut-1-en-1-yl)phenoxy)-3-methyl-4-oxo-7,10,13-trioxa-3-azahexadecan-16-oyl)-L-valyl)-4-hydroxy-N-(4-(4-methylthiazol-5-yl)benzyl)pyrrolidine-2-carboxamide. Provided herein is the compound N1-(2-(4-((Z)-1,2-diphenylbut-1-en-1-yl)phenoxy)ethyl)-N13-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyltridecanediamide. Provided herein is the compound N1-(2-(4-((Z)-1,2-diphenylbut-1-en-1-yl)phenoxy)ethyl)-N13-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyltridecanediamide. Provided herein is the compound N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-4,7,10,13-tetraoxahexadecanediamide. Provided herein is the compound N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyl-4,7,10,13-tetraoxahexadecanediamide. Provided herein is the compound N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylhexadecanediamide. Provided herein is the compound N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methylhexadecanediamide. Provided herein is the compound N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-3,6,9,12,15-pentaoxaheptadecanediamide. Provided herein is the compound N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyl-3,6,9,12,15-pentaoxaheptadecanediamide. Provided herein is the compound N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylheptadecanediamide. Provided herein is the compound N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methylheptadecanediamide.

Provided herein is the compound N1-(2-(4-((Z)-1,2-diphenylbut-1-en-1-yl)phenoxy)ethyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)cyclobutane-1,3-dicarboxamide. Provided herein is the compound N1-(2-(4-((Z)-1,2-diphenylbut-1-en-1-yl)phenoxy)ethyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylcyclobutane-1,3-dicarboxamide. Provided herein is the compound N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N3-(2-(4-((Z)-1-(4-hydroxyphenyl)-2-phenylbut-1-en-1-yl)phenoxy)ethyl)cyclobutane-1,3-dicarboxamide. Provided herein is the compound N2-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N6-(2-(4-((Z)-1-(4-hydroxyphenyl)-2-phenylbut-1-en-1-yl)phenoxy)ethyl)spiro[3.3]heptane-2,6-dicarboxamide. Provided herein is the compound (2S,4R)-1-((S)-2-(2-(4-((2-(4-((Z)-1,2-diphenylbut-1-en-1-yl)phenoxy)ethyl)carbamoyl)phenyl)acetamido)-3,3-dimethylbutanoyl)-4-hydroxy-N-(4-(4-methylthiazol-5-yl)benzyl)pyrrolidine-2-carboxamide. Provided herein is the compound N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N4-(2-(4-((Z)-1-(4-hydroxyphenyl)-2-phenylbut-1-en-1-yl)phenoxy)ethyl)but-2-ynediamide. Provided herein is the compound N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-(2-(4-((Z)-1-(4-hydroxyphenyl)-2-phenylbut-1-en-1-yl)phenoxy)ethyl)hex-2-ynediamide. Provided herein is the compound N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-(2-(4-((Z)-1-(4-hydroxyphenyl)-2-phenylbut-1-en-1-yl)phenoxy)ethyl)oct-2-ynediamide. Provided herein is the compound N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N6-(2-(4-((Z)-1-(4-hydroxyphenyl)-2-phenylbut-1-en-1-yl)phenoxy)ethyl)hexa-2,4-diynediamide. Provided herein is the compound N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide. Provided herein is the compound N1-(3-((2-(4-((Z)-1,2-diphenylbut-1-en-1-yl)phenoxy)ethyl)(methyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide. Provided herein is the compound N1-(3-((2-(4-((Z)-1,2-diphenylbut-1-en-1-yl)phenoxy)ethyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide.

Provided herein is the compound N1-(2-(4-((Z)-1,2-bis(4-hydroxyphenyl)but-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide. Provided herein is the compound N1-(2-(4-((Z)-1,2-bis(4-hydroxyphenyl)but-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide. Provided herein is the compound N1-(3-((2-(4-((Z)-1,2-bis(4-hydroxyphenyl)but-1-en-1-yl)phenoxy)ethyl)(methyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide. Provided herein is the compound (2S,4R)-1-((S)-2-(4-(3-((2-(4-((Z)-1,2-bis(4-hydroxyphenyl)but-1-en-1-yl)phenoxy)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide.

Provided herein is the compound N1-(2-((4-((Z)-1,2-diphenylbut-1-en-1-yl)phenyl)thio)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide. Provided herein is the compound (2S,4R)-1-((S)-2-(4-(3-((2-((4-((Z)-1,2-diphenylbut-1-en-1-yl)phenyl)thio)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide. Provided herein is the compound N1-(2-((4-((Z)-1,2-diphenylbut-1-en-1-yl)phenyl)amino)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide. Provided herein is the compound N1-(3-((2-((4-((Z)-1,2-diphenylbut-1-en-1-yl)phenyl)amino)ethyl)(methyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide. Provided herein is the compound (2S,4R)-1-((S)-2-(4-(3-((2-((4-((Z)-1,2-diphenylbut-1-en-1-yl)phenyl)amino)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide. Provided herein is the compound (2S,4R)-4-hydroxy-1-((S)-2-(4-(3-((2-((4-((E)-1-(4-hydroxyphenyl)-2-phenylbut-1-en-1-yl)phenyl)amino)ethyl)(methyl)amino)-3-oxopropoxy)butanamido)-3,3-dimethylbutanoyl)-N-(4-(4-methylthiazol-5-yl)benzyl)pyrrolidine-2-carboxamide.

Pharmaceutical Compositions

Pharmaceutical compositions of the present disclosure comprise at least one compound of Formulae (I), (II), (III), or (IV), or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules;

as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formulae (I), (II), or (III), or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formulae (I), (II), (III), or (IV), or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

TABLE 1

Equivalent Surface Area Dosage Factors.

| From: | To: Mouse (20 g) | Rat (150 g) | Monkey (3.5 kg) | Dog (8 kg) | Human (60 kg) |
|---|---|---|---|---|---|
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formulae (I), (II), (III), or (IV), or a tautomer, stereoisomer, pharmaceutically acceptable salt or hydrate thereof, is administered to treat cancer in a subject in need thereof. In some embodiments, the cancer is chosen from breast cancer, lung cancer, ovarian cancer, endometrial cancer, prostate cancer, and esophageal cancer. In some embodiments, the cancer is breast cancer. In some embodiments, the cancer is lung cancer. In some embodiments, the cancer is ovarian cancer. In some embodiments, the cancer is endometrial cancer. In some embodiments, the cancer is prostate cancer. In some embodiments, the cancer is esophageal cancer. In some embodiments, the cancer is positive for Estrogen Receptor alpha. In some embodiments, a compound of Formulae (I), (II), or (III), or a tautomer, stereoisomer, pharmaceutically acceptable salt or hydrate thereof, is administered as a pharmaceutical composition. In some embodiments, the subject has been previously treated with tamoxifen.

In some embodiments, herein is provided a use of a compound of Formulae (I), (II), (III), or (IV), or a tautomer, stereoisomer, pharmaceutically acceptable salt or hydrate thereof, in a therapeutic treatment. In some embodiments, the therapeutic treatment is for the treatment of breast cancer, lung cancer, ovarian cancer, endometrial cancer, prostate cancer, and esophageal cancer. In some embodiments, the therapeutic treatment is for the treatment of breast cancer. In some embodiments, the therapeutic treatment is for lung cancer. In some embodiments, the therapeutic treatment is for the treatment of ovarian cancer. In some embodiments, the therapeutic treatment is for the treatment of endometrial cancer. In some embodiments, the therapeutic treatment is for the treatment of prostate cancer. In some embodiments, the therapeutic treatment is for the treatment of esophageal cancer. In some embodiments, the therapeutic treatment is for the treatment of estrogen-related diseases and conditions. In some embodiments, the therapeutic treatment is for the treatment of infertility. In some embodiments, the therapeutic treatment is for the treatment of ovulatory dysfunction. In some embodiments, the therapeutic treatment is for the treatment of postmenopausal osteoporosis. In some embodiments, the therapeutic treatment is for the treatment of estrogen-related gynecomastia. In some embodiments, the therapeutic treatment is for the treatment of dyspareunia due to menopause. In some embodiments, the therapeutic treatment is for the treatment of retroperitoneal fibrosis. In some embodiments, the therapeutic treatment is for the treatment of idiopathic sclerosing mesenteritis.

In some embodiments, herein is provided a use of a compound of Formulae (I), (II), (III), or (IV), or a tautomer, stereoisomer, pharmaceutically acceptable salt or hydrate thereof, in the preparation of a medicament. In some embodiments, herein is provided a method of inhibiting cell growth comprising contacting a cell with a compound of Formulae (I), (II), (III), or (IV), or a tautomer, stereoisomer, pharmaceutically acceptable salt or hydrate thereof. In some embodiments, the cell may express Estrogen Receptor alpha.

In one embodiment, a compound of Formulae (I), (II), (III), or (IV), or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formulae (I), (II), (III), or (IV), or a tautomer, stereoisomer, pharmaceutically acceptable salt or hydrate thereof, may be administered in combination with a hormone or hormonal analog. In some embodiments, a compound of Formulae (I), (II), (III), or (IV), or a tautomer, stereoisomer, pharmaceutically acceptable salt or hydrate thereof, may be administered in combination with a signal transduction pathway inhibitor. In some embodiments, a compound of Formulae (I), (II), (III), or (IV), or a tautomer, stereoisomer, pharmaceutically acceptable salt or hydrate thereof, may be administered in combination with an antimetabolite neoplastic agent. In some embodiments, a compound of Formulae (I), (II), (III), or (IV), or a tautomer, stereoisomer, pharmaceutically acceptable salt or hydrate thereof, may be administered in combination with a topoisomerase I inhibitor. In some embodiments, a compound of Formulae (I), (II), (III), (IV), or a tautomer, stereoisomer, pharmaceutically acceptable salt or hydrate thereof, may be administered in combination with a topoisomerase II inhibitor. In some embodiments, a compound of Formulae (I), (II), (III), or (IV), or a tautomer, stereoisomer, pharmaceutically acceptable salt or hydrate thereof, may be administered in combination with an aromatase inhibitor. In some embodiments, a compound of Formulae (I), (II), (III), or (IV), or a tautomer, stereoisomer, pharmaceutically acceptable salt or hydrate thereof, may be administered in combination with one or more anti-cancer agents.

In some embodiments, a compound of Formulae (I), (II), (III), or (IV), or a tautomer, stereoisomer, pharmaceutically acceptable salt or hydrate thereof, may be administered in combination with an anti-cancer agent, wherein the anti-cancer agent is tamoxifen. In some embodiments, a compound of Formulae (I), (II), (III), or (IV), or a tautomer, stereoisomer, pharmaceutically acceptable salt or hydrate thereof, may be administered in combination with an anti-cancer agent, wherein the anti-cancer agent is fulvestrant.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, 3$^{rd}$ Ed., 1990 New York: Plenum Press; Mundy et al., Name Reaction and Reagents in Organic Synthesis, 2$^{nd}$ Ed., 2005 Hoboken, N.J.: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, 3$^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

The following abbreviations have the definitions set forth below:
1. DCE: 1,2-dichloroethane
2. DCM: dichloromethane
3. DMEM: Dulbecco's Modification of Eagle's Medium
4. DMSO: dimethylsulfoxide
5. DMF: N,N-dimethylformamide
6. EDCI: 1-Ethyl-3-(3-dimethylaminopropyl)carbodiimide
7. EDTA: ethylenediaminetetraacetic acid
8. ESI-TOF: electrospray ionization time-of-flight mass spectrometry
9. EtOAc: ethyl acetate
10. FBS: fetal bovine serum
11. HOAt: 1-hydroxy-7-azabenzotriazole
12. HPLC: high pressure liquid chromatography
13. HRMS: high resolution mass spectrometry
14. LTED: long-term estradiol-deprived cells
15. MeOH: methanol
16. MCF-7: Michigan Cancer Foundation-7 breast cancer cell line 17. NMR: nuclear magnetic resonance
18. PVDF: polyvinylidene fluoride
19. RPMI 1640: Roswell Park Memorial Institute 1640 medium
20. SDS: sodium dodecyl sulfate
21. TBST: tris-buffered saline and Tween 20
22. THF: tetrahydrofuran Example 1. Synthesis of (2S,4R)-1-((S)-2-(tert-butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide Intermediate 1

(Z)-2-(4-(1,2-diphenylbut-1-en-1-yl)phenoxy)-N-methylethan-1-amine

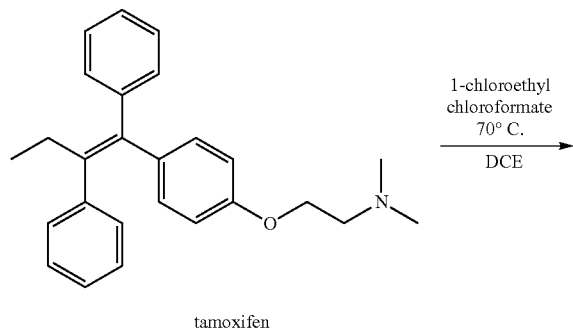

tamoxifen 1-chloroethyl chloroformate
70° C.
DCE

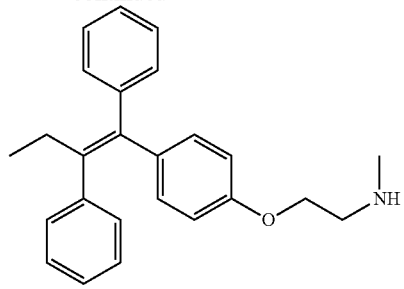

Intermediate 1

To a solution of tamoxifen (10.0 g, 26.91 mmol) in DCE (100 mL) at 0° C. was added 1-chloroethyl chloroformate (4.60 mg, 32.30 mmol). The resulting mixture was stirred at 0° C. for 15 min, and was then stirred at 70° C. overnight. Upon cooling, the mixture was concentrated in vacuo, and the resulting residue was diluted with MeOH (100 mL). The resulting mixture was heated at reflux for 3 h and upon cooling, the mixture was concentrated in vacuo. The resulting residue was crystallized in diethyl ether and MeOH, and Intermediate 1 was obtained was a white solid (8.80 g, 91%). $^1$H-NMR (MeOH-$d_4$) δ 7.35 (t, 2H, J=7.4 Hz), 7.26 (t, 1H, J=7.3 Hz), 7.21 (d, 2H, J=7.2 Hz), 7.12 (m, 5H), 6.82 (d, 2H, J=8.5 Hz), 6.66 (d, 2H, J=8.5 Hz), 4.12 (t, 2H, J=4.5 Hz), 3.36 (t, 2H, J=4.8 Hz), 2.73 (s, 3H), 2.45 (q, 2H, J=7.4 Hz), 0.90 (t, 3H, J=7.4 Hz). HRMS (m/z): 358.22 [M+H]$^+$.

Intermediate 2

(Z)-1-(4-(1,2-diphenylbut-1-en-1-yl)phenoxy)-3-methyl-4-oxo-6,9,12-trioxa-3-azatetradecan-14-oic acid

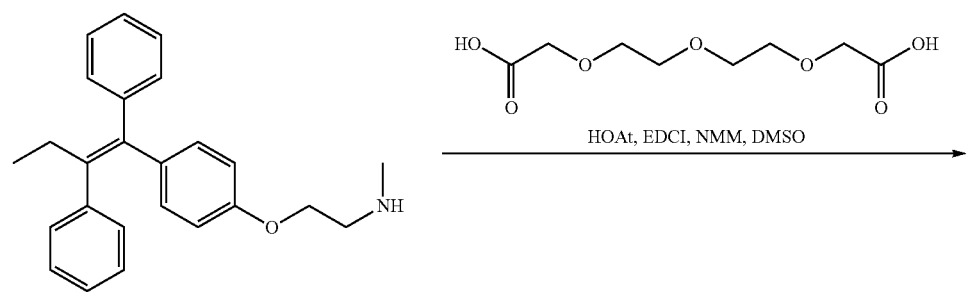

HOAt, EDCI, NMM, DMSO

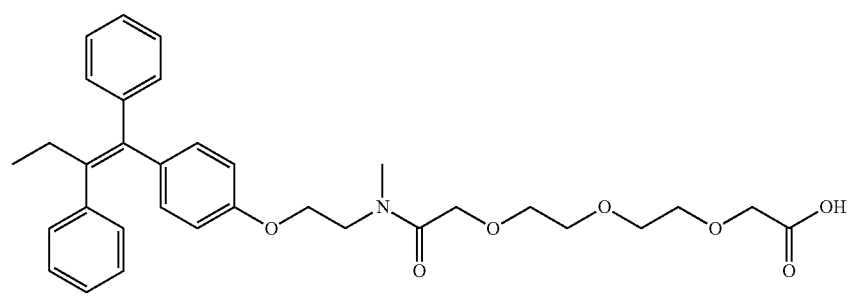

Intermediate 2

To a mixture of Intermediate 1 (230 mg, 0.643 mmol) and DMSO (5 mL) was added N-methylmorpholine (195 mg, 1.93 mmol), 2,2'-((oxybis(ethane-2,1-diyl))bis(oxy))diacetic acid (204 mg, 0.643 mmol), 1-hydroxy-7-azabenzotriazole (131 mg, 0.965 mmol), and EDCI (185 mg, 0.965 mmol). The resulting mixture was stirred at room temperature overnight, and was then concentrated in vacuo. The resulting residue was purified by reverse-phase preparative HPLC to afford Intermediate 2 as colorless oil (259 mg, 71%). $^1$H-NMR (MeOH-$d_4$) δ 7.34 (t, 2H, J=7.5 Hz), 7.26 (t, 1H, J=7.1 Hz), 7.21 (d, 2H, J=7.7 Hz), 7.16 (t, 2H, J=7.5 Hz), 7.10 (m, 3H), 6.77 (t, 2H, J=9.0 Hz), 6.56 (t, 2H, J=9.6 Hz), 4.31 (s, 1H), 4.22 (s, 1H), 4.05 (m, 2H), 4.03 (t, 1H, J=5.1 Hz), 4.00 (t, 1H, J=5.1 Hz), 3.68-3.61 (m, 10H), 3.04 (s, 1.5H), 2.94 (s, 1.5H), 2.44 (q, 2H, J=7.4 Hz), 0.90 (t, 3H, J=7.4 Hz). HRMS (m/z): 562.28 [M+H]$^+$.

Example 1

(2S,4R)-1-((S)-2-(tert-butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide

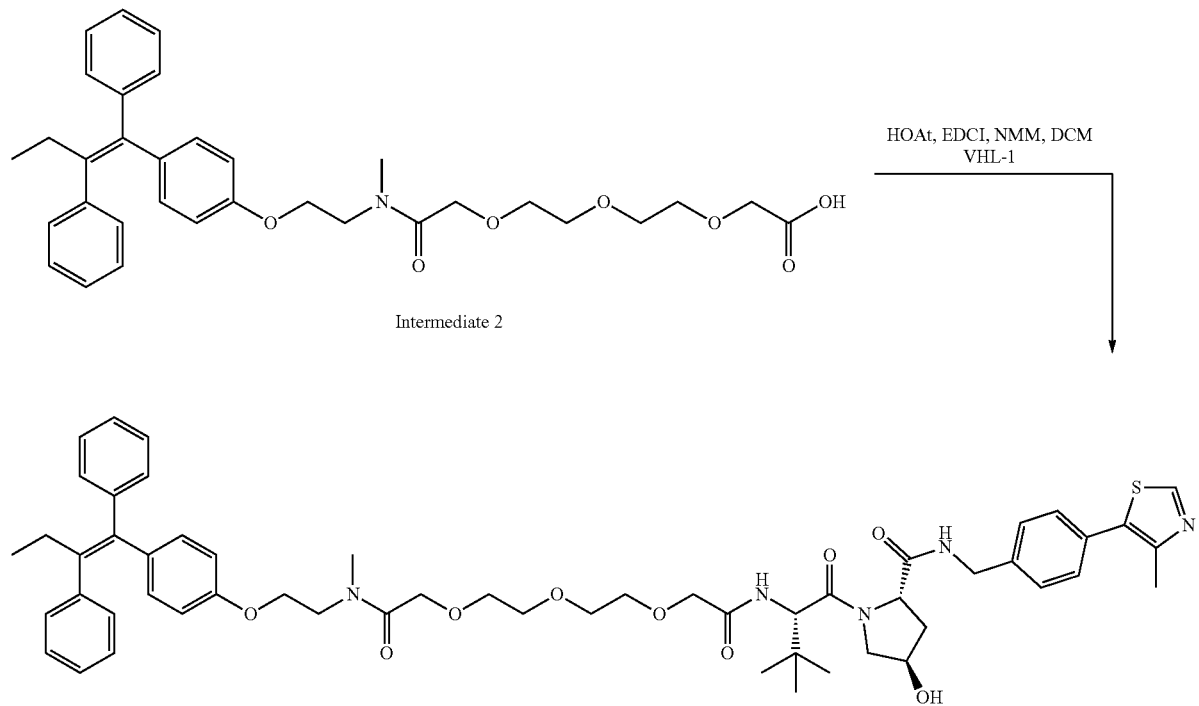

To a mixture of Intermediate 2 (220 mg, 0.392 mmol) and DCM (20 mL) was added N-methylmorpholine (118 mg, 1.176 mmol), (2S,4R)-1-((S)-2-amino-3,3-dimethylbutanoyl)-4-hydroxy-N-(4-(4-methylthiazol-5-yl)benzyl)pyrrolidine-2-carboxamide ("VHL-1", 192 mg, 0.4117 mmol), synthesized according to Galdeano et al., *J. Med. Chem.* (2014) 57: 8657-63, 1-hydroxy-7-azabenzotriazole (64 mg, 0.470 mmol), and EDCI (90 mg, 0.470 mmol). The resulting mixture was stirred at room temperature overnight, and was then concentrated in vacuo. The resulting residue was purified by reverse-phase preparative HPLC to afford Example 1 as a white solid (220 mg, 57%). $^1$H-NMR (MeOH-$d_4$) δ 8.85 (d, 1H, J=2.9 Hz), 7.44 (d, 2H, J=8.1 Hz), 7.40 (d, 2H, J=8.1 Hz), 7.33 (t, 2H, J=7.5 Hz), 7.25 (t, 1H, J=7.3 Hz), 7.20 (d, 2H, J=7.1 Hz), 7.15 (t, 2H, J=7.4 Hz), 7.09 (m, 3H), 6.75 (t, 2H, J=8.0 Hz), 6.54 (t, 2H, J=8.0 Hz), 4.68 (d, 1H, J=2.3 Hz), 4.57-4.47 (m, 3H), 4.33 (dd, 1H, J=4.4 Hz, J=15.5 Hz), 4.28 (s, 1H), 4.18 (s, 1H), 4.05-3.95 (m, 4H), 3.86 (d, 1H, J=11.0 Hz), 3.78 (dd, 1H, J=3.5 Hz, J=10.9 Hz), 3.70-3.60 (m, 10H), 3.01 (s, 1.5H), 2.91 (s, 1H, 1.5H), 2.47-2.41 (m, 5H), 2.21 (m, 1H), 2.07 (m, 1H), 1.02 (d, 9H, J=2.9 Hz), 0.89 (t, 3H, J=7.4 Hz). HRMS (m/z): 974.47 [M+H]$^+$.

Example 2. Synthesis of N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide Intermediate 1 methyl (Z)-8-((2-(4-(1,2-diphenylbut-1-en-1-yl)phenoxy)ethyl)(methyl)amino)-8-oxooctanoate

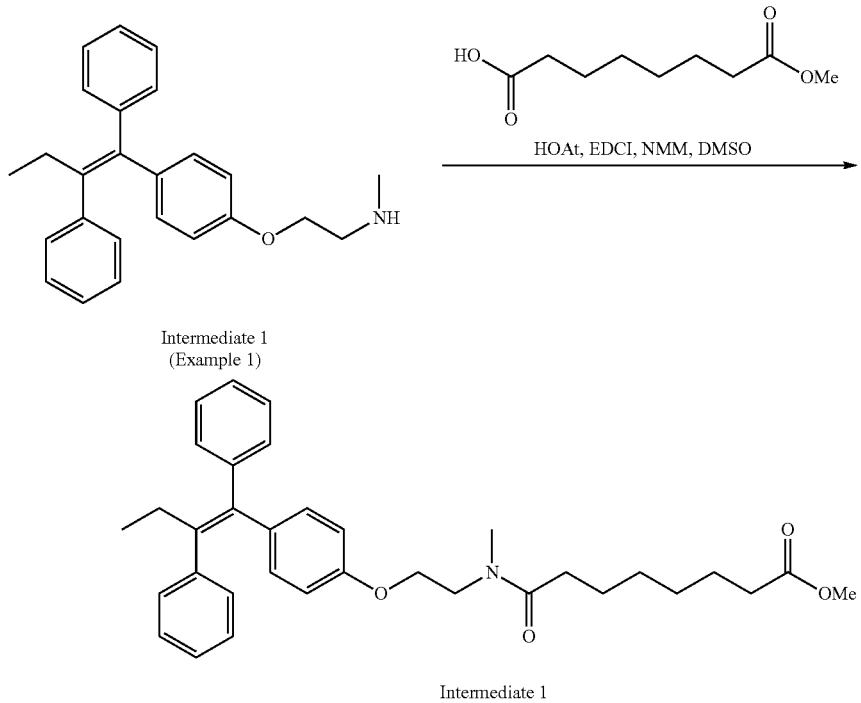

To a mixture of Intermediate 1 (from Example 1) (100 mg, 0.280 mmol) and DCM (20 mL) was added N-methylmorpholine (85 mg, 0.839 mmol), 8-methoxy-8-oxooctanoic acid (63 mg, 0.336 mmol), 1-hydroxy-7-azabenzotriazole (57 mg, 0.420 mmol), and EDCI (80 mg, 0.420 mmol). The mixture was stirred at room temperature overnight. Subsequently, the mixture was concentrated in vacuo and the resulting reside was purified by flash column chromatography on silica gel (gradient from 100% hexane to 50% EtOAc) to afford Intermediate 1 (145 mg, 97%) as a colorless oil. $^1$H-NMR (CDCl$_3$) δ 7.33 (t, 2H, J=7.3 Hz), 7.27-7.23 (m, 3H), 7.19-7.16 (m, 2H), 7.13-7.09 (m, 3H), 6.77 (t, 2H, J=9.6 Hz), 6.51 (m, 2H, J=9.6 Hz), 3.98 (t, 2H, J=5.0 Hz), 3.92 (t, J=5.3 Hz), 3.66-3.60 (m, 5H), 3.05 (s, 2H), 2.94 (s, 1H), 2.47-2.24 (m, 6H), 1.62-1.60 (m, 4H), 1.34-1.32 (m, 4H), 0.92 (d, 3H, J=7.2 Hz). HRMS (m/z): 528.3109 [M+H]$^+$.

Example 2

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide

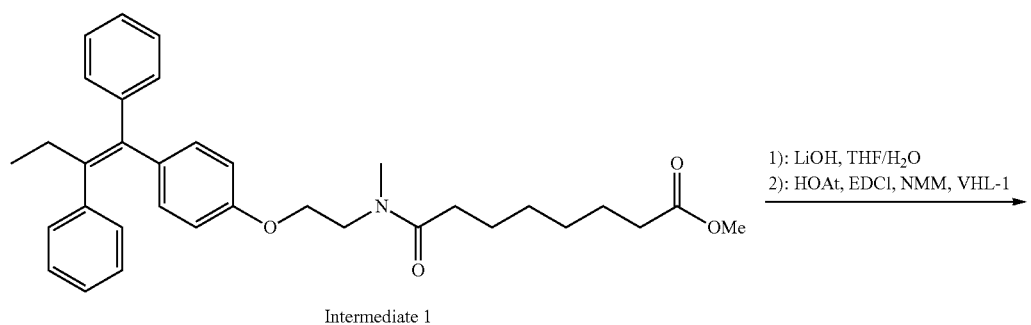

Intermediate 1

-continued

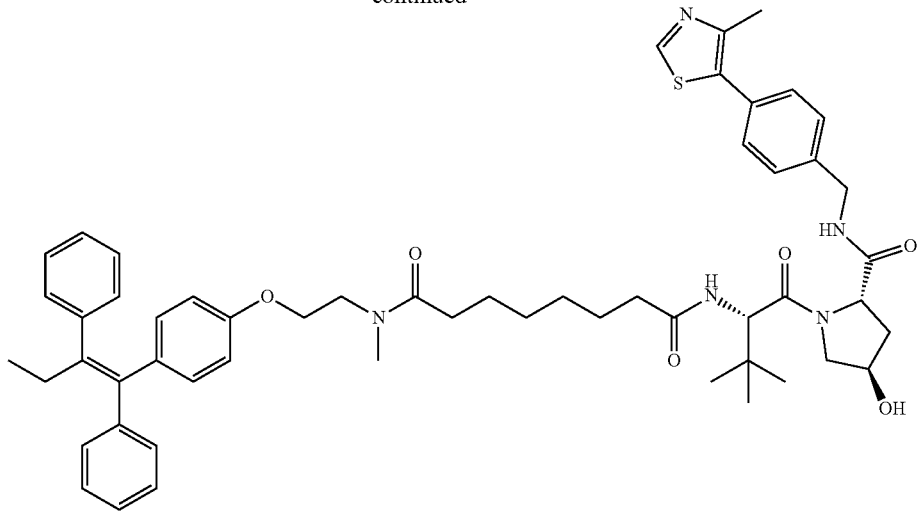

Example 2

To a mixture of Intermediate 1 (85 mg, 0.161 mmol) and THF/H₂O (10 mL/5 mL) was added LiOH (anhydrous, 8 mg, 0.322 mmol), and the resulting mixture was stirred overnight at room temperature. The resulting mixture was the concentrated in vacuo and the residue was diluted with DCM/DMF (10 mL/1 mL), followed by addition of N-methylmorpholine (59 mg, 0.580 mmol), (2S,4R)-1-((S)-2-amino-3,3-dimethylbutanoyl)-4-hydroxy-N-(4-(4-methylthiazol-5-yl)benzyl)pyrrolidine-2-carboxamide (90 mg, 0.193 mmol), 1-hydroxy-7-azabenzotriazole (34 mg, 0.251 mmol), and EDCI (48 mg, 0.251 mmol), and the resulting mixture was stirred overnight at room temperature. Subsequently, the mixture was concentrated in vacuo, and the resulting residue was purified by flash column chromatography on silica gel (gradient from 100% DCM to 10% MeOH in DCM) to afford Example 2 (71 mg, 48%) as a white solid. ¹H-NMR (MeOH-d₄) δ 8.85 (s, 1H), 7.83 (d, 1H, J=8.8 Hz), 7.45 (d, 2H, J=7.8 Hz) 7.40 (t, 2H, J=7.9 Hz), 7.32 (t, 2H, J=7.5 Hz), 7.24 (t, 1H, J=7.4 Hz), 7.19 (d, 2H, J=7.2 Hz), 7.14 (t, 2H, J=7.4 Hz), 7.08 (dd, 3H, J=7.3 Hz, J=15.8 Hz), 6.75 (dd, 2H, J=8.8 Hz, J=11.0 Hz), 6.53 (dd, 2H, J=4.9 Hz, J=8.4 Hz), 4.64 (d, 1H, J=8.5 Hz), 4.58-4.48 (m, 3H), 4.34 (d, 1H, J=15.5 Hz), 3.96 (td, 2H, J=5.1 Hz, J=18.6 Hz), 3.90 (d, 1H, J=10.8 Hz), 3.79 (m, 1H), 3.64 (td, 2H, J=5.1 Hz, J=27.2 Hz), 3.05 (s, 3H), 2.89 (s, 3H), 2.45-2.38 (m, 5H), 2.31-2.19 (m, 4H), 2.09-2.05 (m, 1H), 1.59-1.55 (m, 4H), 1.33-1.31 (m, 4H), 1.03 (d, 9H, J=3.0 Hz), 0.88 (t, 3H, J=7.4 Hz). HRMS (m/z): 926.4880 [M+H]⁺.

Example 3. Synthesis of Exemplary Compounds
General Procedure for Linker Coupling

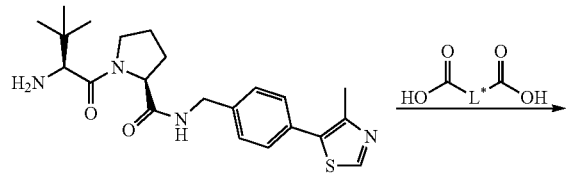

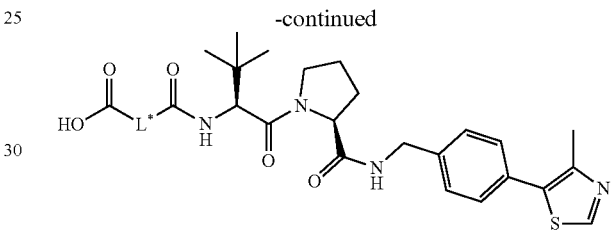

To a solution of a di-acid linker (10 mmol) in DCM/THF (1:1, 200 mL) was added VHL-1 (2 mmol, see Example 1), triethylamine (1 mL, 7.1 mmol), HOAt (300 mg, 2.2 mmol), and EDCI (420 mg, 2.2 mmol) sequentially at 0° C. The resulting mixture was stirred for 2 h at 0° C., before being warmed to room temperature. After stirring overnight at room temperature, water was added to the mixture. The resulting mixture was subsequently concentrated in vacuo and the resulting residue was purified by reverse-phase chromatography to afford the target compound.

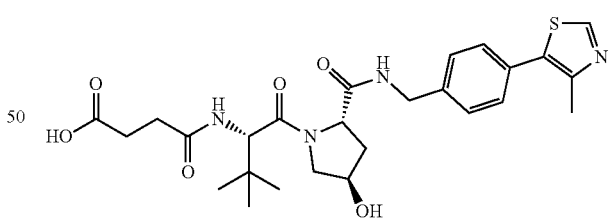

4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid Compound obtained as a white solid (810 mg, 85%). ¹H-NMR (600 MHz, CD₃OD) δ 9.10 (s, 1H), 7.51 (d, J=7.8 Hz, 2H), 7.44 (d, J=8.4 Hz, 2H), 4.64 (s, 1H), 4.60-4.49 (m, 3H), 4.39 (d, J=15.6 Hz, 1H), 3.91 (d, J=10.8 Hz, 1H), 3.82 (dd, J=9.6, 3.6 Hz, 1H), 2.67-2.55 (m, 4H), 2.52 (s, 3H), 2.25-2.22 (m, 1H), 2.12-2.07 (m, 1H), 1.06 (s, 9H). HRMS (ESI-TOF) m/z: [M+H]⁺ 531.2.

63

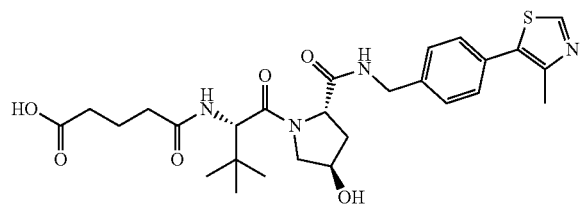 [SMILES: Cc1ncsc1-c1ccc(CNC(=O)[C@@H]2C[C@@H](O)CN2C(=O)[C@@H](NC(=O)CCCC(=O)O)C(C)(C)C)cc1]

5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid Compound obtained as a white solid (230 mg, 43%). ¹H-NMR (600 MHz, CD₃OD) δ 9.14 (s, 1H), 7.51 (d, J=9.0 Hz, 2H), 7.46 (d, J=8.4 Hz, 2H), 4.65 (s, 1H), 4.60-4.57 (m, 1H), 4.56 (d, J=15.6 Hz, 1H), 4.53-4.50 (m, 1H), 4.38 (d, J=15.6 Hz, 1H), 3.94 (d, J=11.4 Hz, 1H), 3.82 (dd, J=11.4, 3.6 Hz, 1H), 2.52 (s, 3H), 2.40-2.30 (m, 4H), 2.26-2.22 (m, 1H), 2.12-2.08 (m, 1H), 1.91 (t, J=7.8 Hz, 2H), 1.06 (s, 9H). HRMS (ESI-TOF) m/z: [M+H]⁺ 545.2432.

64

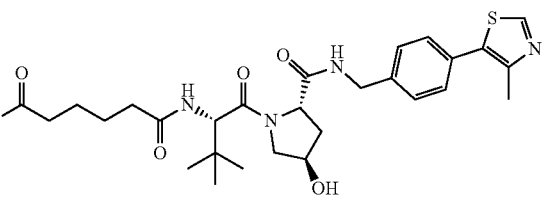

6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid Compound obtained as a white solid (700 mg, 63%). ¹H-NMR (600 MHz, CD₃OD) δ 9.12 (s, 1H), 7.51 (d, J=9.0 Hz, 2H), 7.46 (d, J=8.4 Hz, 2H), 4.65 (s, 1H), 4.60-4.55 (m, 2H), 4.53-4.50 (m, 1H), 4.38 (d, J=16.8 Hz, 1H), 3.93 (d, J=10.8 Hz, 1H), 3.82 (dd, J=11.4, 3.6 Hz, 1H), 2.52 (s, 3H), 2.38-2.21 (m, 5H), 2.12-2.08 (m, 1H), 1.71-1.62 (m, 4H), 1.06 (s, 9H). HRMS (ESI-TOF) m/z: [M+H]⁺ 559.3

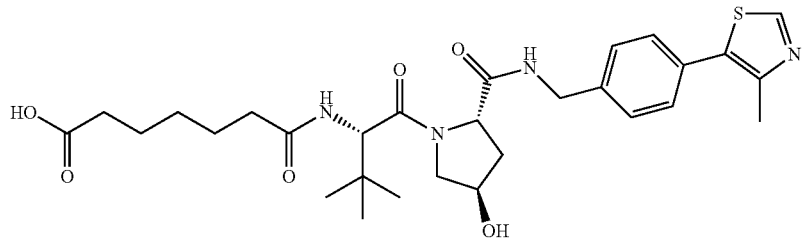 [SMILES: Cc1ncsc1-c1ccc(CNC(=O)[C@@H]2C[C@@H](O)CN2C(=O)[C@@H](NC(=O)CCCCCC(=O)O)C(C)(C)C)cc1]

7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid Compound obtained as a white solid (810 mg, 79%). ¹HNMR (600 MHz, CD₃OD) δ 8.98 (s, 1H), 7.50 (d, J=8.4 Hz, 2H), 7.44 (d, J=9.0 Hz, 2H), 4.65 (s, 1H), 4.60-4.49 (m, 3H), 4.38 (d, J=15.6 Hz, 1H), 3.93 (d, J=10.8 Hz, 1H), 3.82 (dd, J=11.4, 3.6 Hz, 1H), 2.51 (s, 3H), 2.35-2.22 (m, 5H), 2.13-2.08 (m, 1H), 1.68-1.59 (m, 4H), 1.42-1.34 (m, 2H), 1.06 (s, 9H). HRMS (ESI-TOF) m/z: [M+H]⁺ 573.2754.

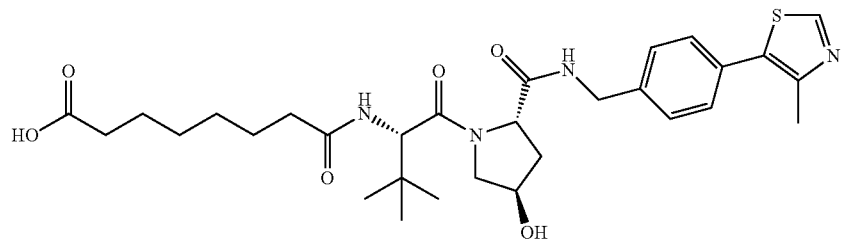 [SMILES: Cc1ncsc1-c1ccc(CNC(=O)[C@@H]2C[C@@H](O)CN2C(=O)[C@@H](NC(=O)CCCCCCC(=O)O)C(C)(C)C)cc1]

8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid Compound obtained as a white solid (980 mg, 78%). ¹H-NMR (600 MHz, CD₃OD) δ 8.94 (s, 1H), 7.47 (d, J=8.1 Hz, 2H), 7.42 (d, J=8.2 Hz, 2H), 4.63 (s, 1H), 4.59-4.47 (m, 3H), 4.35 (d, J=15.4 Hz, 1H), 3.90 (d, J=11.0 Hz, 1H), 3.80 (dd, J=10.9, 3.9 Hz, 1H), 2.48 (s, 3H), 2.32-2.17 (m, 5H), 2.08 (ddd, J=13.3, 9.1, 4.5 Hz, 1H), 1.67-1.55 (m, 4H), 1.40-1.28 (m, 4H), 1.03 (s, 9H). HRMS (ESI-TOF) m/z: [M+H]⁺ 587.3

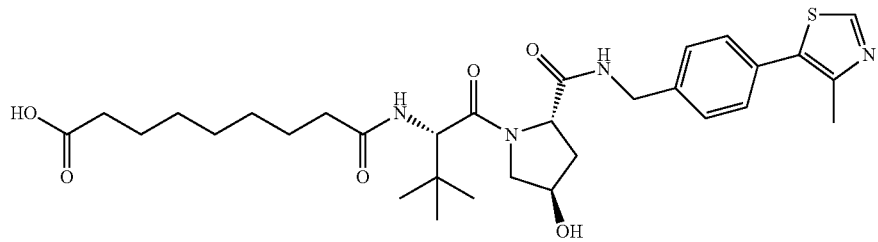 [SMILES: Cc1ncsc1-c1ccc(CNC(=O)[C@@H]2C[C@@H](O)CN2C(=O)[C@@H](NC(=O)CCCCCCCC(=O)O)C(C)(C)C)cc1]

9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid Compound obtained as a white solid (750 mg, 66%). ¹H-NMR (600 MHz CD₃OD) δ 9.09 (s, 1H), 7.51 (d, J=9.0 Hz, 2H), 7.46 (d, J=8.4 Hz, 2H), 4.66 (s, 1H), 4.61-4.50 (m, 3H), 4.38 (d, J=15.6 Hz, 11H), 3.93 (d, J=10.8 Hz, 1H), 3.82 (dd, J=11.4, 3.6 Hz, 1H), 2.52 (s, 3H), 2.36-2.22 (m, 5H), 2.12-2.07 (m, 1H), 1.68-1.59 (m, 4H), 1.40-1.34 (m, 8H), 1.06 (s, 9H); HRMS (ESI-TOF) [M+H]⁺ 601.3

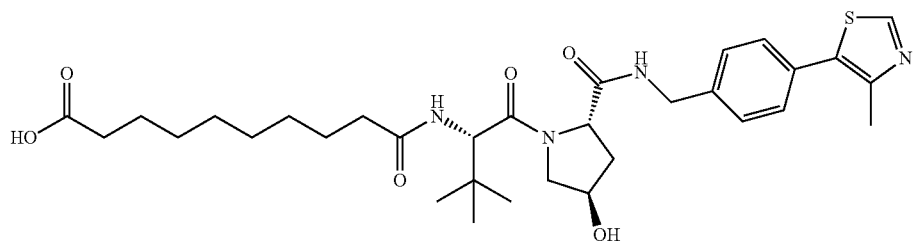 [SMILES: Cc1ncsc1-c1ccc(CNC(=O)[C@@H]2C[C@@H](O)CN2C(=O)[C@@H](NC(=O)CCCCCCCCC(=O)O)C(C)(C)C)cc1]

10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid Compound obtained as a white solid (900 mg, 73%). ¹H-NMR (600 MHz CD₃OD) δ 8.98 (s, 1H), 7.50 (d, J=8.4 Hz, 2H), 7.45 (d, J=9.0 Hz, 2H), 4.66 (s, 1H), 4.61-4.50 (m, 3H), 4.38 (d, J=14.4 Hz, 11H), 3.93 (d, J=10.8 Hz, 1H), 3.83 (dd, J=11.4, 3.6 Hz, 1H), 2.51 (s, 3H), 2.35-2.22 (m, 5H), 2.13-2.08 (m, 1H), 1.66-1.58 (m, 4H), 1.38-1.32 (m, 10H), 1.06 (s, 9H). HRMS (ESI-TOF) [M+H]⁺ 615.3

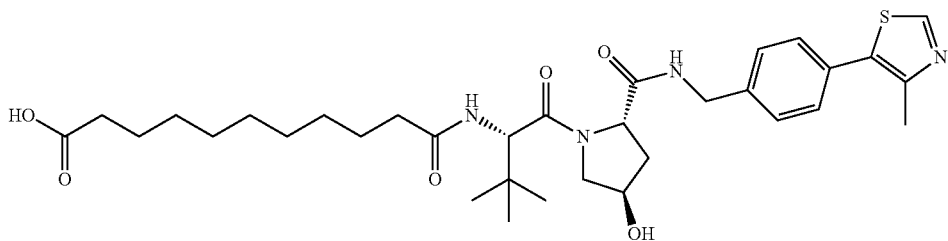 [SMILES: Cc1ncsc1-c1ccc(CNC(=O)[C@@H]2C[C@@H](O)CN2C(=O)[C@@H](NC(=O)CCCCCCCCCC(=O)O)C(C)(C)C)cc1]

11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid Compound obtained as a white solid (930 mg, 78%). $^1$HNMR (600 MHz CD$_3$OD) δ 8.95 (s, 1H), 7.49 (d, J=8.4 Hz, 2H), 7.44 (d, J=7.8 Hz, 2H), 4.66 (s, 1H), 4.61-4.50 (m, 3H), 4.38 (d, J=15.6 Hz, 1H), 3.93 (d, J=9.6 Hz, 1H), 3.82 (dd, J=11.4, 3.6 Hz, 1H), 2.50 (s, 3H), 2.35-2.21 (m, 5H), 2.12-2.07 (m, 1H), 1.66-1.57 (m, 4H), 1.37-1.29 (m, 12H), 1.06 (s, 9H). HRMS (ESI-TOF) [M+H]$^+$ 629.3

General Procedure for Linker Coupling

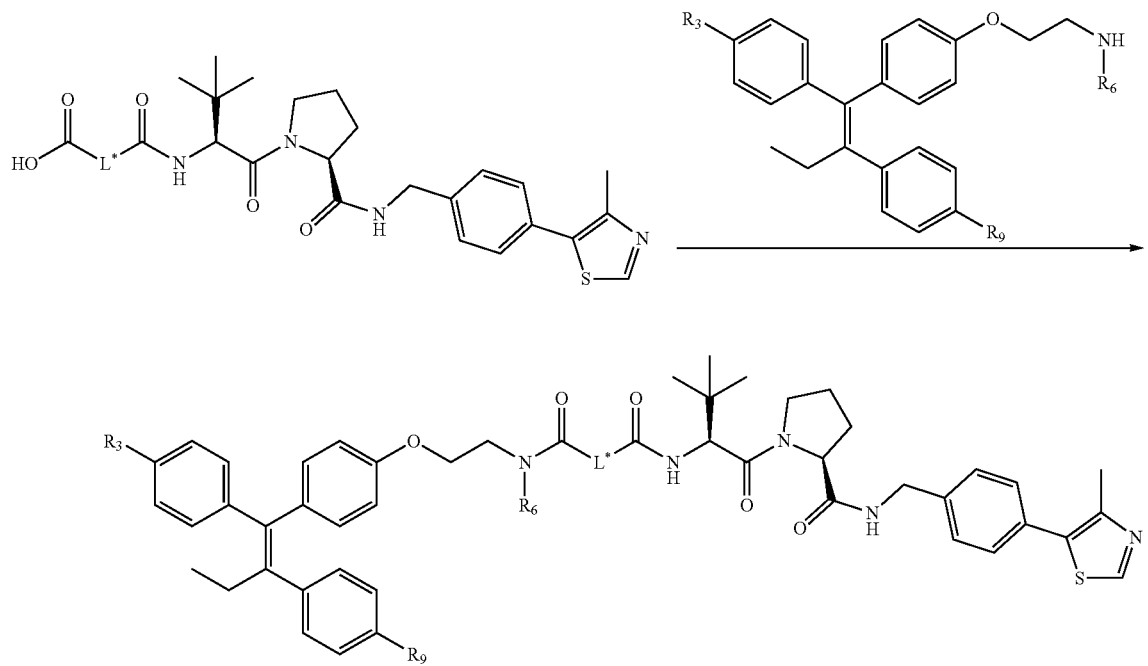

To a mixture of a tamoxifen derivative (0.1 mmol) in DMSO/DCM (1 mL/5 mL) was added NMM (0.2 mmol), linker compound (0.1 mmol; general synthesis described above), HOAt (0.15 mmol) and EDCI (0.15 mmol). The mixture was stirred at room temperature overnight. The resulting mixture was concentrated in vacuo and purified by preparative-HPLC to afford the desired compound.

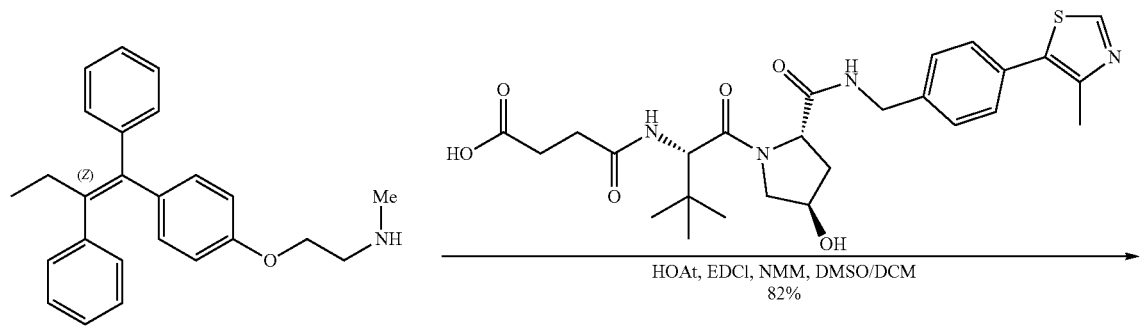
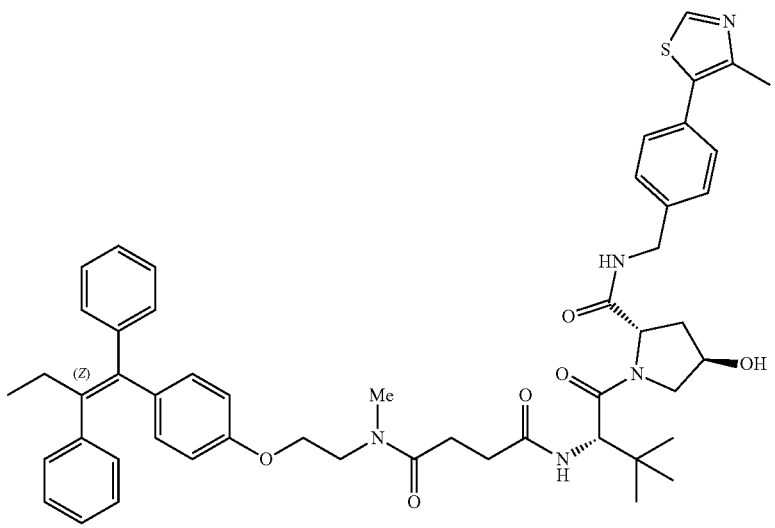
N[1]-(2-(4-((Z)-1,2-Diphenylbut-1-en-1-yl)phenoxy)ethyl)-N[4]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[1]-methylsuccinamide
Obtained as a white solid (20 mg, 82%). $^1$H NMR (600 MHz, Methanol-$d_4$) δ 9.07 (s, 1H), 7.47 (d, J=7.9 Hz, 2H), 7.42 (dd, J=8.2, 1.6 Hz, 2H), 7.33 (td, J=7.5, 1.7 Hz, 2H), 7.26-7.22 (m, 1H), 7.19 (d, J=8.1 Hz, 2H), 7.16-7.12 (m, 2H), 7.12-7.06 (m, 3H), 6.79-6.71 (m, 2H), 6.58-6.52 (m, 2H), 4.60-4.50 (m, 3H), 4.45 (s, 1H), 4.36 (d, J=15.5 Hz, 1H), 4.00 (t, J=5.2 Hz, 1H), 3.95 (t, J=5.5 Hz, 1H), 3.86 (d, J=11.0 Hz, 1H), 3.79-3.65 (m, 2H), 3.65-3.60 (m, 1H), 3.07 (s, 1.5H, NH3), 2.91 (s, 1.5H, NH3), 2.84-2.54 (m, 3H), 2.51-2.40 (m, 6H), 2.22-2.17 (m, 1H), 2.09-2.02 (m, 1H), 1.00 (d, J=6.3 Hz, 9H), 0.89 (t, J=7.4 Hz, 3H). HRMS (ESI-TOF) m/z: [M+H]$^+$ 870.4
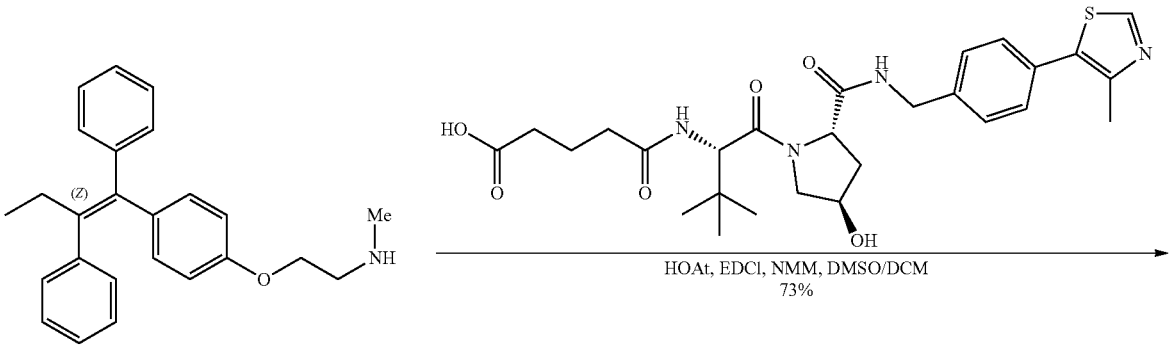

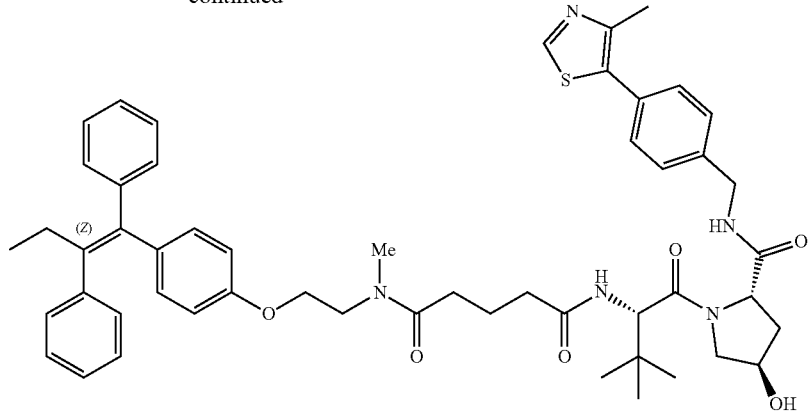

N[1]-(2-(4-((Z)-1,2-Diphenylbut-1-en-1-yl)phenoxy)ethyl)-N[5]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[1]-methylglutaramide Obtained as a white solid (18 mg, 73%). $^1$H NMR (600 MHz, Methanol-$d_4$) δ 9.02 (s, 1H), 7.47 (d, J=6.5 Hz, 2H), 7.41 (d, J=8.2 Hz, 2H), 7.32 (t, J=7.5 Hz, 2H), 7.27-7.22 (m, 1H), 7.19 (d, J=8.2 Hz, 2H), 7.14 (t, J=7.7 Hz, 2H), 7.11-7.05 (m, 3H), 6.75 (dd, J=11.9, 8.8 Hz, 2H), 6.55 (dd, J=12.9, 8.8 Hz, 2H), 4.59 (d, J=22.4 Hz, 1H), 4.56-4.51 (m, 2H), 4.50-4.43 (m, 1H), 4.34 (dd, J=15.5, 4.6 Hz, 1H), 3.98 (dt, J=11.1, 5.3 Hz, 2H), 3.90 (t, J=10.6 Hz, 1H), 3.76 (ddd, J=31.3, 11.0, 3.9 Hz, 1H), 3.68 (t, J=5.3 Hz, 1H), 3.64 (q, J=5.4 Hz, 1H), 3.05 (s, 1.5H, 0.5NH3), 2.91 (s, 1.5H, 0.5NH3), 2.49-2.40 (m, 6H), 2.37-2.24 (m, 3H), 2.23-2.16 (m, 1H), 2.10-2.03 (m, 1H), 1.91-1.82 (m, 2H), 1.01 (d, J=12.2 Hz, 9H), 0.89 (t, J=7.4 Hz, 3H). HRMS (ESI-TOF) m/z: [M+H]+ 884.4

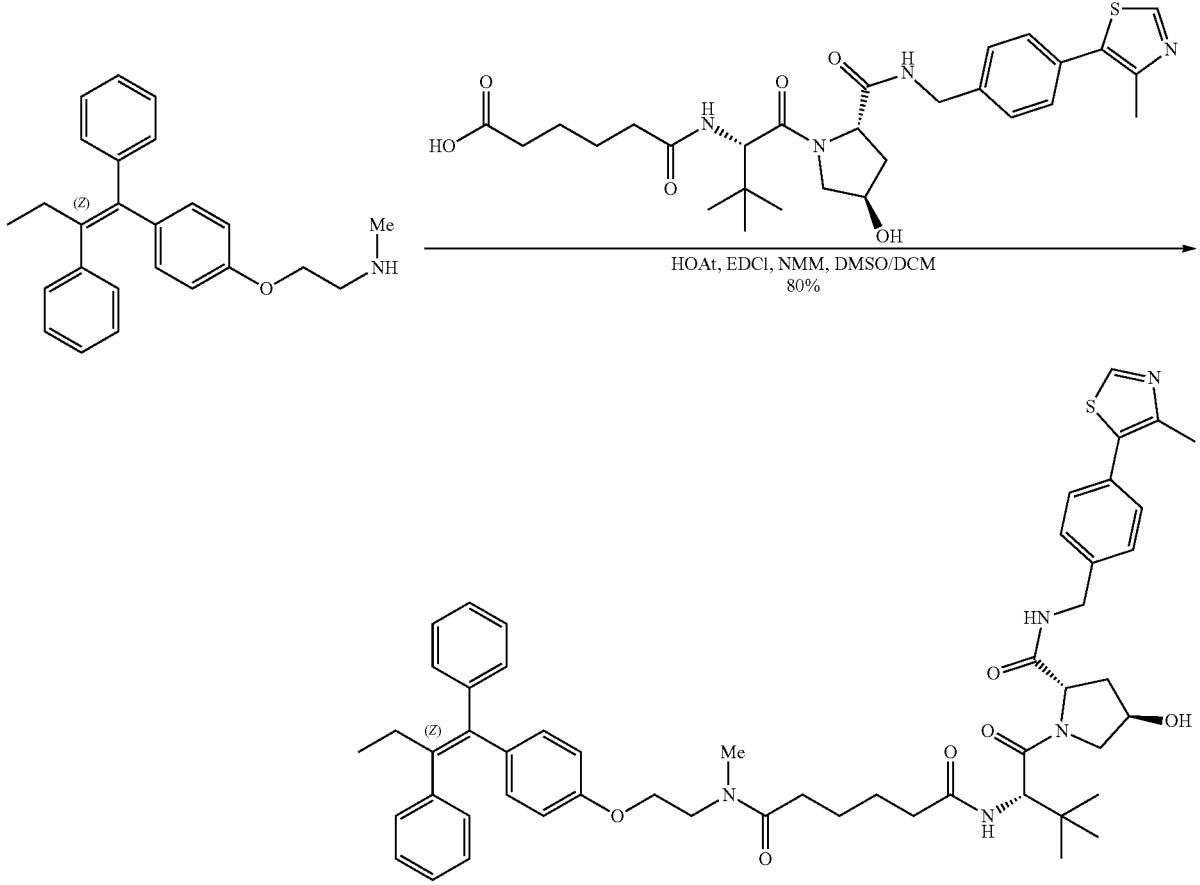

N[1]-(2-(4-((Z)-1,2-diphenylbut-1-en-1-yl)phenoxy)ethyl)-N[6]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[1]-methyladipamide Obtained as a white solid (20 mg, 80%). $^1$H NMR (600 MHz, Methanol-$d_4$) δ 8.98 (s, 1H), 7.47 (dd, J=8.1, 1.9 Hz, 2H), 7.41 (dd, J=8.3, 1.7 Hz, 2H), 7.32 (t, J=7.6 Hz, 2H), 7.24 (t, J=6.8 Hz, 1H), 7.19 (d, J=6.8 Hz, 2H), 7.16-7.12 (m, 2H), 7.12-7.04 (m, 3H), 6.75 (dd, J=12.0, 8.8 Hz, 2H), 6.54 (t, J=8.9 Hz, 2H), 4.61 (d, J=7.2 Hz, 1H), 4.58-4.51 (m, 2H), 4.50-4.46 (m, 1H), 4.35 (d, J=15.5 Hz, 1H), 3.99 (t, J=5.2 Hz, 1H), 3.96 (t, J=5.5 Hz, 1H), 3.89 (d, J=11.0 Hz, 1H), 3.81-3.75 (m, 1H), 3.68 (t, J=5.2 Hz, 1H), 3.63 (t, J=5.5 Hz, 1H), 3.06 (s, 1.5H, 0.5 NH3), 2.90 (s, 1.5H, 0.5 NH3), 2.49-2.40 (m, 5H), 2.36-2.18 (m, 5H), 2.10-2.04 (m, 1H), 1.67-1.54 (m, 4H), 1.01 (s, 9H), 0.89 (t, J=7.5 Hz, 3H). HRMS (ESI-TOF) m/z: [M+H]$^+$ 898.5

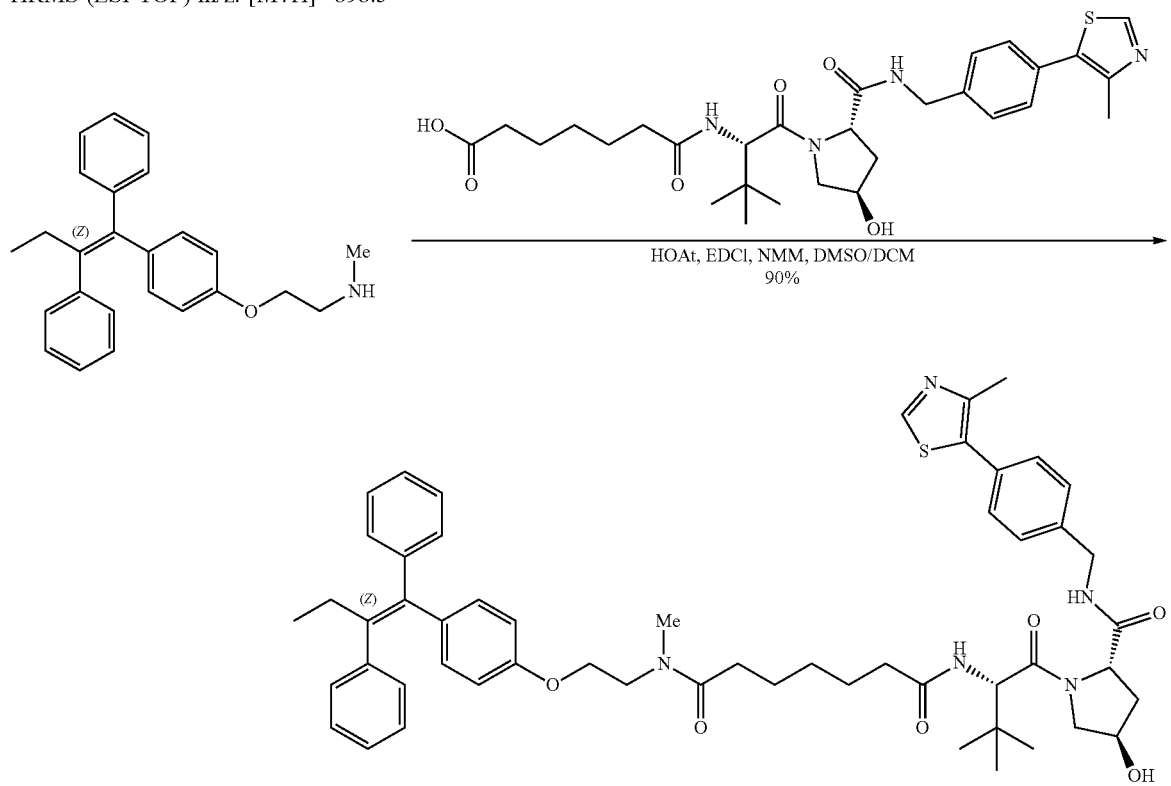

N[1]-(2-(4-((Z)-1,2-diphenylbut-1-en-1-yl)phenoxy)ethyl)-N[7]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[1]-methylheptanediamide Obtained as a white solid (23 mg, 90%). $^1$H NMR (600 MHz, Methanol-$d_4$) δ 8.99 (s, 1H), 7.47 (d, J=8.2 Hz, 2H), 7.41 (d, J=8.1 Hz, 2H), 7.33 (t, J=7.6 Hz, 2H), 7.27-7.21 (m, 1H), 7.19 (d, J=6.7 Hz, 2H), 7.16-7.12 (m, 2H), 7.11-7.06 (m, 3H), 6.79-6.72 (m, 2H), 6.54 (dd, J=8.9, 2.4 Hz, 2H), 4.62 (d, J=2.5 Hz, 1H), 4.59-4.51 (m, 2H), 4.49-4.46 (m, 1H), 4.35 (dd, J=15.5, 2.1 Hz, 1H), 3.99 (t, J=5.2 Hz, 1H), 3.97 (t, J=5.5 Hz, 1H), 3.90 (d, J=11.1 Hz, 1H), 3.82-3.75 (m, 1H), 3.70-3.62 (m, 2H), 3.06 (s, 1.5H, 0.5NH3), 2.91 (s, 1.5H, 0.5NH3), 2.47 (s, 3H), 2.46-2.37 (m, 3H), 2.34-2.17 (m, 4H), 2.10-2.04 (m, 1H), 1.65-1.54 (m, 4H), 1.37-1.28 (m, 2H), 1.02 (d, J=4.6 Hz, 9H), 0.89 (t, J=7.4 Hz, 3H). HRMS (ESI-TOF) m/z: [M+H]$^+$ 912.5

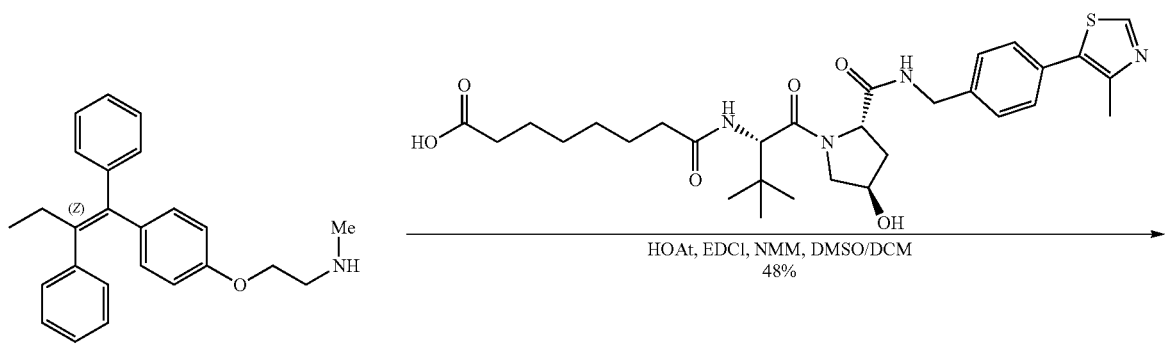

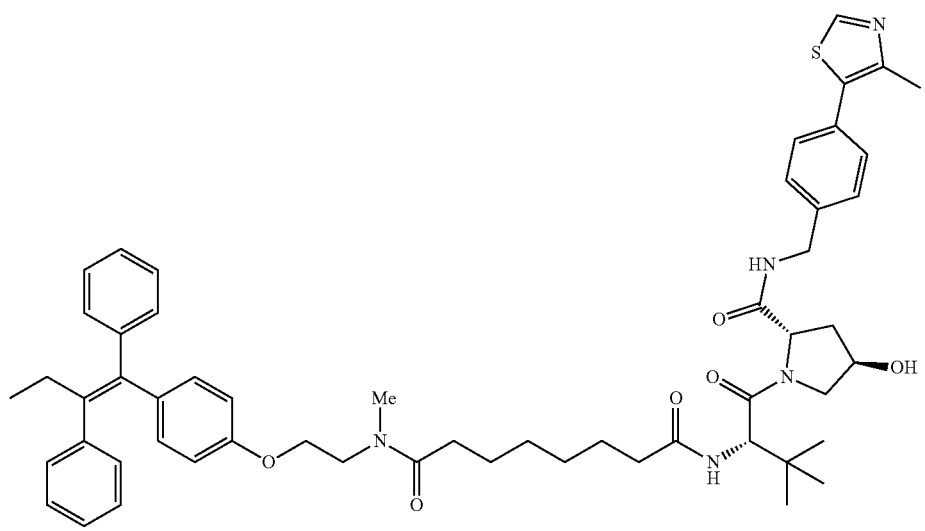

N[1]-(2-(4-((Z)-1,2-Diphenylbut-1-en-1-yl)phenoxy) ethyl)-N[8]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide Obtained as a white solid (71 mg, 48%). $^1$H NMR (600 MHz, Methanol-$d_4$) δ 8.85 (s, 1H), 7.45 (d, J=8.2 Hz, 2H), 7.40 (t, J=15.5 Hz, 2H), 7.32 (t, J=7.5 Hz, 2H), 7.24 (t, J=7.5 Hz, 1H), 7.19 (d, J=7.0 Hz, 2H), 7.14 (t, J=7.5 Hz, 2H), 7.11-7.04 (m, 2H), 6.75 (dd, J=8.5, 11.4 Hz, 2H), 6.53 (dd, J=4.9, 8.5 Hz, 2H), 4.64 (d, J=8.8 Hz, 1H), 4.57 (t, J=8.4 Hz, 1H), 4.53 (d, J=15.6 Hz, 1H), 4.48 (s, 1H), 4.34 (d, J=15.5 Hz, 1H), 3.98 (t, J=5.2 Hz, 1H), 3.95 (t, J=5.4 Hz, 1H), 3.90 (d, J=11.0 Hz, 1H), 3.81-3.76 (m, 1H), 3.67 (t, J=5.2 Hz, 1H), 3.62 (t, J=5.5 Hz, 1H), 3.04 (s, 1.5H, 0.5NCH$_3$), 2.89 (s, 1.5H, 0.5NCH$_3$), 2.45 (s, 3H), 2.45-2.36 (m, 3H), 2.32-2.17 (m, 4H), 2.10-2.04 (m, 1H), 1.64-1.51 (m, 4H), 1.38-1.27 (m, 4H), 1.03 (d, J=3.5 Hz, 9H), 0.88 (t, J=7.4 Hz, 3H). HRMS (ESI-TOF) m/z: [M+H]$^+$ 926.5

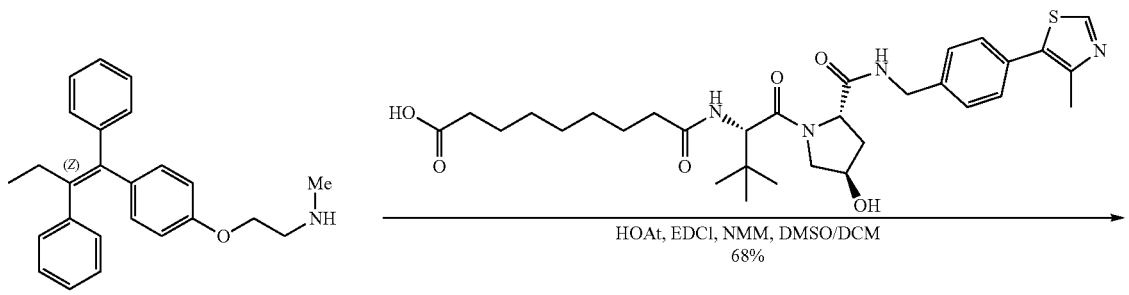

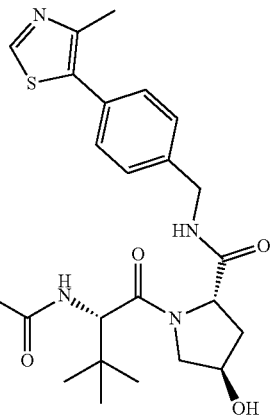

N[1]-(2-(4-((Z)-1,2-Diphenylbut-1-en-1-yl)phenoxy)ethyl)-N[9]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[1]-methylnonanediamide Obtained as a white solid (16 mg, 68%). ¹H-NMR (600 MHz, Methanol-$d_4$) δ 8.93 (s, 1H), 7.46 (dd, J=8.1, 2.2 Hz, 2H), 7.40 (dd, J=8.3, 1.8 Hz, 2H), 7.33 (t, J=7.6 Hz, 2H), 7.24 (t, J=7.5 Hz, 1H), 7.20 (d, J=6.7 Hz, 2H), 7.15 (t, J=7.7 Hz, 2H), 7.12-7.06 (m, 3H), 6.75 (dd, J=11.3, 8.7 Hz, 2H), 6.53 (dd, J=8.8, 6.4 Hz, 2H), 4.63 (s, 1H), 4.57 (ddd, J=9.4, 7.6, 2.1 Hz, 1H), 4.53 (dd, J=15.4, 2.6 Hz, 1H), 4.48 (dp, J=4.1, 2.5, 1.9 Hz, 1H), 4.35 (d, J=15.5 Hz, 1H), 4.00 (t, J=5.2 Hz, 1H), 3.96 (t, J=5.4 Hz, 1H), 3.90 (d, J=11.1 Hz, 1H), 3.79 (dd, J=10.9, 3.9 Hz, 1H), 3.68 (t, J=5.2 Hz, 1H), 3.63 (td, J=5.3, 2.4 Hz, 1H), 3.06 (s, 1.5H, 0.5NH3), 2.90 (s, 1.5H, 0.5NH3), 2.47 (s, 3H), 2.43 (q, J=7.3 Hz, 2H), 2.39 (t, J=7.6 Hz, 1H), 2.33-2.17 (m, 4H), 2.11-2.03 (m, 1H), 1.64-1.51 (m, 4H), 1.30 (dd, J=5.2, 2.7 Hz, 6H), 1.03 (s, 9H), 0.89 (t, J=7.4 Hz, 3H). HRMS (ESI-TOF) m/z: [M+H]⁺ 940.5

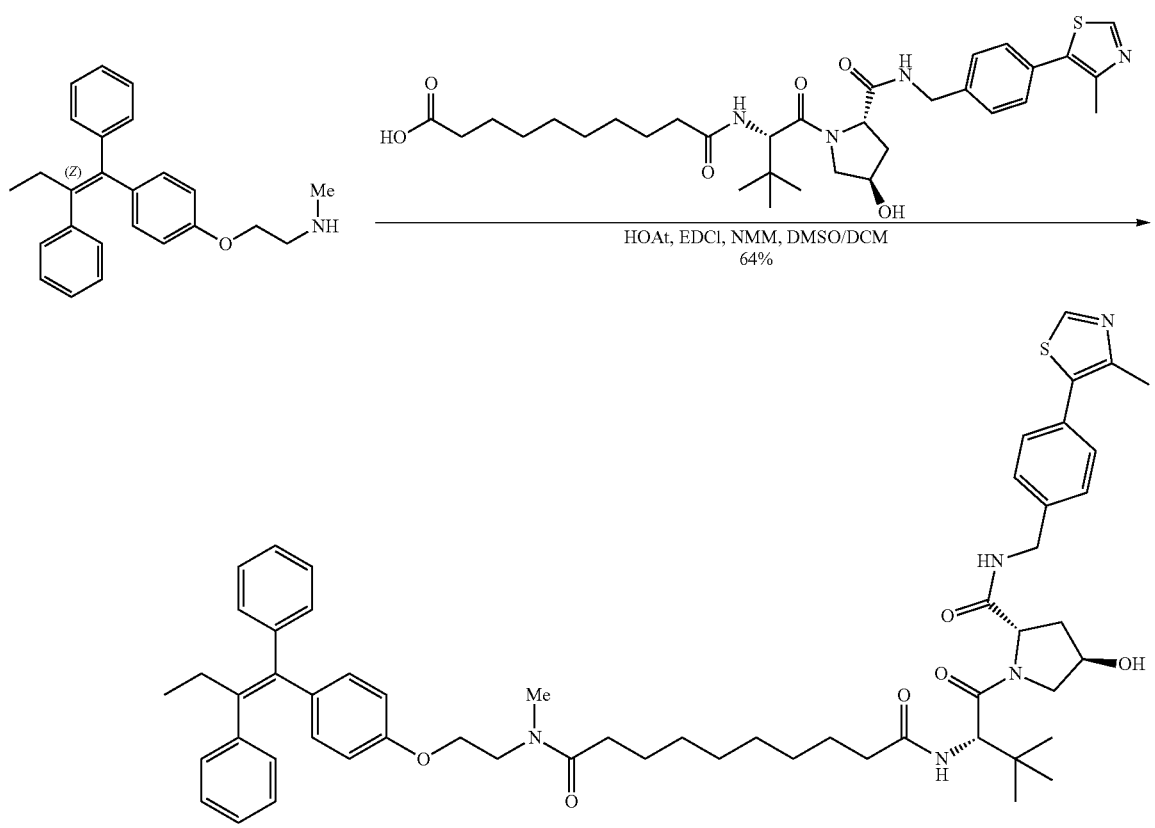

N$^1$-(2-(4-((Z)-1,2-Diphenylbut-1-en-1-yl)phenoxy)ethyl)-N$^{10}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N$^1$-methyldecanediamide Obtained as a white solid (15 mg, 64%). $^1$H NMR (600 MHz, Methanol-d$_4$) δ 8.97 (s, 1H), 7.47 (d, J=8.2 Hz, 2H), 7.41 (dd, J=8.3, 1.5 Hz, 2H), 7.33 (t, J=7.6 Hz, 2H), 7.25 (t, J=7.4 Hz, 1H), 7.20 (d, J=6.7 Hz, 2H), 7.17-7.13 (m, 2H), 7.12-7.06 (m, 3H), 6.75 (dd, J=10.0, 8.8 Hz, 2H), 6.53 (dd, J=8.8, 4.1 Hz, 2H), 4.63 (s, 1H), 4.60-4.47 (m, 3H), 4.35 (d, J=15.5 Hz, 1H), 4.00 (t, J=5.1 Hz, 1H), 3.97 (t, J=5.4 Hz, 1H), 3.90 (d, J=10.9 Hz, 1H), 3.79 (dd, J=11.0, 3.9 Hz, 1H), 3.68 (t, J=5.2 Hz, 1H), 3.63 (t, J=5.4 Hz, 1H), 3.06 (s, 1.5H, 0.5NH3), 2.91 (s, 1.5H, 0.5NH3), 2.47 (s, 3H), 2.43 (q, J=7.5 Hz, 2H), 2.39 (t, J=7.6 Hz, 1H), 2.33-2.18 (m, 4H), 2.10-2.04 (m, 1H), 1.64-1.51 (m, 4H), 1.36-1.24 (m, 8H), 1.03 (s, 9H), 0.89 (t, J=7.5 Hz, 3H). HRMS (ESI-TOF) m/z: [M+H]$^+$ 954.5

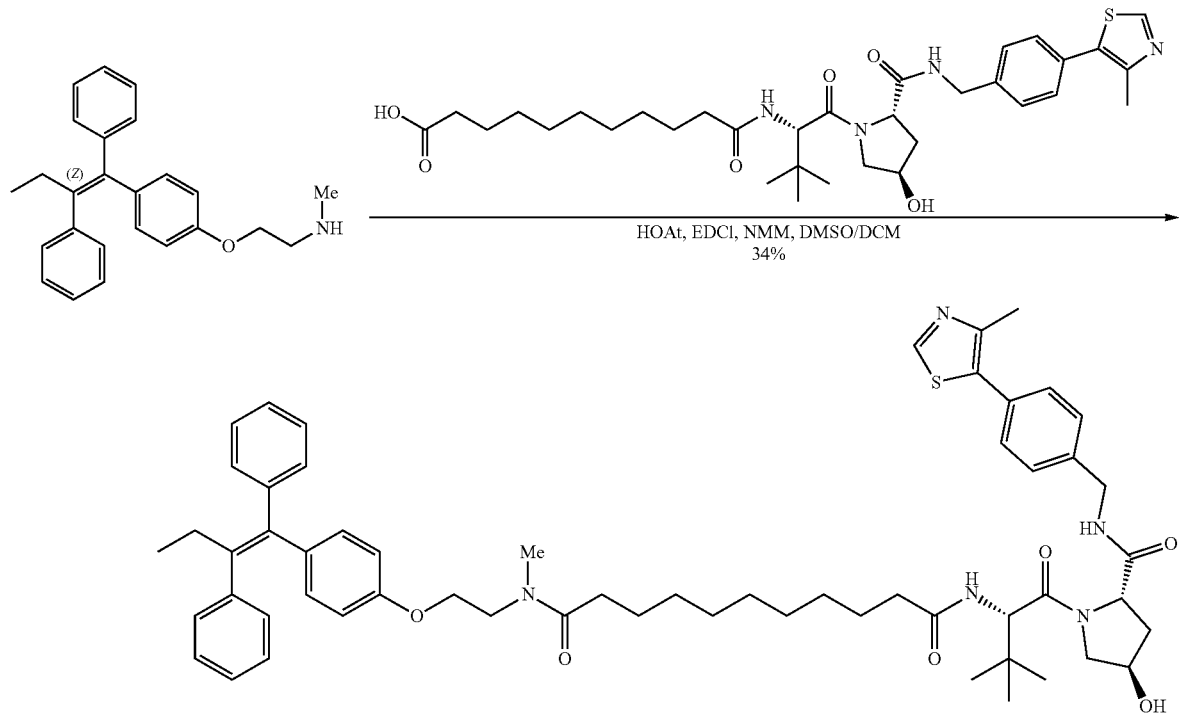

N$^1$-(2-(4-((Z)-1,2-diphenylbut-1-en-1-yl)phenoxy)ethyl)-N$^{11}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N$^1$-methylundecanediamide Obtained as a white solid (30 mg, 34%). $^1$H NMR (600 MHz, Methanol-d$_4$) δ 8.86 (s, 1H), 7.45 (d, J=7.5 Hz, 2H), 7.40 (d, J=7.9 Hz, 2H), 7.33 (t, J=7.5 Hz, 2H), 7.25 (t, J=7.4 Hz, 1H), 7.19 (d, J=7.4 Hz, 2H), 7.15 (t, J=7.5 Hz, 2H), 7.12-7.05 (m, 3H), 6.75 (t, J=9.0 Hz, 2H), 6.53 (dd, J=3.6, 8.8 Hz, 2H), 4.64 (s, 1H), 4.60-4.46 (m, 3H), 4.35 (d, J=15.5 Hz, 1H), 4.00 (t, J=5.1 Hz, 1H), 3.96 (t, J=5.4 Hz, 1H), 3.90 (d, J=11.1 Hz, 1H), 3.80 (dd, J=3.8, 11.1 Hz, 1H), 3.68 (t, J=5.1 Hz, 1H), 3.63 (t, J=5.3 Hz, 1H), 3.05 (s, 1.5H, 0.5NCH$_3$), 2.90 (s, 1.5H, 0.5NCH$_3$), 2.48-2.41 (m, 5H), 2.25-2.18 (m, 1H), 2.10-2.04 (m, 1H), 1.66-1.49 (m, 4H), 1.41-1.21 (m, 14H), 1.03 (s, 9H), 0.89 (t, J=7.4 Hz, 3H). HRMS (ESI-TOF) m/z: [M+H]$^+$ 968.5

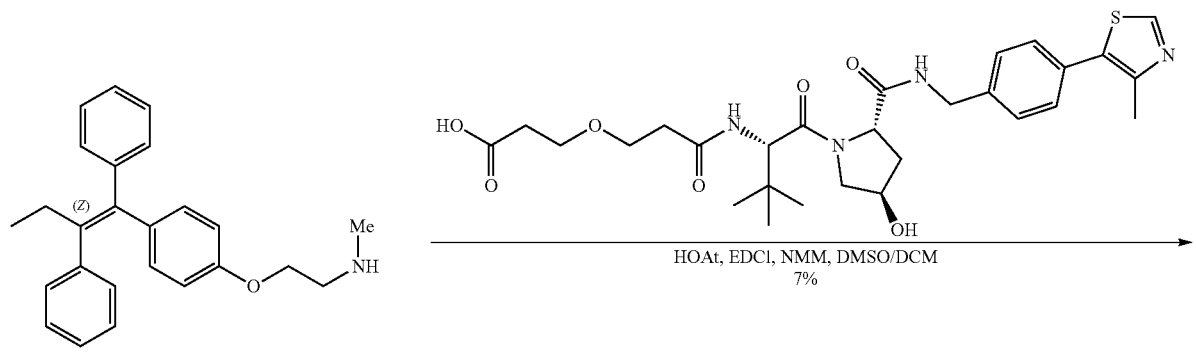

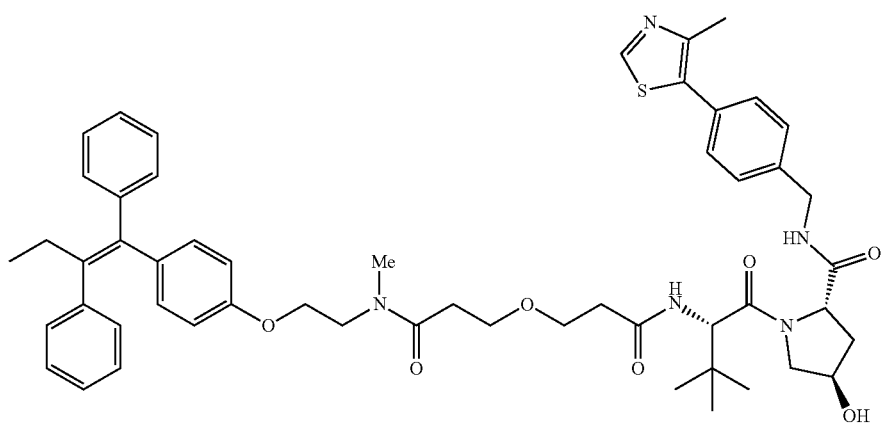

(2S,4R)-1-((S)-2-(3-(3-((2-(4-((Z)-1,2-Diphenylbut-1-en-1-yl)phenoxy)ethyl)(methyl)amino)-3-oxo-propoxy)propanamido)-3,3-dimethylbutanoyl)-4-hydroxy-N-(4-(4-methylthiazol-5-yl)benzyl)pyrrolidine-2-carboxamide Obtained as a white solid (29 mg, 7%). $^1$H NMR (600 MHz, Methanol-$d_4$) δ 9.03 (s, 1H), 7.46 (t, J=8.1 Hz, 2H), 7.40 (dd, J=3.4, 8.2 Hz, 2H), 7.33 (t, J=7.6 Hz, 2H), 7.24 (t, J=7.5 Hz, 1H), 7.19 (d, J=7.5 Hz, 2H), 7.17-7.05 (m, 5H), 6.75 (dd, J=4.2, 8.7 Hz, 2H), 6.53 (d, J=9.0 Hz, 2H), 4.63 (d, J=4.7 Hz, 1H), 4.58-4.45 (m, 3H), 4.33 (dd, J=9.3, 15.6 Hz, 1H), 3.98 (d, J=5.2 Hz, 1H), 3.95 (t, J=5.5 Hz, 1H), 3.87 (d, J=11.0 Hz, 1H), 3.80-3.75 (m, 1H), 3.75-3.59 (m, 8H), 3.07 (s, 1.5H, 0.5NCH$_3$), 2.92 (s, 1.5H, 0.5NCH$_3$), 2.71 (t, J=5.4 Hz, 1H), 2.60 (t, J=6.5 Hz, 1H), 2.47 (s, 3H), 2.43 (q, J=7.5 Hz, 2H), 2.23-2.17 (m, 1H), 2.09-2.03 (m, 1H), 1.00 (d, J=7.3 Hz, 9H), 0.89 (t, J=7.5 Hz, 3H). HRMS (ESI-TOF) m/z: [M+H]$^+$ 914.4

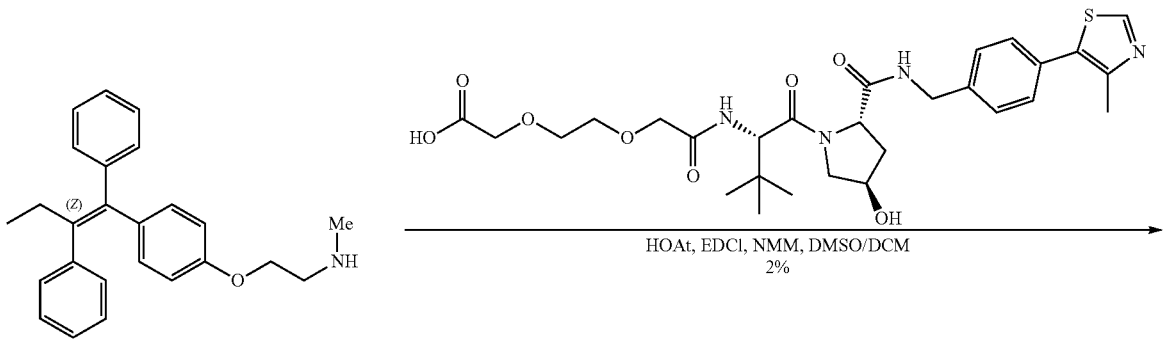

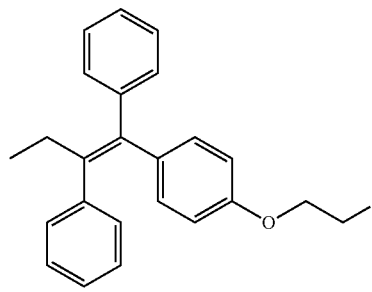
(2S,4R)-1-((S)-2-(tert-Butyl)-14-(4-((Z)-1,2-diphenylbut-1-en-1-yl)phenoxy)-12-methyl-4,11-dioxo-6,9-dioxa-3,12-diazatetradecanoyl)-4-hydroxy-N-(4-(4-methylthiazol-5-yl)benzyl)pyrrolidine-2-carboxamide
Obtained as a white solid (3.3 mg, 2%). $^1$H NMR (600 MHz, Methanol-d$_4$) δ 8.93 (s, 1H), 7.47-7.30 (m, 6H), 7.27-7.23 (m, 1H), 7.22-7.06 (m, 7H), 6.75 (t, J=7.9 Hz, 2H), 6.52 (dd, J=8.5, 11.8 Hz, 2H), 4.69 (d, J=6.8 Hz, 1H), 4.58-4.47 (m, 2H), 4.38-4.22 (m, 4H), 4.07-3.94 (m, 4H), 3.86 (d, J=11.1 Hz, 1H), 3.79 (d, J=11.0 Hz, 1H), 3.75-3.59 (m, 6H), 3.02 (s, 1.5H, NCH$_3$), 2.90 (s, 1.5H, NCH$_3$), 2.49-2.40 (m, 5H), 2.24-2.18 (m, 1H), 2.11-2.04 (m, 1H), 1.01 (d, J=5.1 Hz, 9H), 0.89 (t, J=7.4 Hz, 3H). HRMS (ESI-TOF) m/z: [M+H]$^+$ 930.4
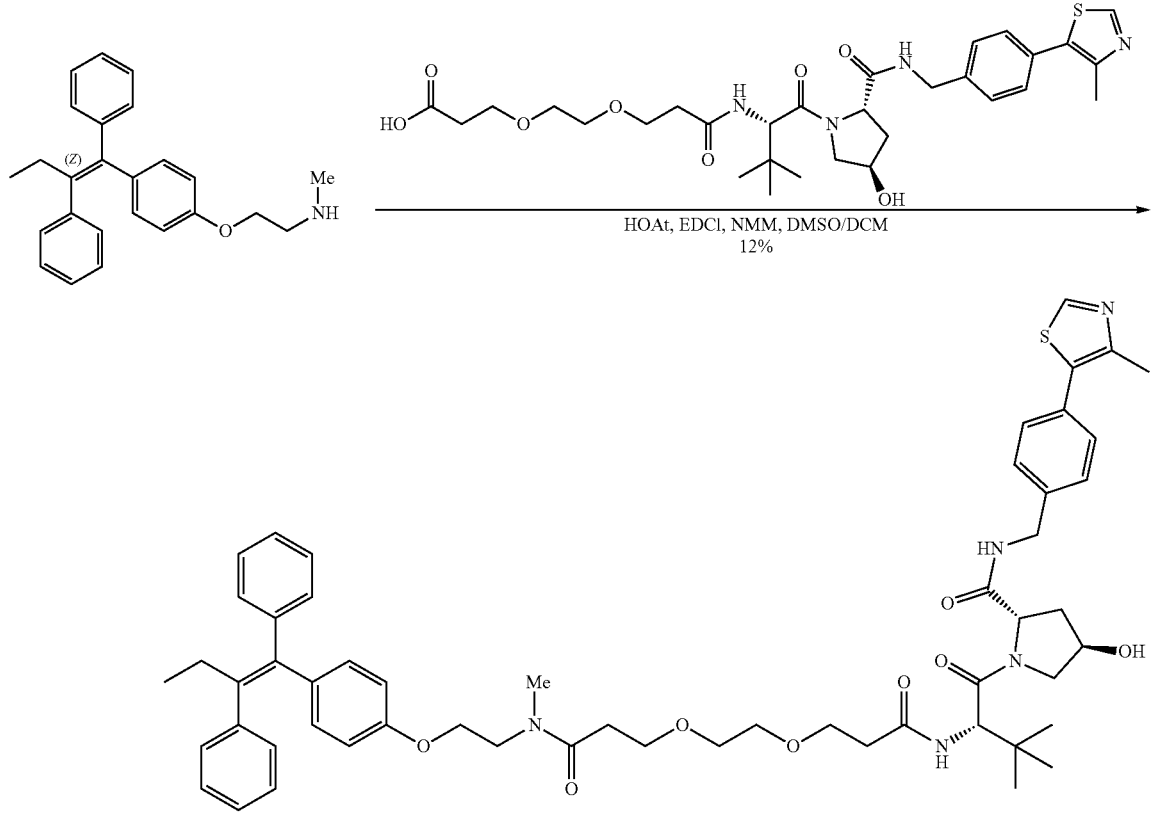

(2S,4R)-1-((S)-2-(tert-Butyl)-16-(4-((Z)-1,2-diphenylbut-1-en-1-yl)phenoxy)-14-methyl-4,13-dioxo-7,10-dioxa-3,14-diazahexadecanoyl)-4-hydroxy-N-(4-(4-methylthiazol-5-yl)benzyl)pyrrolidine-2-carboxamide Obtained as a white solid (23 mg, 12%). $^1$H NMR (600 MHz, Methanol-$d_4$) δ 9.16 (s, 1H), 7.48 (d, J=7.0 Hz, 2H), 7.42 (d, J=8.1 Hz, 2H), 7.33 (t, J=7.5 Hz, 2H), 7.25 (t, J=7.5 Hz, 1H), 7.20 (d, J=6.9 Hz, 2H), 7.15 (t, J=7.6 Hz, 2H), 7.12-7.06 (m, 3H), 6.75 (dd, J=6.1, 8.4 Hz, 2H), 6.54 (dd, J=8.7, 12.1 Hz, 2H), 4.64 (d, J=3.5 Hz, 1H), 4.58-4.46 (m, 3H), 4.34 (d, J=15.6 Hz, 1H), 4.01 (t, J=5.2 Hz, 1H), 3.96 (t, J=5.5 Hz, 1H), 3.88 (d, J=11.0 Hz, 1H), 3.81-3.76 (m, 1H), 3.75-3.62 (m, 7H), 3.58-3.51 (m, 4H), 3.08 (s, 1.5H, NCH$_3$), 2.92 (s, 1.5H, NCH$_3$), 2.69 (t, J=6.5 Hz, 1H), 2.59 (t, J=6.5 Hz, 1H), 2.49 (s, 3H), 2.43 (q, J=7.8 Hz, 3H), 2.24-2.17 (m, 1H), 2.10-2.02 (m, 1H), 1.02 (d, J=4.0 Hz, 9H), 0.89 (t, J=7.4 Hz, 3H). HRMS (ESI-TOF) m/z: [M+H]$^+$ 958.5

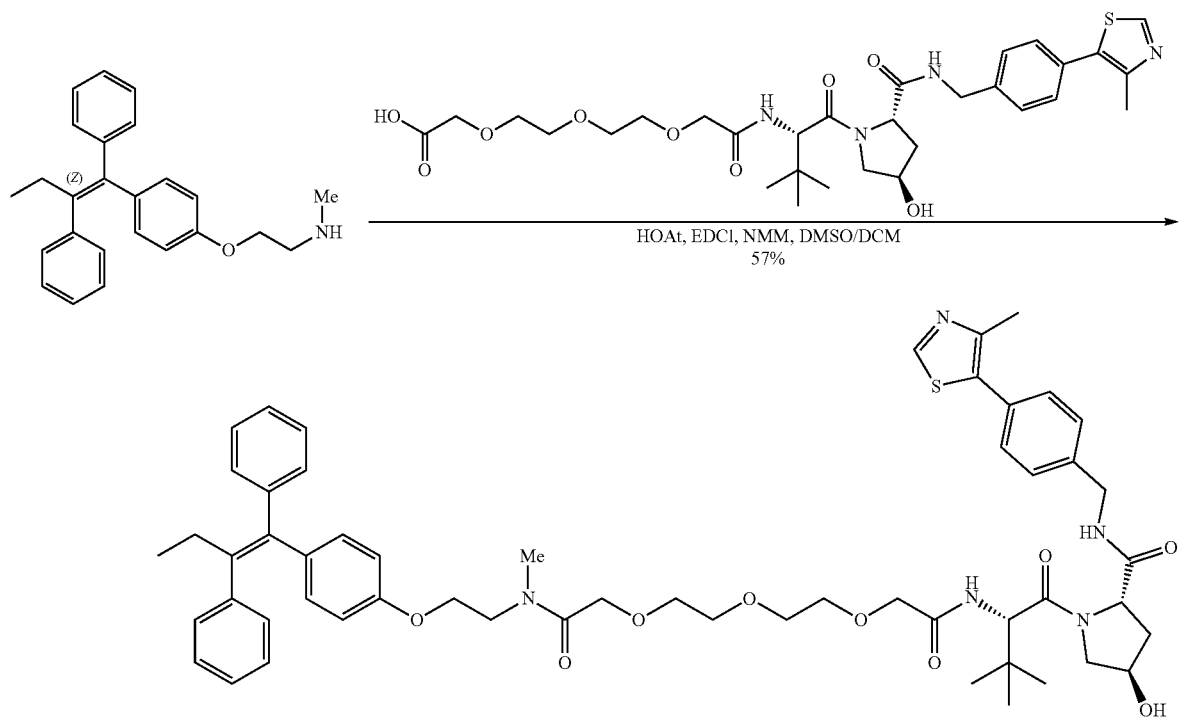

(2S,4R)-1-((S)-2-(tert-Butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide Obtained as a white solid (220 mg, 57%). $^1$H-NMR (600 MHz, Methanol-$d_4$) δ 8.85 (d, 1H, J=2.9 Hz), 7.44 (d, 2H, J=8.1 Hz), 7.40 (d, 2H, J=8.1 Hz), 7.33 (t, 2H, J=7.5 Hz), 7.25 (t, 1H, J=7.3 Hz), 7.20 (d, 2H, J=7.1 Hz), 7.15 (t, 2H, J=7.4 Hz), 7.09 (m, 3H), 6.75 (t, 2H, J=8.0 Hz), 6.54 (t, 2H, J=8.0 Hz), 4.68 (d, 1H, J=2.3 Hz), 4.57-4.47 (m, 3H), 4.33 (dd, 1H, J=4.4 Hz, J=15.5 Hz), 4.28 (s, 1H), 4.18 (s, 1H), 4.05-3.95 (m, 4H), 3.86 (d, 1H, J=11.0 Hz), 3.78 (dd, 1H, J=3.5 Hz, J=10.9 Hz), 3.70-3.60 (m, 1 OH), 3.01 (s, 1.5H, 0.5NCH$_3$), 2.91 (s, 1H, 1.5H, 0.5NCH$_3$), 2.47-2.41 (m, 5H), 2.21 (m, 1H), 2.07 (m, 1H), 1.02 (d, 9H, J=2.9 Hz), 0.89 (t, 3H, J=7.4 Hz). HRMS (ESI-TOF) m/z: [M+H]$^+$ 974.5

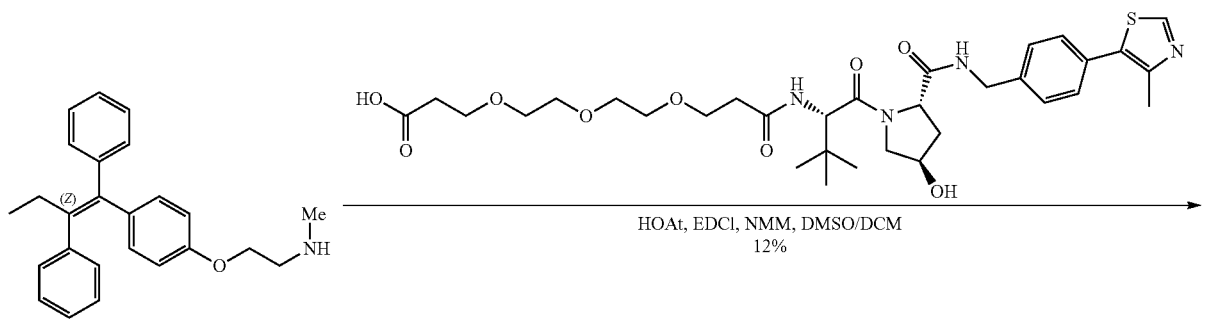

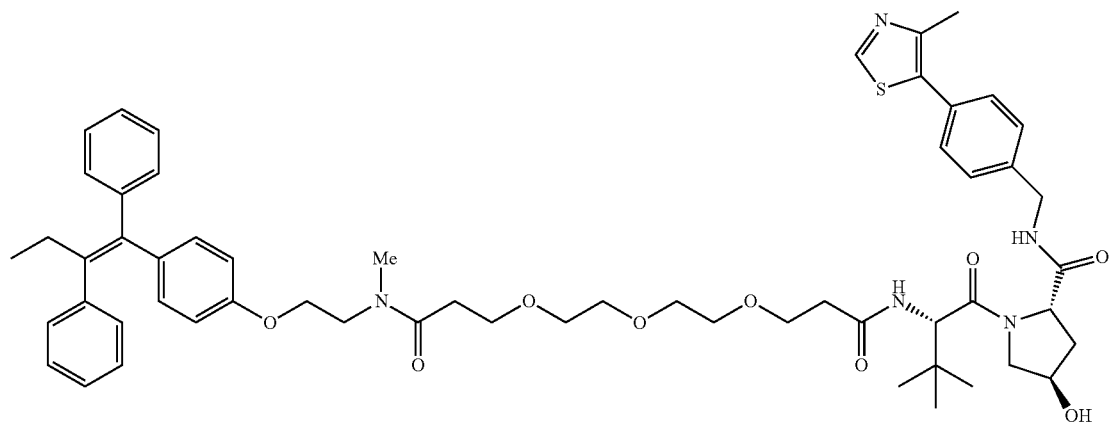

(2S,4R)-1-((S)-2-(tert-Butyl)-19-(4-((Z)-1,2-diphenylbut-1-en-1-yl)phenoxy)-17-methyl-4,16-dioxo-7,10,13-trioxa-3,17-diazanonadecanoyl)-4-hydroxy-N-(4-(4-methylthiazol-5-yl)benzyl)pyrrolidine-2-carboxamide Obtained as a white solid (20 mg, 12%). $^1$H-NMR (600 MHz, Methanol-$d_4$) δ 9.14 (s, 1H), 7.48 (d, J=7.9 Hz, 2H), 7.42 (d, J=7.9 Hz, 2H), 7.33 (t, J=7.6 Hz, 2H), 7.25 (t, J=7.5 Hz, 1H), 7.20 (d, J=7.4 Hz, 2H), 7.15 (t, J=7.5 Hz, 2H), 7.13-7.06 (m, 3H), 6.75 (t, J=7.4 Hz, 2H), 6.55 (dd, J=8.6, 11.6 Hz, 2H), 4.64 (s, 1H), 4.59-4.46 (m, 3H), 4.35 (d, J=15.5 Hz, 1H), 4.01 (t, J=5.3 Hz, 1H), 3.97 (t, J=5.4 Hz, 1H), 3.89 (d, J=11.0 Hz, 1H), 3.79 (dd, J=3.7, 11.1 Hz, 1H), 3.76-3.51 (m, 16H), 3.09 (s, 1.5H, NCH$_3$), 2.93 (s, 1.5H, NCH$_3$), 2.69 (t, J=6.4 Hz, 1H), 2.58 (t, J=6.4 Hz, 1H), 2.49 (s, 3H), 2.43 (q, J=7.2 Hz, 2H), 2.24-2.17 (m, 1H), 2.10-2.02 (m, 1H), 1.03 (s, 9H), 0.89 (t, J=7.5 Hz, 3H). HRMS (ESI-TOF) m/z: [M+H]$^+$ 1002.5

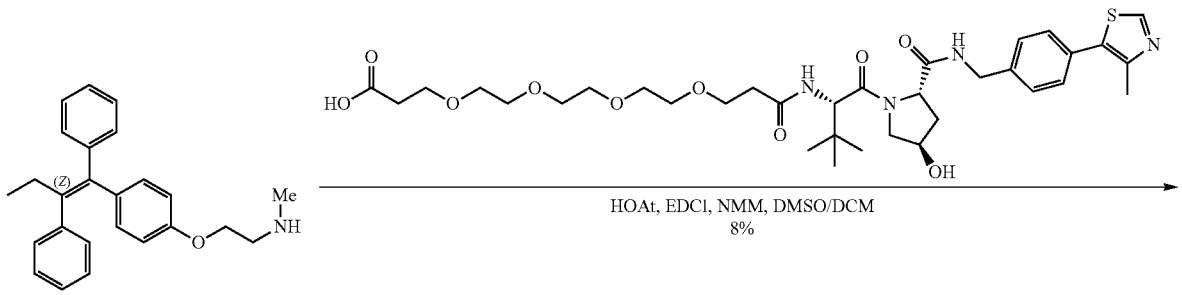

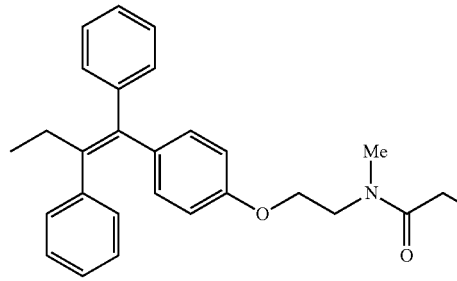

N[1]-(2-(4-((Z)-1,2-Diphenylbut-1-en-1-yl)phenoxy)ethyl)-N[16]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[1]-methyl-4,7,10,13-tetraoxahexadecanediamide Obtained as a white solid (12 mg, 8.6%). $^1$H NMR (600 MHz, Methanol-$d_4$) 9.13 (s, 1H), 7.49 (d, J=7.9 Hz, 2H), 7.43 (d, J=7.9 Hz, 2H), 7.34 (t, J=7.5 Hz, 2H), 7.25 (t, J=7.5 Hz, 1H), 7.20 (d, J=7.4 Hz, 2H), 7.15 (t, J=7.5 Hz, 2H), 7.13-7.07 (m, 3H), 6.76 (dd, J=6.6, 8.7 Hz, 2H), 6.55 (dd, J=8.7, 12.1 Hz, 2H), 4.64 (s, 1H), 4.59-4.46 (m, 3H), 4.35 (d, J=15.5 Hz, 1H), 4.02 (t, J=5.3 Hz, 1H), 3.98 (t, J=5.5 Hz, 1H), 3.88 (d, J=11.0 Hz, 1H), 3.79 (dd, J=3.7, 11.1 Hz, 1H), 3.75-3.63 (m, 7H), 3.63-3.49 (m, 13H), 3.10 (s, 1.5H, 0.5NCH$_3$), 2.93 (s, 1.5H, 0.5NCH$_3$), 2.69 (t, J=6.3 Hz, 1H), 2.59 (t, J=6.4 Hz, 1H), 2.49 (s, 3H), 2.43 (q, J=6.9, 7.5 Hz, 2H), 2.25-2.18 (m, 1H), 2.10-2.02 (m, 1H), 1.03 (s, 9H), 0.89 (t, J=7.4 Hz, 3H). HRMS (ESI-TOF) m/z: [M+H]$^+$ 1046.5

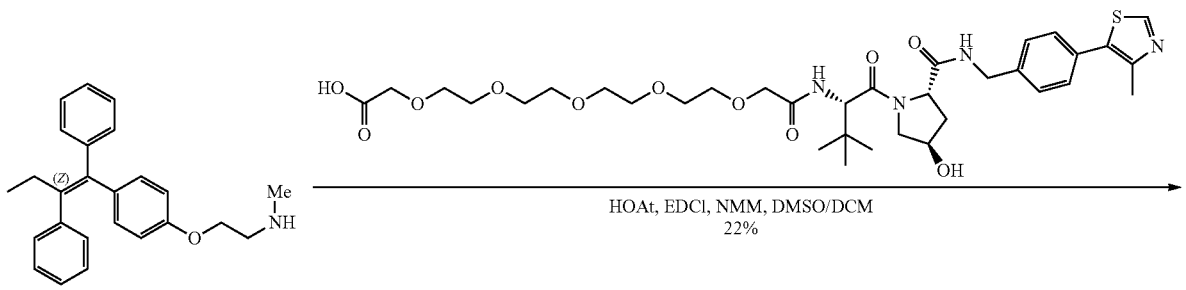

HOAt, EDCl, NMM, DMSO/DCM
22%

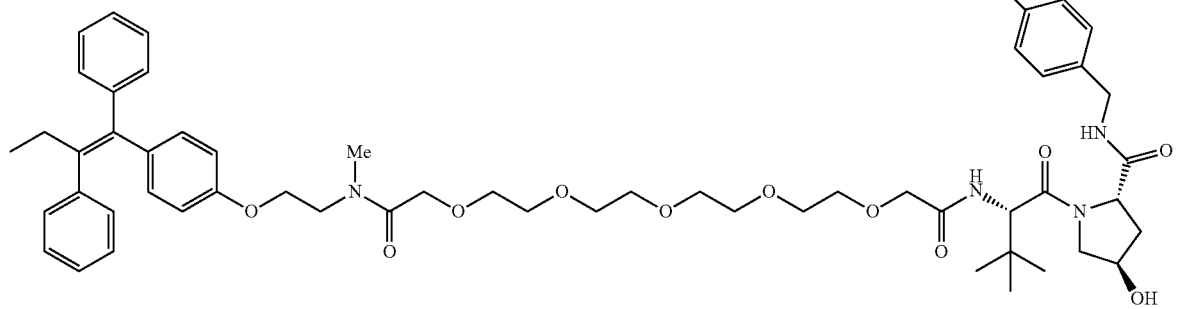

N¹-(2-(4-((Z)-1,2-Diphenylbut-1-en-1-yl)phenoxy) ethyl)-N¹⁷—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹-methyl-3,6,9,12,15-pentaoxaheptadecanediamide Obtained as a white solid (34 mg, 22%). ¹H NMR (600 MHz, Methanol-d₄) δ 9.29 (s, 1H), 7.49 (d, J=7.9 Hz, 2H), 7.43 (d, J=7.8 Hz, 2H), 7.33 (t, J=7.4 Hz, 2H), 7.24 (t, J=7.4 Hz, 1H), 7.19 (d, J=7.4 Hz, 2H), 7.15 (t, J=7.1 Hz, 2H), 7.12-7.05 (m, 3H), 6.76 (t, J=9.6 Hz, 2H), 6.54 (t, J=9.5 Hz, 2H), 4.69 (s, 1H), 4.61-4.53 (m, 2H), 4.49 (s, 1H), 4.34 (d, J=15.7 Hz, 1H), 4.30 (s, 1H), 4.20 (s, 1H), 4.05-3.94 (m, 4H), 3.87 (d, J=11.1 Hz, 1H), 1H), 3.79 (dd, J=3.6, 11.0 Hz, 1H), 3.71-3.50 (m, 18H), 3.00 (s, 1.5H, 0.5NCH₃), 2.92 (s, 1.5H, 0.5NCH₃), 2.50 (s, 3H), 2.43 (q, J=7.4 Hz, 2H), 2.28-2.18 (m, 1H), 2.12-2.04 (m, 1H), 1.03 (s, 9H), 0.88 (t, J=7.4 Hz, 3H). HRMS (ESI-TOF) m/z: [M+H]⁺ 1062.5

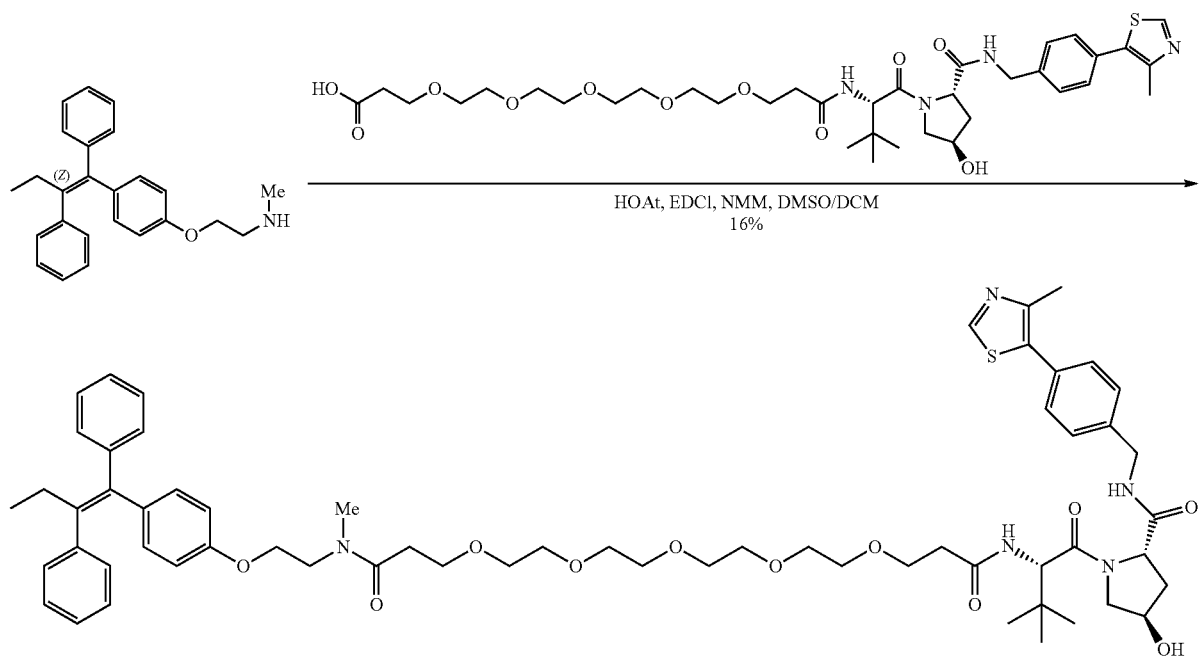

N¹-(2-(4-((Z)-1,2-diphenylbut-1-en-1-yl)phenoxy) ethyl)-N¹⁹—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N¹-methyl-4,7,10,13,16-pentaoxanonadecanediamide Obtained as a white solid (24 mg, 16%). ¹H NMR (600 MHz, Methanol-d₄) δ 9.18 (s, 1H), 7.49 (d, J=7.9 Hz, 2H), 7.43 (d, J=7.8 Hz, 2H), 7.33 (t, J=7.6 Hz, 2H), 7.25 (t, J=7.4 Hz, 1H), 7.20 (d, J=7.5 Hz, 2H), 7.15 (t, J=7.4 Hz, 2H), 7.12-7.06 (m, 3H), 6.76 (dd, J=6.8, 8.9 Hz, 2H), 6.55 (dd, J=8.3, 11.7 Hz, 2H), 4.64 (s, 1H), 4.59-4.51 (m, 2H), 4.48 (s, 1H), 4.35 (d, J=15.5 Hz, 1H), 4.01 (t, J=5.2 Hz, 1H), 3.97 (t, J=5.6 Hz, 1H), 3.89 (d, J=11.0 Hz, 1H), 3.79 (dd, J=3.7, 11.1 Hz, 1H), 3.75-3.49 (m, 24H), 3.09 (s, 1.5H, 0.5NCH₃), 2.93 (s, 1.5H, 0.5NCH₃), 2.69 (t, J=6.3 Hz, 1H), 2.59 (t, J=6.4 Hz, 1H), 2.49 (s, 3H), 2.43 (q, J=6.1 Hz, 2H), 2.25-2.18 (m, 1H), 2.11-2.03 (m, 1H), 1.03 (s, 9H), 0.89 (t, J=7.4 Hz, 3H). HRMS (ESI-TOF) m/z: [M+H]⁺ 1090.6

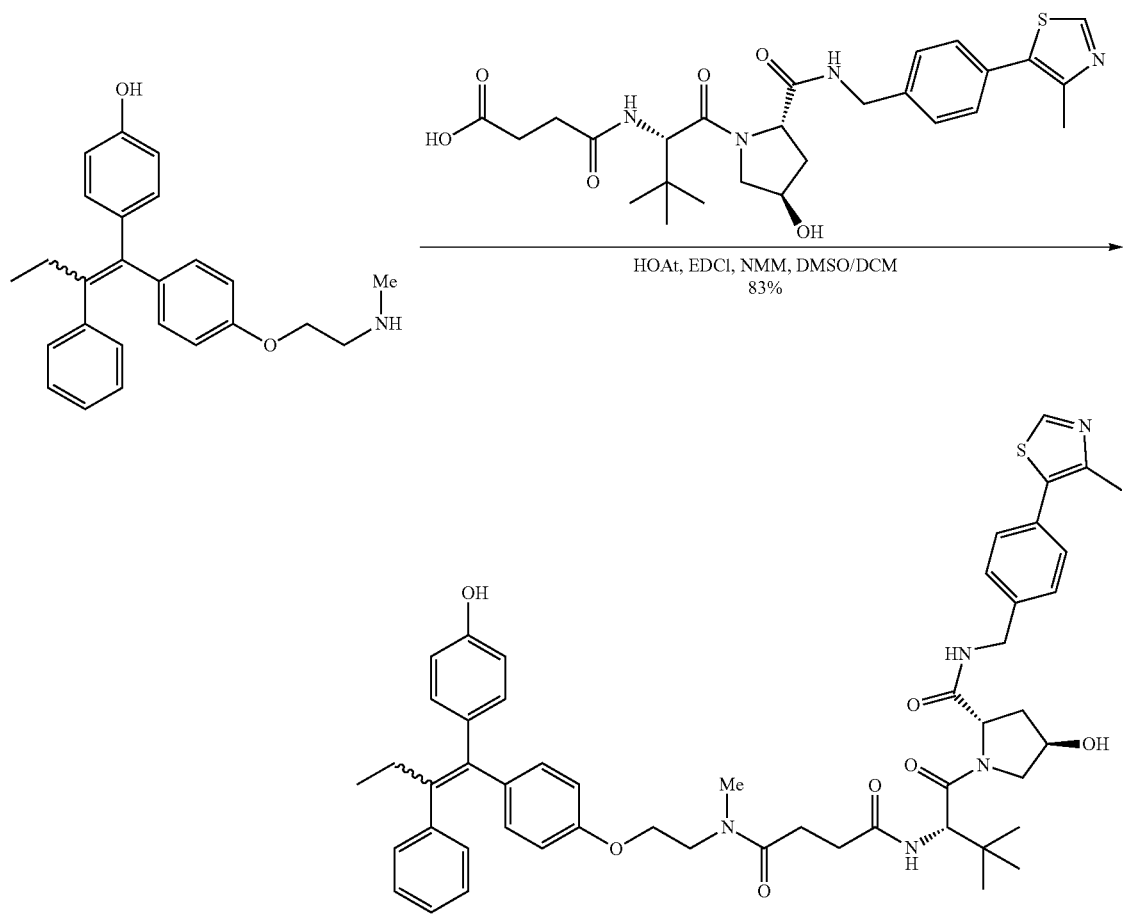
N[1]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[4]-(2-(4-(1-(4-hydroxyphenyl)-2-phenylbut-1-en-1-yl)phenoxy)ethyl)-N[4]-methylsuccinamide
Obtained as a white solid (20 mg, 83%). $^1$H NMR (600 MHz, Methanol-$d_4$) δ 9.11 (s, 1H), 7.48 (d, J=7.9 Hz, 2H), 7.42 (d, J=8.2 Hz, 2H), 7.16-7.03 (m, 6H), 7.00 (d, J=8.5 Hz, 1H), 6.90 (dd, J=18.7, 8.7 Hz, 1H), 6.77-6.72 (m, 2H), 6.63 (d, J=8.7 Hz, 1H), 6.54 (dd, J=19.6, 8.8 Hz, 1H), 6.39 (dd, J=8.6, 1.6 Hz, 1H), 4.61-4.50 (m, 3H), 4.48-4.43 (m, 1H), 4.36 (dd, J=15.5, 2.1 Hz, 1H), 4.14 (dt, J=32.5, 5.3 Hz, 1H), 3.98 (dt, J=28.0, 5.4 Hz, 1H), 3.90-3.84 (m, 1H), 3.83-3.70 (m, 2H), 3.70-3.61 (m, 1H), 3.18 (s, 0.8H), 3.07 (s, 0.8H), 3.00 (s, 0.7H), 2.91 (s, 0.7H), 2.84-2.51 (m, 4H), 2.50-2.42 (m, 5H), 2.24-2.16 (m, 1H), 2.10-2.02 (m, 1H), 1.03-0.97 (m, 9H), 0.91-0.87 (m, 3H). HRMS (ESI-TOF) m/z: [M+H]$^+$ 886.4
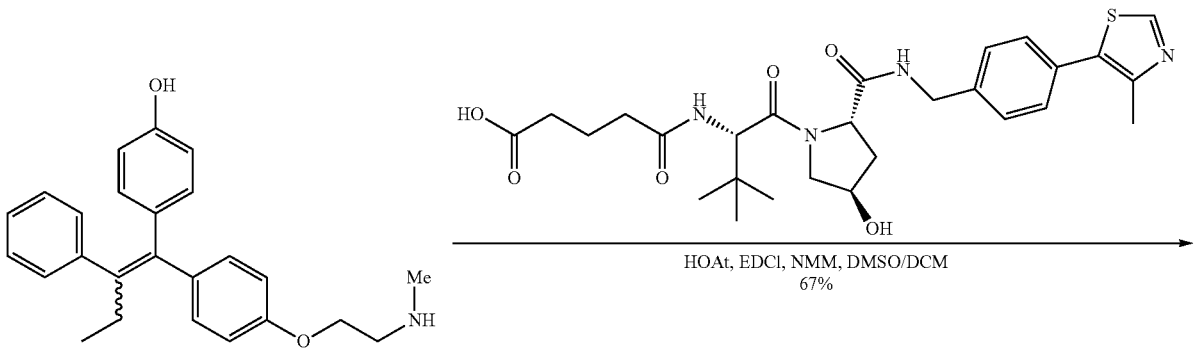

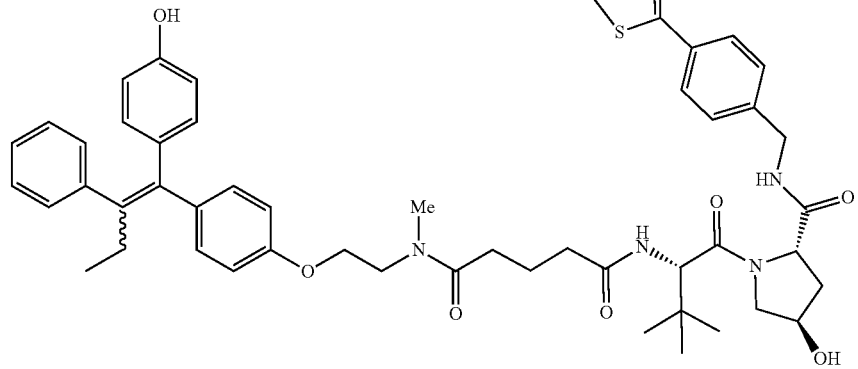

N[1]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[5]-(2-(4-(1-(4-hydroxyphenyl)-2-phenylbut-1-en-1-yl)phenoxy)ethyl)-N[5]-methylglutaramide Obtained as a white solid (16 mg, 67%). $^1$H NMR (600 MHz, Methanol-$d_4$) δ 9.09 (d, J=3.3 Hz, 1H), 7.48 (d, J=8.2 Hz, 2H), 7.42 (dd, J=8.3, 2.2 Hz, 2H), 7.16-7.04 (m, 6H), 7.00 (d, J=8.4 Hz, 1H), 6.90 (dd, J=12.6, 8.7 Hz, 1H), 6.77-6.72 (m, 2H), 6.63 (dd, J=8.6, 1.6 Hz, 1H), 6.54 (dd, J=13.8, 8.8 Hz, 1H), 6.39 (d, J=8.6 Hz, 1H), 4.63-4.50 (m, 3H), 4.50-4.42 (m, 1H), 4.34 (dd, J=15.5, 4.1 Hz, 1H), 4.15 (dt, J=14.0, 5.3 Hz, 1H), 3.98 (dt, J=9.1, 5.3 Hz, 1H), 3.94-3.87 (m, 1H), 3.81-3.60 (m, 3H), 3.15 (s, 0.8H), 3.05 (s, 0.8H), 3.00 (s, 0.7H), 2.92 (s, 0.7H), 2.59-2.40 (m, 6H), 2.38-2.25 (m, 3H), 2.23-2.16 (m, 1H), 2.11-2.03 (m, 1H), 1.98-1.83 (m, 2H), 1.04-0.98 (m, 9H), 0.92-0.86 (m, 3H). HRMS (ESI-TOF) m/z: [M+H]$^+$ 900.4

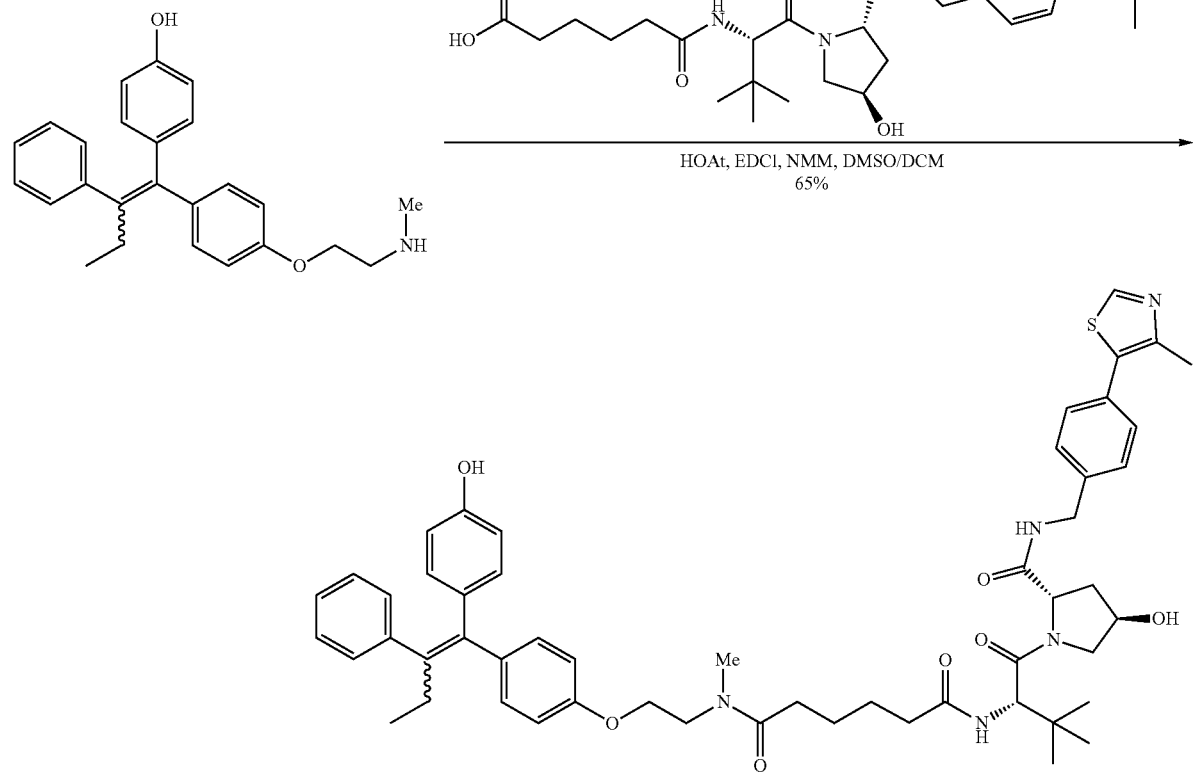

N¹—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁶-(2-(4-(1-(4-hydroxyphenyl)-2-phenylbut-1-en-1-yl)phenoxy)ethyl)-N⁶-methyladipamide Obtained as a white solid (16 mg, 65%). ¹H-NMR (600 MHz, Methanol-d₄) δ 8.97 (d, J=1.5 Hz, 1H), 7.46 (d, J=8.2 Hz, 2H), 7.41 (d, J=8.3 Hz, 2H), 7.17-7.04 (m, 6H), 7.00 (d, J=8.6 Hz, 1H), 6.90 (t, J=8.9 Hz, 1H), 6.77-6.72 (m, 2H), 6.65-6.61 (m, 1H), 6.53 (t, J=9.1 Hz, 1H), 6.39 (dd, J=8.6, 1.4 Hz, 1H), 4.64-4.51 (m, 3H), 4.49-4.46 (m, 1H), 4.35 (d, J=15.6 Hz, 1H), 4.15 (dt, J=23.3, 5.3 Hz, 1H), 3.98 (dt, J=17.9, 5.3 Hz, 1H), 3.90 (d, J=11.6 Hz, 1H), 3.81-3.73 (m, 2H), 3.66 (dt, J=28.7, 5.4 Hz, 1H), 3.16 (s, 0.8H), 3.06 (s, 0.8H), 2.99 (s, 0.7H), 2.91 (s, 0.7H), 2.55-2.37 (m, 6H), 2.36-2.17 (m, 4H), 2.11-2.04 (m, 1H), 1.72-1.55 (m, 4H), 1.01 (s, 9H), 0.89 (td, J=7.5, 2.9 Hz, 3H). HRMS (ESI-TOF) m/z: [M+H]⁺ 914.4

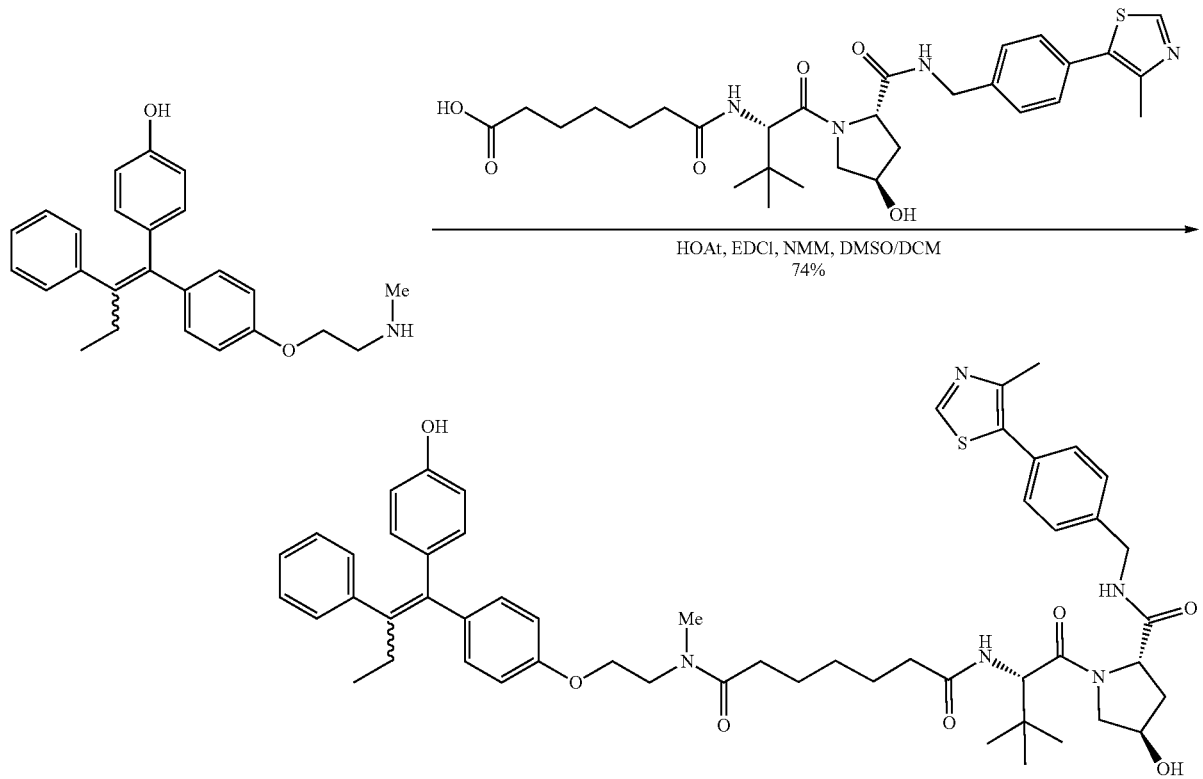

N¹—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁷-(2-(4-(1-(4-hydroxyphenyl)-2-phenylbut-1-en-1-yl)phenoxy)ethyl)-N⁷-methylheptanediamide Obtained as a white solid (18 mg, 74%). ¹H-NMR (600 MHz, Methanol-d₄) δ 8.98 (s, 1H), 7.47 (d, J=8.2 Hz, 2H), 7.41 (d, J=8.2 Hz, 2H), 7.17-7.04 (m, 6H), 7.00 (d, J=8.5 Hz, 1H), 6.90 (dd, J=8.8, 2.4 Hz, 1H), 6.77-6.72 (m, 2H), 6.63 (d, J=8.6 Hz, 1H), 6.53 (dd, J=9.0, 2.5 Hz, 1H), 6.39 (d, J=8.7 Hz, 1H), 4.65-4.45 (m, 4H), 4.35 (d, J=15.5 Hz, 1H), 4.15 (dt, J=21.6, 5.3 Hz, 1H), 3.98 (dt, J=15.5, 5.3 Hz, 1H), 3.90 (d, J=10.9 Hz, 1H), 3.81-3.61 (m, 3H), 3.16 (s, 0.8H), 3.06 (s, 0.8H), 2.99 (s, 0.7H), 2.91 (s, 0.7H), 2.52-2.34 (m, 6H), 2.35-2.17 (m, 4H), 2.11-2.03 (m, 1H), 1.69-1.54 (m, 4H), 1.41-1.31 (m, 2H), 1.02 (d, J=4.4 Hz, 9H), 0.89 (td, J=6.8, 6.3, 2.1 Hz, 3H). HRMS (ESI-TOF) m/z: [M+H]⁺ 928.5

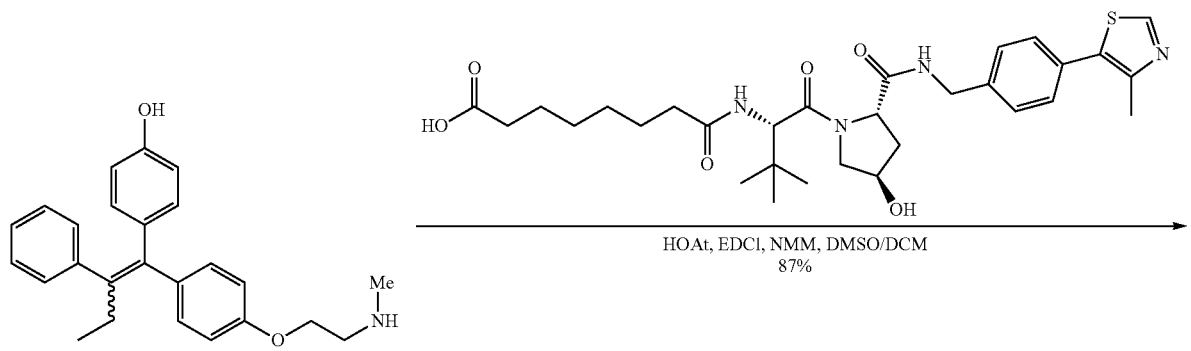

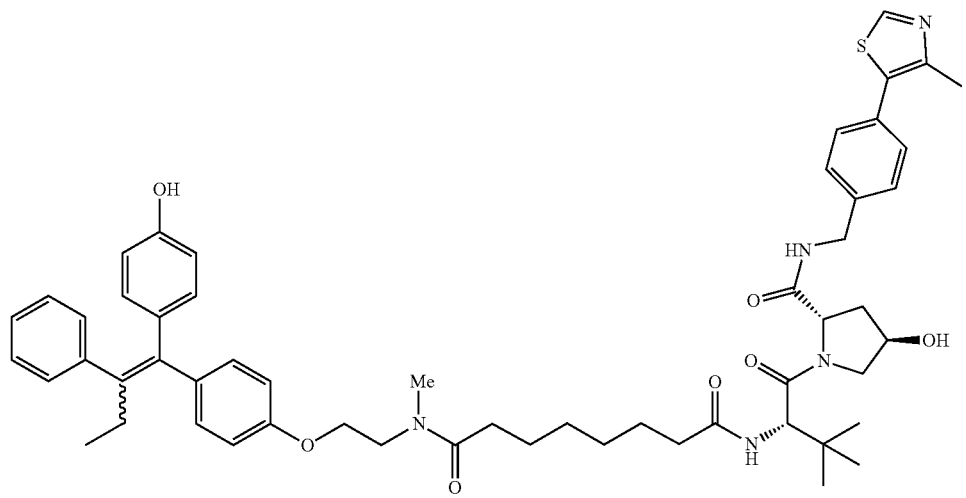

N[1]—((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)-N[8]-(2-(4-(1-(4-hydroxyphenyl)-2-phenylbut-1-en-1-yl)phenoxy)ethyl)-N[8]-methyloctanediamide Obtained as a white solid (28 mg, 87%). $^1$H NMR (600 MHz, Methanol-$d_4$) δ 9.15 (s, 1H), 7.48 (d, J=8.2 Hz, 2H), 7.42 (d, J=8.2 Hz, 2H), 7.16-7.03 (m, 6H), 7.00 (d, J=8.5 Hz, 1H), 6.89 (dd, J=8.5, 5.7 Hz, 1H), 6.74 (dd, J=12.2, 8.6 Hz, 2H), 6.63 (d, J=8.6 Hz, 1H), 6.52 (dd, J=8.7, 5.6 Hz, 1H), 6.39 (d, J=8.7 Hz, 1H), 4.63 (d, J=2.5 Hz, 1H), 4.59-4.51 (m, 2H), 4.50-4.46 (m, 1H), 4.35 (d, J=15.4 Hz, 1H), 4.15 (dt, J=24.2, 5.3 Hz, 1H), 3.98 (dt, J=18.8, 5.3 Hz, 1H), 3.90 (d, J=11.1 Hz, 1H), 3.81-3.72 (m, 2H), 3.65 (dt, J=27.4, 5.3 Hz, 1H), 3.15 (s, 0.8H), 3.05 (s, 0.8H), 2.98 (s, 0.7H), 2.90 (s, 0.7H), 2.52-2.42 (m, 5H), 2.38 (dt, J=15.2, 7.6 Hz, 1H), 2.33-2.17 (m, 4H), 2.11-2.03 (m, 1H), 1.67-1.52 (m, 4H), 1.39-1.27 (m, 4H), 1.02 (d, J=3.8 Hz, 9H), 0.89 (td, J=7.4, 2.0 Hz, 3H). HRMS (ESI-TOF) m/z: [M+H]$^+$ 942.5

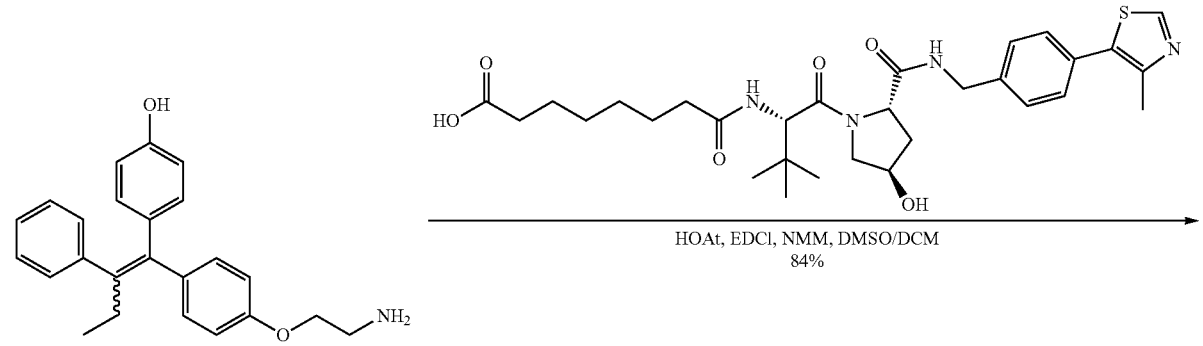

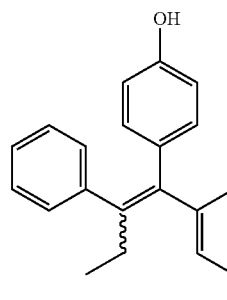

N¹—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁸-(2-(4-(1-(4-hydroxyphenyl)-2-phenylbut-1-en-1-yl)phenoxy)ethyl) octanediamide Obtained as a white solid (27 mg, 84%). ¹H NMR (600 MHz, Methanol-d₄) δ 9.09 (s, 1H), 7.48 (d, J=8.1 Hz, 2H), 7.42 (d, J=8.3 Hz, 2H), 7.16-7.04 (m, 6H), 7.00 (d, J=8.5 Hz, 1H), 6.90 (d, J=8.7 Hz, 1H), 6.75 (t, J=8.7 Hz, 2H), 6.63 (d, J=8.7 Hz, 1H), 6.54 (d, J=8.8 Hz, 1H), 6.39 (d, J=8.6 Hz, 1H), 4.62 (d, J=1.4 Hz, 1H), 4.59-4.46 (m, 3H), 4.35 (d, J=15.5 Hz, 1H), 4.05 (t, J=5.5 Hz, 1H), 3.90 (d, J=11.8 Hz, 1H), 3.88 (t, J=5.5 Hz, 1H), 3.79 (dd, J=11.0, 3.9 Hz, 1H), 3.55 (t, J=5.4 Hz, 1H), 3.45 (t, J=5.4 Hz, 1H), 2.52-2.42 (m, 5H), 2.29-2.13 (m, 5H), 2.10-2.04 (m, 1H), 1.64-1.52 (m, 4H), 1.37-1.25 (m, 4H), 1.02 (s, 9H), 0.89 (td, J=7.4, 1.9 Hz, 3H). HRMS (ESI-TOF) m/z: [M+H]⁺ 928.5

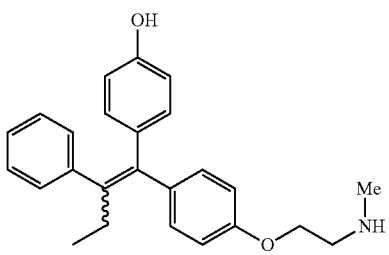
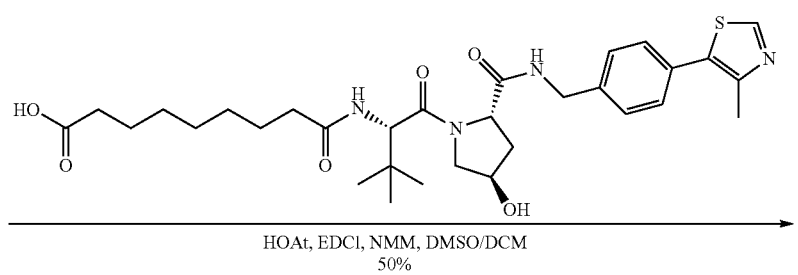

HOAt, EDCl, NMM, DMSO/DCM
50%

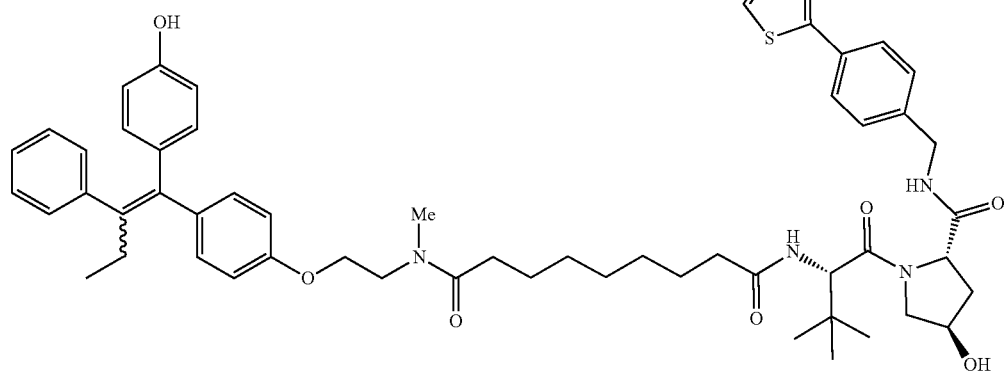

N[1]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[9]-(2-(4-(1-(4-hydroxyphenyl)-2-phenylbut-1-en-1-yl)phenoxy)ethyl)-N[9]-methylnonanediamide Obtained as a white solid (12 mg, 50%). $^1$H NMR (600 MHz, Methanol-$d_4$) δ 8.98 (s, 1H), 7.47 (d, J=8.2 Hz, 2H), 7.41 (d, J=8.3 Hz, 2H), 7.16-7.04 (m, 6H), 7.00 (d, J=8.5 Hz, 1H), 6.89 (dd, J=8.7, 7.0 Hz, 1H), 6.74 (dd, J=12.9, 8.7 Hz, 2H), 6.63 (d, J=8.6 Hz, 1H), 6.52 (dd, J=8.9, 7.0 Hz, 1H), 6.39 (d, J=8.6 Hz, 1H), 4.63 (s, 1H), 4.60-4.46 (m, 3H), 4.35 (d, J=15.5 Hz, 1H), 4.15 (dt, J=30.4, 5.3 Hz, 1H), 3.98 (dt, J=25.1, 5.3 Hz, 1H), 3.90 (d, J=10.9 Hz, 1H), 3.82-3.72 (m, 2H), 3.70-3.61 (m, 1H), 3.16 (s, 0.8H), 3.06 (s, 0.8H), 2.98 (s, 0.7H), 2.90 (s, 0.7H), 2.50-2.42 (m, 5H), 2.40-2.35 (m, 1H), 2.33-2.18 (m, 4H), 2.10-2.04 (m, 1H), 1.65-1.53 (m, 4H), 1.39-1.25 (m, 6H), 1.03 (s, 9H), 0.89 (td, J=7.4, 1.7 Hz, 3H). HRMS (ESI-TOF) m/z: [M+H]$^+$ 956.5

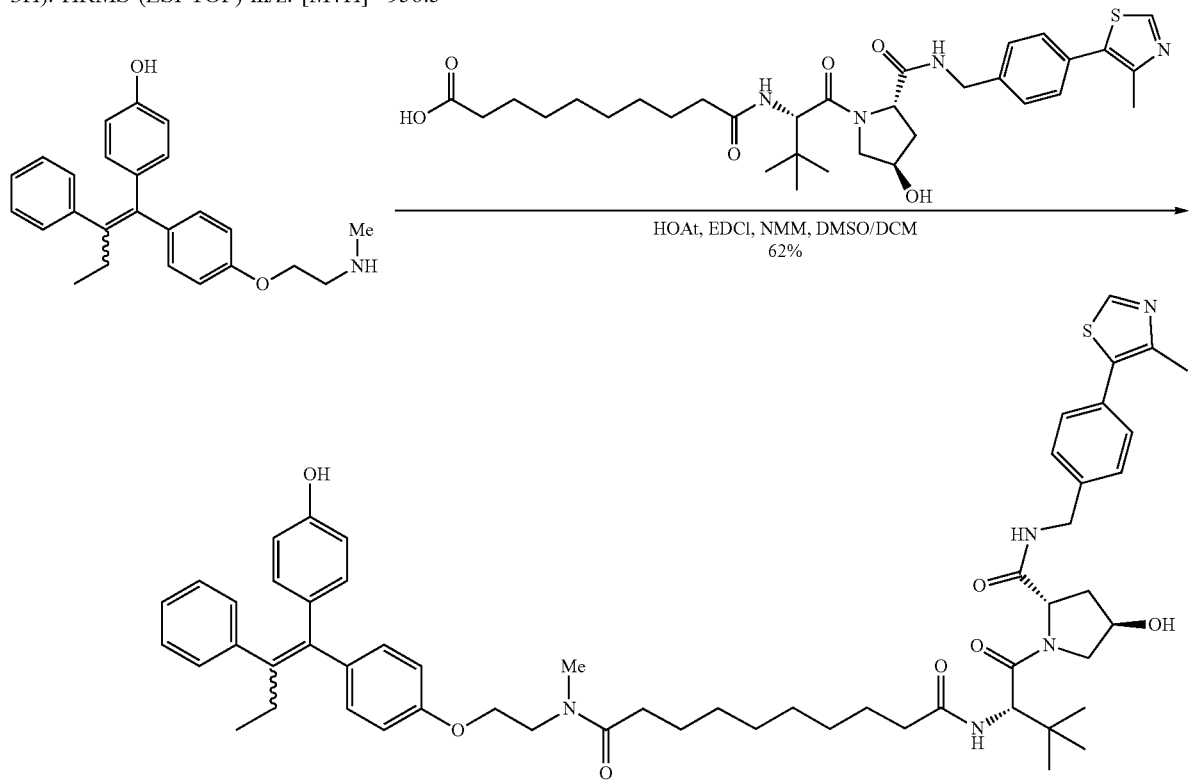

N[1]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[10]-(2-(4-(1-(4-hydroxyphenyl)-2-phenylbut-1-en-1-yl)phenoxy)ethyl)-N[10]-methyldecanediamide Obtained as a white solid (15 mg, 62%). $^1$H NMR (600 MHz, Methanol-$d_4$) δ 8.95 (s, 1H), 7.46 (d, J=8.0 Hz, 2H), 7.41 (d, J=7.9 Hz, 2H), 7.16-7.04 (m, 6H), 7.00 (d, J=8.5 Hz, 1H), 6.89 (dd, J=8.5, 5.3 Hz, 1H), 6.79-6.71 (m, 2H), 6.63 (d, J=8.7 Hz, 1H), 6.54-6.50 (m, 1H), 6.39 (d, J=8.6 Hz, 1H), 4.63 (s, 1H), 4.60-4.52 (m, 2H), 4.50-4.47 (m, 1H), 4.35 (d, J=15.4 Hz, 1H), 4.15 (dt, J=28.2, 5.2 Hz, 1H), 3.99 (dt, J=22.4, 5.3 Hz, 1H), 3.90 (dd, J=11.3, 2.1 Hz, 1H), 3.82-3.73 (m, 2H), 3.66 (dt, J=28.3, 5.3 Hz, 1H), 3.16 (s, 0.8H), 3.06 (s, 0.8H), 2.99 (s, 0.7H), 2.91 (s, 0.7H), 2.50-2.42 (m, 5H), 2.41-2.35 (m, 1H), 2.33-2.18 (m, 4H), 2.10-2.04 (m, 1H), 1.64-1.52 (m, 4H), 1.38-1.25 (m, 8H), 1.02 (d, J=3.4 Hz, 9H), 0.89 (td, J=7.5, 1.3 Hz, 3H). HRMS (ESI-TOF) m/z: [M+H]$^+$ 970.5

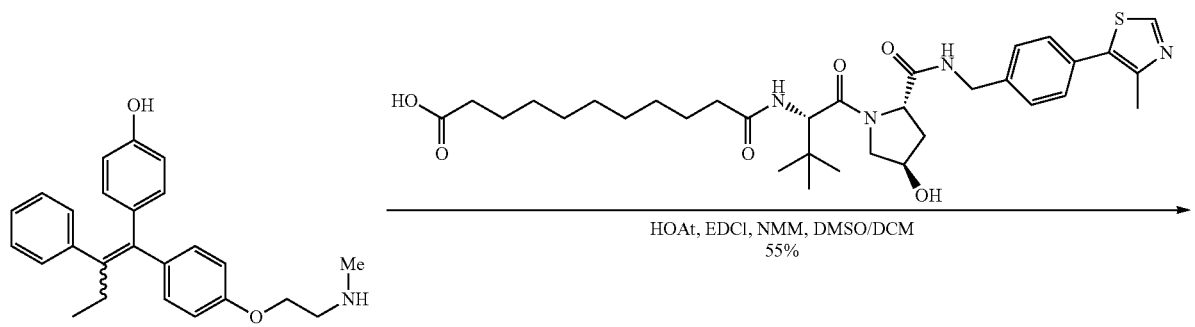

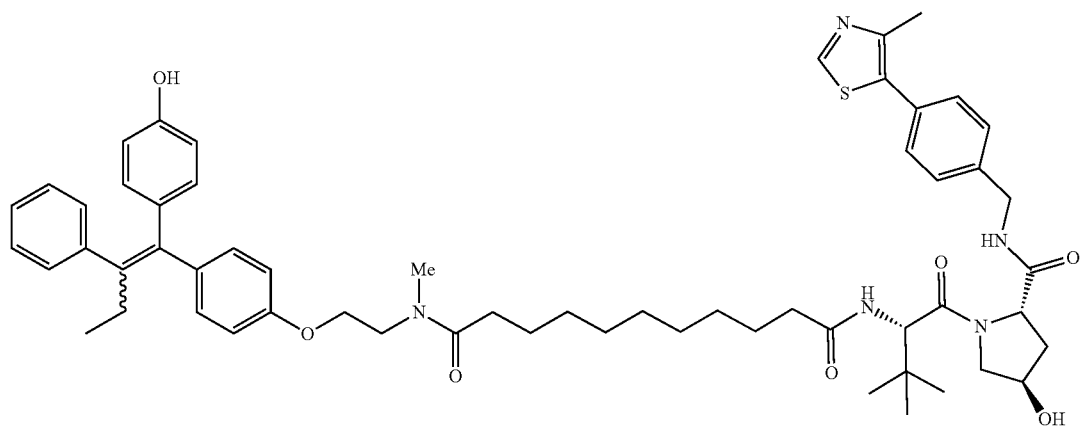

N[1]—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N[11]-(2-(4-(1-(4-hydroxyphenyl)-2-phenyl-but-1-en-1-yl)phenoxy)ethyl)-N[11]-methylundecanediamide Obtained as a white solid (13 mg, 55%). $^1$H NMR (600 MHz, Methanol-$d_4$) δ 8.94 (s, 1H), 7.46 (d, J=8.0 Hz, 2H), 7.41 (d, J=8.2 Hz, 2H), 7.16-7.04 (m, 6H), 7.00 (d, J=8.5 Hz, 1H), 6.92-6.85 (m, 1H), 6.80-6.69 (m, 2H), 6.63 (d, J=8.6 Hz, 1H), 6.52 (dd, J=8.8, 4.0 Hz, 1H), 6.39 (d, J=8.6 Hz, 1H), 4.63 (d, J=4.1 Hz, 1H), 4.59-4.51 (m, 2H), 4.50-4.47 (m, 1H), 4.35 (d, J=15.5 Hz, 1H), 4.16 (dt, J=26.4, 5.3 Hz, 1H), 3.99 (dt, J=20.6, 5.3 Hz, 1H), 3.90 (dd, J=11.3, 1.7 Hz, 1H), 3.82-3.73 (m, 2H), 3.66 (dt, J=26.5, 5.3 Hz, 1H), 3.16 (s, 0.8H), 3.06 (s, 0.8H), 2.99 (s, 0.7H), 2.91 (s, 0.7H), 2.50-2.42 (m, 5H), 2.40-2.34 (m, 1H), 2.32-2.18 (m, 4H), 2.11-2.04 (m, 1H), 1.64-1.52 (m, 4H), 1.37-1.25 (m, 10H), 1.03 (d, J=3.5 Hz, 9H), 0.89 (t, J=7.6 Hz, 3H). HRMS (ESI-TOF) m/z: [M+H]$^+$ 984.5

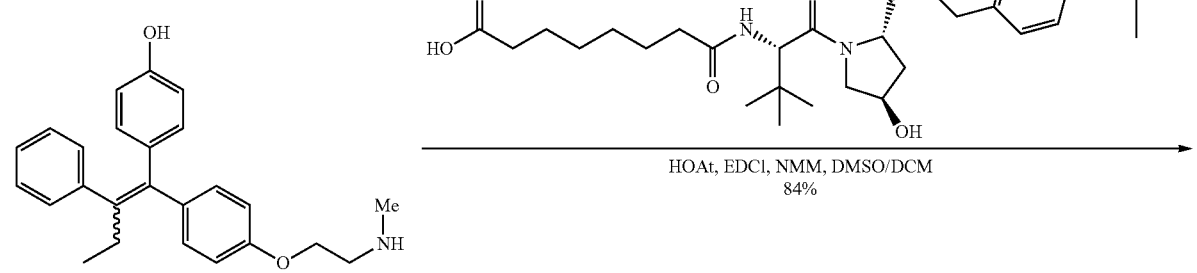

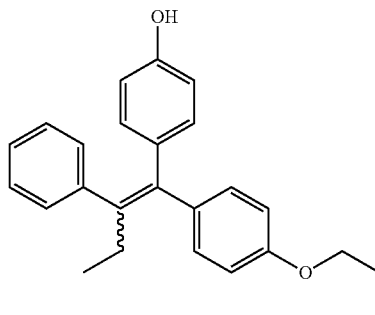

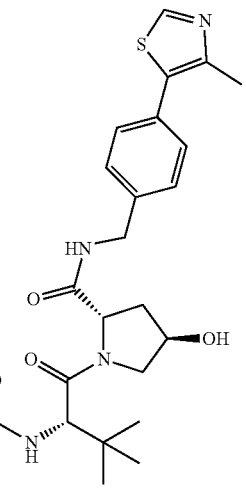

N¹—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N⁸-(2-(4-(1-(4-hydroxyphenyl)-2-phenylbut-1-en-1-yl)phenoxy)ethyl)octanediamide Obtained as a white solid (27 mg, 84%). ¹H NMR (600 MHz, Methanol-d₄) δ 9.09 (s, 1H), 7.48 (d, J=8.1 Hz, 2H), 7.42 (d, J=8.3 Hz, 2H), 7.16-7.04 (m, 6H), 7.00 (d, J=8.5 Hz, 1H), 6.90 (d, J=8.7 Hz, 1H), 6.75 (t, J=8.7 Hz, 2H), 6.63 (d, J=8.7 Hz, 1H), 6.54 (d, J=8.8 Hz, 1H), 6.39 (d, J=8.6 Hz, 1H), 4.62 (d, J=1.4 Hz, 1H), 4.59-4.46 (m, 3H), 4.35 (d, J=15.5 Hz, 1H), 4.05 (t, J=5.5 Hz, 1H), 3.90 (d, J=11.8 Hz, 1H), 3.88 (t, J=5.5 Hz, 1H), 3.79 (dd, J=11.0, 3.9 Hz, 1H), 3.55 (t, J=5.4 Hz, 1H), 3.45 (t, J=5.4 Hz, 1H), 2.52-2.42 (m, 5H), 2.29-2.13 (m, 5H), 2.10-2.04 (m, 1H), 1.64-1.52 (m, 4H), 1.37-1.25 (m, 4H), 1.02 (s, 9H), 0.89 (td, J=7.4, 1.9 Hz, 3H). HRMS (ESI-TOF) m/z: [M+H]⁺ 928.5.

Example 4. N¹-(2-(4-((Z)-1,2-Diphenylbut-1-en-1-yl)phenoxy)ethyl)-N¹¹—((S)-1-((2S,4R)-4-hydroxy-2-((4-(quinazolin-6-yl)benzyl)pyrrolidin-1-yl)-3,3-dimethyl-1-oxobutan-2-yl)-N¹-methylundecanediamide

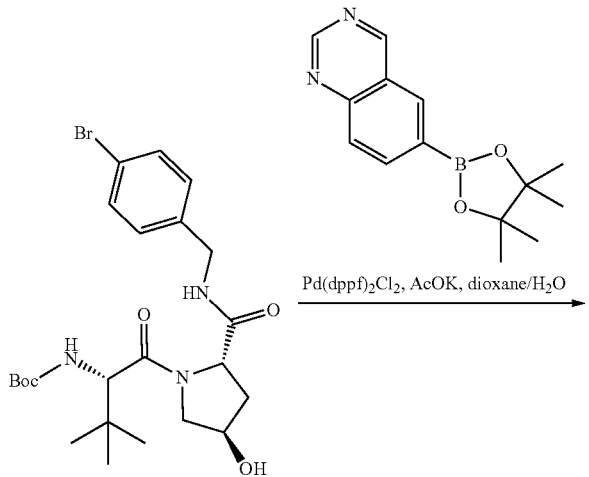

-continued

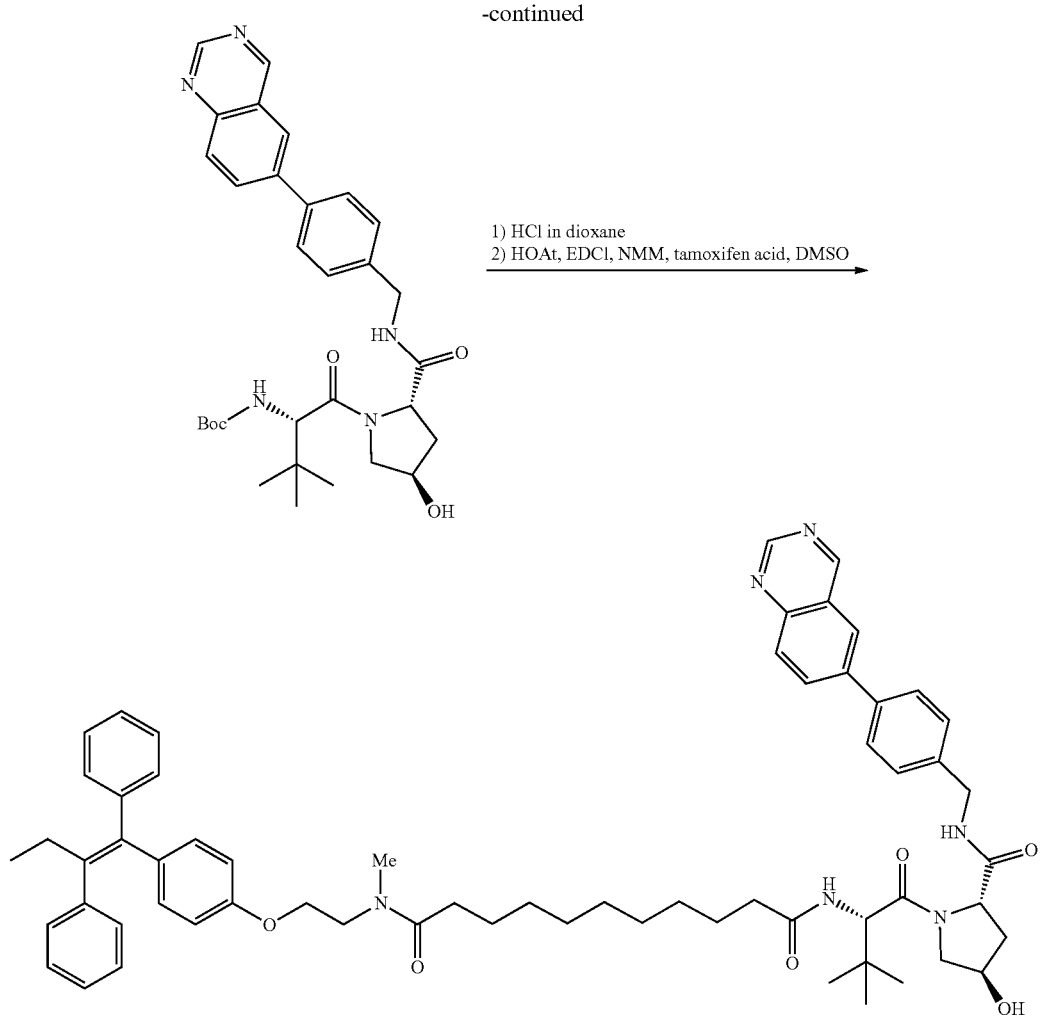

N[1]-(2-(4-((Z)-1,2-Diphenylbut-1-en-1-yl)phenoxy)ethyl)-N[11]—((S)-1-((2S,4R)-4-hydroxy-2-((4-(quinazolin-6-yl)benzyl)carbamoyl)pyrrolidin-1-yl)-3,3-dimethyl-1-oxobutan-2-yl)-N[1]-methylundecanediamide A mixture of 6-(4,4,5,5-tetramethyl-1,3,2-dioxaborolan-2-yl)quinazoline (100 mg, 0.390 mmol), tert-butyl ((S)-1-((2S,4R)-2-((4-bromobenzyl)carbamoyl)-4-hydroxypyrrolidin-1-yl)-3,3-dimethyl-1-oxobutan-2-yl)carbamate (200 mg, 0.390 mmol), Pd(dppf)$_2$Cl$_2$ (30 mg, 0.039 mmol) and potassium acetate (114 mg, 1.17 mmol) in dioxane (30 mL) and H$_2$O (5 mL) was heated at 90° C. for 3 hours. Upon cooling, the mixture was concentrated in vacuo, and then purified by flash column chromatography (gradient from 100% ethyl acetate to 10% methanol) to afford the Suzuki coupling intermediate as a solid (120 mg, 55%). HRMS (ESI-TOF) m/z: [M+H]$^+$ 562.3. To a mixture of the Suzuki coupling intermediate (9 mg, 0.016 mmol) in methanol (5 mL) was added HCl in dioxane (4.0 M, 2 mL), and then the solution was stirred overnight at room temperature. Subsequently, the mixture was concentrated under reduced pressure and the resulting residue was dissolved in DMSO (1 mL). To the resulting mixture were added tamoxifen acid (9 mg, 0.016 mmol), N-methylmorpholine (16 mg, 0.16 mmol), HOAt (3.3 mg, 0.024 mmol) and EDCI (4.6 mg, 0.024 mmol), and the resulting mixture was stirred overnight at room temperature. Subsequently, the mixture was concentrated under reduced pressure, and the resulting residue was purified by preparative-HPLC to afford the title compound (8 mg, 50%) as a white solid. $^1$H-NMR (600 MHz, Methanol-d$_4$) δ 8.61 (s, 1H), 7.82 (dd, J=8.4, 2.1 Hz, 1H), 7.77 (d, J=2.0 Hz, 1H), 7.60 (d, J=7.0 Hz, 2H), 7.46 (d, J=6.8 Hz, 2H), 7.38 (d, J=8.4 Hz, 1H), 7.33 (t, J=7.6 Hz, 2H), 7.25 (t, J=7.4 Hz, 1H), 7.20 (d, J=6.7 Hz, 2H), 7.17-7.06 (m, 5H), 6.75 (dd, J=10.3, 8.8 Hz, 2H), 6.64-6.47 (m, 2H), 6.25 (s, 1H), 4.63 (s, 1H), 4.60-4.47 (m, 3H), 4.38 (d, J=15.4 Hz, 1H), 4.01 (t, J=5.1 Hz, 1H), 3.97 (t, J=5.4 Hz, 1H), 3.90 (d, J=11.3 Hz, 1H), 3.80 (dd, J=10.9, 3.9 Hz, 1H), 3.68 (t, J=5.1 Hz, 1H), 3.64 (t, J=5.5 Hz, 1H), 3.06 (s, 1.5H, 0.5NH3), 2.91 (s, 1.5H, 0.5NH3), 2.48-2.16 (m, 7H), 2.10-2.03 (m, 1H), 1.65-1.50 (m, 4H), 1.38-1.22 (m, 10H), 1.04 (s, 9H), 0.89 (t, J=7.4 Hz, 3H). HRMS (ESI-TOF) m/z: [M+H]$^+$ 999.6.

Example 5. Degradative Activity of Compounds of the Present Disclosure Toward MCF-7 Cells MCF-7 cells were maintained in high glucose DMEM (Corning cellgro, 15-013-CM), supplemented with 10% FBS, 1× L-Glutamine (29.2 mg/mL) and 1× Penicillin Streptomycin (10,000 I.U./mL Penicillin; 10,000 µg/mL Streptomycin; Corning, 30-009-CI). The resulting MCF-7 cells were plated into a 24-well plate at 1×10$^5$ cells/well, and the following day, compound was added to the cell medium at various concentrations. After treating the cell medium with compound, the cell plates were incubated for 20 hours at 37° C. Upon cooling, cells were lysed by addition of SDS loading buffer. The resulting cell lysates were subjected to immunoblotting by standard protocol. with primary antibodies of mouse anti-human ERα monoclonal antibody (Santa Cruz Biotechnology Inc., #SC-8002) and 1:1000 goat anti-human actin polyclonal antibody (Santa Cruz Biotechnology Inc. #SC-1616). Western blot results visualized using pico-LUCENT™ PLUS-HRP ECL (G Biosciences, 786-165) and LI-CORC digit imaging system.

TABLE 2

Exemplary Compounds Tested for Biological Activity.

| Compound # | Structure |
|---|---|
| 1 | 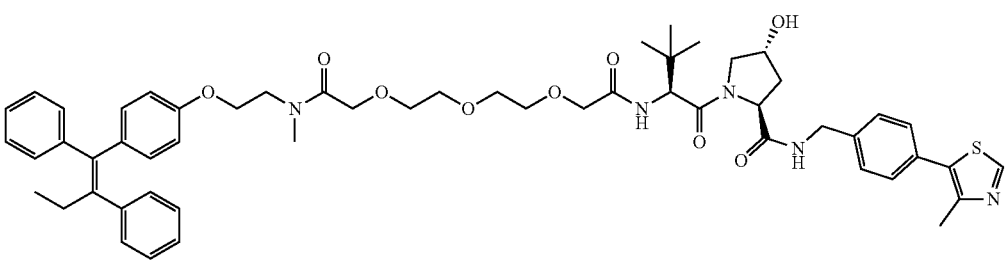 [SMILES: CC/C(=C(\c1ccccc1)c1ccc(OCCN(C)C(=O)COCCOCCOCC(=O)N[C@H](C(=O)N2C[C@H](O)C[C@H]2C(=O)NCc2ccc(-c3scnc3C)cc2)C(C)(C)C)cc1)c1ccccc1] |
| 2 | 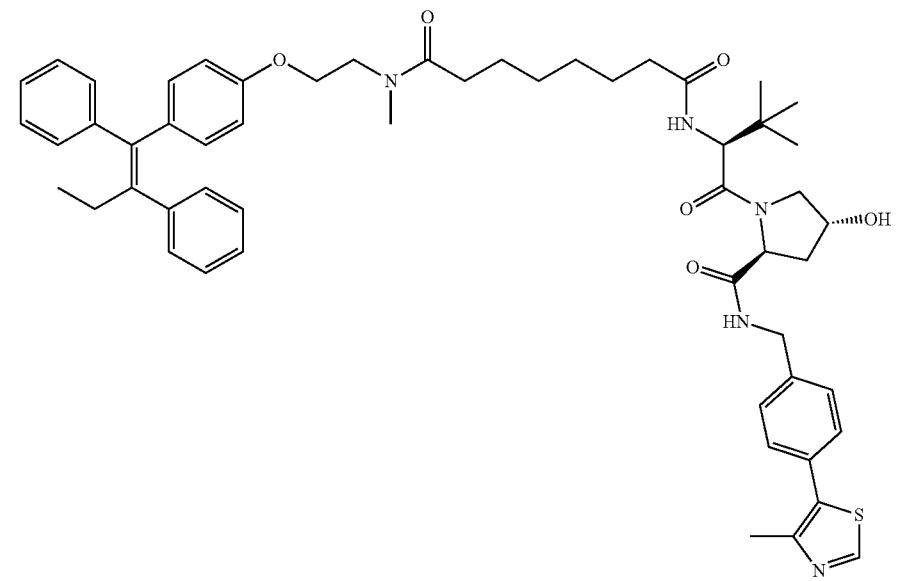 [SMILES: CC/C(=C(\c1ccccc1)c1ccc(OCCN(C)C(=O)CCCCCCC(=O)N[C@H](C(=O)N2C[C@H](O)C[C@H]2C(=O)NCc2ccc(-c3scnc3C)cc2)C(C)(C)C)cc1)c1ccccc1] |
| 3 | 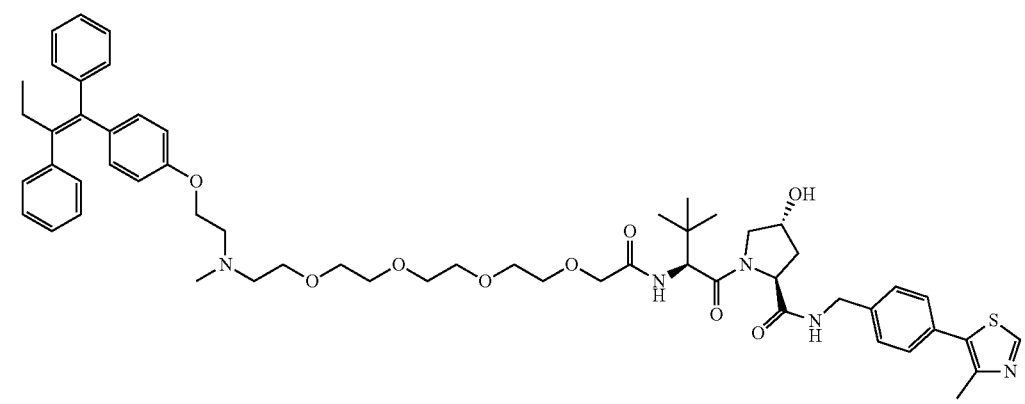 [SMILES: CC/C(=C(\c1ccccc1)c1ccc(OCCN(C)CCOCCOCCOCCOCC(=O)N[C@H](C(=O)N2C[C@H](O)C[C@H]2C(=O)NCc2ccc(-c3scnc3C)cc2)C(C)(C)C)cc1)c1ccccc1] |

TABLE 2-continued

Exemplary Compounds Tested for Biological Activity.

| Compound # | Structure |
|---|---|
| 4 | 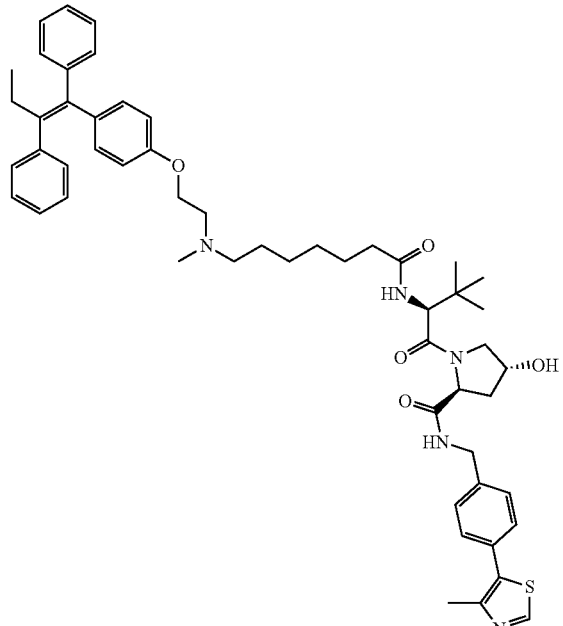 |

Figure 2:
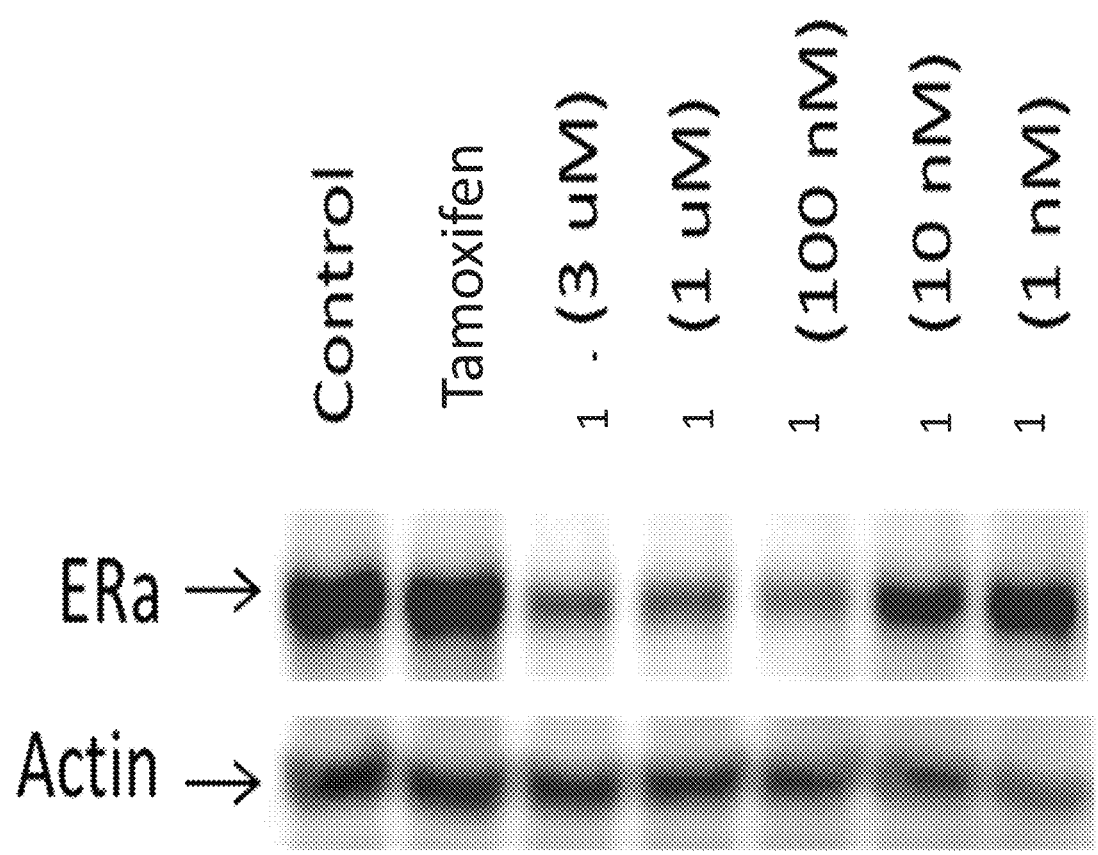
FIG. 2 illustrates the degradative activity of a compound of the present disclosure toward Estrogen Receptor alpha.
Figure 3A:
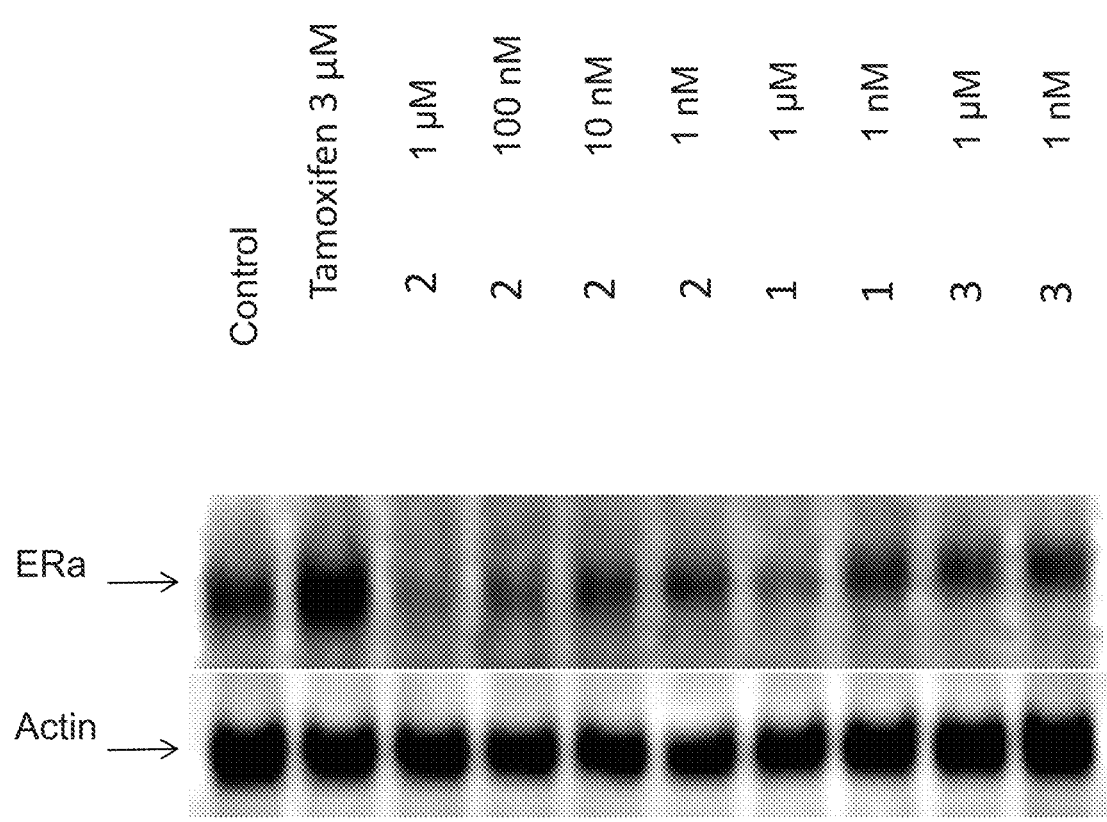
FIG. 3A illustrates the comparative degradative activity of several compounds of the present disclosure toward Estrogen Receptor alpha.
Figure 3B:
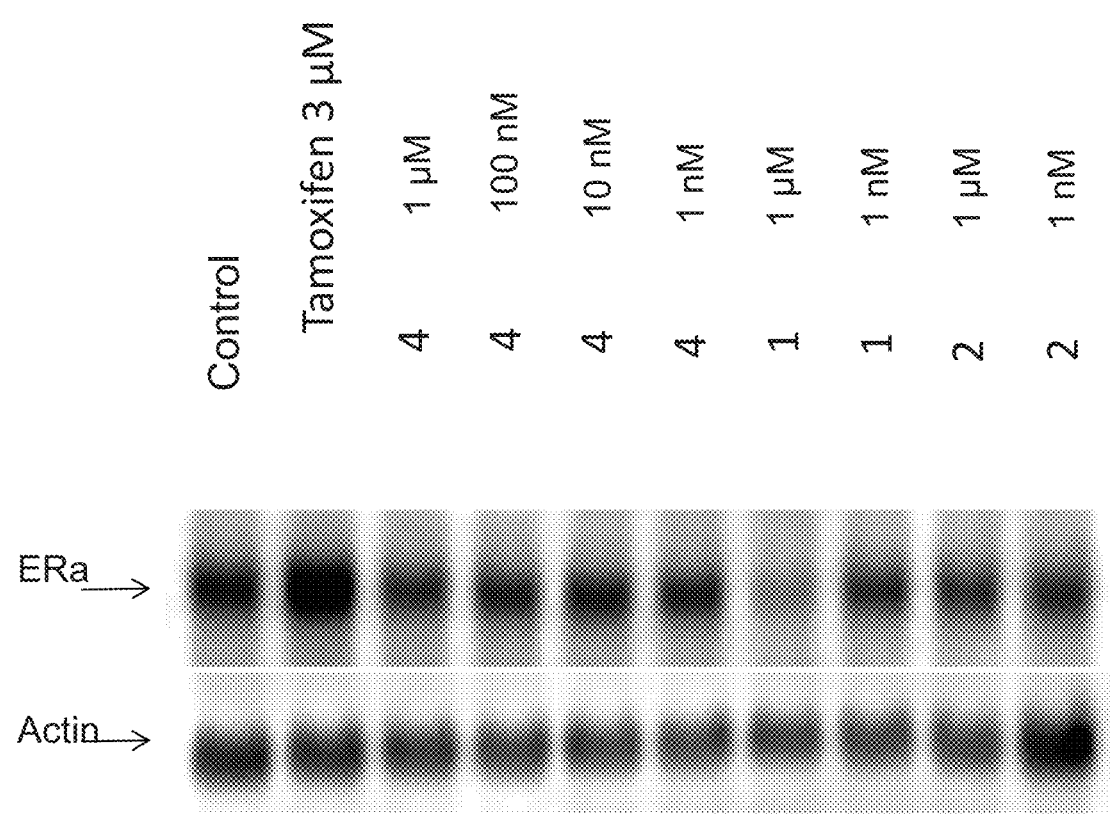
FIG. 3B illustrates the comparative degradative activity of several compounds of the present disclosure toward Estrogen Receptor alpha.

In FIG. 2, Compound 1 was added at concentrations of 1 nM, 10 nM, 100 nM, 1 μM, and 3 μM, resulting in Estrogen Receptor alpha degradation. In FIGS. 3A and 3B, Compounds 1, 2, 3, and 4 were added at concentrations varying from 1 nM to 1 μM. Treatment with Compounds 1, 2, 3, and 4 all resulted in degradation of Estrogen Receptor alpha when compared with the control. Compounds 1 and 2 are more potent at inducing Estrogen Receptor alpha degradation than Compounds 3 and 4.

The effect of chain length on potency was studied. MCF7 or LTED cells were plated and grown to 90% confluence overnight. Cells were treated with different compounds, as shown below. To collect protein from cells, cells were washed with PBS and proteins were collected in Laemmli sample buffer (1×) (VWR international). Proteins in cell lysate (25 μg) were separated by SDS-PAGE and transferred to PVDF membranes. Nonspecific binding was blocked by incubation with blocking buffer (5% milk in 1×TBST) at room temperature for 30 minutes. The membranes were then incubated with Primary antibodies mouse anti-ERα (1:500, Santa Cruz Biotechnology), or goat anti-actin (1:4,000, Santa Cruz Biotechnology) overnight at 4° C., followed by washing 3 times with TBST, and then incubated with horseradish peroxidase-conjugated rabbit anti-mouse or anti-goat IgG (1:5,000) for 1 hour. After TBST washes, blots were developed with an enhanced chemiluminescence kit (Thermo Fisher Scientific). The bands were imaged by chemidock touch system (Bio-Rad) and quantified by ImageJ.

Figure 4A:
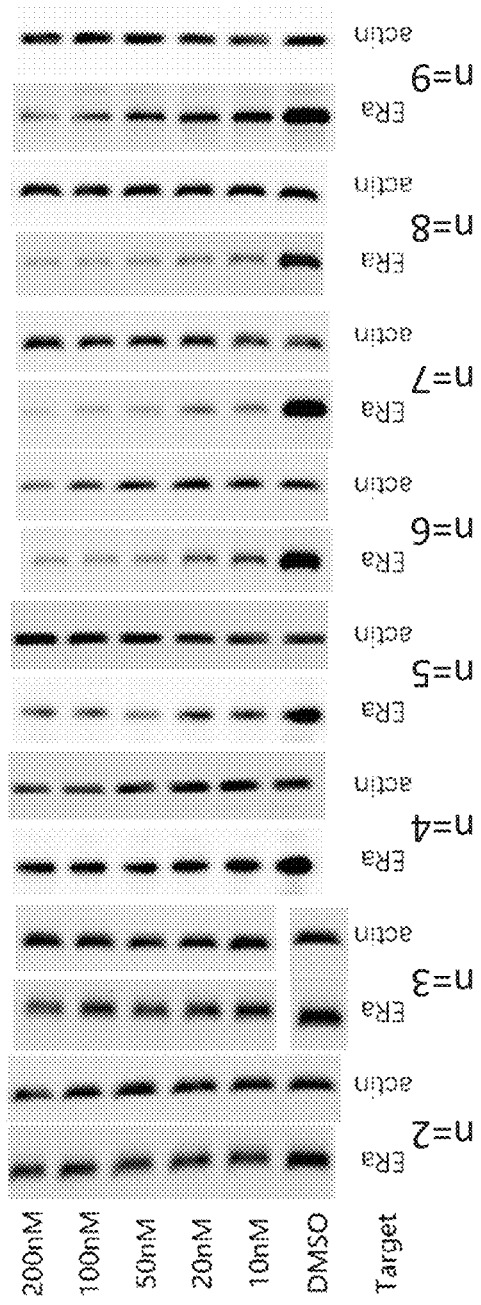
FIGS. 4A, 4B, and 4C show Estrogen Receptor alpha activity as a function of varying linker length.

FIG. 4A shows Estrogen Receptor alpha degradation as a function of linker length for compounds of the formula:

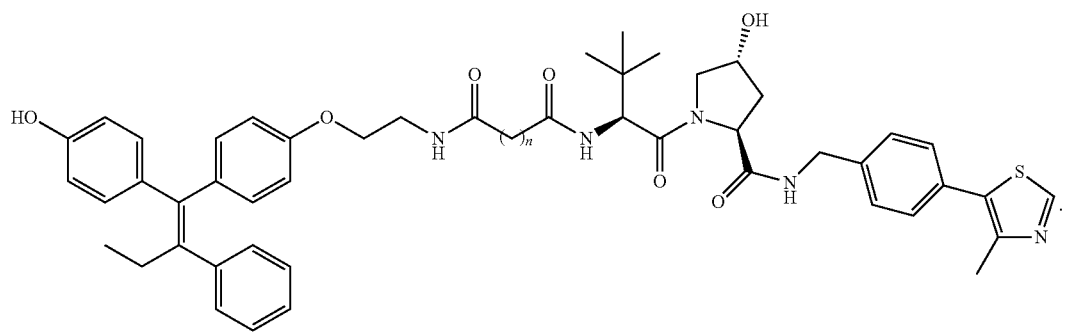

Figure 4B:
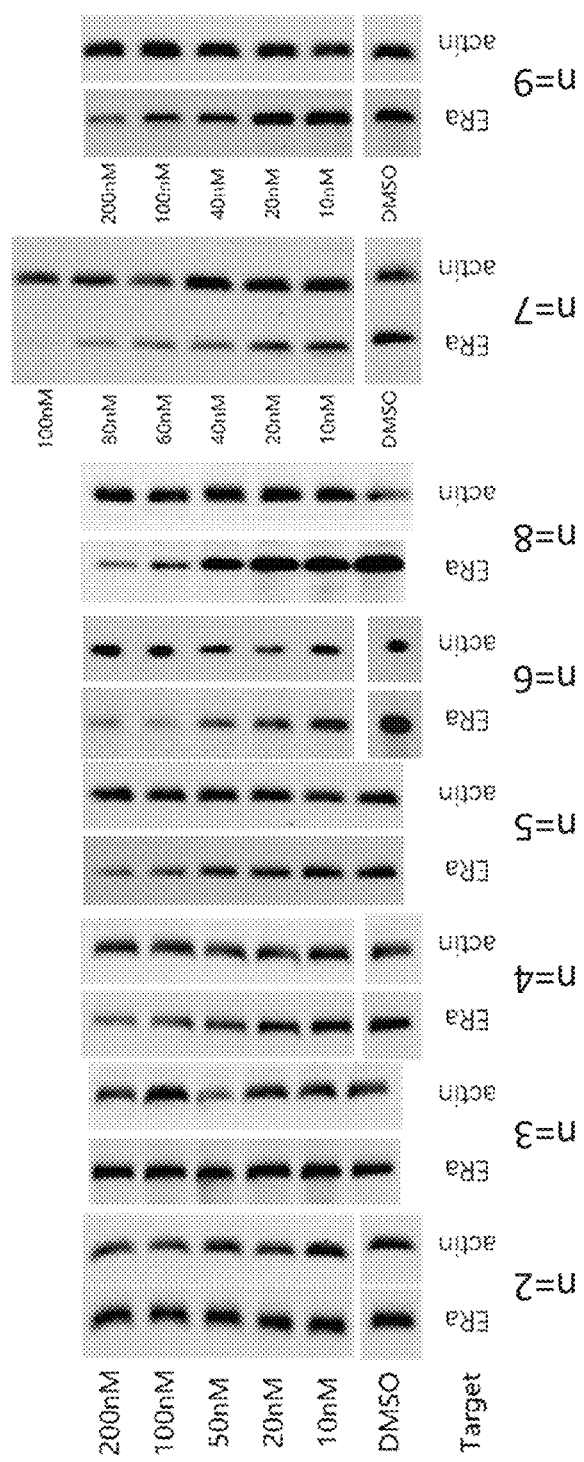
Figure 4C:
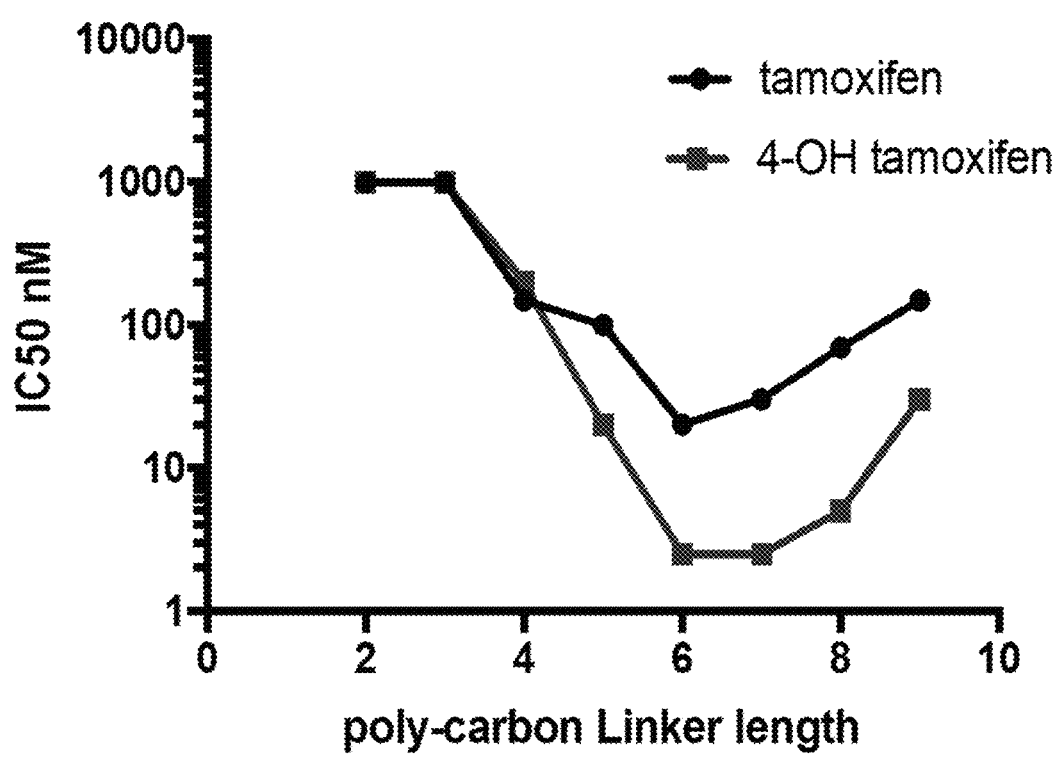

Similarly, FIG. 4B shows Estrogen Receptor alpha degradation as a function of linker length for compounds of the formula:

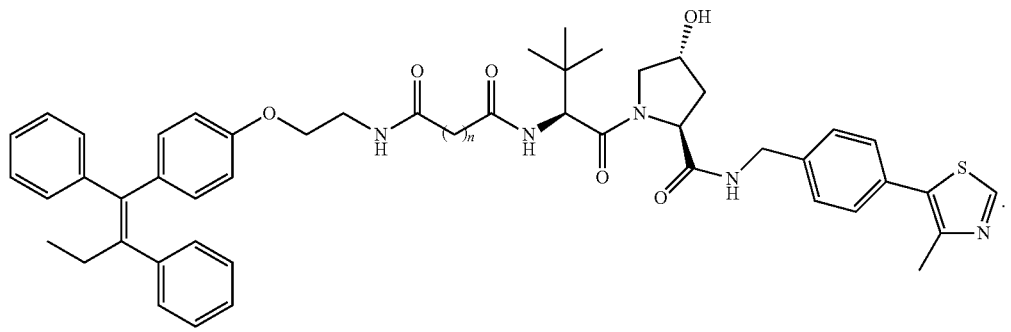
FIG. 4C shows the relationship between Estrogen Receptor alpha degradation IC$_{50}$ and linker length.
Table 3 contains the IC$_{50}$ values depicted in FIG. 4C:
TABLE 3
IC$_{50}$ Values as a function of linker length.
| Linker Length (# carbon atoms) | tamoxifen IC$_{50}$ (nM) | 4-OH tamoxifen IC$_{50}$ (nM) |
|---|---|---|
| 2 | 1000 | 1000 |
| 3 | 1000 | 1000 |
| 4 | 300 | 1000 |
| 5 | 250 | 300 |
| 6 | 100 | 2.5 |
| 7 | 150 | 2.5 |
| 8 | 150 | 10 |
| 9 | 300 | 10 |
Using the same procedure described above, the activity of compound A
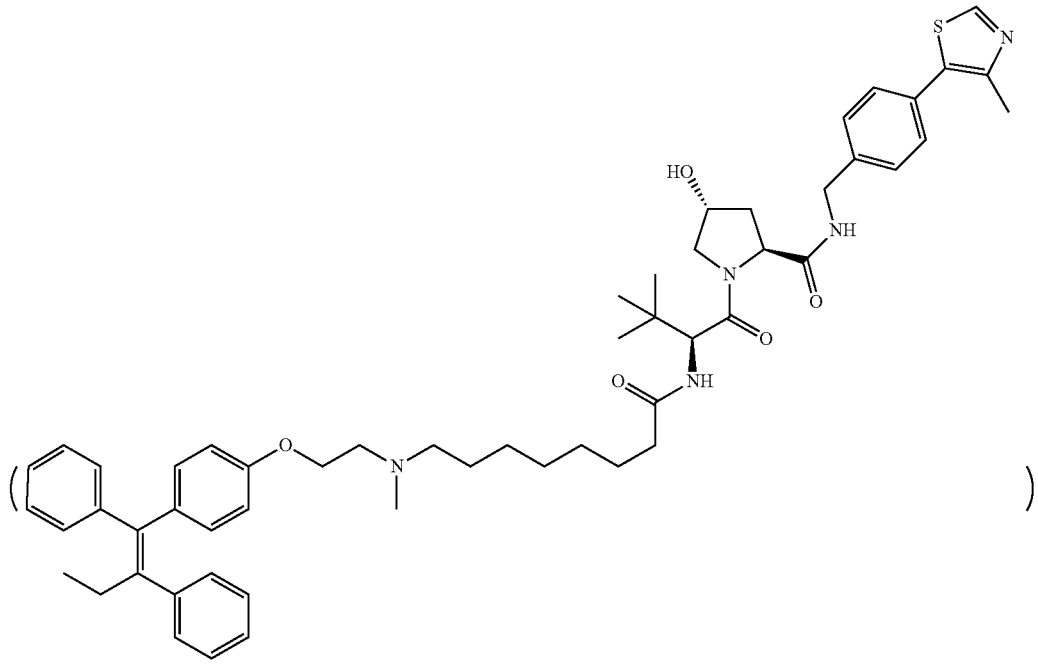

and compound B

Figure 5:
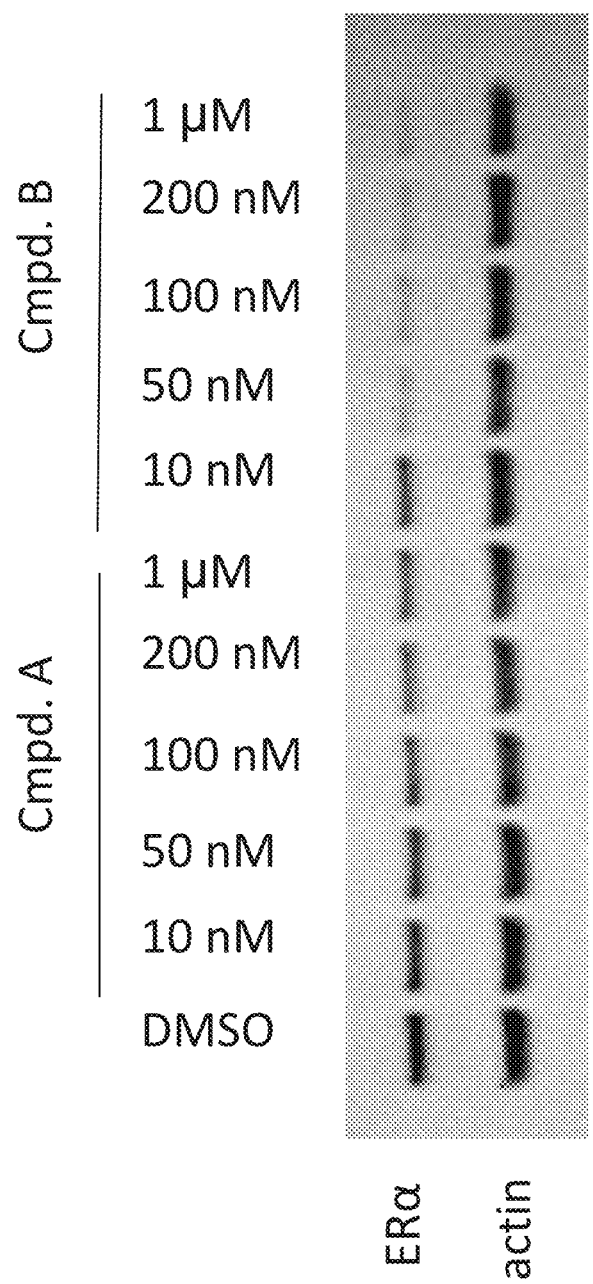
FIG. 5 illustrates a comparison of Estrogen Receptor alpha activity when cells are treated with compounds of high structural similarity.
Figure 6:
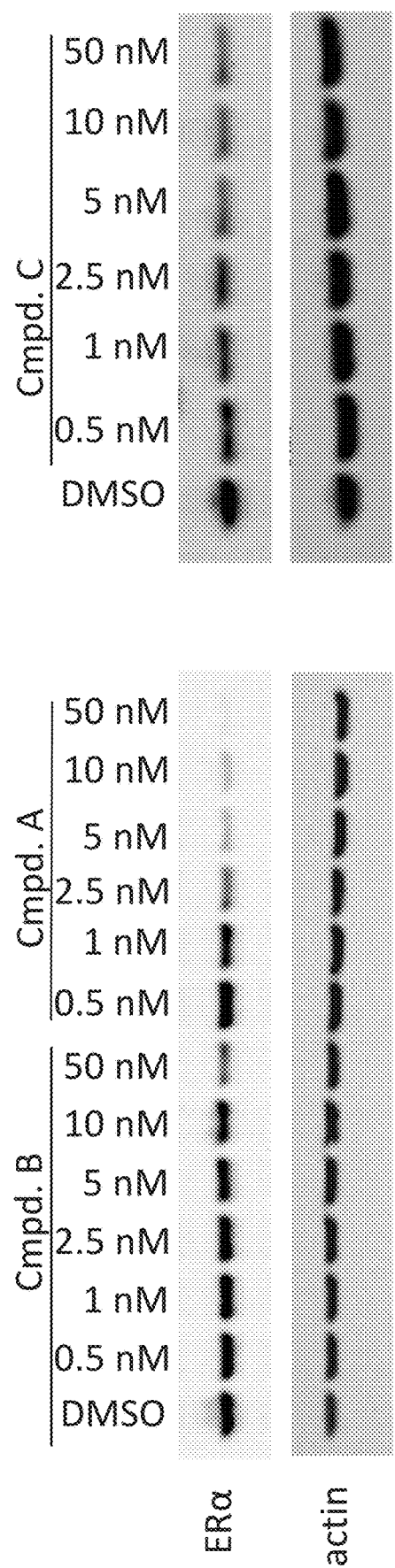
FIG. 6 illustrates the Estrogen Receptor alpha activity of cells after treatment with various compounds.

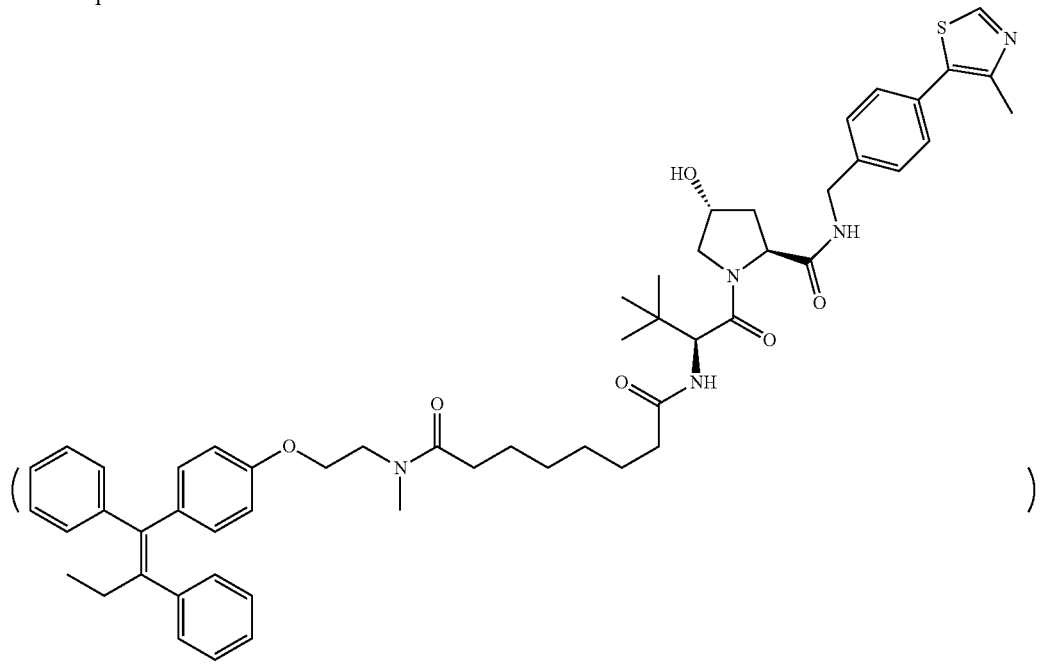

toward Estrogen Receptor alpha was studied. It was surprisingly found that the presence of the carbonyl adjacent to the tamoxifen moiety is critical, as shown in FIG. 5. Compound B was found to be ten-fold more potent than Compound A, lacking the critical carbonyl group.

Example 6. Comparison of Estrogen Receptor Alpha Degradation Activity of Compounds of the Present Disclosure and Various Literature Compounds The following compounds were used in this study:

TABLE 4

Compounds tested for biological activity.

| Compound ID | Structure |
|---|---|
| A | 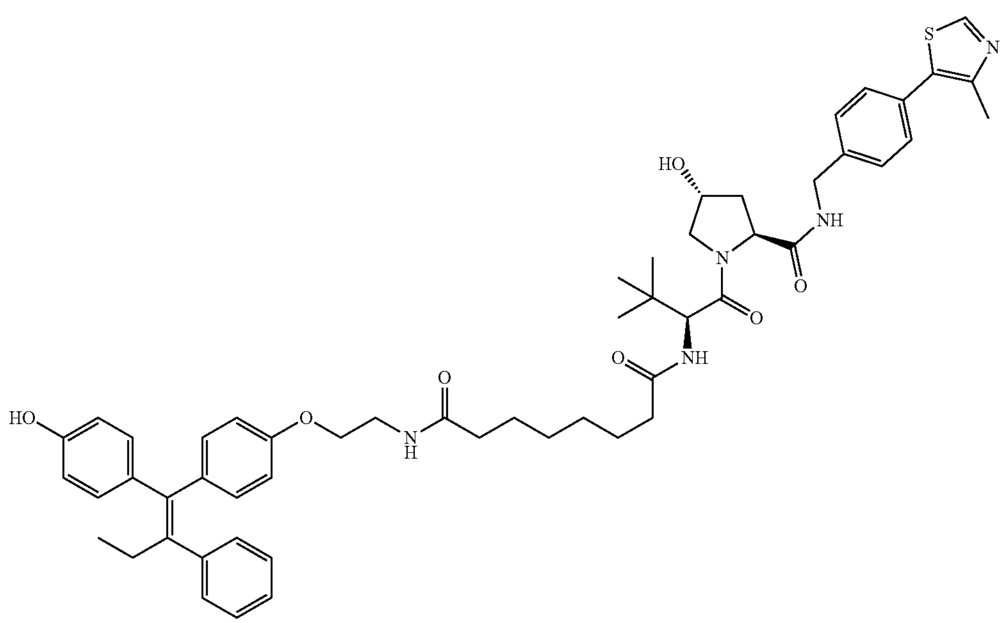 [SMILES: CC/C(=C(\c1ccc(O)cc1)c1ccc(OCCNC(=O)CCCCCCC(=O)N[C@H](C(=O)N2C[C@H](O)C[C@H]2C(=O)NCc2ccc(-c3scnc3C)cc2)C(C)(C)C)cc1)c1ccccc1] |

TABLE 4-continued

Compounds tested for biological activity.

| Compound ID | Structure |
|---|---|
| B (ARN-810) | *(structure shown)* |
| C (fulvestrant) | *(structure shown)* |

MCF-7 cells were treated with compounds A, B, and C, as described in Example 5. As shown in FIG. 5, compound A, of the present disclosure, is more potent than both compounds B and C.

Example 7. Estrogen Receptor Alpha Degradation Time-Dependence Study

Figure 7:
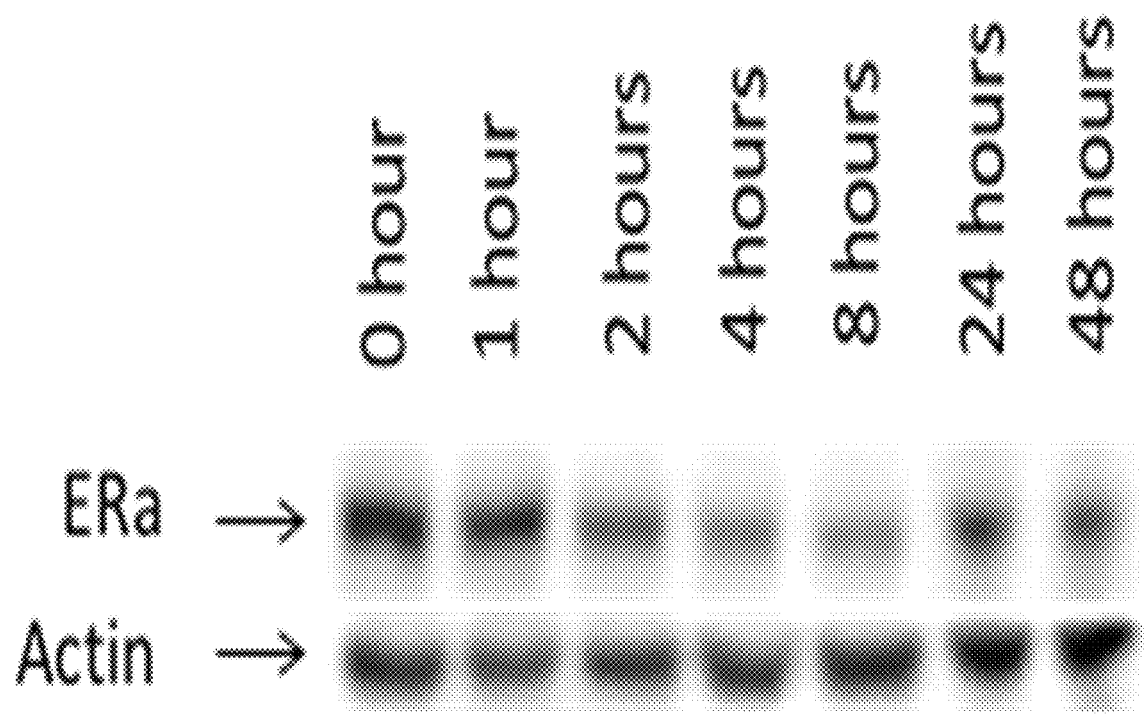
FIG. 7 illustrates the time course of Estrogen Receptor alpha degradation induced by a compound of the present disclosure.

MCF-7 cells were maintained in high glucose DMEM (Corning cellgro, 15-013-CM), supplemented with 10% FBS, 1× L-Glutamine (29.2 mg/mL), and Penicillin Streptomycin (10,000 I.U./mL Penicillin; 10,000 µg/mL Streptomycin; Corning, 30-009-CI). These cells were then plated into 24-well plate at 1×10$^5$ cells/well, and Compound 1 was added to each well of the 24-well plate at a final concentration of 100 nM the following day. The cells were lysed at 1, 2, 4, 8, 24, and 48 hours. Once the cells were lysed, Estrogen Receptor alpha and actin were detected with 1:500 mouse anti-human ERα monoclonal antibody (Santa Cruz Biotechnology Inc., #SC-8002) and 1:1000 goat anti-human actin polyclonal antibody (Santa Cruz Biotechnology Inc. #SC-1616). FIG. 7 depicts the degradative activity of Compound 1 at various time points over the course of 48 hours.

Similarly, the Estrogen Receptor alpha degradation time-dependence was studied for the compounds listed in Table 5.

TABLE 5
Compounds tested in this example.
| Compound ID | Structure |
|---|---|
| A | 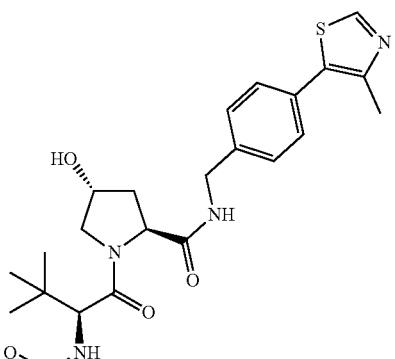 |
| B | 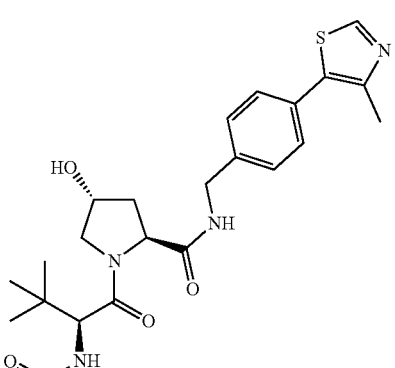 |

TABLE 5-continued

Compounds tested in this example.

| Compound ID | Structure |
|---|---|
| C (ARN-810) | 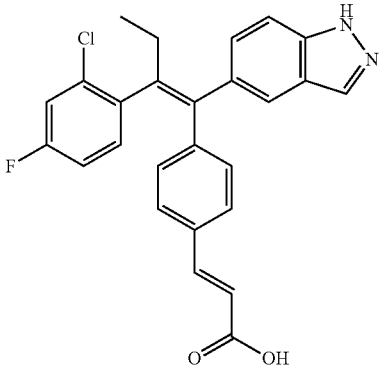 [SMILES: CC/C(=C(/c1ccc(/C=C/C(=O)O)cc1)c1ccc2[nH]ncc2c1)c1ccc(F)cc1Cl] |
| D (fulvestrant) | 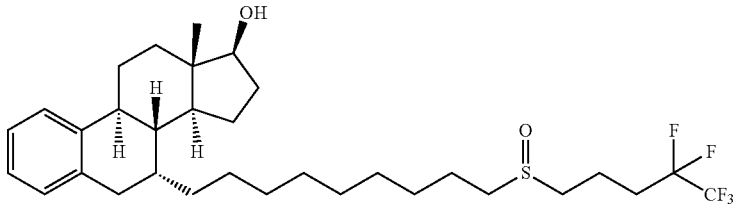 |

Figure 8:
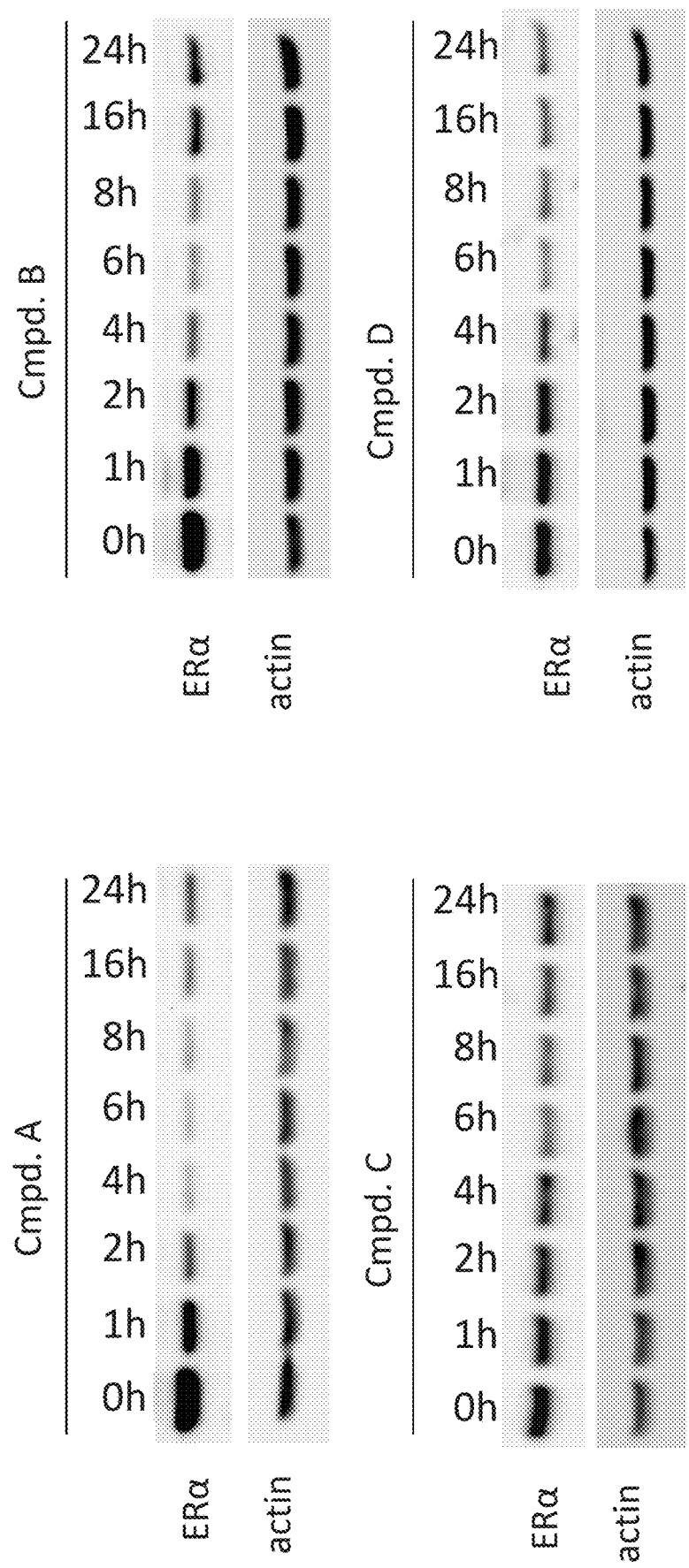
FIG. 8 illustrates the time course of Estrogen Receptor alpha degradation induced by various compounds.

Estrogen Receptor alpha, as a function of time, is shown in FIG. 8, for compounds A-D.

Example 8. Proteasome-Dependence of Estrogen Receptor Alpha Degradation

MCF-7 cells were maintained in high glucose DMEM (Corning cellgro, 15-013-CM) supplemented with 10% FBS, 1× L-Glutamine (29.2 mg/mL), and Penicilin Streptomycin (10,000 I.U./mL Penicillin; 10,000 µg/mL Streptomycin; Corning, 30-009-CI). These cells were plated into 24-well plates at 1×10$^5$ cells/well, and the following day Compound 1

Figure 9A:
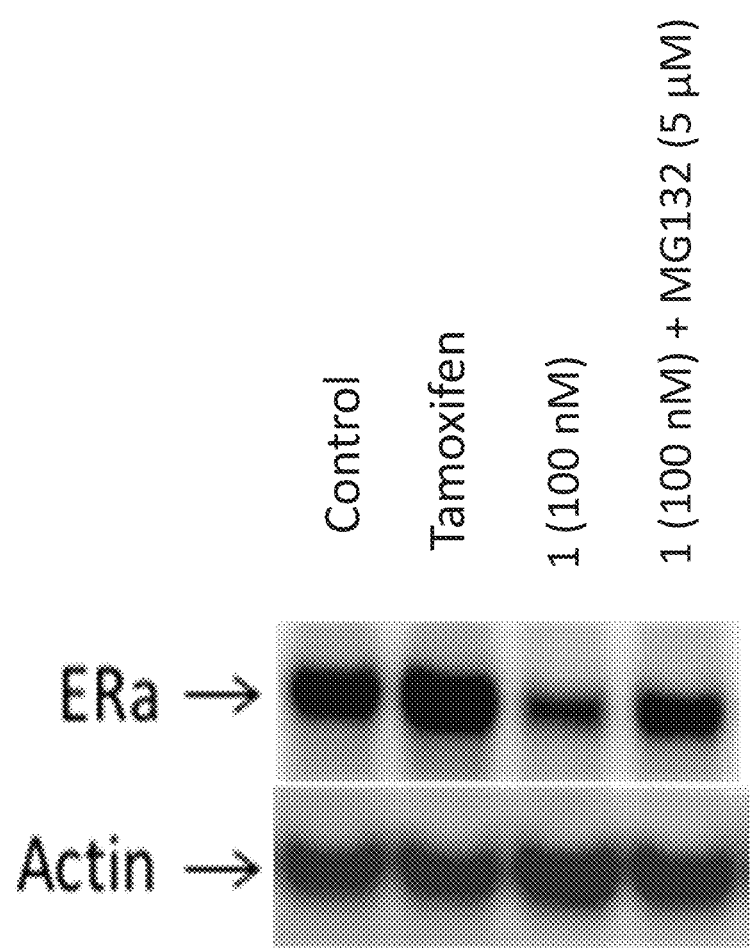
FIG. 9A illustrates the proteasome-dependence of Estrogen Receptor alpha degradation.
Figure 9B:
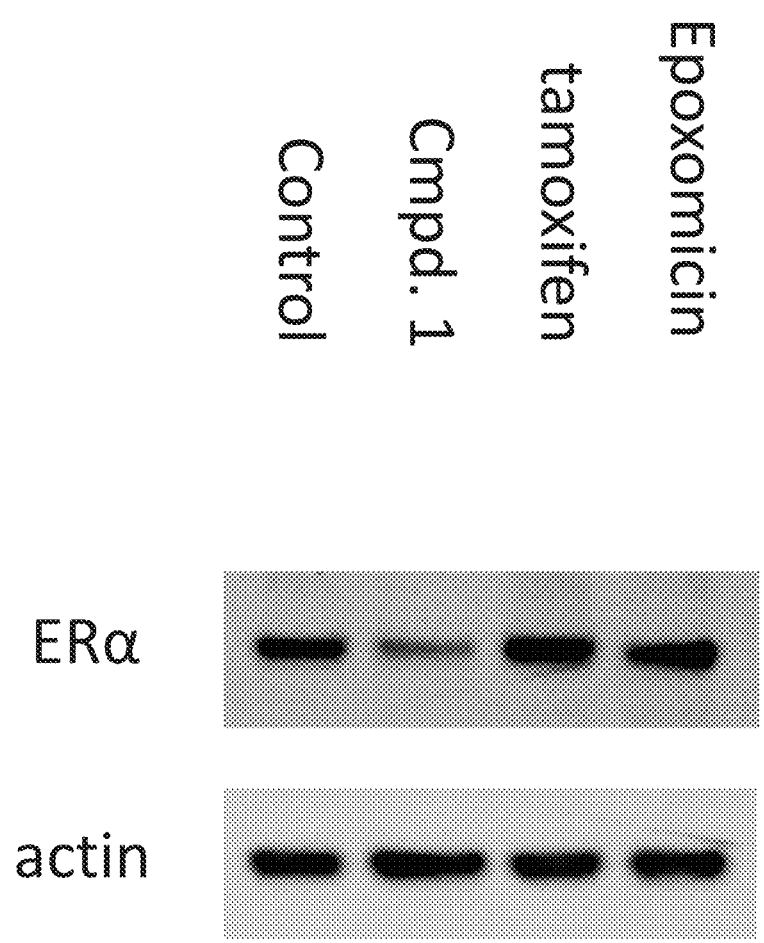
FIG. 9B illustrates the proteasome-dependence of Estrogen Receptor alpha degradation.

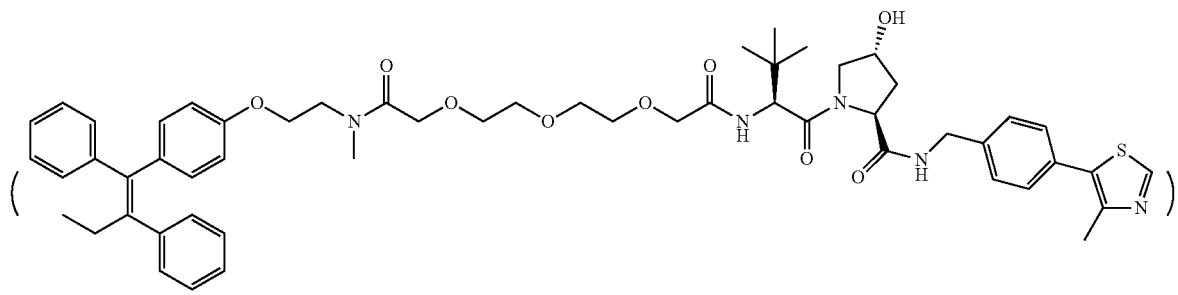

was added at 100 nM, alone or in combination with 5 μM of MG-132A (Selleckchem, S2619). The cells were then incubated at 37° C. for 20 hours, and upon cooling, the cells were lysed. The cell lysates were subjected to immunoblotting by standard protocol with primary antibodies of mouse anti-human Estrogen Receptor alpha monoclonal antibody (Santa Cruz Biotechnology Inc., #SC-8002) and 1:1000 goat anti-human actin polyclonal antibody (Santa Cruz Biotechnology Inc. #SC-1616). Western blot results visualized using picoLUCENT™ PLUS-HRP ECL (G Biosciences, 786-165) and LI-COR C digit imaging system. FIG. 9A illustrates the proteasome dependence of Estrogen Receptor alpha degradation induced by compounds of the present disclosure. Similarly, FIG. 9B shows the effect of treatment using Compound 1 alone and in the presence of tamoxifen and expomicin, at 100 nM, 10 μM, and 1 μM respectively.

Example 9. Compounds of the Present Disclosure Demonstrate Selectivity for Cells with Estrogen Receptor Alpha MCF-7 cells were maintained in high glucose DMEM (Corning cellgro, 15-013-CM) supplemented with 10% FBS, 1× L-Glutamine (29.2 mg/mL), and Penicilin Streptomycin (10,000 I.U./mL Penicillin; 10,000 μg/mL Streptomycin; Corning, 30-009-CI). These cells were plated into 24-well plates at 2×10⁴ cells/well, and the following day Compound 1

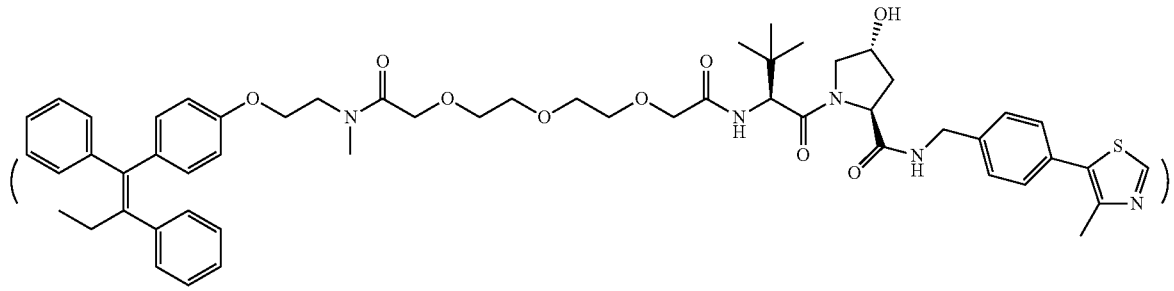

was added to the medium at various concentrations (1 μM, 100 nM, 10 nM, and 1 nM), with each concentration being added in quadruplicate. At each 24 hour time point, one set of cells at each concentration was trypsinized and mixed with 0.4% trypan blue solution (Corning, 25-900-CI) 1:1 (v/v). The live cells were counted under a microscope using a hemocytometer. The same procedure was repeated using the triple negative breast cancer cell line MDA-MB-231.

Figure 10A:
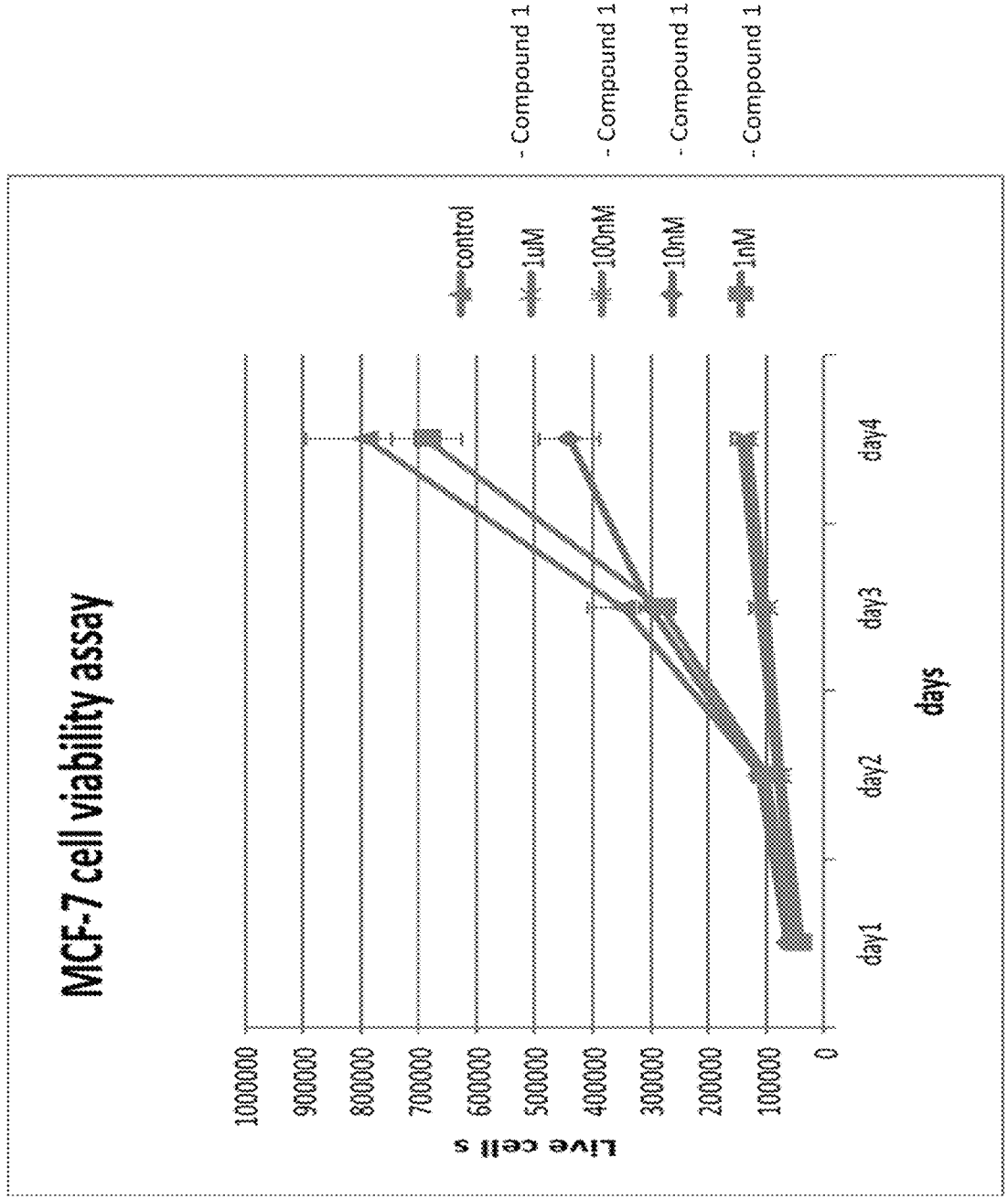
FIG. 10A illustrates the anti-proliferation activity of a compound of the present disclosure toward the Estrogen Receptor alpha positive cell line MCF-7.
Figure 10B:
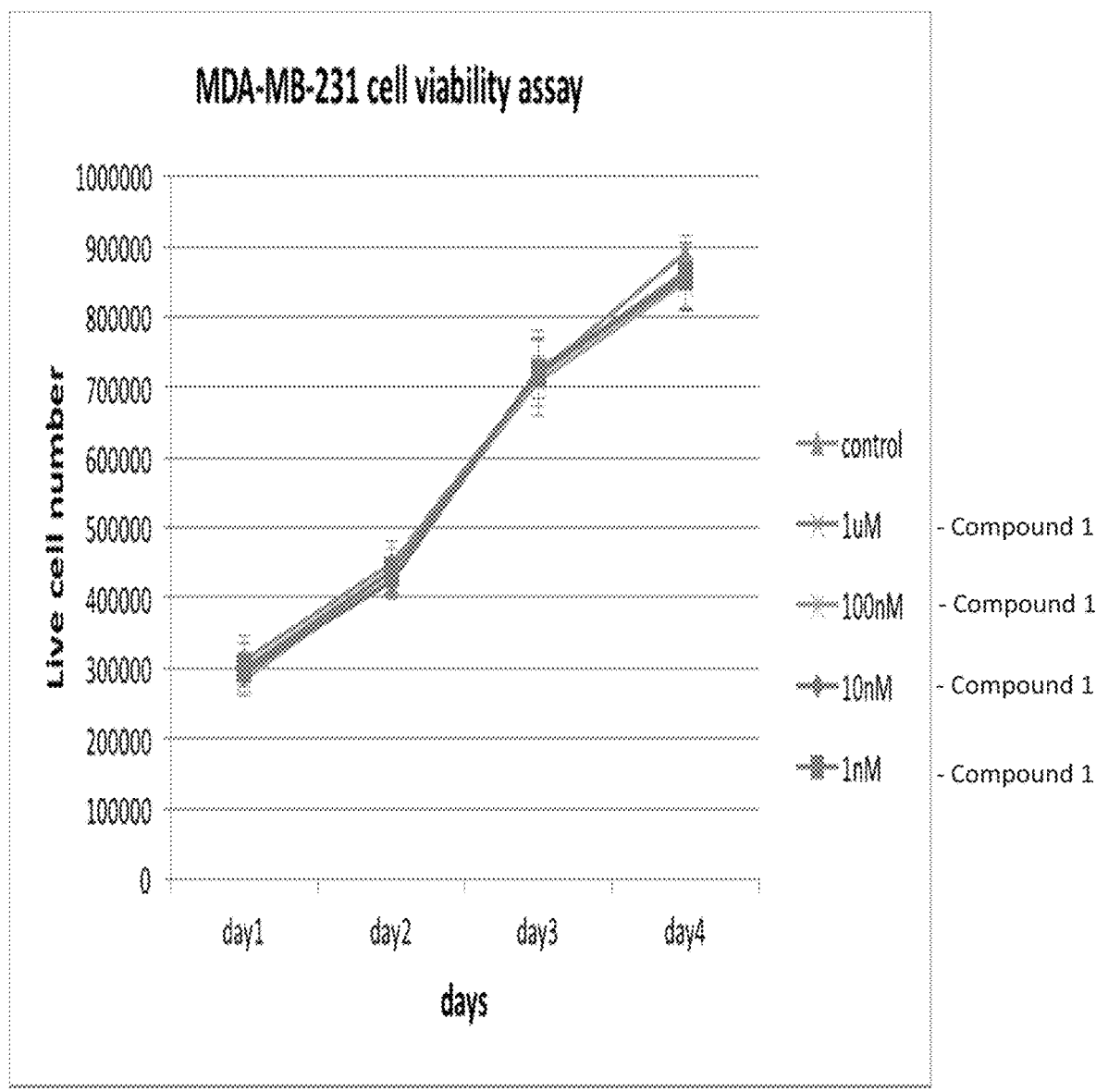
FIG. 10B illustrates the lack of anti-proliferation activity toward the triple negative (i.e., Estrogen Receptor alpha negative breast cancer MB-231 cell line.

FIGS. 11A and 10B demonstrate the compounds of the present disclosure for cells that are selective for Estrogen Receptor alpha positive (10A) over Estrogen Receptor alpha negative (10B).

Figure 11:
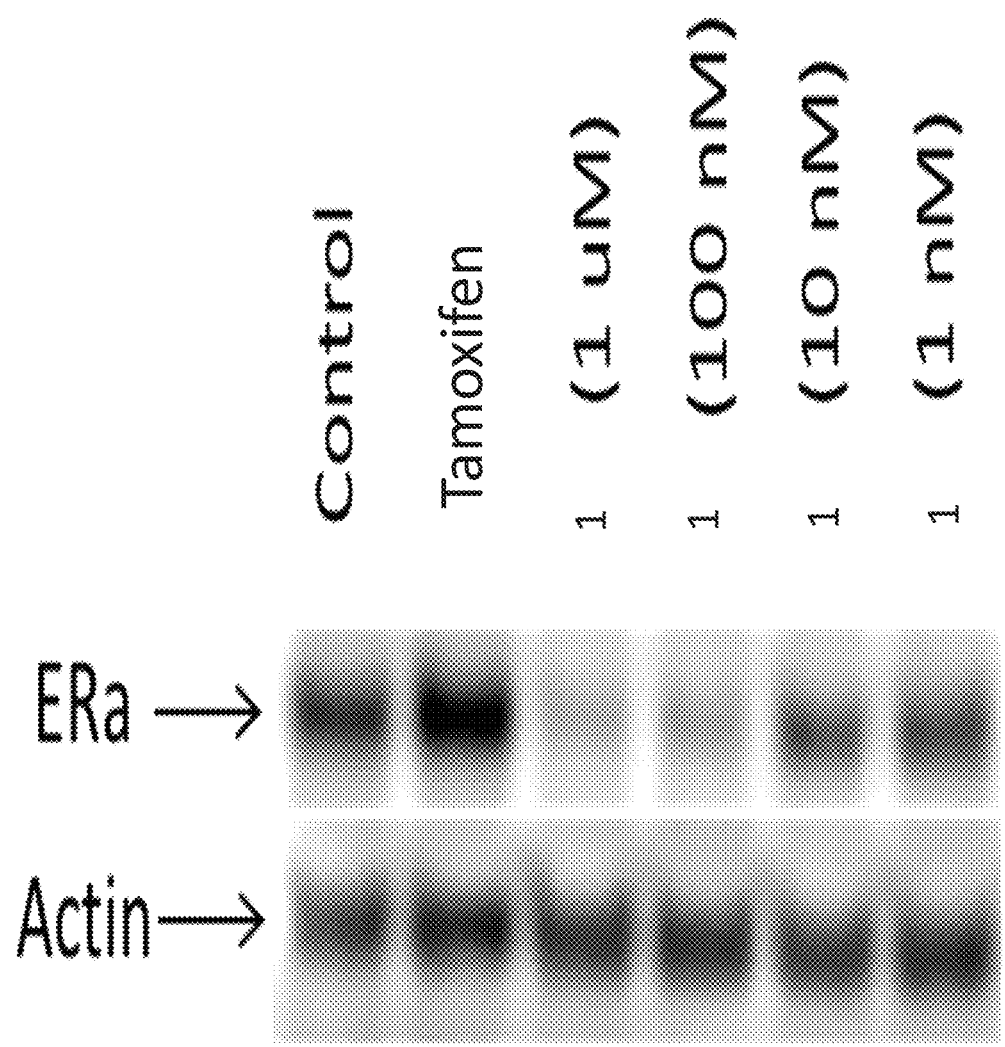
FIG. 11 illustrates the degradative activity of a compound of the present disclosure in another Estrogen Receptor alpha positive cell line T-47D.

Example 10. Compounds of the Present Disclosure are Active Against Other Cell Types that are Positive for Estrogen Receptor Alpha T47D cells were maintained in RPMI 1640, supplemented with 10% FBS, 1× L-Glutamine (29.2 mg/mL), and Penicillin Streptomycin (10,000 I.U./mL Penicillin; 10,000 μg/mL Streptomycin; Corning, 30-009-CI) and 5 μg/mL Bovine insulin. The resulting T47D cells were plated into a 24-well plate at 1×10⁵ cells/well, and the following day, compound was added to the cell medium at various concentrations. After treating the cell medium with compound, the cell plates were incubated for 20 hours. Upon cooling, cells were lysed. The resulting cell lysates were subjected to immunoblotting by standard protocol with primary antibodies of mouse anti-human ERα monoclonal antibody (Santa Cruz Biotechnology Inc., #SC-8002) and 1:1000 goat anti-human actin polyclonal antibody (Santa Cruz Biotechnology Inc. #sc-1616). Western blot results visualized using picoLUCENT™ PLUS-HRP ECL (G Biosciences, 786-165) and LI-COR C digit imaging system. FIG. 11 shows the effect induce by Compound 1 on Estrogen Receptor alpha degradation at various concentrations.

Example 11. Pharmacokinetic Study of a Compound of the Present Disclosure

Compound 1

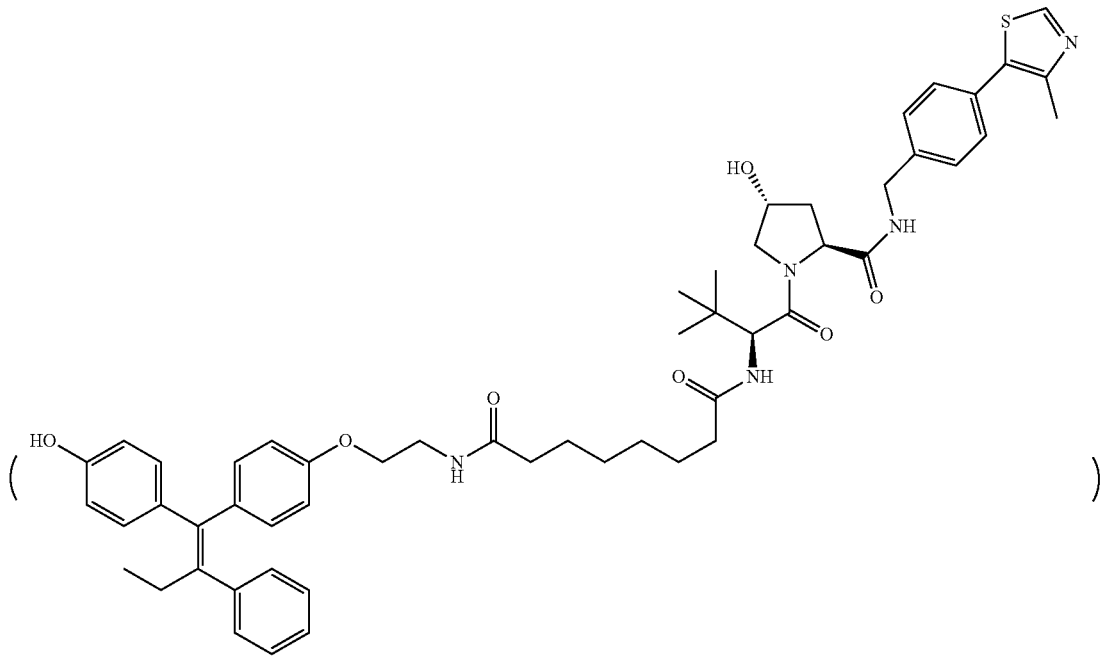

was formulated as shown in Table 6.

TABLE 6

Formulations of Compound 1 for oral administration.

| Component | Formulation 1 (5 mg/mL) | Formulation 2 (5 mg/mL) | Formulation 3 (5 mg/mL) |
|---|---|---|---|
| Compound 1 | 5.24 mg | 5.44 mg | 5.20 mg |
| DMSO | — | — | 0.051 mL |
| Ethanol | 0.103 mL | 0.107 mL | — |
| Captisol | 0.103 mL | — | — |
| PEG-400 | — | — | 0.408 mL |
| Sesame oil | 0.821 mL | 0.960 mL | — |
| 0.1% Tween 80 in deionized water | — | — | 0.561 mL |

Nine mice were divided into three groups, with three mice per group. Each mouse was orally administered one of the formulations described above, at 50 mg/kg. The dosing volume administered was 10 mL/kg. Group 1 was administered Formulation 1, and the mice in group 1 were in a fed state. Group 2 was administered Formulation 2, and the mice in group 2 were in a fasted state. Group 3 was administered Formulation 3, and the mice in group 3 were in a fed state.

After administration, blood samples were collected from each mouse at 0.25, 1, 2, and 4 hours. The samples were collected with $K_2EDTA$ as an anticoagulant (10 µL of 20% $K_2EDTA$ of solution per mL of blood). The plasma was immediately isolated via centrifugation and stored at −70±10° C., until analyzed using LC/MS.

Figure 12:
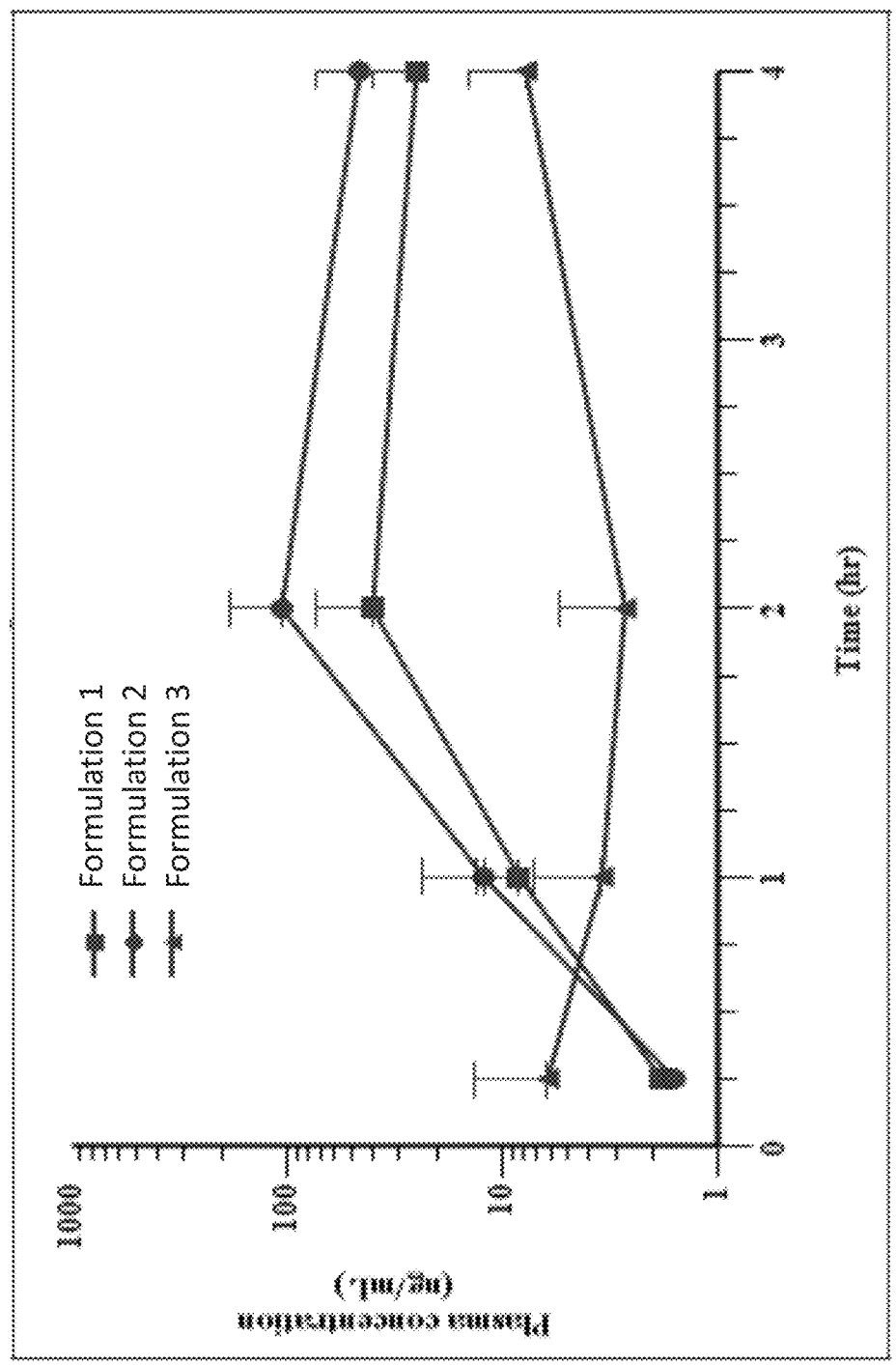
FIG. 12 illustrates the plasma concentration of Compound 1 as a function of time after administration of various formulations.

FIG. 12 (semi-log scale) shows that administration of Formulations 1 and 2 resulted in appreciable amounts of Compound 1 in the blood at the 4 hour time point. Table 7 shows the pharmacokinetic parameters for the various formulations.

TABLE 7

Pharmacokinetic parameters of oral administration of Formulations 1, 2, and 3.

| Formulation | $T_{max}$ (hr) | $C_{max}$ (ng/mL) | $AUC_{last}$ (hr * ng/mL) |
|---|---|---|---|
| 1 | 2 | 40.24 | 93.51 |
| 2 | 2 | 105.74 | 216.24 |
| 3 | 4 | 7.85 | 18.09 |

Example 12. Measurement of Estrogen Receptor Alpha Expression in MCF-7 Breast Cancer Xenoraft Model Animal experiments were performed according to the guidelines approved by the Institutional Animal Care and Use Committee (IACUC) following the guidance of the Association for Assessment and Accreditation of Laboratory Animal Care (AAALAC).

For the short time challenge assay, female BALB/c nude mice (with supplemental 17-β estradiol) bearing MCF-7 tumors (mean tumor volume 200 mm³) were treated with Compound 1 (5 mg/kg, 3 doses/day, i.p.) in vehicle or by vehicle only for 1 day. (The vehicle solution is: 10% Ethanol, 20% Solutol, 20% PG, 50% Captisol. At the end of the 1-day treatment, tumor tissues from each animal were collected and subjected to western blot analysis for ERα and Actin.

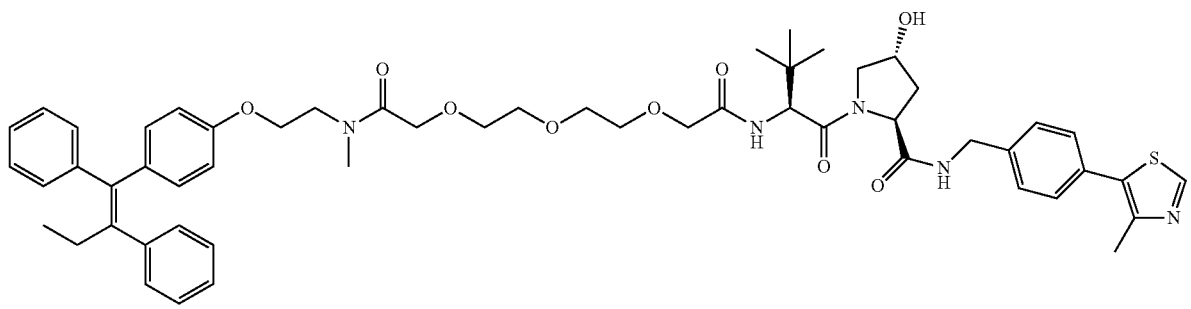

Compound 1

For the tumor growth inhibition study, female BALB/c nude mice (with supplemental 17-β estradiol) bearing MCF-7 tumors (mean tumor volume 211 mm³) were i.p. treated with Accutar-153 (10 mg/day) in vehicle or by vehicle only for 3 weeks. Body weight and tumor volume (tumor volume=[length×width²]/2) were monitored twice weekly. At the end of study, plasma, tumor tissues and organs (brain, liver, kidney) for each animal were collected for further analysis.

Figure 13:
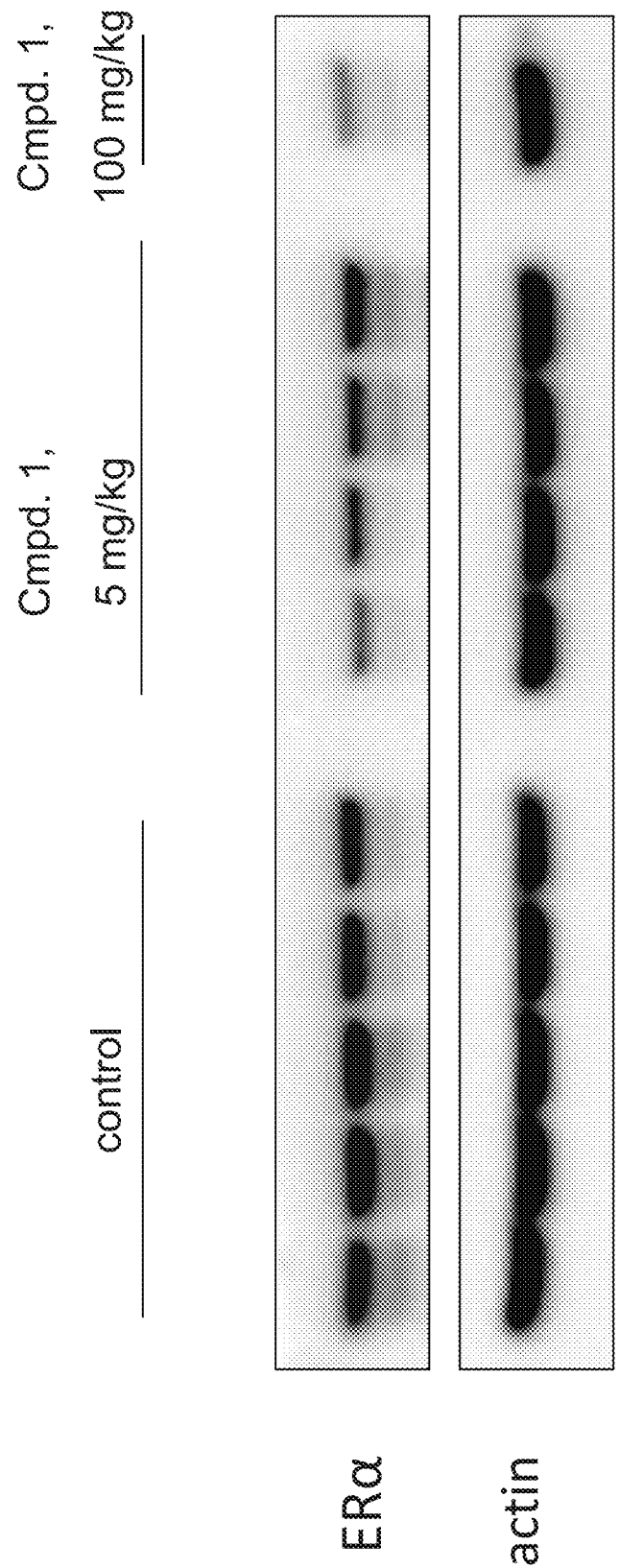
FIG. 13 illustrates the Estrogen Receptor alpha degradation in a tumor.

As shown in FIG. 13, administration of Compound 1 at 100 mg/kg resulted in a 90% decrease in Estrogen Receptor alpha expression, demonstrating that compounds of the present disclosure can penetrate the tissue of various organs.

Example 13. Compounds of the Present Disclosure Inhibit Cancer Cell Growth in a MCF-7 Breast Cancer-Derived Mouse Xenograft Model Female BALB/c nude mice (supplemented with 17-β estradiol) bearing MCF-7 tumors (mean tumor volume was 211 mm³) were treated with the compound:

(10 mg/day, i.p.) in vehicle, or by vehicle only, for 3 weeks. Body weight and tumor volume (tumor volume=[length×width²]/2) were monitored twice weekly. At the end of study, plasma, tumor tissues and organs (brain, liver, kidney) for each animal were collected for further analysis. The tumor growth inhibition studies were performed twice.

Figure 14A:
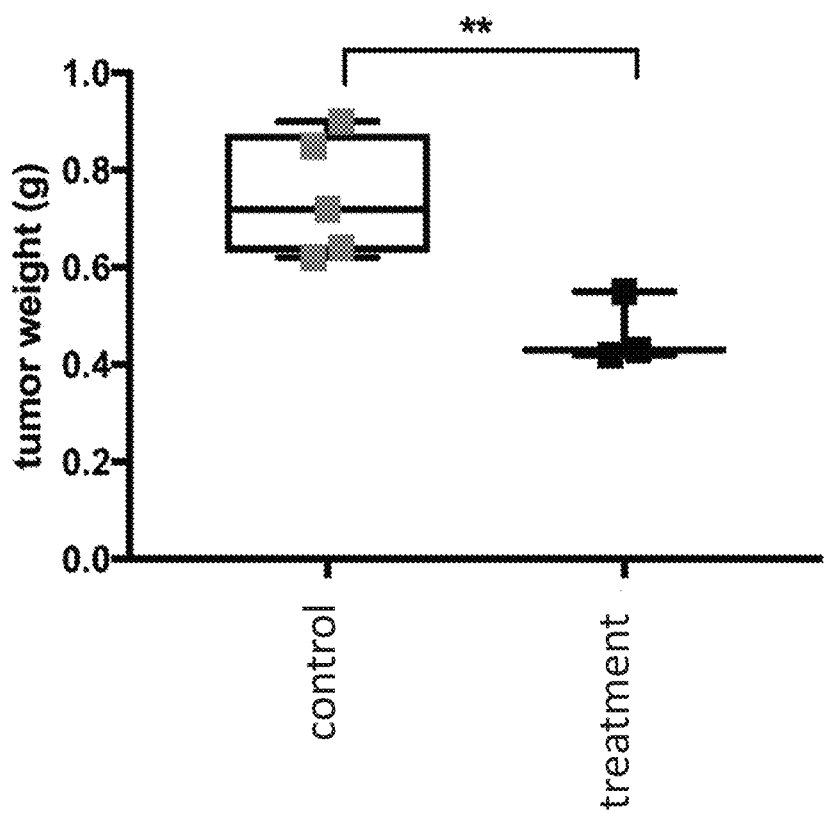
FIGS. 14A, 14B, and 14C show the effect of treatment on tumor weight and volume.
Figure 14B:
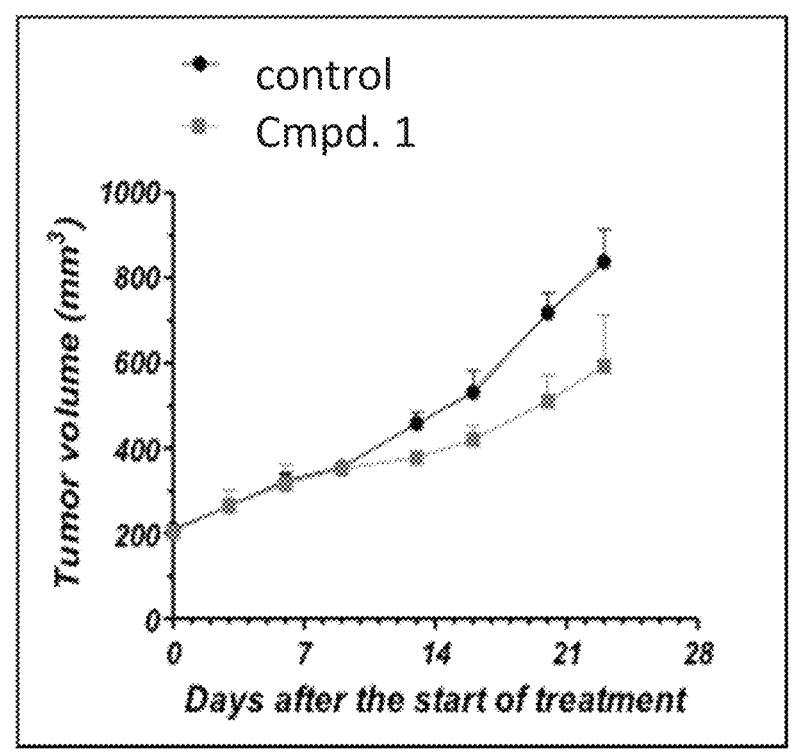
Figure 14C:
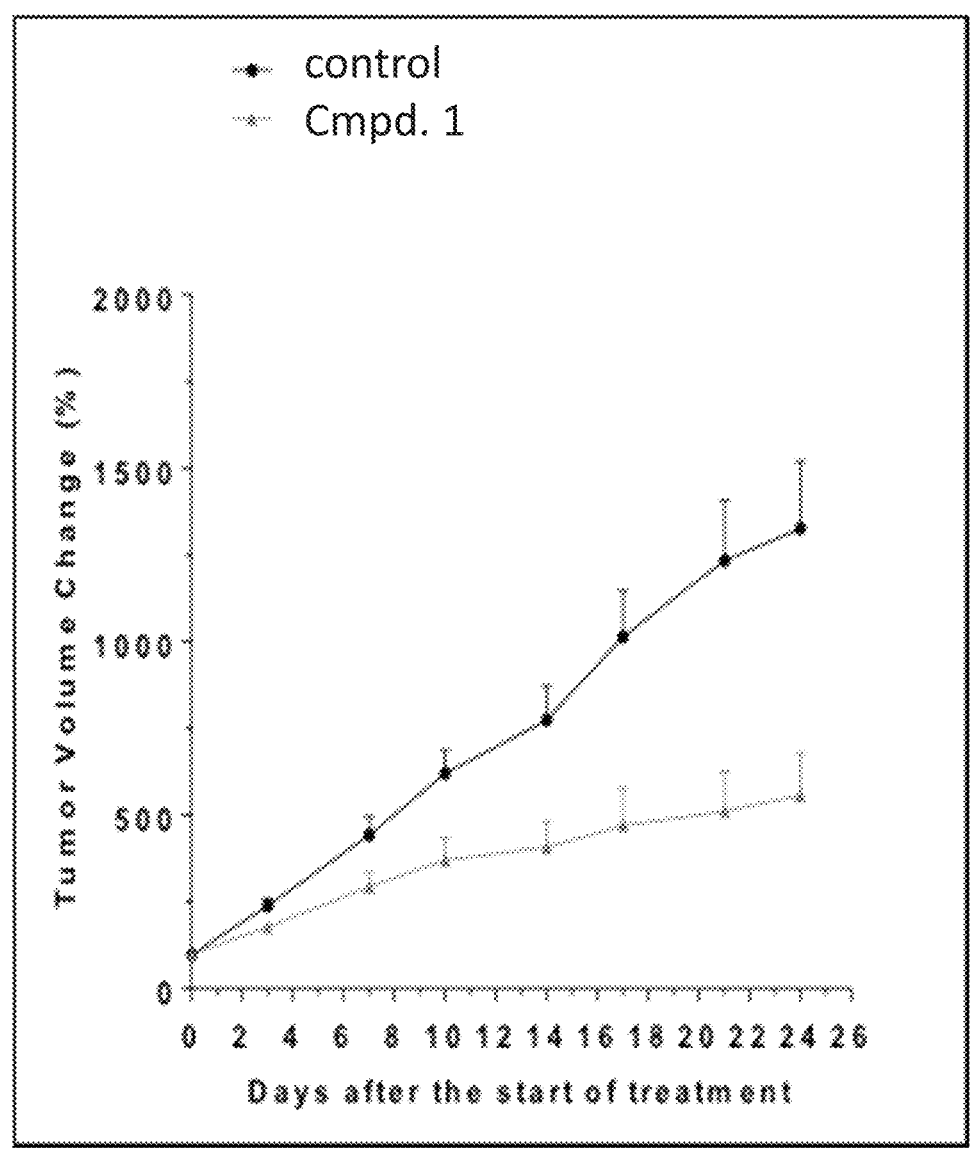

FIG. 14A shows a significant decrease in tumor weight for the mice in the treatment group versus the mice in the control group. Similarly, FIGS. 14B and 14C show tumor volume and tumor volume percent change, respectively, as a function of time for the mice in the treatment group versus mice in the control group.

Example 14. Assessment of Compound Activity in Tamoxifen-Resistant Tumor Cells In a long-term estrogen deprived (LTED) cell line based cell proliferation assay, a tamoxifen-resistant cell line, the inhibitory activity of Compound 1,

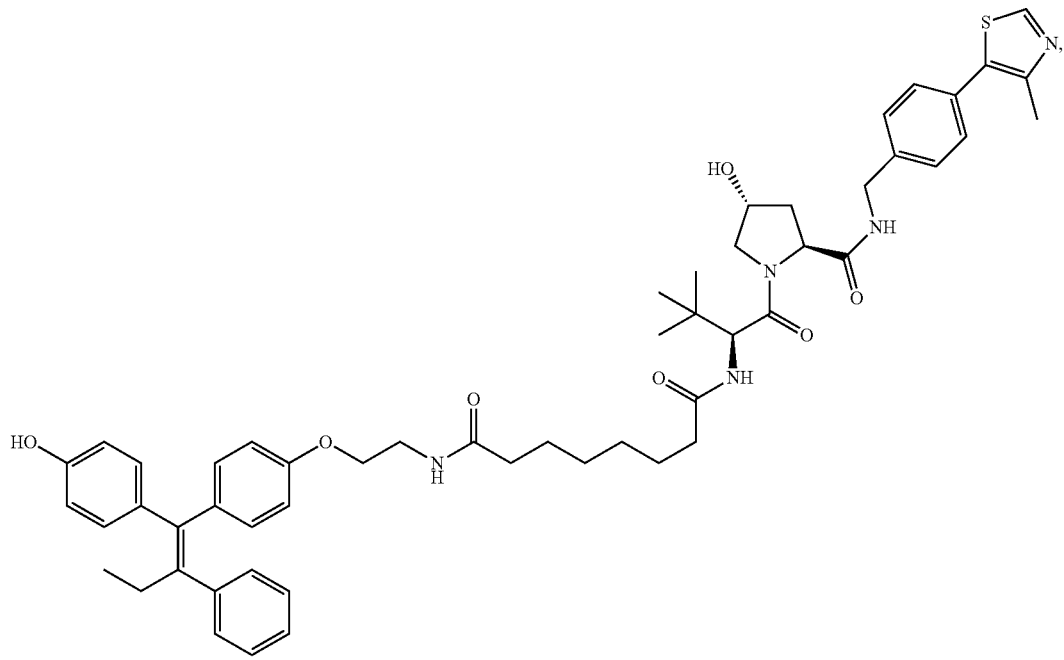 [SMILES: CC/C(=C(\c1ccc(O)cc1)c1ccc(OCCNC(=O)CCCCCCC(=O)N[C@H](C(=O)N2C[C@H](O)C[C@H]2C(=O)NCc2ccc(-c3scnc3C)cc2)C(C)(C)C)cc1)c1ccccc1]

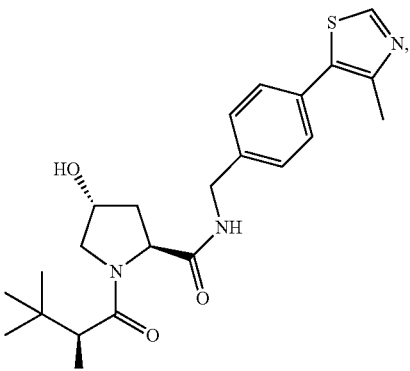
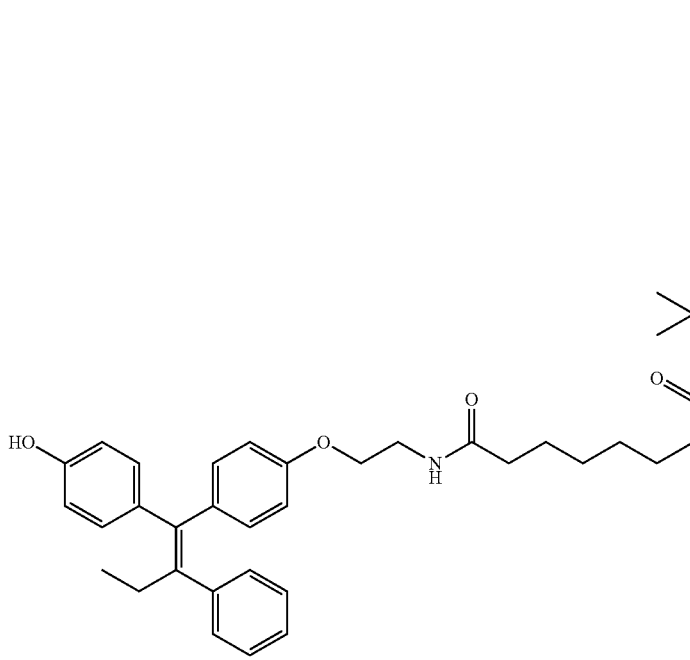

was compared with that of tamoxifen and fulvestrant. LTED cells were plated into 96-well plates at $0.3 \times 10^4$ cells/well and assayed for 4 days. Compounds were added to medium at different final concentrations as indicated in the results. Media were replaced each day during compound exposure.

The relative cell number was determined using the Cell Titer Glo reagent (Promega) for cell viability assay according to the protocol. After compound exposure, Cell Titer Glo (100 μL) was added to the cells, and the relative luminescence units (RLU) of each well were determined. CellTiter-Glo (100 μL) was added to medium without cells to obtain a background value. The luminescence was determined by a luminometer (Perkin Elmer EnSpire). The relative viability (in percentage) of each sample was determined according to the equation:

$$((RLU_{sample} - RLU_{background})/(RLU_{untreated} - RLU_{background})) \times 100 = \text{\%-viability}$$

Figure 15A:
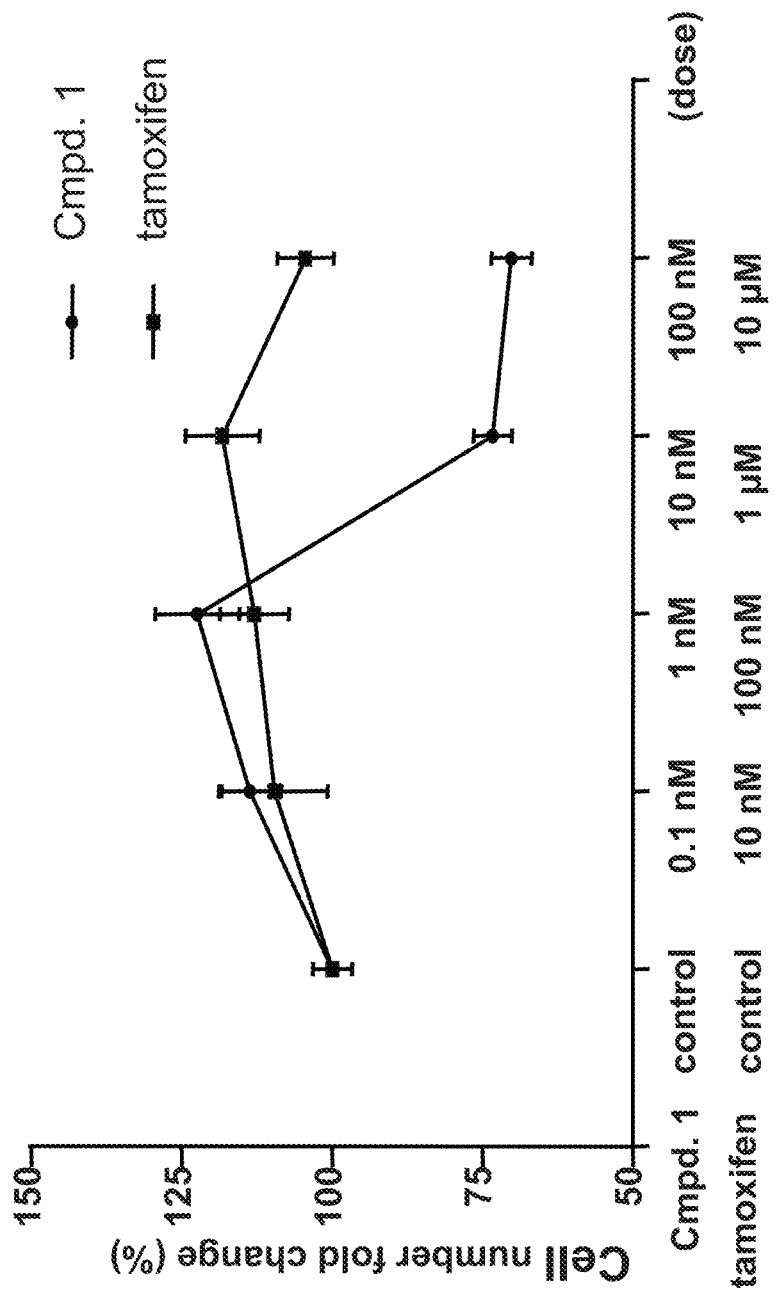
FIG. 15A illustrates the effect on cell proliferation after administration of either Compound 1 or tamoxifen.
Figure 15B:
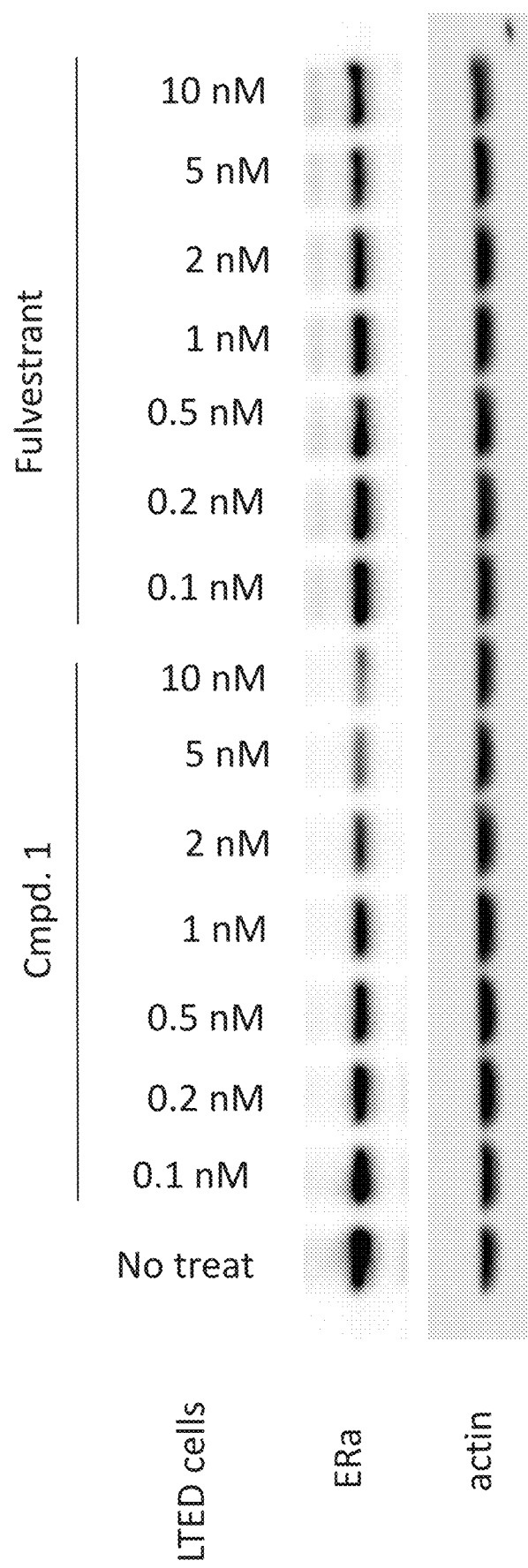
FIG. 15B illustrates the effect on Estrogen Receptor alpha degradation after administration of either Compound 1 or tamoxifen.

FIG. 15A shows change in cell number as a function of inhibitor concentration. FIG. 15B shows change in Estrogen Receptor alpha expression as a function of inhibitor concentration.

OTHER EMBODIMENTS

Embodiment 1

A compound of Formula (I), and pharmaceutically acceptable salts thereof:

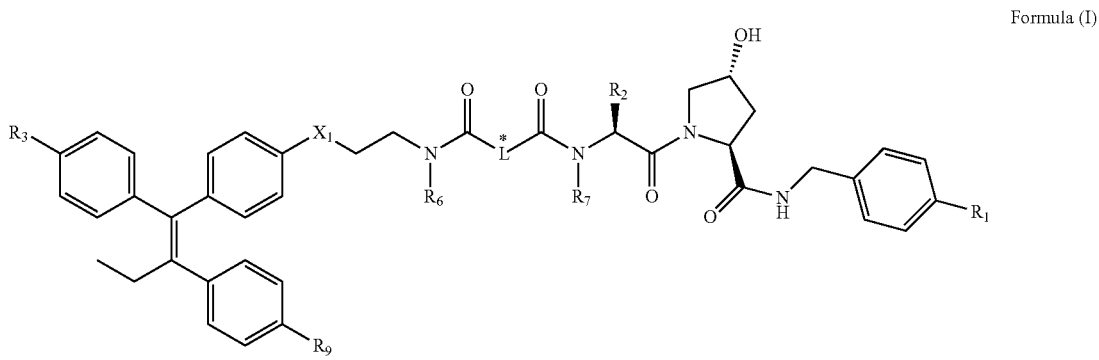

Formula (I)

wherein $X^1$ is selected from $CH_2$, $NR^8$, O, and S;

$R^1$ is selected from H, $C_1$-$C_6$ alkyl, halo, heterocycle, and heteroaryl, each of which is substituted with 0, 1, 2, or 3 $R^5$;

$R^2$ is selected from H, $C_1$-$C_6$ alkyl, and $C_3$-$C_6$ cycloalkyl, each of which is substituted with 0, 1, 2, or 3 $R^5$;

$R^3$ is selected from H, $C_1$-$C_6$ alkyl, halo, hydroxy, and sulfhydryl, each of which is substituted with 0, 1, 2, or 3 $R^5$;

$R^4$ is selected from H, $C_1$-$C_6$ alkyl, and acyl, each of which is substituted with 0, 1, 2, or 3 $R^5$;

each $R^5$ is independently selected from $C_1$-$C_6$ alkyl, halo, cyano, and hydroxy;

$R^6$, $R^7$, and $R^8$ are each independently selected from H, $C_1$-$C_6$ alkyl, and acyl, each of which is substituted with 0, 1, 2, or 3 $R^5$;

$R^9$ is selected from H, $C_1$-$C_6$ alkyl, halo, hydroxy, and sulfhydryl, each of which is substituted with 0, 1, 2, or 3 $R^5$; and L* is a linker of 1 to 16 carbon atoms in length, wherein one or more carbon atoms are optionally replaced by C(O), O, $NR^4$, S, $C_2$-alkenyl, $C_2$-alkynyl, cycloalkyl, aryl, heterocycle, or heteroaryl.

Embodiment 2

The compound according to embodiment 1, wherein L* is

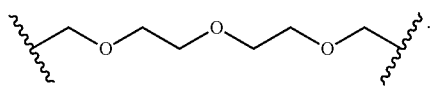

Embodiment 3

The compound according to Embodiment 1, wherein L* is

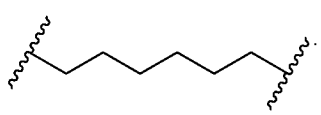 [SMILES: *CCCCCC*]

Embodiment 4

The compound according to Embodiment 1, wherein L* is a linker of 6 to 16 carbon atoms in length.

Embodiment 5

The compound according to Embodiment 1, wherein L* is a linker of 9 to 10 carbon atoms in length.

Embodiment 6

The compound according to Embodiment 1, wherein L* is a linker of 6 to 7 carbon atoms in length.

Embodiment 7

A compound of Formula (II), and pharmaceutically acceptable salts thereof:

Formula (II)

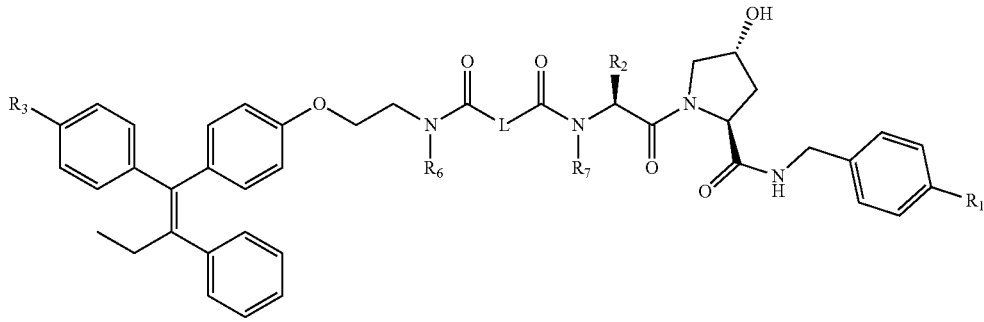

wherein:

$R^1$ is selected from H, $C_1$-$C_6$ alkyl, halo, heterocycle, and heteroaryl, each of which is substituted with 0, 1, 2, or 3 $R^5$;

$R^2$ is selected from H, $C_1$-$C_6$ alkyl, and $C_3$-$C_6$ cycloalkyl, each of which is substituted with 0, 1, 2, or 3 $R^5$;

$R^3$ is selected from H, $C_1$-$C_6$ alkyl, halo, and hydroxy, each of which is substituted with 0, 1, 2, or 3 $R^5$;

$R^4$ is selected from H, $C_1$-$C_6$ alkyl, and acyl, each of which is substituted with 0, 1, 2, or 3 $R^5$;

each $R^5$ is independently selected from $C_1$-$C_6$ alkyl, halo, cyano, and hydroxy;

$R^6$ and $R^7$ are each independently selected from H, $C_1$-$C_6$ alkyl, and acyl, each of which is substituted with 0, 1, 2, or 3 $R^5$; and L is a linker of 6 to 16 carbon atoms in length, wherein one or more carbon atoms are optionally replaced by O, $NR^4$, S, $C_2$-alkenyl, $C_2$-alkynyl, cycloalkyl, aryl, heterocycle, or heteroaryl.

Embodiment 8

A compound of Formula (III), and pharmaceutically acceptable salts thereof:

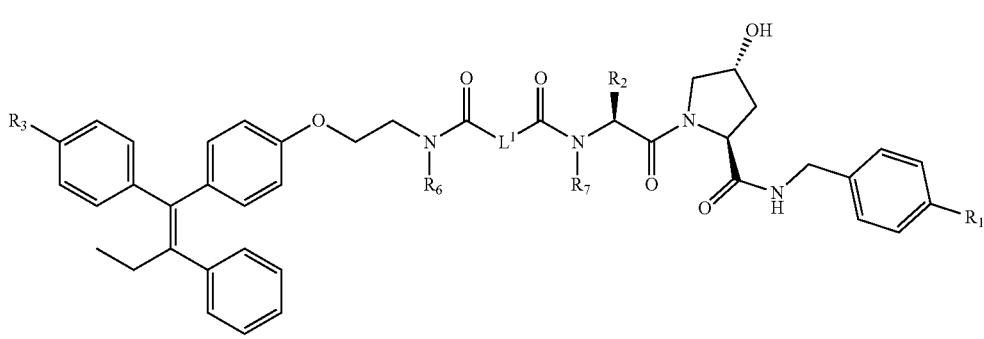
Formula (III)

wherein:

R[1] is selected from H, $C_1$-$C_6$ alkyl, halo, heterocycle, and heteroaryl, each of which is substituted with 0, 1, 2, or 3 R[5];

R[2] is selected from H, $C_1$-$C_6$ alkyl, and $C_3$-$C_6$ cycloalkyl, each of which is substituted with 0, 1, 2, or 3 R[5];

R[3] is selected from H, $C_1$-$C_6$ alkyl, halo, and hydroxy, each of which is substituted with 0, 1, 2, or 3 R[5];

R[4] is selected from H, $C_1$-$C_6$ alkyl, and acyl, each of which is substituted with 0, 1, 2, or 3 R[5];

each R[5] is independently selected from $C_1$-$C_6$ alkyl, halo, cyano, and hydroxy;

R[6] and R[7] are each independently selected from H, $C_1$-$C_6$ alkyl, and acyl, each of which is substituted with 0, 1, 2, or 3 R[5]; and L[1] is a linker of 9 to 10 carbon atoms in length, wherein one or more carbon atoms are optionally replaced by O, NR[4], S, $C_2$-alkenyl, $C_2$-alkynyl, cycloalkyl, aryl, heterocycle, or heteroaryl.

Embodiment 9

The compound according to embodiment 2, wherein L[1] is

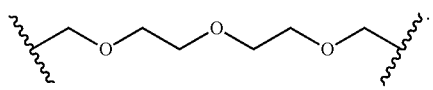 [SMILES: *COCCOCCOC*]

Embodiment 10

A compound of Formula (IV), and pharmaceutically acceptable salts thereof:

wherein:

R[1] is selected from H, $C_1$-$C_6$ alkyl, halo, heterocycle, and heteroaryl, each of which is substituted with 0, 1, 2, or 3 R[5];

R[2] is selected from H, $C_1$-$C_6$ alkyl, and $C_3$-$C_6$ cycloalkyl, each of which is substituted with 0, 1, 2, or 3 R[5];

R[3] is selected from H, $C_1$-$C_6$ alkyl, halo, and hydroxy, each of which is substituted with 0, 1, 2, or 3 R[5];

R[4] is selected from H, $C_1$-$C_6$ alkyl, and acyl, each of which is substituted with 0, 1, 2, or 3 R[5];

each R[5] is independently selected from $C_1$-$C_6$ alkyl, halo, cyano, and hydroxy;

R[6] and R[7] are each independently selected from H, $C_1$-$C_6$ alkyl, and acyl, each of which is substituted with 0, 1, 2, or 3 R[5]; and L[2] is a linker of 6 to 7 carbon atoms in length, wherein one or more carbon atoms are optionally replaced by O, NR[4], S, $C_2$-alkenyl, $C_2$-alkynyl, cycloalkyl, aryl, heterocycle, or heteroaryl.

Embodiment 11

The compound according to embodiment 10, wherein L[2] is

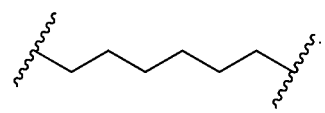

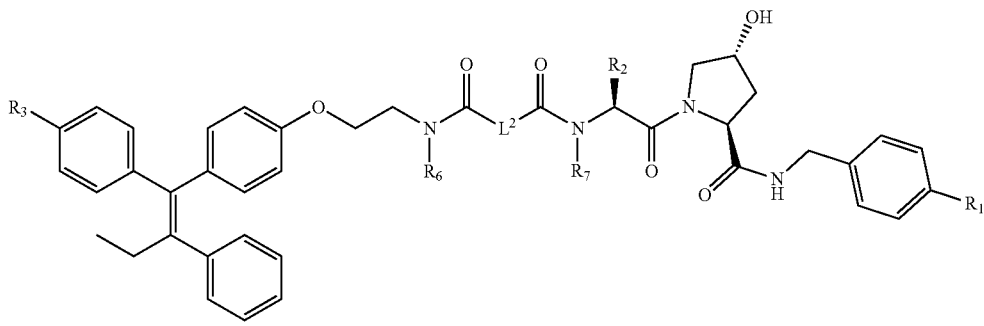
Formula (IV)

Embodiment 12

The compound according to embodiment 7, wherein L contains at least one O atom.

Embodiment 13

The compound according to embodiment 7, wherein L contains at least one aryl.

Embodiment 14

The compound according to embodiment 7, wherein L contains at least one $C_2$-alkenyl.

Embodiment 15

The compound according to embodiment 7, wherein L contains at least one $C_2$-alkynyl.

Embodiment 16

The compound according to embodiment 7, wherein L contains at least one 5-membered heteroaryl.

Embodiment 17

The compound according to embodiment 16, wherein the at least one 5-membered heteroaryl is a triazole.

Embodiment 18

The compound according to embodiment 8, wherein $L^1$ contains at least one O atom.

Embodiment 19

The compound according to embodiment 8, wherein $L^1$ contains at least one aryl.

Embodiment 20

The compound according to embodiment 8, wherein L contains at least one $C_2$-alkenyl.

Embodiment 21

The compound according to embodiment 8, wherein L contains at least one $C_2$-alkynyl.

Embodiment 22

The compound according to embodiment 8, wherein L contains at least one 5-membered heteroaryl.

Embodiment 23

The compound according to embodiment 22, wherein the at least one 5-membered heteroaryl is a triazole.

Embodiment 24

The compound according to embodiment 10, wherein $L^2$ contains at least one O atom.

Embodiment 25

The compound according to embodiment 10, wherein $L^2$ contains at least one aryl.

Embodiment 26

The compound according to embodiment 10, wherein $L^2$ contains at least one $C_2$-alkenyl.

Embodiment 27

The compound according to embodiment 10, wherein $L^2$ contains at least one $C_2$-alkynyl.

Embodiment 28

The compound according to embodiment 10, wherein $L^2$ contains at least one 5-membered heteroaryl.

Embodiment 29

The compound according to embodiment 28, wherein the at least one 5-membered heteroaryl is a triazole.

Embodiment 30

The compound according to any one of embodiment 1-29, wherein $R^1$ is selected from halo and heteroaryl.

Embodiment 31

The compound according to embodiment 30, wherein $R^1$ is 5-membered heteroaryl.

Embodiment 32

The compound according to embodiment 30, wherein $R^1$ is methylthiazole.

Embodiment 33

The compound according to embodiment 30, wherein $R^1$ is 4-methylthiazole.

Embodiment 34

The compound according to embodiment 30, wherein $R^1$ is

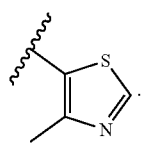 [SMILES: *c1scnc1C]

Embodiment 35

The compound according to any one of embodiments 1-34, wherein $R^2$ is $C_1$-$C_6$ alkyl.

Embodiment 36

The compound according to embodiment 35, wherein $R^2$ is tert-butyl.

Embodiment 37

The compound according to embodiment 35, wherein $R^2$ is iso-propyl.

Embodiment 38

The compound according to any one of embodiments 1-37, wherein $R^3$ is H.

Embodiment 39

The compound according to any one of embodiments 1-37, wherein $R^3$ is $C_1$-$C_6$ alkyl.

Embodiment 40

The compound according to any one of embodiments 1-37, wherein $R^3$ is hydroxy.

Embodiment 41

The compound according to any one of embodiments 1, 7, 8, 10, and 12-38, wherein $R^4$ is H.

Embodiment 42

The compound according to any one of embodiments 1, 7, 8, 10, and 12-38, wherein $R^4$ is $C_1$-$C_3$ alkyl.

Embodiment 43

The compound according to embodiment 42, wherein the $C_1$-$C_3$ is methyl.

Embodiment 44

The compound according to any one of embodiments 1, 7, 8, 6, and 12-38, wherein $R^4$ is acyl.

Embodiment 45

The compound according to embodiment 44, wherein the acyl is acetyl.

Embodiment 46

The compound according to any one of embodiments 1-45, wherein $R^6$ is $C_1$-$C_3$ alkyl.

Embodiment 47

The compound according to embodiment 46, wherein the $C_1$-$C_3$ alkyl is methyl.

Embodiment 48

The compound according to any one of embodiments 1-45, wherein $R^6$ is H.

Embodiment 49

The compound according to any one of embodiments 1-48, wherein $R^7$ is selected from H and $C_1$-$C_3$ alkyl.

Embodiment 50

The compound according to embodiment 48, wherein $R^7$ is H.

Embodiment 51

The compound according to embodiment 48, wherein $R^7$ is $C_1$-$C_3$ alkyl.

Embodiment 52

The compound according to embodiment 51, wherein the $C_1$-$C_3$ alkyl is methyl.

Embodiment 53

The compound according to embodiment 9, wherein the compound is:

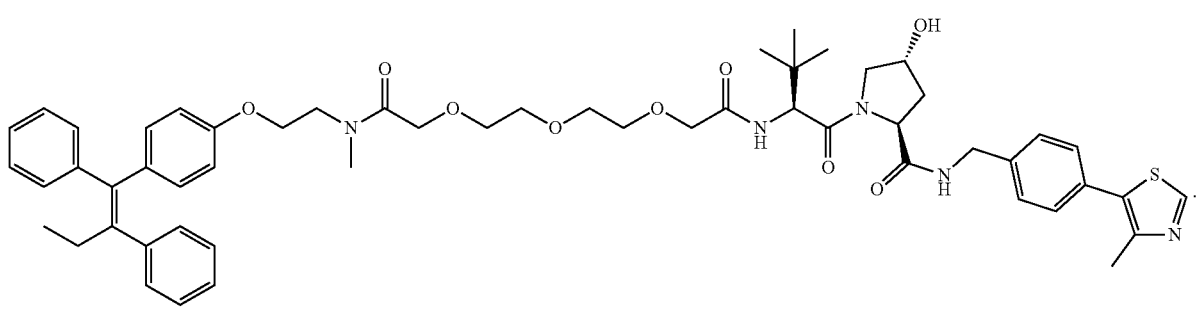 [SMILES: CC/C(=C(\c1ccccc1)c1ccc(OCCN(C)C(=O)COCCOCCOCC(=O)N[C@H](C(=O)N2C[C@H](O)C[C@H]2C(=O)NCc2ccc(-c3scnc3C)cc2)C(C)(C)C)cc1)c1ccccc1]

Embodiment 54
The compound according to embodiment 11, wherein the compound is:
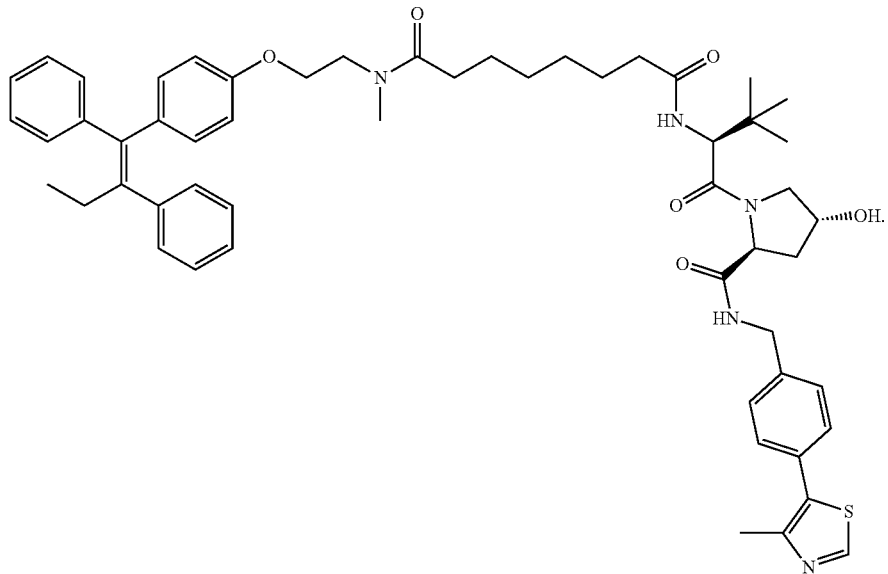 [SMILES: CC/C(=C(\c1ccccc1)c1ccc(OCCN(C)C(=O)CCCCCCC(=O)N[C@H](C(=O)N2C[C@H](O)C[C@H]2C(=O)NCc2ccc(-c3scnc3C)cc2)C(C)(C)C)cc1)c1ccccc1]
Embodiment 55
The compound according to embodiment 11, wherein the compound is:
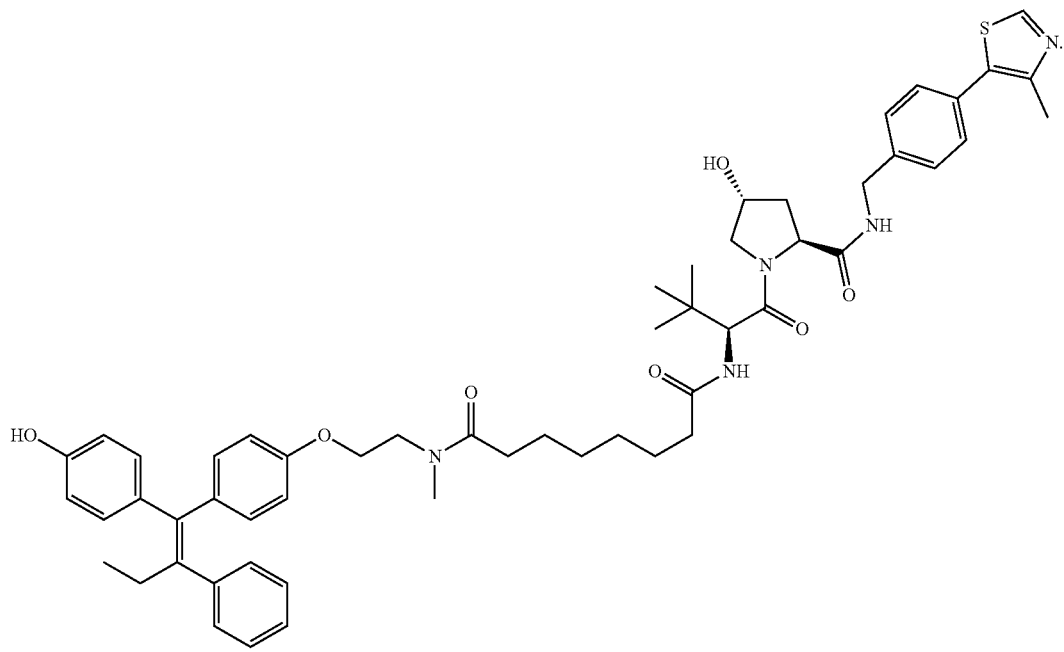 [SMILES: CC/C(=C(\c1ccc(O)cc1)c1ccc(OCCN(C)C(=O)CCCCCCC(=O)N[C@H](C(=O)N2C[C@H](O)C[C@H]2C(=O)NCc2ccc(-c3scnc3C)cc2)C(C)(C)C)cc1)c1ccccc1]
Embodiment 56
The compound according to embodiment 11, wherein the compound is:

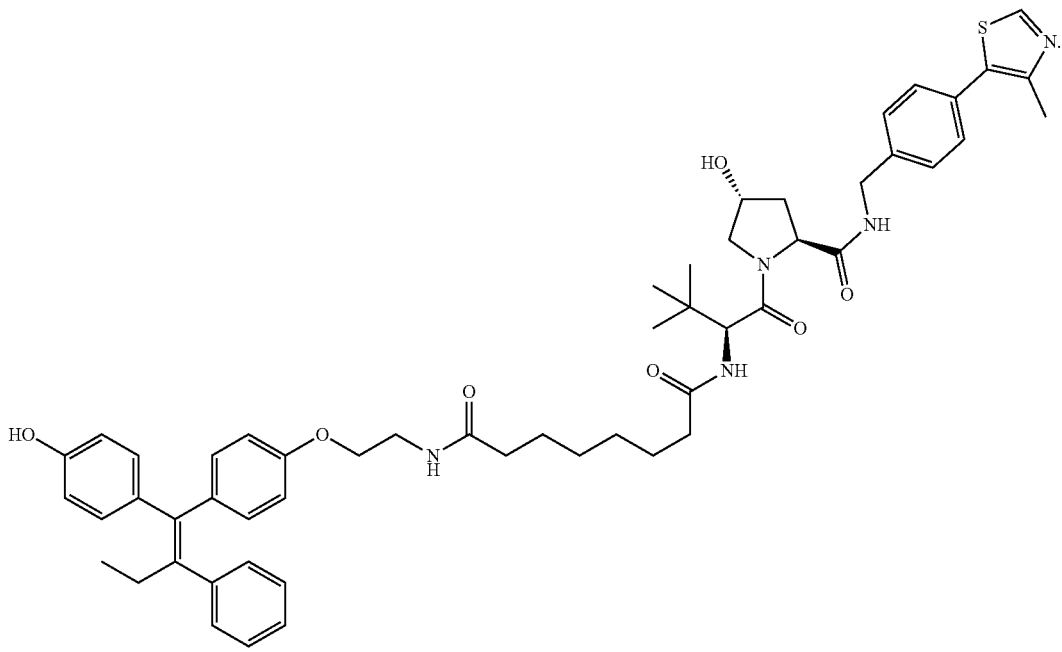 [SMILES: CC/C(=C(\c1ccc(O)cc1)c1ccc(OCCNC(=O)CCCCCCC(=O)N[C@H](C(=O)N2C[C@H](O)C[C@H]2C(=O)NCc2ccc(-c3scnc3C)cc2)C(C)(C)C)cc1)c1ccccc1]

Embodiment 57

A pharmaceutical composition comprising the compound according to any one of embodiments 1-56 and at least one additional component selected from pharmaceutically acceptable carriers, pharmaceutically acceptable vehicles, and pharmaceutically acceptable excipients.

Embodiment 58

The pharmaceutical composition according to embodiment 57, wherein the compound is present in a therapeutically effective amount.

Embodiment 59

A method of treating cancer in a subject in need thereof, comprising administering to said subject an effective amount of the compound according to any one of embodiments 1-56 or of the pharmaceutical composition according to any one of embodiments 57-58, wherein the cancer is chosen from breast cancer, lung cancer, ovarian cancer, endometrial cancer, prostate cancer, and esophageal cancer.

Embodiment 60

The method according to embodiment 59, wherein the cancer is breast cancer.

Embodiment 61

The method according to any one of embodiments 59-60, wherein the cancer is positive for Estrogen Receptor alpha.

Embodiment 62

The method according to any one of embodiments 59-61, wherein the subject has been previously treated with an anti-cancer agent.

Embodiment 63

The method according to embodiment 62, wherein the anti-cancer agent is tamoxifen.

Embodiment 64

A use of the compound according to any one of embodiments 1-56 in a method of therapeutic treatment, wherein said therapeutic treatment is chosen from treatment of breast cancer, lung cancer, ovarian cancer, endometrial cancer, prostate cancer, esophageal cancer, infertility, ovulatory dysfunction, postmenopausal osteoporosis, estrogen-related gynecomastia, dyspareunia due to menopause, retroperitoneal fibrosis, and idiopathic sclerosing mesenteritis.

Embodiment 65

A use of the compound according to any one of embodiments 1-56 in the preparation of a medicament.

Embodiment 66

A method of inhibiting cell growth, comprising contacting a cell with the compound according to any one of embodiments 1-56 or the pharmaceutical composition according to any one of embodiments 57-58.

Embodiment 67

The method according to embodiment 66, wherein the cell is a cancer cell.

Embodiment 68

The method according to any one of embodiments 66-67, wherein the cell expresses Estrogen Receptor alpha.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

What is claimed is:

1. A compound of Formula (I) or tautomer, stereoisomer, pharmaceutically acceptable salt or hydrate thereof:

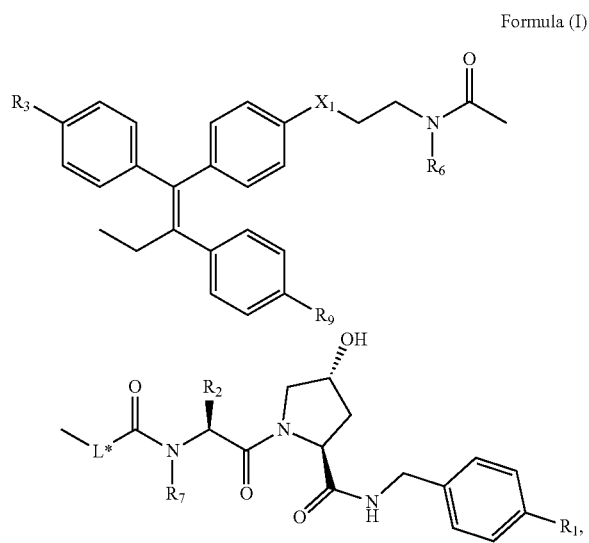

Formula (I)

wherein:
- $X^1$ is selected from $CH_2$, $NR^8$, O, and S;
- $R^1$ is selected from H, $C_1$-$C_6$ alkyl, halo, heterocycle, and heteroaryl, each of which is substituted with 0, 1, 2, or 3 $R^5$;
- $R^2$ is selected from H, $C_1$-$C_6$ alkyl, and $C_3$-$C_6$ cycloalkyl, each of which is substituted with 0, 1, 2, or 3 $R^5$;
- $R^3$ is selected from H, $C_1$-$C_6$ alkyl, halo, hydroxy, and sulfhydryl, each of which is substituted with 0, 1, 2, or 3 $R^5$;
- $R^4$ is selected from H, $C_1$-$C_6$ alkyl, and acyl, each of which is substituted with 0, 1, 2, or 3 $R^5$;
- each $R^5$ is independently selected from $C_1$-$C_6$ alkyl, halo, cyano, and hydroxy;
- $R^6$, $R^7$, and $R^8$ are each independently selected from H, $C_1$-$C_6$ alkyl, and acyl, each of which is substituted with 0, 1, 2, or 3 $R^5$;
- $R^9$ is selected from H, $C_1$-$C_6$ alkyl, halo, hydroxy, and sulfhydryl, each of which is substituted with 0, 1, 2, or 3 $R^5$; and
- L* is a linker of 1 to 16 carbon atoms in length, wherein one or more carbon atoms are optionally replaced by C(O), O, $NR^4$, S, $C_2$-alkenyl, $C_2$-alkynyl, cycloalkyl, aryl, heterocycle, or heteroaryl.

2. The compound according to claim 1, or tautomer, stereoisomer, pharmaceutically acceptable salt or hydrate thereof, wherein L* is

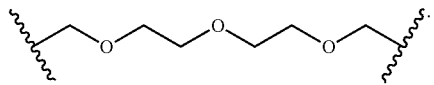 [SMILES: *COCCOCCOC*]

3. The compound according to claim 1, or tautomer, stereoisomer, pharmaceutically acceptable salt or hydrate thereof, wherein L* is

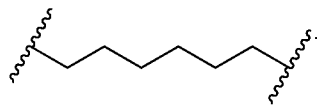 [SMILES: *CCCCCC*]

4. The compound according to claim 1, or tautomer, stereoisomer, pharmaceutically acceptable salt or hydrate thereof, wherein L* is a linker of 6 to 16 carbon atoms in length.

5. The compound according to claim 1, or tautomer, stereoisomer, pharmaceutically acceptable salt or hydrate thereof, wherein L* is a linker of 9 to 10 carbon atoms in length.

6. The compound according to claim 1, or tautomer, stereoisomer, pharmaceutically acceptable salt or hydrate thereof, wherein L* is a linker of 6 to 7 carbon atoms in length.

7. The compound according to claim 1, or tautomer, stereoisomer, pharmaceutically acceptable salt or hydrate thereof, wherein $R^1$ is selected from halo and heteroaryl.

8. The compound according to claim 7, or tautomer, stereoisomer, pharmaceutically acceptable salt or hydrate thereof, wherein $R^1$ is 5-membered heteroaryl.

9. The compound according to claim 8, or tautomer, stereoisomer, pharmaceutically acceptable salt or hydrate thereof, wherein $R^1$ is methylthiazole.

10. The compound according to claim 9, or tautomer, stereoisomer, pharmaceutically acceptable salt or hydrate thereof, wherein $R^1$ is 4-methylthiazole.

11. The compound according to claim 10, or tautomer, stereoisomer, pharmaceutically acceptable salt or hydrate thereof, wherein $R^1$ is

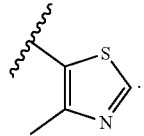 [SMILES: *c1scnc1C]

12. The compound according to claim 1, or tautomer, stereoisomer, pharmaceutically acceptable salt or hydrate thereof, wherein $R^2$ is $C_1$-$C_6$ alkyl.

13. The compound according to claim 12, or tautomer, stereoisomer, pharmaceutically acceptable salt or hydrate thereof, wherein $R^2$ is tert-butyl.

14. The compound according to claim 12, or tautomer, stereoisomer, pharmaceutically acceptable salt or hydrate thereof, wherein $R^2$ is iso-propyl.

15. The compound according to claim 1, or tautomer, stereoisomer, pharmaceutically acceptable salt or hydrate thereof, wherein $R^3$ is H.

16. The compound according to claim 1, or tautomer, stereoisomer, pharmaceutically acceptable salt or hydrate thereof, wherein $R^3$ is $C_1$-$C_6$ alkyl.

17. The compound according to claim 1, or tautomer, stereoisomer, pharmaceutically acceptable salt or hydrate thereof, wherein $R^3$ is hydroxy.

18. The compound according to claim 1, or tautomer, stereoisomer, pharmaceutically acceptable salt or hydrate thereof, wherein $R^4$ is H.

19. The compound according to any claim 1, or tautomer, stereoisomer, pharmaceutically acceptable salt or hydrate thereof, wherein $R^4$ is $C_1$-$C_3$ alkyl.

20. The compound according to claim 19, or tautomer, stereoisomer, pharmaceutically acceptable salt or hydrate thereof, wherein the $C_1$-$C_3$ alkyl is methyl.

21. The compound according to claim 1, or tautomer, stereoisomer, pharmaceutically acceptable salt or hydrate thereof, wherein $R^4$ is acyl.

22. The compound according to claim 21, or tautomer, stereoisomer, pharmaceutically acceptable salt or hydrate thereof, wherein the acyl is acetyl.

23. The compound according to claim 1, or tautomer, stereoisomer, pharmaceutically acceptable salt or hydrate thereof, wherein $R^6$ is $C_1$-$C_3$ alkyl.

24. The compound according to claim 23, or tautomer, stereoisomer, pharmaceutically acceptable salt or hydrate thereof, wherein the $C_1$-$C_3$ alkyl is methyl.

25. The compound according to claim 1, or tautomer, stereoisomer, pharmaceutically acceptable salt or hydrate thereof, wherein $R^6$ is H.

26. The compound according to claim 1, or tautomer, stereoisomer, pharmaceutically acceptable salt or hydrate thereof, wherein $R^7$ is selected from H and $C_1$-$C_3$ alkyl.

27. The compound according to claim 26, or tautomer, stereoisomer, pharmaceutically acceptable salt or hydrate thereof, wherein $R^7$ is H.

28. The compound according to claim 26, or tautomer, stereoisomer, pharmaceutically acceptable salt or hydrate thereof, wherein $R^7$ is $C_1$-$C_3$ alkyl.

29. The compound according to claim 28, or tautomer, stereoisomer, pharmaceutically acceptable salt or hydrate thereof, wherein the $C_1$-$C_3$ alkyl is methyl.

30. The compound according to claim 1, wherein the compound is:

(2S,4R)-1-((S)-2-(tert-butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide;

(2S,4R)-1-((S)-2-(2-(2-(4-(3-((2-(4-((Z)-1,2-diphenylbut-1-en-1-yl)phenoxy)ethyl)(methyl)amino)-3-oxopropyl)-1H-1,2,3-triazol-1-yl)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(4-(2-((2-(4-((Z)-1,2-diphenylbut-1-en-1-yl)phenoxy)ethyl)(methyl)amino)-2-oxoethyl)-1H-1,2,3-triazol-1-yl)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(3-((2-(4-((Z)-1,2-diphenylbut-1-en-1-yl)phenoxy)ethyl)(methyl)amino)-3-oxopropyl)phenethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(4-(2-((2-(4-((Z)-1,2-diphenylbut-1-en-1-yl)phenoxy)ethyl)(methyl)amino)-2-oxoethyl)phenyl)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(5-(4-(3-((2-(4-((Z)-1,2-diphenylbut-1-en-1-yl)phenoxy)ethyl)(methyl)amino)-3-oxopropyl)phenyl)pentanamido)-3,3-dimethylbutanoyl)-4-hydroxy-N-(4-(4-methylthiazol-5-yl)benzyl)pyrrolidine-2-carboxamide;

4-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)oxy)phenyl (2-(4-((Z)-1,2-diphenylbut-1-en-1-yl)phenoxy)ethyl)(methyl)carbamate;

4-(3-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)propyl)phenyl (2-(4-((Z)-1,2-diphenylbut-1-en-1-yl)phenoxy)ethyl)(methyl)carbamate;

(2S,4R)-1-((S)-2-(6-(4-(2-((2-(4-((Z)-1,2-diphenylbut-1-en-1-yl)phenoxy)ethyl)(methyl)amino)-2-oxoethyl)phenyl)hexanamido)-3,3-dimethylbutanoyl)-4-hydroxy-N-(4-(4-methylthiazol-5-yl)benzyl)pyrrolidine-2-carboxamide;

4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)benzyl (2-(4-((Z)-1,2-diphenylbut-1-en-1-yl)phenoxy)ethyl)(methyl)carbamate;

(2S,4R)-1-((S)-2-(2-(2-(4-(2-((2-(4-((Z)-1,2-diphenylbut-1-en-1-yl)phenoxy)ethyl)(methyl)amino)-2-oxoethyl)phenoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-((2-(4-((Z)-1,2-diphenylbut-1-en-1-yl)phenoxy)ethyl)(methyl)amino)-2-oxoethoxy)phenethoxy)acetamido)-3,3-dimethylbutanoyl)-4-hydroxy-N-(4-(4-methylthiazol-5-yl)benzyl)pyrrolidine-2-carboxamide;

4-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)methyl)phenethyl (2-(4-((Z)-1,2-diphenylbut-1-en-1-yl)phenoxy)ethyl)(methyl)carbamate;

4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutoxy)benzyl (2-(4-((Z)-1,2-diphenylbut-1-en-1-yl)phenoxy)ethyl)(methyl)carbamate;

4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)benzyl (2-(4-((Z)-1,2-diphenylbut-1-en-1-yl)phenoxy)ethyl)(methyl)carbamate;

4-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)methyl)benzyl (2-(4-((Z)-1,2-diphenylbut-1-en-1-yl)phenoxy)ethyl)(methyl)carbamate;

6-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)hex-3-yn-1-yl (2-(4-((Z)-1,2-diphenylbut-1-en-1-yl)phenoxy)ethyl)(methyl)carbamate;

6-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)hex-4-yn-1-yl (2-(4-((Z)-1,2-diphenylbut-1-en-1-yl)phenoxy)ethyl)(methyl)carbamate;

(2S,4R)-1-((S)-2-(tert-butyl)-17-(4-((Z)-1,2-diphenylbut-1-en-1-yl)phenoxy)-15-methyl-4,14-dioxo-6,12-dioxa-3,15-diazaheptadec-9-ynoyl)-4-hydroxy-N-(4-(4-methylthiazol-5-yl)benzyl)pyrrolidine-2-carboxamide;

9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxonon-3-yn-1-yl (2-(4-((Z)-1,2-diphenylbut-1-en-1-yl)phenoxy)ethyl)(methyl)carbamate;

9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxonon-4-yn-1-yl (2-(4-((Z)-1,2-diphenylbut-1-en-1-yl)phenoxy)ethyl)(methyl)carbamate;

(2S,4R)-1-((S,E)-2-(tert-butyl)-17-(4-((Z)-1,2-diphenylbut-1-en-1-yl)phenoxy)-15-methyl-4,14-dioxo-6,12-dioxa-3,15-diazaheptadec-9-enoyl)-4-hydroxy-N-(4-(4-methylthiazol-5-yl)benzyl)pyrrolidine-2-carboxamide;

(2S,4R)-1-((S,E)-2-(tert-butyl)-17-(4-((Z)-1,2-diphenylbut-1-en-1-yl)phenoxy)-15-methyl-4,14-dioxo-6,12-dioxa-3,15-diazaheptadec-8-enoyl)-4-hydroxy-N-(4-(4-methylthiazol-5-yl)benzyl)pyrrolidine-2-carboxamide;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

(2S,4R)-1-((S)-2-(3-(4-((2-(4-((Z)-1,2-diphenylbut-1-en-1-yl)phenoxy)ethyl)(methyl)amino)-4-oxobutoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(3-((2-(4-((Z)-1,2-diphenylbut-1-en-1-yl)phenoxy)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide;

6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl (2-(4-((Z)-1,2-diphenylbut-1-en-1-yl)phenoxy)ethyl)(methyl)carbamate;

2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl (2-(4-((Z)-1,2-diphenylbut-1-en-1-yl)phenoxy)ethyl)(methyl)carbamate;

(E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-3-enediamide;

(E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-4-enediamide;

(E)-N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-methyloct-3-enediamide;

(E)-6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-2-en-1-yl (2-(4-((Z)-1,2-diphenylbut-1-en-1-yl)phenoxy)ethyl)(methyl)carbamate;

(E)-6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-3-en-1-yl (2-(4-((Z)-1,2-diphenylbut-1-en-1-yl)phenoxy)ethyl)(methyl)carbamate;

6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohex-2-yn-1-yl (2-(4-((Z)-1,2-diphenylbut-1-en-1-yl)phenoxy)ethyl)(methyl)carbamate;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-3-ynediamide;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloct-4-ynediamide;

N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-methyloct-3-ynediamide;

4-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)phenyl (2-(4-((Z)-1,2-diphenylbut-1-en-1-yl)phenoxy)ethyl)(methyl)carbamate;

(2S,4R)-1-((S)-2-(3-(4-(2-((2-(4-((Z)-1,2-diphenylbut-1-en-1-yl)phenoxy)ethyl)(methyl)amino)-2-oxoethyl)phenyl)propanamido)-3,3-dimethylbutanoyl)-4-hydroxy-N-(4-(4-methylthiazol-5-yl)benzyl)pyrrolidine-2-carboxamide;

4-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)phenyl (2-(4-((Z)-1,2-diphenylbut-1-en-1-yl)phenoxy)ethyl)(methyl)carbamate;

(2S,4R)-1-((S)-2-(2-(4-(2-((2-(4-((Z)-1,2-diphenylbut-1-en-1-yl)phenoxy)ethyl)(methyl)amino)-2-oxoethyl)phenoxy)acetamido)-3,3-dimethylbutanoyl)-4-hydroxy-N-(4-(4-methylthiazol-5-yl)benzyl)pyrrolidine-2-carboxamide;

(2S,4R)-1-((1-(4-((Z)-1,2-diphenylbut-1-en-1-yl)phenoxy)-3-methyl-4-oxo-6,9,12-trioxa-3-azatetradecan-14-oyl)-L-valyl)-4-hydroxy-N-(4-(4-methylthiazol-5-yl)benzyl)pyrrolidine-2-carboxamide;

(2S,4R)-1-((2-(2-(4-(3-((2-(4-((Z)-1,2-diphenylbut-1-en-1-yl)phenoxy)ethyl)(methyl)amino)-3-oxopropyl)-1H-1,2,3-triazol-1-yl)ethoxy)acetyl)-L-valyl)-4-hydroxy-N-(4-(4-methylthiazol-5-yl)benzyl)pyrrolidine-2-carboxamide;

(2S,4R)-1-((2-(3-(4-(2-((2-(4-((Z)-1,2-diphenylbut-1-en-1-yl)phenoxy)ethyl)(methyl)amino)-2-oxoethyl)-1H-1,2,3-triazol-1-yl)propoxy)acetyl)-L-valyl)-4-hydroxy-N-(4-(4-methylthiazol-5-yl)benzyl)pyrrolidine-2-carboxamide;

(2S,4R)-1-((2-(4-(3-((2-(4-((Z)-1,2-diphenylbut-1-en-1-yl)phenoxy)ethyl)(methyl)amino)-3-oxopropyl)phenethoxy)acetyl)-L-valyl)-4-hydroxy-N-(4-(4-methylthiazol-5-yl)benzyl)pyrrolidine-2-carboxamide;

(2S,4R)-1-((2-(3-(4-(2-((2-(4-((Z)-1,2-diphenylbut-1-en-1-yl)phenoxy)ethyl)(methyl)amino)-2-oxoethyl)phenyl)propoxy)acetyl)-L-valyl)-4-hydroxy-N-(4-(4-methylthiazol-5-yl)benzyl)pyrrolidine-2-carboxamide;

(2S,4R)-1-((5-(4-(3-((2-(4-((Z)-1,2-diphenylbut-1-en-1-yl)phenoxy)ethyl)(methyl)amino)-3-oxopropyl)phenyl)pentanoyl)-L-valyl)-4-hydroxy-N-(4-(4-methylthiazol-5-yl)benzyl)pyrrolidine-2-carboxamide;

4-((5-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-5-oxopentyl)oxy)phenyl (2-(4-((Z)-1,2-diphenylbut-1-en-1-yl)phenoxy)ethyl)(methyl)carbamate;

4-(3-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)propyl)phenyl (2-(4-((Z)-1,2-diphenylbut-1-en-1-yl)phenoxy)ethyl)(methyl)carbamate;

(2S,4R)-1-((6-(4-(2-((2-(4-((Z)-1,2-diphenylbut-1-en-1-yl)phenoxy)ethyl)(methyl)amino)-2-oxoethyl)phenyl)hexanoyl)-L-valyl)-4-hydroxy-N-(4-(4-methylthiazol-5-yl)benzyl)pyrrolidine-2-carboxamide;

4-(2-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)ethyl)benzyl (2-(4-((Z)-1,2-diphenylbut-1-en-1-yl)phenoxy)ethyl)(methyl)carbamate;

(2S,4R)-1-((2-(2-(4-(2-((2-(4-((Z)-1,2-diphenylbut-1-en-1-yl)phenoxy)ethyl)(methyl)amino)-2-oxoethyl)phenoxy)ethoxy)acetyl)-L-valyl)-4-hydroxy-N-(4-(4-methylthiazol-5-yl)benzyl)pyrrolidine-2-carboxamide;

(2S,4R)-1-((2-(4-(2-((2-(4-((Z)-1,2-diphenylbut-1-en-1-yl)phenoxy)ethyl)(methyl)amino)-2-oxoethoxy)phenethoxy)acetyl)-L-valyl)-4-hydroxy-N-(4-(4-methylthiazol-5-yl)benzyl)pyrrolidine-2-carboxamide;

4-((2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)methyl)phenethyl (2-(4-((Z)-1,2-diphenylbut-1-en-1-yl)phenoxy)ethyl)(methyl)carbamate;

4-(4-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-4-oxobutoxy)benzyl (2-(4-((Z)-1,2-diphenylbut-1-en-1-yl)phenoxy)ethyl)(methyl)carbamate;

4-(5-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-5-oxopentyl)benzyl (2-(4-((Z)-1,2-diphenylbut-1-en-1-yl)phenoxy)ethyl)(methyl)carbamate;

4-((3-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-3-oxopropoxy)methyl)benzyl (2-(4-((Z)-1,2-diphenylbut-1-en-1-yl)phenoxy)ethyl)(methyl)carbamate;

6-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)hex-3-yn-1-yl (2-(4-((Z)-1,2-diphenylbut-1-en-1-yl)phenoxy)ethyl)(methyl)carbamate;

6-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)hex-4-yn-1-yl (2-(4-((Z)-1,2-diphenylbut-1-en-1-yl)phenoxy)ethyl)(methyl)carbamate;

(2S,4R)-1-((2-((5-(2-((2-(4-((Z)-1,2-diphenylbut-1-en-1-yl)phenoxy)ethyl)(methyl)amino)-2-oxoethoxy)pent-3-yn-1-yl)oxy)acetyl)-L-valyl)-4-hydroxy-N-(4-(4-methylthiazol-5-yl)benzyl)pyrrolidine-2-carboxamide;

(2S,4R)-1-((2-((5-(2-((2-(4-((Z)-1,2-diphenylbut-1-en-1-yl)phenoxy)ethyl)(methyl)amino)-2-oxoethoxy)pent-2-yn-1-yl)oxy)acetyl)-L-valyl)-4-hydroxy-N-(4-(4-methylthiazol-5-yl)benzyl)pyrrolidine-2-carboxamide;

9-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-9-oxonon-3-yn-1-yl (2-(4-((Z)-1,2-diphenylbut-1-en-1-yl)phenoxy)ethyl)(methyl)carbamate;

9-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-9-oxonon-4-yn-1-yl (2-(4-((Z)-1,2-diphenylbut-1-en-1-yl)phenoxy)ethyl)(methyl)carbamate;

(2S,4R)-1-((2-(((E)-5-(2-((2-(4-((Z)-1,2-diphenylbut-1-en-1-yl)phenoxy)ethyl)(methyl)amino)-2-oxoethoxy)pent-3-en-1-yl)oxy)acetyl)-L-valyl)-4-hydroxy-N-(4-(4-methylthiazol-5-yl)benzyl)pyrrolidine-2-carboxamide;

(2S,4R)-1-((2-(((E)-5-(2-((2-(4-((Z)-1,2-diphenylbut-1-en-1-yl)phenoxy)ethyl)(methyl)amino)-2-oxoethoxy)pent-2-en-1-yl)oxy)acetyl)-L-valyl)-4-hydroxy-N-(4-(4-methylthiazol-5-yl)benzyl)pyrrolidine-2-carboxamide;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloctanediamide;

(2S,4R)-1-((3-(4-((2-(4-((Z)-1,2-diphenylbut-1-en-1-yl)phenoxy)ethyl)(methyl)amino)-4-oxobutoxy)propanoyl)-L-valyl)-4-hydroxy-N-(4-(4-methylthiazol-5-yl)benzyl)pyrrolidine-2-carboxamide;

(2S,4R)-1-((4-(3-((2-(4-((Z)-1,2-diphenylbut-1-en-1-yl)phenoxy)ethyl)(methyl)amino)-3-oxopropoxy)butanoyl)-L-valyl)-4-hydroxy-N-(4-(4-methylthiazol-5-yl)benzyl)pyrrolidine-2-carboxamide;

6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohexyl (2-(4-((Z)-1,2-diphenylbut-1-en-1-yl)phenoxy)ethyl)(methyl)carbamate;

2-(3-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-3-oxopropoxy)ethyl (2-(4-((Z)-1,2-diphenylbut-1-en-1-yl)phenoxy)ethyl)(methyl)carbamate;

(E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-3-enediamide;

(E)-N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-4-enediamide;

(E)-N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N8-methyloct-3-enediamide;

(E)-6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-2-en-1-yl (2-(4-((Z)-1,2-diphenylbut-1-en-1-yl)phenoxy)ethyl)(methyl)carbamate;

(E)-6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-3-en-1-yl (2-(4-((Z)-1,2-diphenylbut-1-en-1-yl)phenoxy)ethyl)(methyl)carbamate;

6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-2-yn-1-yl (2-(4-((Z)-1,2-diphenylbut-1-en-1-yl)phenoxy)ethyl)(methyl)carbamate;

6-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-6-oxohex-3-yn-1-yl (2-(4-((Z)-1,2-diphenylbut-1-en-1-yl)phenoxy)ethyl)(methyl)carbamate;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-3-ynediamide;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyloct-4-ynediamide;

N8-(2-(4-((Z)-1,2-diphenylbut-1-en-1-yl)phenoxy)ethyl)-N1-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N8-methyloct-3-ynediamide;

4-(2-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-2-oxoethoxy)phenyl (2-(4-((Z)-1,2-diphenylbut-1-en-1-yl)phenoxy)ethyl)(methyl)carbamate;

(2S,4R)-1-((3-(4-(2-((2-(4-((Z)-1,2-diphenylbut-1-en-1-yl)phenoxy)ethyl)(methyl)amino)-2-oxoethyl)phenyl)propanoyl)-L-valyl)-4-hydroxy-N-(4-(4-methylthiazol-5-yl)benzyl)pyrrolidine-2-carboxamide;

4-(3-(((S)-1-((2S,4R)-4-hydroxy-2-((4-(4-methylthiazol-5-yl)benzyl)carbamoyl)pyrrolidin-1-yl)-3-methyl-1-oxobutan-2-yl)amino)-3-oxopropyl)phenyl (2-(4-((Z)-1,2-diphenylbut-1-en-1-yl)phenoxy)ethyl)(methyl)carbamate;

(2S,4R)-1-((2-(4-(2-((2-(4-((Z)-1,2-diphenylbut-1-en-1-yl)phenoxy)ethyl)(methyl)amino)-2-oxoethyl)phenoxy)acetyl)-L-valyl)-4-hydroxy-N-(4-(4-methylthiazol-5-yl)benzyl)pyrrolidine-2-carboxamide;

(2S,4R)-1-((S)-2-(tert-butyl)-14-(4-((Z)-1,2-diphenylbut-1-en-1-yl)phenoxy)-12-methyl-4,11-dioxo-6,9-dioxa-3,12-diazatetradecanoyl)-4-hydroxy-N-(4-(4-methylthiazol-5-yl)benzyl)pyrrolidine-2-carboxamide;

(2S,4R)-1-((2-(2-(2-((2-(4-((Z)-1,2-diphenylbut-1-en-1-yl)phenoxy)ethyl)(methyl)amino)-2-oxoethoxy)ethoxy)acetyl)-L-valyl)-4-hydroxy-N-(4-(4-methylthiazol-5-yl)benzyl)pyrrolidine-2-carboxamide;

(2S,4R)-1-((S)-2-(tert-butyl)-16-(4-((Z)-1,2-diphenylbut-1-en-1-yl)phenoxy)-14-methyl-4,13-dioxo-7,10-dioxa-3,14-diazahexadecanoyl)-4-hydroxy-N-(4-(4-methylthiazol-5-yl)benzyl)pyrrolidine-2-carboxamide;

(2S,4R)-1-((3-(2-(3-((2-(4-((Z)-1,2-diphenylbut-1-en-1-yl)phenoxy)ethyl)(methyl)amino)-3-oxopropoxy)ethoxy)propanoyl)-L-valyl)-4-hydroxy-N-(4-(4-methylthiazol-5-yl)benzyl)pyrrolidine-2-carboxamide;

N1-(2-(4-((Z)-1,2-diphenylbut-1-en-1-yl)phenoxy)ethyl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyldecanediamide;

N1-(2-(4-((Z)-1,2-diphenylbut-1-en-1-yl)phenoxy)ethyl)-N10-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyldecanediamide;

(2S,4R)-1-((1-(4-((Z)-1,2-diphenylbut-1-en-1-yl)phenoxy)-3-methyl-4-oxo-6,9,12-trioxa-3-azatetradecan-14-oyl)-L-valyl)-4-hydroxy-N-(4-(4-methylthiazol-5-yl)benzyl)pyrrolidine-2-carboxamide;

N1-(2-(4-((Z)-1,2-diphenylbut-1-en-1-yl)phenoxy)ethyl)-N11-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylundecanediamide;

N1-(2-(4-((Z)-1,2-diphenylbut-1-en-1-yl)phenoxy)ethyl)-N11-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methylundecanediamide;

(2S,4R)-1-((S)-2-(tert-butyl)-19-(4-((Z)-1,2-diphenylbut-1-en-1-yl)phenoxy)-17-methyl-4,16-dioxo-7,10,13-trioxa-3,17-diazanonadecanoyl)-4-hydroxy-N-(4-(4-methylthiazol-5-yl)benzyl)pyrrolidine-2-carboxamide;

(2S,4R)-1-((1-(4-((Z)-1,2-diphenylbut-1-en-1-yl)phenoxy)-3-methyl-4-oxo-7,10,13-trioxa-3-azahexadecan-16-oyl)-L-valyl)-4-hydroxy-N-(4-(4-methylthiazol-5-yl)benzyl)pyrrolidine-2-carboxamide;

N1-(2-(4-((Z)-1,2-diphenylbut-1-en-1-yl)phenoxy)ethyl)-N13-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyltridecanediamide;

N1-(2-(4-((Z)-1,2-diphenylbut-1-en-1-yl)phenoxy)ethyl)-N13-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyltridecanediamide;

N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-4,7,10,13-tetraoxahexadecanediamide;

N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyl-4,7,10,13-tetraoxahexadecanediamide;

N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylhexadecanediamide;

N1-(2-(4-((Z)-1,2-diphenylbut-1-en-1-yl)phenoxy)ethyl)-N16-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methylhexadecanediamide;

N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-3,6,9,12,15-pentaoxaheptadecanediamide;

N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methyl-3,6,9,12,15-pentaoxaheptadecanediamide;

N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylheptadecanediamide;

N1-(2-(4-((Z)-1,2-diphenylbut-1-en-1-yl)phenoxy)ethyl)-N17-((S)-1-((2S,4R)-4-hydroxy-2-((4-(4-methylthiazol-5-yl)benzyl)carbamoyl)pyrrolidin-1-yl)-3-methyl-1-oxobutan-2-yl)-N1-methylheptadecanediamide;

N1-(2-(4-((Z)-1,2-diphenylbut-1-en-1-yl)phenoxy)ethyl)-N3-((S)-1-((2S,4R)-4-hydroxy-2-((4-(4-meththiazol-5-yl)benzyl)carbamoyl)pyrrolidin-1-yl)-3,3-dimethyl-1-oxobutan-2-yl)cyclobutane-1,3-dicarboxamide;

N1-(2-(4-((Z)-1,2-diphenylbut-1-en-1-yl)phenoxy)ethyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylcyclobutane-1,3-dicarboxamide;

N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N3-(2-(4-((Z)-1-(4-hydroxyphenyl)-2-phenylbut-1-en-1-yl)phenoxy)ethyl)cyclobutane-1,3-dicarboxamide;

N2-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N6-(2-(4-((Z)-1-(4-hydroxyphenyl)-2-phenylbut-1-en-1-yl)phenoxy)ethyl)spiro[3.3]heptane-2,6-dicarboxamide;

(2S,4R)-1-((S)-2-(2-(4-((2-(4-((Z)-1,2-diphenylbut-1-en-1-yl)phenoxy)ethyl)carbamoyl)phenyl)acetamido)-3,3-dimethylbutanoyl)-4-hydroxy-N-(4-(4-methylthiazol-5-yl)benzyl)pyrrolidine-2-carboxamide;

N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N4-(2-(4-((Z)-1-(4-hydroxyphenyl)-2-phenylbut-1-en-1-yl)phenoxy)ethyl)but-2-ynediamide;

N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-(2-(4-((Z)-1-(4-hydroxyphenyl)-2-phenylbut-1-en-1-yl)phenoxy)ethyl)hex-2-ynediamide;

N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-(2-(4-((Z)-1-(4-hydroxyphenyl)-2-phenylbut-1-en-1-yl)phenoxy)ethyl)oct-2-ynediamide;

N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N6-(2-(4-((Z)-1-(4-hydroxyphenyl)-2-phenylbut-1-en-1-yl)phenoxy)ethyl)hexa-2,4-diynediamide;

N1-(3-((2-(4-((Z)-1,2-diphenylbut-1-en-1-yl)phenoxy)ethyl)(methyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinimide;

N$^1$-(3-((2-(4-((Z)-1,2-diphenylbut-1-en-1-yl)phenoxy)ethyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinimide;

N1-(2-(4-((Z)-1,2-bis(4-hydroxyphenyl)but-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

N1-(2-(4-((Z)-1,2-bis(4-hydroxyphenyl)but-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide;

N$^1$-(3-((2-(4-((Z)-1,2-bis(4-hydroxyphenyl)but-1-en-1-yl)phenoxy)ethyl)(methyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinimide;

(2S,4R)-1-((S)-2-(4-(3-((2-(4-((Z)-1,2-bis(4-hydroxyphenyl)but-1-en-1-yl)phenoxy)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide;

N1-(2-((4-((Z)-1,2-diphenylbut-1-en-1-yl)phenyl)thio)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-(2-(4-((Z)-1-(4-hydroxyphenyl)-2-phenylbut-1-en-1-yl)phenoxy)ethyl)octanediamide;

(2S,4R)-1-((S)-2-(4-3-((2-((4-((Z)-1,2-diphenylbut-1-en-1-yl)phenyl)thio)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide;

N1-(2-((4-((Z)-1,2-diphenylbut-1-en-1-yl)phenyl)amino)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

N1-(3-((2-((4-((Z)-1,2-diphenylbut-1-en-1-yl)phenyl)amino)ethyl)(methyl)amino)-3-oxopropyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinimide;

(2S,4R)-1-((S)-2-(4-(3-((2-((4-((Z)-1,2-diphenylbut-1-en-1-yl)phenyl)amino)ethyl)(methyl)amino)-3-oxopropoxy)butanamido)-3,3-dimethylbutanoyl)-4-hydroxy-N-(4-(4-methylthiazol-5-yl)benzyl)pyrrolidine-2-carboxamide;

N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-(2-(4-((Z)-1-(4-hydroxyphenyl)-2-phenylbut-1-en-1-yl)phenoxy)ethyl)-N8-methyloctanediamide; or (2S,4R)-4-hydroxy-1-((S)-2-(4-(3-((2-((4-((E)-1-(4-hydroxyphenyl)-2-phenylbut-1-en-1-yl)phenyl)amino)ethyl)(methyl)amino)-3-oxopropoxy)butanamido)-3,3-dimethylbutanoyl)-N-(4-(4-methylthiazol-5-yl)benzyl)pyrrolidine-2-carboxamide; or tautomer, stereoisomer, pharmaceutically acceptable salt, or hydrate thereof.

31. The compound according to claim 9, wherein the compound is:

(2S,4R)-1-((S)-2-(tert-butyl)-17-(4-((Z)-1,2-diphenylbut-1-en-1-yl)phenoxy)-15-methyl-4,14-dioxo-6,9,12-trioxa-3,15-diazaheptadecanoyl)-4-hydroxy-N-(4-(4-methylthiazol-5-yl)benzyl)pyrrolidine-2-carboxamide;

N1-(2-(4-((Z)-1,2-diphenylbut-1-en-1-yl)phenoxy)ethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-(2-(4-((Z)-1-(4-hydroxyphenyl)-2-phenylbut-1-en-1-yl)phenoxy)ethyl)-N8-methyloctanediamide; or N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-(2-(4-((Z)-1-(4-hydroxyphenyl)-2-phenylbut-1-en-1-yl)phenoxy)ethyl)octanediamide, or tautomer, stereoisomer, pharmaceutically acceptable salt or hydrate thereof.

32. A pharmaceutical composition comprising the compound according to 1, or tautomer, stereoisomer, pharmaceutically acceptable salt or hydrate thereof, and at least one additional component selected from pharmaceutically acceptable carriers, pharmaceutically acceptable vehicles, and pharmaceutically acceptable excipients.

33. The pharmaceutical composition according to claim 32, wherein the compound or tautomer, stereoisomer, pharmaceutically acceptable salt or hydrate thereof is present in a therapeutically effective amount.

34. A pharmaceutical composition comprising the compound according to claim 30, or tautomer, stereoisomer, pharmaceutically acceptable salt or hydrate thereof, and at least one additional component selected from pharmaceutically acceptable carriers, pharmaceutically acceptable vehicles, and pharmaceutically acceptable excipients.

35. A pharmaceutical composition comprising the compound according to claim 31, or tautomer, stereoisomer, pharmaceutically acceptable salt or hydrate thereof, and at least one additional component selected from pharmaceutically acceptable carriers, pharmaceutically acceptable vehicles, and pharmaceutically acceptable excipients.

36. A method of treating cancer in a subject in need thereof, comprising administering to said subject an effective amount of the compound according to claim 1, or tautomer, stereoisomer, pharmaceutically acceptable salt or hydrate thereof, wherein the cancer is chosen from breast cancer, lung cancer, ovarian cancer, endometrial cancer, prostate cancer, and esophageal cancer.

37. The method according to claim 36, wherein the cancer is breast cancer.

38. The method according to claim 36, wherein the cancer is positive for Estrogen Receptor alpha.

39. The method according to claim 36, wherein the subject has been previously treated with an anti-cancer agent.

40. The method according to claim 39, wherein the anti-cancer agent is tamoxifen.

41. A method of treating cancer in a subject in need thereof, comprising administering to said subject an effective amount of the compound according to claim 30, or tautomer, stereoisomer, pharmaceutically acceptable salt or hydrate thereof, wherein the cancer is chosen from breast cancer, lung cancer, ovarian cancer, endometrial cancer, prostate cancer, and esophageal cancer.

42. The method according to claim 41, wherein the cancer is breast cancer.

43. The method according to claim 41, wherein the cancer is positive for Estrogen Receptor alpha.

44. The method according to claim 41, wherein the subject has been previously treated with an anti-cancer agent.

45. The method according to claim 44, wherein the anti-cancer agent is tamoxifen.

46. A method of inhibiting cell growth, comprising contacting a cell with the compound according to claim 1, or tautomer, stereoisomer, pharmaceutically acceptable salt or hydrate thereof.

47. The method according to claim 46, wherein the cell is a cancer cell.

48. The method according to claim 46, wherein the cell expresses Estrogen Receptor alpha.

* * * * *

UNITED STATES PATENT AND TRADEMARK OFFICE
CERTIFICATE OF CORRECTION

PATENT NO. : 10,968,212 B2
APPLICATION NO. : 16/560178
DATED : April 6, 2021
INVENTOR(S) : Jie Fan et al.

It is certified that error appears in the above-identified patent and that said Letters Patent is hereby corrected as shown below:

In the Claims

In Claim 30, Column 155, Line 46, "$N^1$" should read as --N1--.

In Claim 30, Column 155, Line 60, "$N^1$" should read as --N1--.

Signed and Sealed this
Tenth Day of January, 2023

Katherine Kelly Vidal
*Director of the United States Patent and Trademark Office*